(12) United States Patent
Chen et al.

(10) Patent No.: US 10,308,660 B2
(45) Date of Patent: Jun. 4, 2019

(54) COMPOUNDS AND COMPOSITIONS FOR INHIBITING THE ACTIVITY OF SHP2

(71) Applicants: Zhuoliang Chen, Belmont, MA (US); Jorge Garcia Fortanet, Wilmington, MA (US); Matthew J. LaMarche, Reading, MA (US); Martin Sendzik, Belmont, MA (US); Victoriano Tamez, Jr., Hull, MA (US); Bing Yu, Belmont, MA (US)

(72) Inventors: Zhuoliang Chen, Belmont, MA (US); Jorge Garcia Fortanet, Wilmington, MA (US); Matthew J. LaMarche, Reading, MA (US); Martin Sendzik, Belmont, MA (US); Victoriano Tamez, Jr., Hull, MA (US); Bing Yu, Belmont, MA (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 15/736,989

(22) PCT Filed: Jun. 15, 2016

(86) PCT No.: PCT/IB2016/053549
§ 371 (c)(1),
(2) Date: Dec. 15, 2017

(87) PCT Pub. No.: WO2016/203405
PCT Pub. Date: Dec. 22, 2016

(65) Prior Publication Data
US 2018/0251471 A1 Sep. 6, 2018

Related U.S. Application Data

(60) Provisional application No. 62/181,871, filed on Jun. 19, 2015.

(51) Int. Cl.
| | |
|---|---|
| *C07D 401/04* | (2006.01) |
| *C07D 491/107* | (2006.01) |
| *C07D 401/14* | (2006.01) |
| *A61P 35/00* | (2006.01) |

(52) U.S. Cl.
CPC .......... *C07D 491/107* (2013.01); *A61P 35/00* (2018.01); *C07D 401/04* (2013.01); *C07D 401/14* (2013.01)

(58) Field of Classification Search
CPC .......................... C07D 491/107; C07D 401/04
See application file for complete search history.

(56) References Cited

U.S. PATENT DOCUMENTS

| | | | |
|---|---|---|---|
| 4,613,603 A | 9/1986 | Biziere et al. | |
| 2003/0171359 A1 | 9/2003 | Dahmann et al. | |
| 2005/0222159 A1 | 10/2005 | Tsutsumi et al. | |
| 2008/0024964 A1 | 1/2008 | Lev et al. | |
| 2010/0029941 A1* | 2/2010 | Wallace | C07D 211/56 544/310 |
| 2011/0306606 A1 | 12/2011 | Ryu et al. | |
| 2011/0319381 A1 | 12/2011 | Abouabdellah et al. | |
| 2013/0116430 A1 | 5/2013 | Fujiwara et al. | |
| 2015/0315207 A1 | 11/2015 | Morales et al. | |

FOREIGN PATENT DOCUMENTS

| | | |
|---|---|---|
| EP | 799617 A2 | 10/1997 |
| WO | 1991019305 A1 | 5/1991 |
| WO | 2000059893 A1 | 10/2000 |
| WO | 2002024679 A1 | 3/2002 |

(Continued)

OTHER PUBLICATIONS

Cancer and Metastasis Reviews (1998), 17(1), 91-106.*
Science (1999), vol. 286, 531-537.*
Cancer [online], [retrieved on Jul. 6, 2007]. Retrieved from the internet, URL http://www.nlm.nih.gov/medlineplus/cancer.html>.*
Whelligan, et al., "Aminopyrazine Inhibitors Binding to an Unusual Inactive Conformation of the Mitotic Kinase Nek2: SAR and Structural Characterization", Journal of Medicinal Chemistry, 2010, vol. 53, No. 21, pp. 7682-7698, American Chemical Society.
Ellingboe, et al., (Pyrimidinyloxy)acetic Acids and Pyrimidineacetic Acids as a Novel Class of Aldose Reductase Inhibitors, Journal of Medicinal Chemistry, 1990, vol. 33, pp. 2892-2899, American Chemical Society.

(Continued)

*Primary Examiner* — Shawquia Jackson
(74) *Attorney, Agent, or Firm* — Scott W. Reid

(57) ABSTRACT

The present invention relates to compounds of formula I:

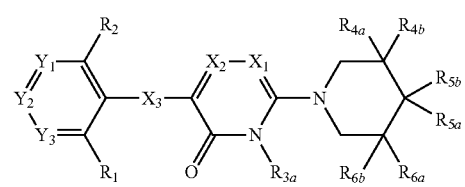

in which $X_1$, $X_2$, $X_3$, $Y_1$, $Y_2$, $Y_3$, $R_1$, $R_2$, $R_{3a}$, $R_{4a}$, $R_{4b}$, $R_{5a}$, $R_{5b}$, $R_{6a}$ and $R_{6b}$ are defined in the Summary of the Invention; capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

20 Claims, No Drawings
Specification includes a Sequence Listing.

(56) References Cited

FOREIGN PATENT DOCUMENTS

| WO | 2005117909 A2 | 12/2005 |
| WO | 2007031529 A1 | 3/2007 |
| WO | 2008055959 A1 | 5/2008 |
| WO | 2008100412 A1 | 8/2008 |
| WO | 2008110611 A1 | 9/2008 |
| WO | 2009131687 A2 | 10/2009 |
| WO | 2009150230 A1 | 12/2009 |
| WO | 2009158571 A1 | 12/2009 |
| WO | 2010008739 A2 | 1/2010 |
| WO | 2010048149 A2 | 4/2010 |
| WO | 2010121212 A2 | 10/2010 |
| WO | 2011078143 A1 | 6/2011 |
| WO | 2012009217 A1 | 1/2012 |
| WO | 2012016217 A1 | 2/2012 |
| WO | 2012027495 A1 | 3/2012 |
| WO | 2012052948 A1 | 4/2012 |
| WO | 2013040044 A1 | 3/2013 |
| WO | 2013096093 A1 | 6/2013 |
| WO | 2013182546 A1 | 12/2013 |
| WO | 2014054053 A1 | 4/2014 |
| WO | 2014160521 A1 | 10/2014 |
| WO | 2015107493 A1 | 7/2015 |
| WO | 2015107494 A1 | 7/2015 |
| WO | 2015168466 A1 | 11/2015 |
| WO | 2016203404 A1 | 12/2016 |
| WO | 2016203406 A1 | 12/2016 |

OTHER PUBLICATIONS

Aso, et al., "Discovery of pyrrolo[2,3-d]pyrimidin-4-ones as corticotropin-releasing factor 1 receptor agonists with a carbonyl-based hydrogen bonding acceptor", Bioorganic & Medicinal Chemistry Letters, 2011, pp. 2365-237, vol. 21, Elsevier Ltd.

Fortanet, et al., "Allosteric Inhibition of SHP2: Identification of a Potent, Selective, and Orally Efficacious Phosphatase Inhibitor", Journal of Medicinal Chemistry, Jun. 27, 2016, pp. 7773-7782, vol. 59, American Chemical Society.

* cited by examiner

COMPOUNDS AND COMPOSITIONS FOR INHIBITING THE ACTIVITY OF SHP2

CROSS REFERENCE TO RELATED APPLICATIONS

This application is a 371 U.S. national phase application of international application number PCT/IB2016/053549 filed 15 Jun. 2016, which application claims the benefit of priority under 35 U.S.C. § 119(e) to U.S. Provisional Patent Application No. 62/181,871, filed 19 Jun. 2015, the disclosures of which are incorporated herein by reference in their entirety and for all purposes.

BACKGROUND

Field of the Invention

The present invention relates to compounds capable of inhibiting the activity of SHP2. The invention further provides a process for the preparation of compounds of the invention, pharmaceutical preparations comprising such compounds and methods of using such compounds and compositions in the management of diseases or disorders associated with the aberrant activity of SHP2.

Background of the Invention

The Src Homolgy-2 phosphatase (SHP2) is a non-receptor protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive, self-inhibited conformation stabilized by a binding network involving residues from both the N-SH2 and PTP domains. Stimulation by, for example, cytokines or growth factors leads to exposure of the catalytic site resulting in enzymatic activation of SHP2.

Mutations in the PTPN11 gene and subsequently in SHP2 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2, therefore, represents a highly attractive target for the development of novel therapies for the treatment of various diseases. The compounds of the present invention fulfill the need of small molecules to that inhibit the activity of SHP2.

SUMMARY OF THE INVENTION

In one aspect, the present invention provides compounds, or the pharmaceutically acceptable salts thereof, of Formula I:

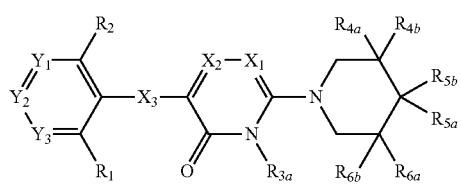

in which:
$X_1$ is selected from N and CH; $X_2$ is $CR_{3b}$; $X_3$ is selected from S and a bond; $Y_1$ is selected from N and $CR_7$; wherein $R_7$ is selected from hydrogen, amino, halo, $C_{1-3}$alkyl, $C_{1-3}$alkoxy and hydroxy; $Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; $Y_3$ is selected from N and $CR_9$; wherein $R_9$ is selected from hydrogen, amino, halo, $C_{1-3}$alkyl, —NH($C_{3-5}$cycloalkyl), $C_{1-3}$alkoxy and hydroxy; $R_1$ is selected from hydrogen, halo, halo-substituted-$C_{1-2}$alkyl, halo-substituted-$C_{1-2}$alkoxy, $C_{1-2}$alkyl-hydroxy and cyano; or $R_1$ and $R_8$ together with the carbon atoms to which $R_1$ and $R_8$ are attached form a ring selected from 1,3-dioxole, phenyl, pyridine, cyclopentene, dihydrofuran, dihydropyrane; wherein said 1,3-dioxole, phenyl, pyridine, cyclopentene, 2,3-dihydrofuran, 2,3-dihydropyrrole, or dihydropyrane can be unsubstituted or substituted 1 to 2 halo groups; $R_2$ is selected from hydrogen and halo; $R_{3a}$ is selected from hydrogen, methyl and halo-substituted-$C_{1-2}$alkyl; $R_{3b}$ is selected from hydrogen, methyl and amino; $R_{4a}$ and $R_{4b}$ are each independently selected from hydrogen, hydroxy and fluoro; with proviso that $R_{4a}$ and $R_{4b}$ cannot both be OH; with the proviso that $R_{4a}$ and $R_{4b}$ cannot be OH and F simultaneously; $R_{5a}$ is selected from amino and amino-methyl; $R_{5b}$ is selected from OH, amino, fluoro, $C_{1-6}$alkyl, methoxy-carbonyl, $C_{3-6}$cycloalkyl-$C_{1-3}$alkyl, hydroxy-substituted $C_{1-3}$alkyl, $C_{1-2}$alkoxy-substituted $C_{1-3}$alkyl and a 5 to 6 member heteroaryl ring containing 1 to 4 heteroatoms selected from O, S and N; wherein said $C_{1-6}$alkyl or $C_{1-2}$alkoxy-substituted $C_{1-3}$alkyl of $R_{5b}$ is unsubstituted or substituted with 1-3 fluorines; with the proviso that if $R_{5a}$ is amino, $R_{5b}$ cannot be OH, amino or fluoro; or $R_{5a}$ and $R_{5b}$, together with the carbon atom to which $R_{5a}$ and $R_{5b}$ are attached, form a group selected from:

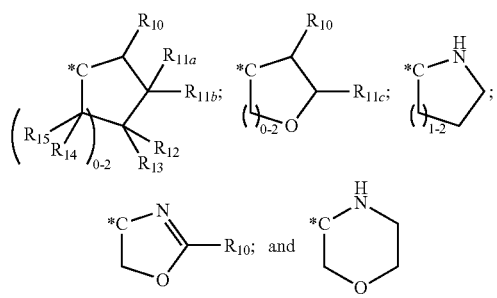

wherein *C represents the carbon atom to which $R_{5a}$ and $R_{5b}$ are attached; $R_{10}$ is amino; $R_{11a}$ is selected from hydrogen, hydroxy, fluoro, $C_{1-3}$alkyl and hydroxy-methyl; $R_{11b}$ is selected from fluoro, methyl and hydrogen; with proviso that $R_{11a}$ and $R_{11b}$ cannot both be OH and fluoro simultaneously; $R_{11c}$ is selected from hydrogen, $C_{1-3}$alkyl and hydroxy-methyl; $R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy; $R_{13}$ is selected from hydrogen, halo and $C_{1-3}$alkyl; $R_{14}$ is selected from hydrogen and fluoro; with proviso that $R_{12}$ and $R_{13}$ cannot both be OH and fluoro simultaneously; $R_{15}$ is selected from hydrogen and fluoro; and $R_{6a}$ and $R_{6b}$ are each independently selected from hydrogen, hydroxy and fluoro; with proviso that $R_{6a}$ and $R_{6b}$ cannot both be OH; with proviso that $R_{6a}$ and $R_{6b}$ cannot both be OH and fluoro simultaneously; or the pharmaceutically acceptable salts thereof; with the proviso that a compound of formula I does not include a compound selected from:

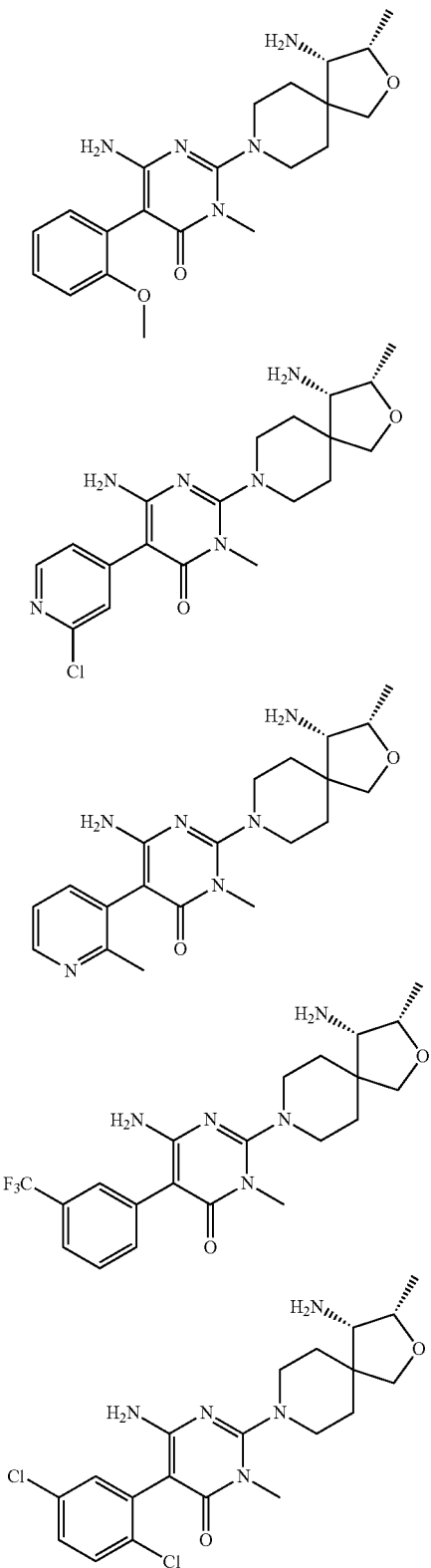

In a second aspect, the present invention provides a pharmaceutical composition which contains a compound of Formula I or a N-oxide derivative, tautomer, individual isomers and mixture of isomers thereof; or a pharmaceutically acceptable salt thereof, in admixture with one or more suitable excipients.

In a third aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof.

In a fourth aspect, the present invention provides a method of treating a disease in an animal in which modulation of SHP2 activity can prevent, inhibit or ameliorate the pathology and/or symptomology of the diseases, which method comprises administering to the animal a therapeutically effective amount of a compound of Formula I or a N-oxide derivative, individual isomers and mixture of isomers thereof, or a pharmaceutically acceptable salt thereof, in simultaneous or sequential combination with an anti-cancer therapeutic.

In a fifth aspect, the present invention provides the use of a compound of Formula I in the manufacture of a medicament for treating a disease in an animal in which SHP2 activity contributes to the pathology and/or symptomology of the disease.

In a sixth aspect, the present invention provides a process for preparing compounds of Formula I and the N-oxide derivatives, prodrug derivatives, protected derivatives, individual isomers and mixture of isomers thereof, and the pharmaceutically acceptable salts thereof.

Definitions

The general terms used hereinbefore and hereinafter preferably have within the context of this disclosure the following meanings, unless otherwise indicated, where more general terms wherever used may, independently of each other, be replaced by more specific definitions or remain, thus defining more detailed embodiments of the invention:

"Alkyl" refers to a fully saturated branched or unbranched hydrocarbon moiety having up to 20 carbon atoms. Unless otherwise provided, alkyl refers to hydrocarbon moieties having 1 to 7 carbon atoms ($C_{1-7}$alkyl), or 1 to 4 carbon atoms ($C_{1-4}$alkyl). Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, n-decyl and the like. A substituted alkyl is an alkyl group containing one or more, such as one, two or three substituents selected from halogen, hydroxy or alkoxy groups. Halo-substituted-alkyl and halo-substituted-alkoxy, can be either straight-chained or branched and includes, methoxy, ethoxy, difluoromethyl, trifluoromethyl, pentafluoroethyl, difluoromethoxy, trifluoromethoxy, and the like.

"Aryl" means a monocyclic or fused bicyclic aromatic ring assembly containing six to ten ring carbon atoms. For example, aryl may be phenyl or naphthyl, preferably phenyl. "Arylene" means a divalent radical derived from an aryl group.

"Heteroaryl" is as defined for aryl above where one or more of the ring members is a heteroatom. For example $C_{5-10}$heteroaryl is a minimum of 5 members as indicated by the carbon atoms but that these carbon atoms can be replaced by a heteroatom. Consequently, $C_{5-10}$heteroaryl includes pyridyl, indolyl, indazolyl, quinoxalinyl, quinolinyl, benzofuranyl, benzopyranyl, benzothiopyranyl, benzo[1,3]dioxole, imidazolyl, benzo-imidazolyl, pyrimidinyl, furanyl, oxazolyl, isoxazolyl, triazolyl, tetrazolyl, pyrazolyl, thienyl, etc.

"Cycloalkyl" means a saturated or partially unsaturated, monocyclic, fused bicyclic or bridged polycyclic ring assembly containing the number of ring atoms indicated. For example, $C_{3-10}$cycloalkyl includes cyclopropyl, cyclobutyl, cyclopentyl, cyclohexyl, cyclohexenyl, etc.

"Heterocycloalkyl" means cycloalkyl, as defined in this application, provided that one or more of the ring carbons indicated, are replaced by a moiety selected from —O—, —N═, —NR—, —C(O)—, —S—, —S(O)— or —S(O)$_2$—, wherein R is hydrogen, $C_{1-4}$alkyl or a nitrogen protecting group. For example, $C_{3-8}$heterocycloalkyl as used in this application to describe compounds of the invention includes morpholino, pyrrolidinyl, pyrrolidinyl-2-one, piperazinyl, piperidinyl, piperidinylone, 1,4-dioxa-8-aza-spiro [4.5]dec-8-yl, thiomorpholino, sulfanomorpholino, sulfonomorpholino, etc.

"Halogen" (or halo) preferably represents chloro or fluoro, but may also be bromo or iodo.

"SHP2" means "Src Homolgy-2 phosphatase" and is also known as SH-PTP2, SH-PTP3, Syp, PTP1D, PTP2C, SAP-2 or PTPN11.

Cancers harboring "PTPN11 mutations" include but are not limited to: N58Y; D61Y, V; E69K; A72V, T, D; E76G, Q, K (ALL); G60A; D61Y; E69V; F71K; A72V; T73I; E76G, K; R289G; G503V (AML); G60R, D61Y, V, N; Y62D; E69K; A72T, V; T73I; E76K, V, G, A, Q; E139D; G503A, R; Q506P (JMML); G60V; D61V; E69K; F71L; A72V; E76A (MDS); Y63C (CMML); Y62C; E69K; T507K (neuroblastoma); V46L; N58S; E76V (Lung cancer); R138Q (melanoma); E76G (colon cancer).

Compounds of formula I may have different isomeric forms. For example, any asymmetric carbon atom may be present in the (R)-, (S)- or (R,S)-configuration, preferably in the (R)- or (S)-configuration. Substituents at a double bond or especially a ring may be present in cis-(═Z-) or trans (═E-) form. The compounds may thus be present as mixtures of isomers or preferably as pure isomers, preferably as pure diastereomers or pure enantiomers.

Where the plural form (e.g. compounds, salts) is used, this includes the singular (e.g. a single compound, a single salt). "A compound" does not exclude that (e.g. in a pharmaceutical formulation) more than one compound of the formula I (or a salt thereof) is present, the "a" merely representing the indefinite article. "A" can thus preferably be read as "one or more", less preferably alternatively as "one".

Wherever a compound or compounds of the formula I are mentioned, this is further also intended to include N-oxides of such compounds and/or tautomers thereof.

The term "and/or an N-oxide thereof, a tautomer thereof and/or a (preferably pharmaceutically acceptable) salt thereof" especially means that a compound of the formula I may be present as such or in mixture with its N-oxide, as tautomer (e.g. due to keto-enol, lactam-lactim, amide-imidic acid or enamine-imine tautomerism) or in (e.g. equivalency reaction caused) mixture with its tautomer, or as a salt of the compound of the formula I and/or any of these forms or mixtures of two or more of such forms.

The present invention also includes all suitable isotopic variations of the compounds of the invention, or pharmaceutically acceptable salts thereof. An isotopic variation of a compound of the invention or a pharmaceutically acceptable salt thereof is defined as one in which at least one atom is replaced by an atom having the same atomic number but an atomic mass different from the atomic mass usually found in nature. Examples of isotopes that may be incorporated into the compounds of the invention and pharmaceutically acceptable salts thereof include, but are not limited to, isotopes of hydrogen, carbon, nitrogen and oxygen such as $^2$H, $^3$H, $^{11}$C, $^{13}$C, $^{14}$C, $^{15}$N, $^{17}$O, $^{18}$O, $^{35}$S, $^{18}$F, $^{36}$Cl and $^{123}$I. Certain isotopic variations of the compounds of the invention and pharmaceutically acceptable salts thereof, for example, those in which a radioactive isotope such as $^3$H or $^{14}$C is incorporated, are useful in drug and/or substrate tissue distribution studies. In particular examples, $^3$H and $^{14}$C isotopes may be used for their ease of preparation and detectability. In other examples, substitution with isotopes such as $^2$H may afford certain therapeutic advantages resulting from greater metabolic stability, such as increased in vivo half-life or reduced dosage requirements. Isotopic variations of the compounds of the invention or pharmaceutically acceptable salts thereof can generally be prepared by conventional procedures using appropriate isotopic variations of suitable reagents.

DESCRIPTION OF PREFERRED EMBODIMENTS

The present invention relates to compounds capable of inhibiting the activity of SHP2. In one aspect of the invention, with respect to compounds of formula I, are compounds of formula Ia:

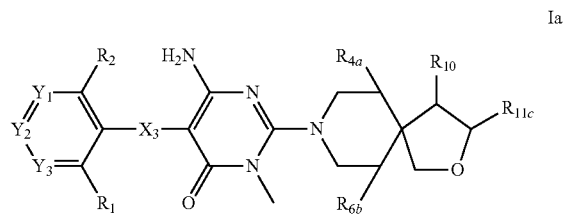

in which: $X_3$ is selected from S; $Y_1$ is selected from N and $CR_7$; wherein $R_7$ is selected from hydrogen, amino, halo, $C_{1-3}$alkyl, $C_{1-3}$alkoxy; $Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole; $Y_3$ is selected from N and $CR_9$; wherein $R_9$ is selected from hydrogen, amino, halo, $C_{1-3}$alkyl, $C_{1-3}$alkoxy and hydroxy; $R_1$ is selected from hydrogen, halo, halo-substituted-$C_{1-2}$alkyl; $R_2$ is selected from hydrogen and chloro; $R_{4a}$ is selected from hydrogen, hydroxy and fluoro; $R_{6b}$ is selected from hydrogen, hydroxy and fluoro; $R_{10}$ is amino; and $R_{11c}$ is selected from hydrogen and $C_{1-3}$alkyl; or the pharmaceutically acceptable salts thereof.

In a further aspect of the invention: $Y_1$ is selected from N and $CR_7$; wherein $R_7$ is selected from hydrogen, halo and amino; $Y_2$ is selected from N and $CR_8$; wherein $R_8$ is selected from hydrogen, halo, amino, dimethyl-amino, cyano, halo-substituted-$C_{1-2}$alkyl, $C_{1-2}$alkoxy, cyclopropyl, cyclopentyl, cyclopentyl-methoxy, halo-substituted-$C_{1-2}$alkoxy, phenyl, methoxy-ethoxy, tetrahydro-2H-pyran-4-yl, phenoxy and benzoxy; $Y_3$ is selected from N and $CR_9$; wherein $R_9$ is selected from hydrogen, amino, halo, $C_{1-2}$alkoxy, cyclopropyl, trifluoromethyl, trifluoromethyl-sulfanyl, isopropyl and hydroxy; $R_1$ is selected from hydrogen, halo, trifluoromethyl, trifluoromethoxy, $C_{1-2}$alkyl and cyano; $R_2$ is selected from hydrogen, fluoro and chloro; $R_{4a}$ is hydrogen; $R_{6b}$ is hydrogen; $R_{10}$ is amino; and $R_{11c}$ is selected from hydrogen, methyl and ethyl; or the pharmaceutically acceptable salts thereof.

In a further aspect of the invention are compounds, or a pharmaceutically acceptable salt thereof, selected from:

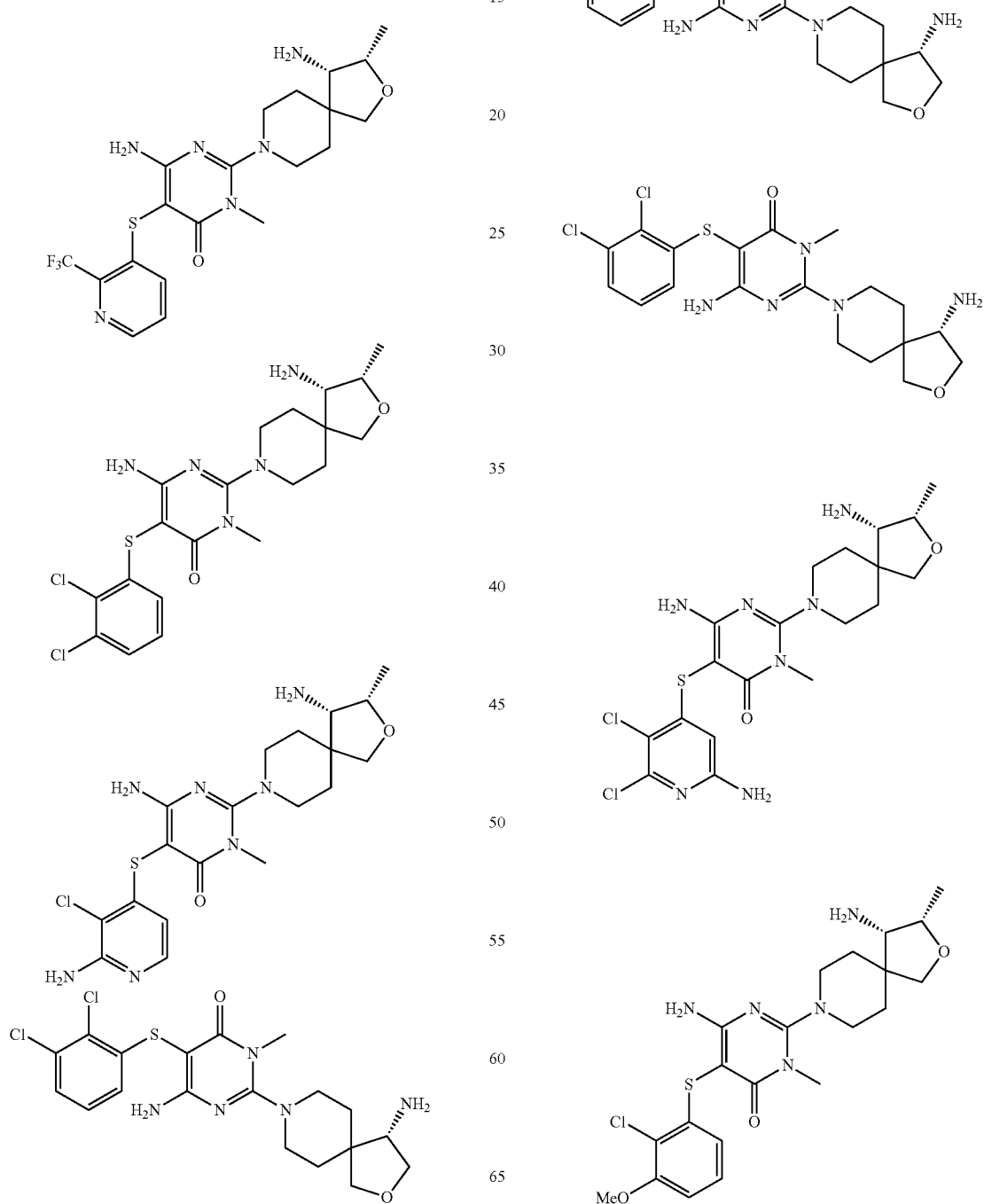

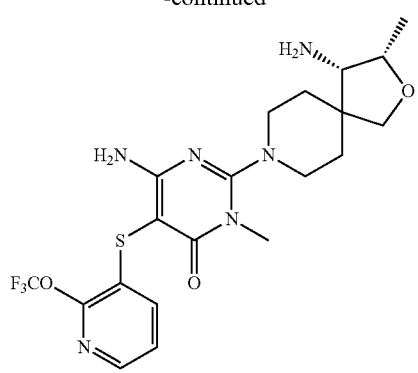
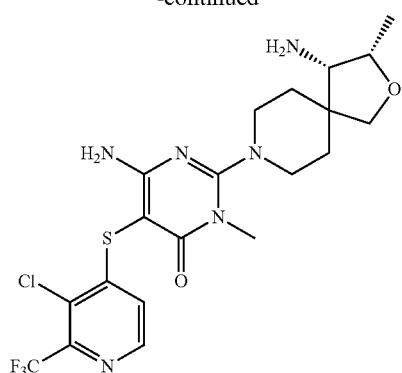
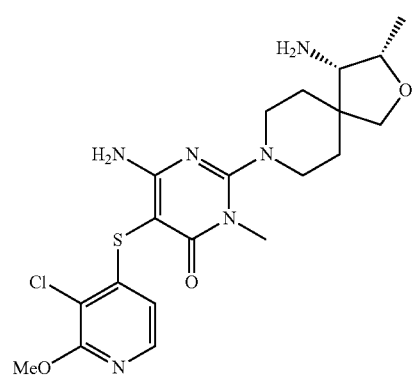
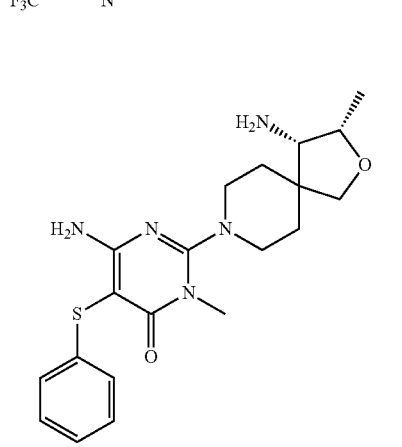
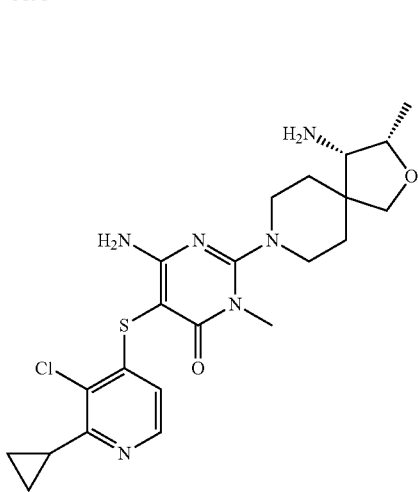
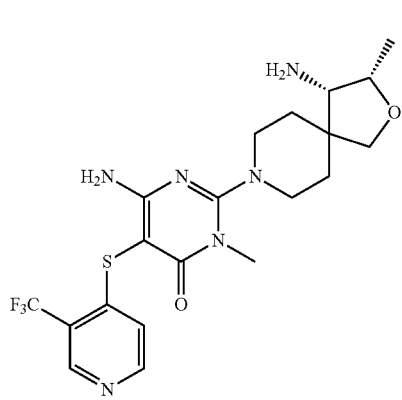
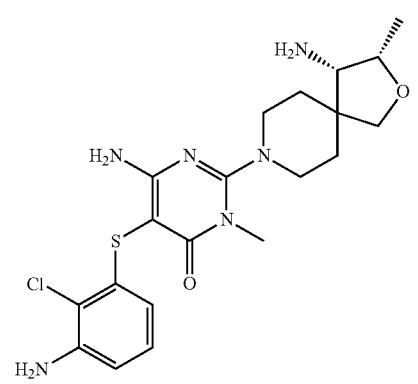
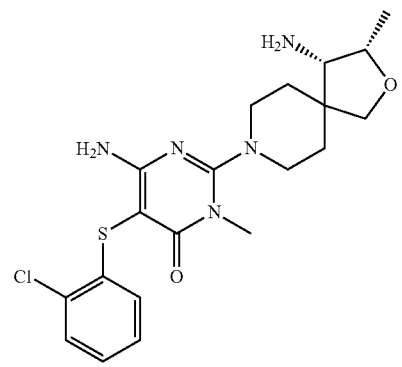

-continued
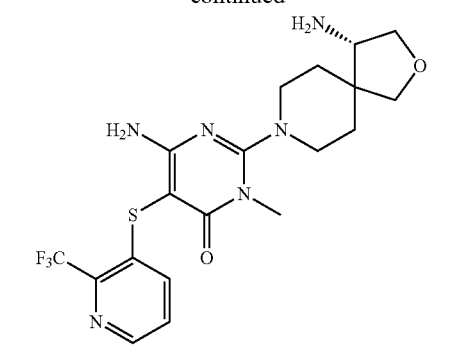
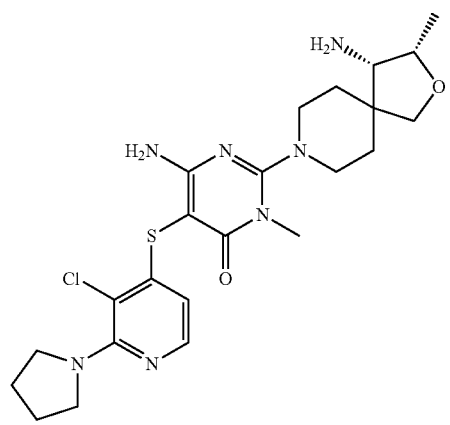
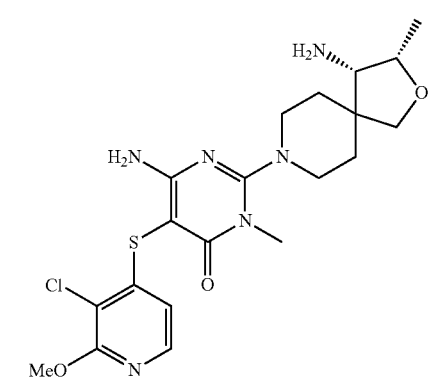
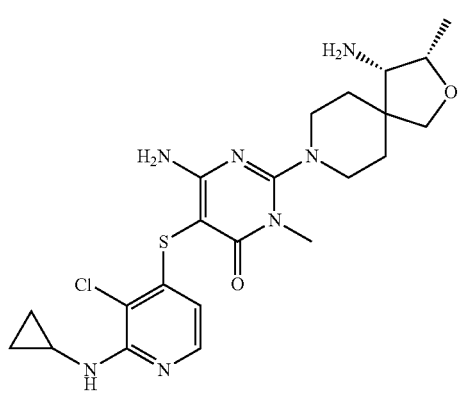
-continued
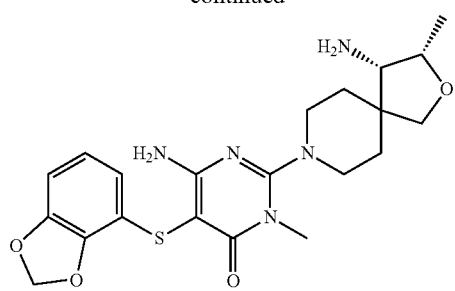
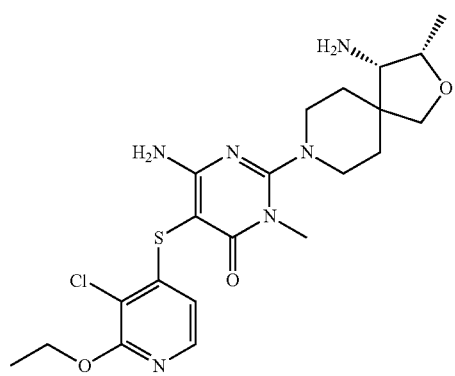
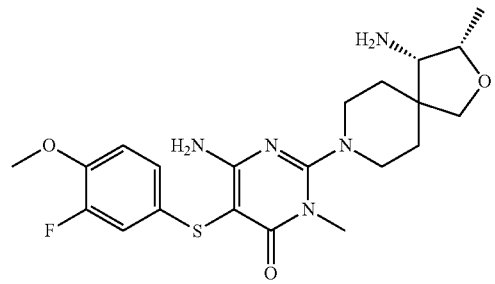
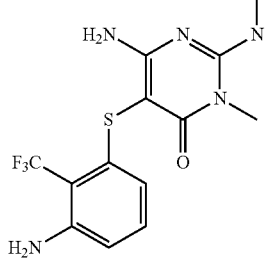
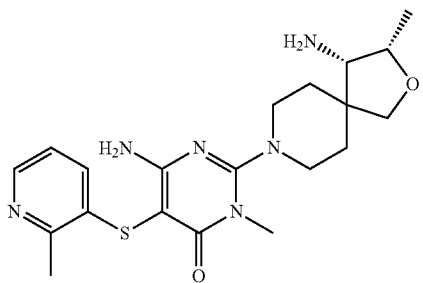

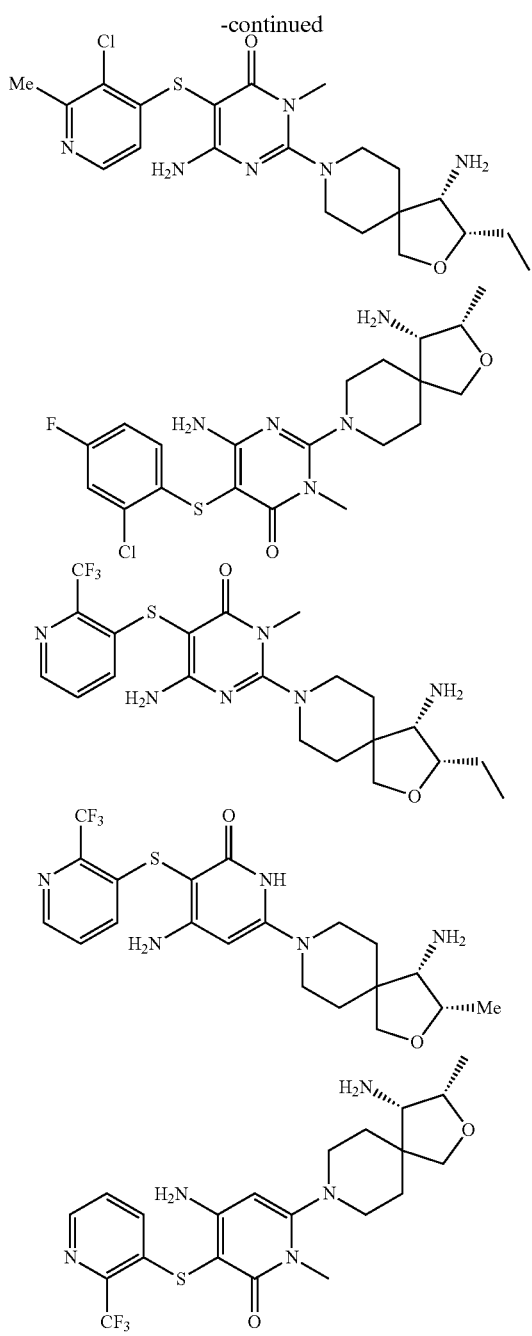

In another aspect of the invention are compounds of formula Ia:

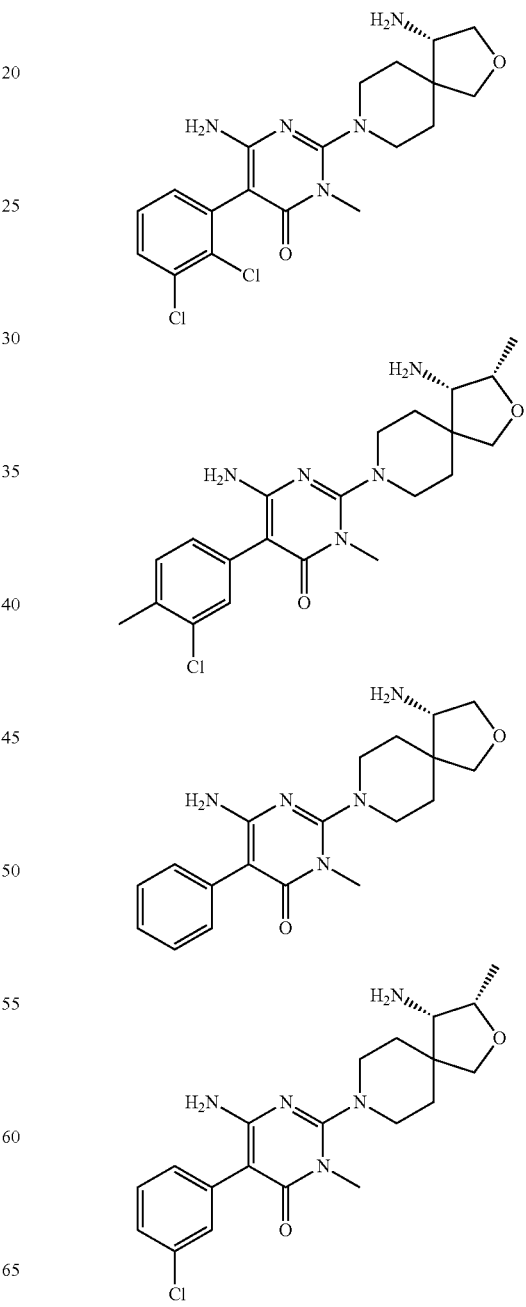

in which: $X_3$ is selected from a bond; $Y_1$ is $CR_7$; wherein $R_7$ is selected from hydrogen, chloro and fluoro; $Y_2$ is $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_6$aryl and $C_6$aryl-$C_{0-1}$alkoxy; $Y_3$ is selected from $CR_9$; wherein $R_9$ is selected from hydrogen, chloro, fluoro and methyl; $R_1$ is selected from hydrogen, chloro, fluoro; $R_2$ is selected from hydrogen; $R_{4a}$ is selected from hydrogen, hydroxy and fluoro; $R_{6b}$ is selected from hydrogen, hydroxy and fluoro; $R_{10}$ is amino; and $R_{11c}$ is selected from hydrogen, $C_{1-3}$alkyl and hydroxy-methyl; or the pharmaceutically acceptable salts thereof.

In a further aspect of the invention are compounds, or a pharmaceutically acceptable salt thereof, selected from:

-continued
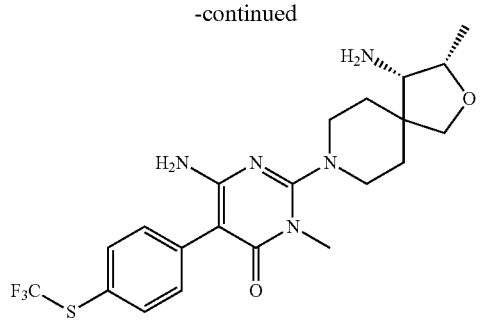
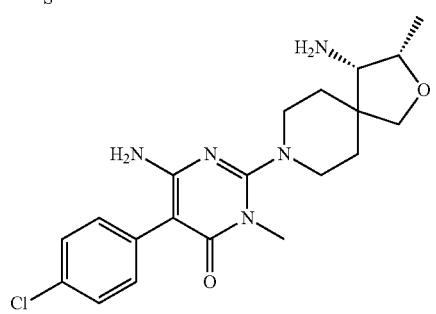
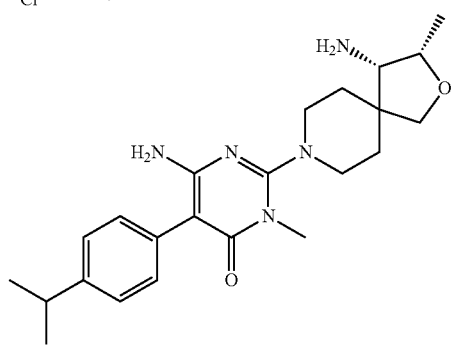
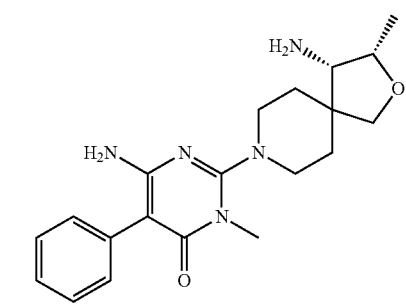
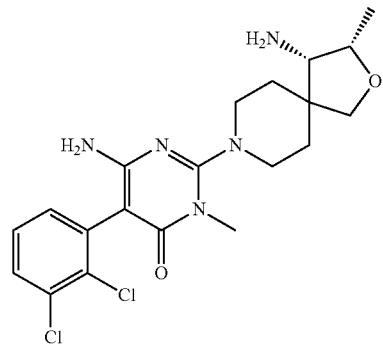
-continued
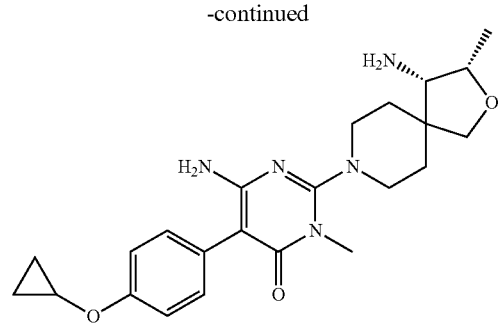
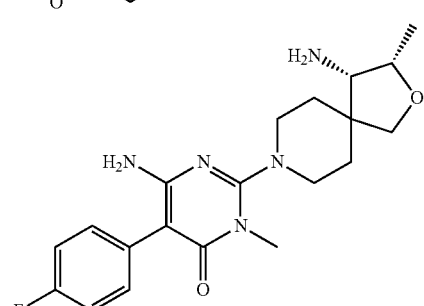
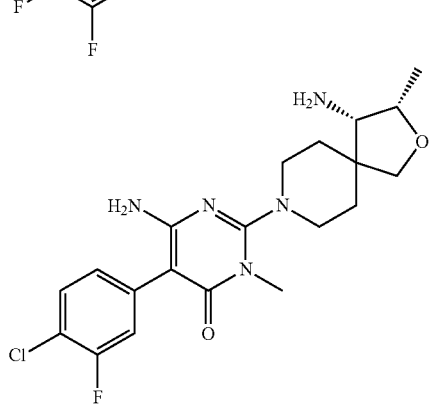
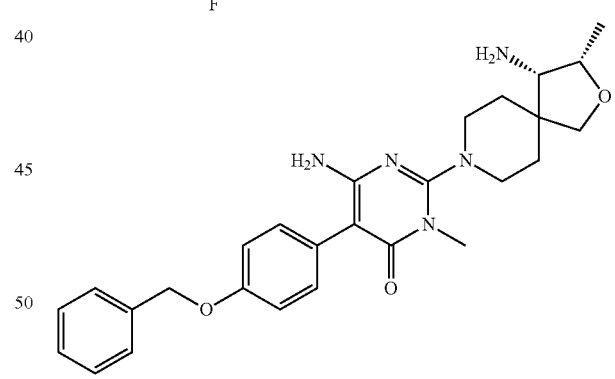
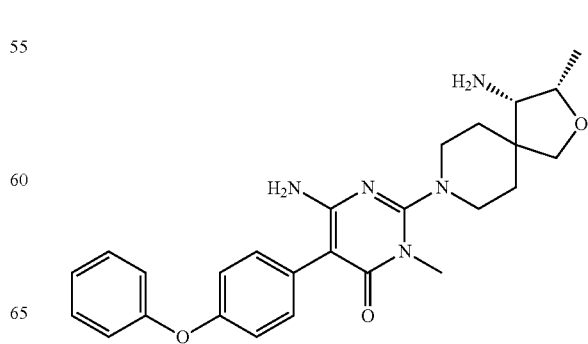

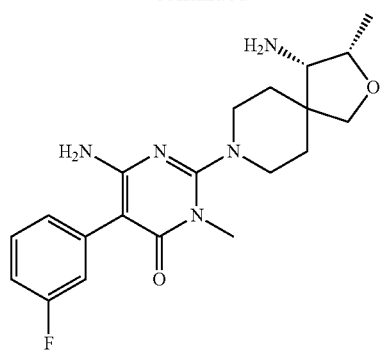
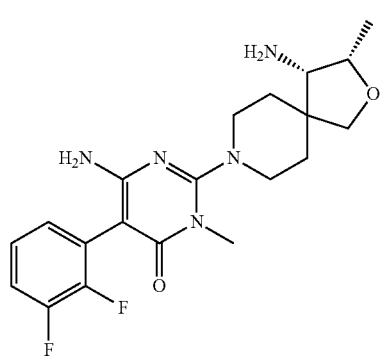
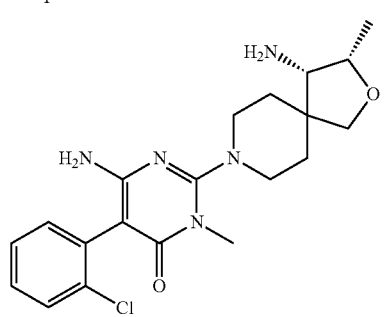
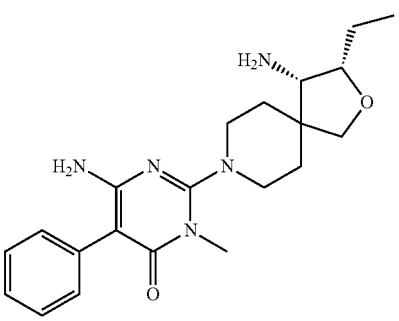
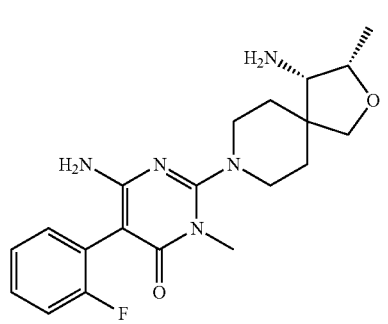
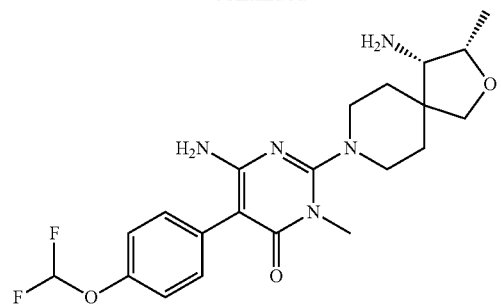
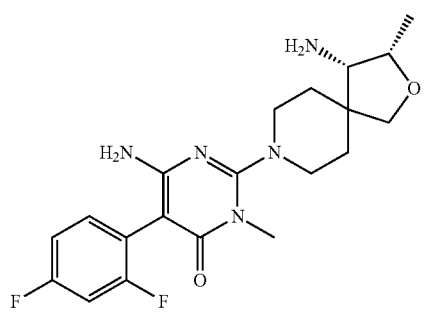
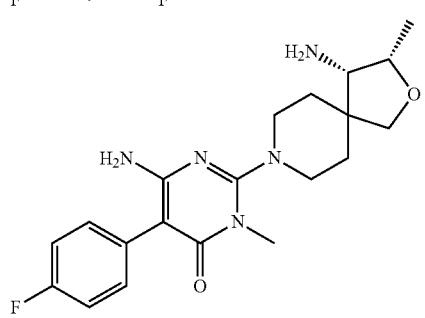
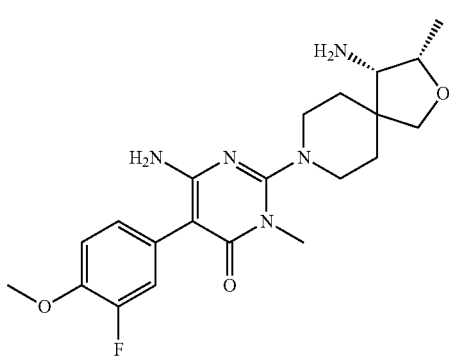
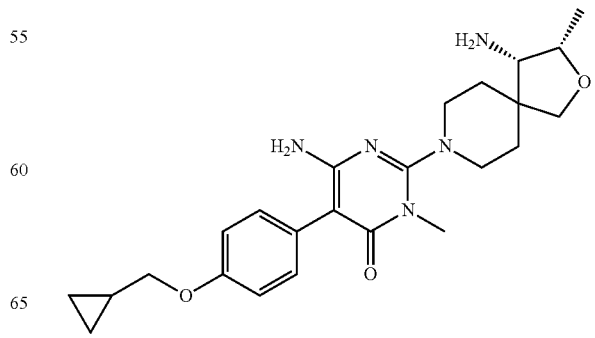

-continued
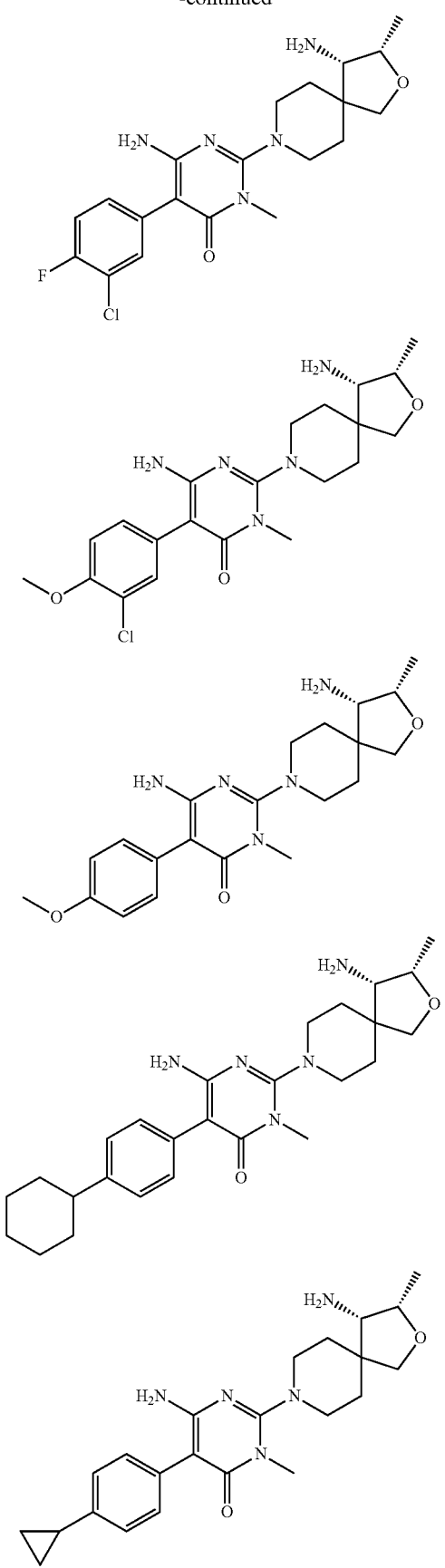
-continued
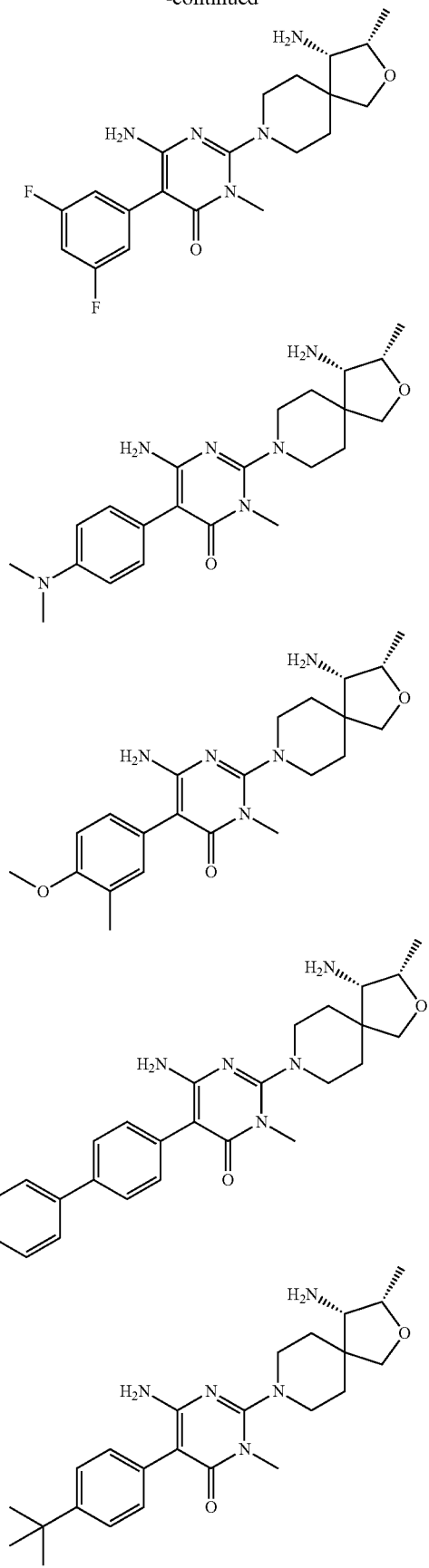

-continued
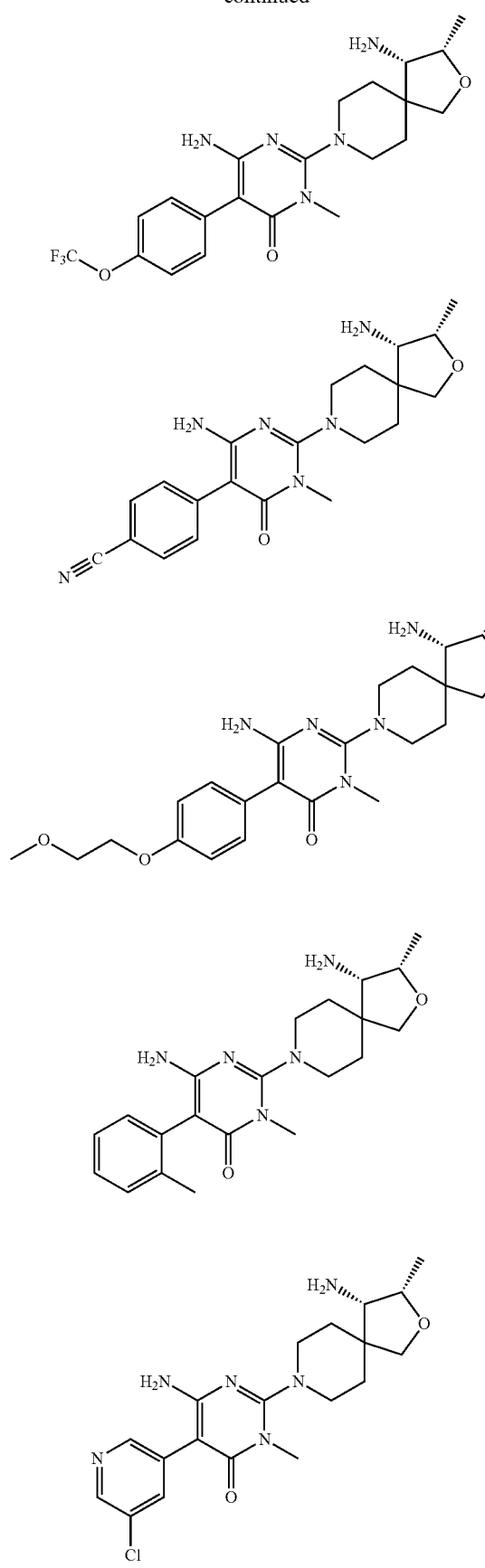
-continued
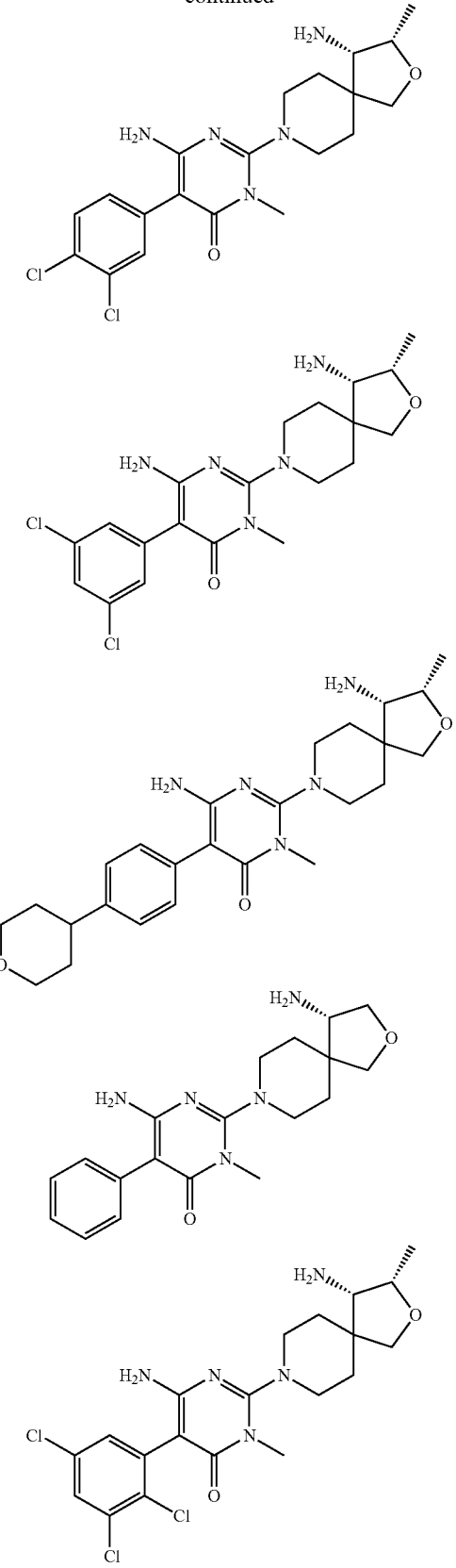
In another aspect of the invention are compounds of formula Ib:

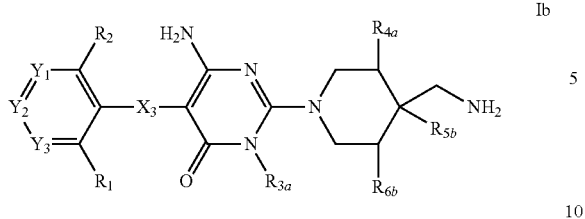

Ib in which: $X_3$ is selected from S; $Y_1$ is selected from N and $CR_7$; wherein $R_7$ is selected from hydrogen, amino, halo, $C_{1-3}$alkyl, $C_{1-3}$alkoxy; $Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole; $Y_3$ is selected from N and $CR_9$; wherein $R_9$ is selected from hydrogen, amino, halo, $C_{1-3}$alkyl, $C_{1-3}$alkoxy and hydroxy; $R_1$ is selected from hydrogen, halo, halo-substituted-$C_{1-2}$alkyl and halo-substituted-$C_{1-2}$alkoxy; $R_2$ is selected from hydrogen and halo; $R_{3a}$ is selected from hydrogen and methyl; $R_{4a}$ is selected from hydrogen, hydroxy and fluoro; $R_{5b}$ is selected from $C_{1-6}$alkyl; $R_{6b}$ is selected from hydrogen, hydroxy and fluoro; or the pharmaceutically acceptable salts thereof.

In a further aspect of the invention: $Y_1$ is selected from N and $CR_7$; wherein $R_7$ is selected from hydrogen, halo and amino; $Y_2$ is selected from N and $CR_8$; wherein $R_8$ is selected from hydrogen, halo, amino, cyano, halo-substituted-$C_{1-2}$alkyl, $C_{1-2}$alkoxy and halo-substituted-$C_{1-2}$alkoxy; $Y_3$ is selected from N and $CR_9$; wherein $R_9$ is selected from hydrogen, amino, halo, $C_{1-2}$alkoxy and hydroxy; $R_1$ is selected from halo, trifluoromethyl, trifluoromethoxy, $C_{1-2}$alkyl, nitro, hydroxy and cyano; or $R_1$ and $R_8$ together with the carbon atoms to which $R_1$ and $R_8$ are attached form a ring selected from 1,3-dioxolane and pyridine; wherein said 1,3-dioxolane or pyridine can be unsubstituted or substituted 1 to 2 halo groups; $R_2$ is selected from hydrogen, fluoro and chloro; $R_{3a}$ is selected from hydrogen and methyl; $R_{4a}$ is hydrogen; $R_{6b}$ is hydrogen; or the pharmaceutically acceptable salts thereof.

In a further aspect of the invention are compounds, or a pharmaceutically acceptable salt thereof, selected from:

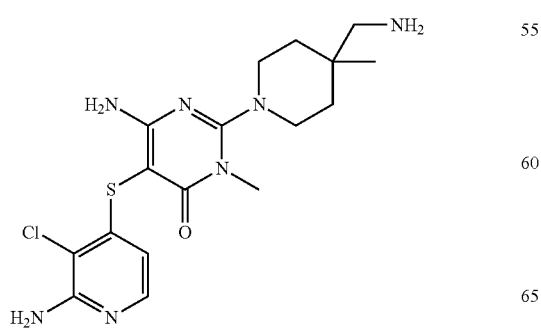

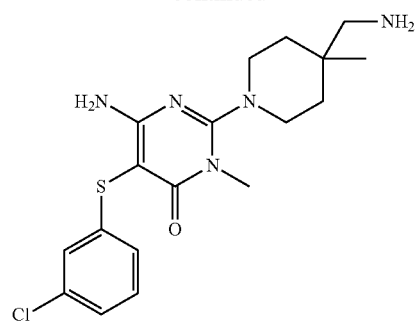

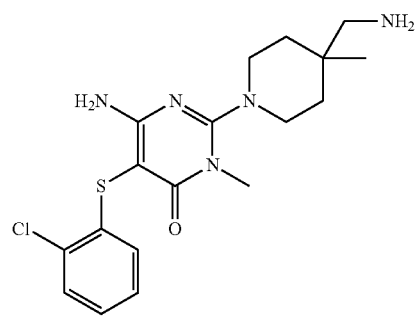

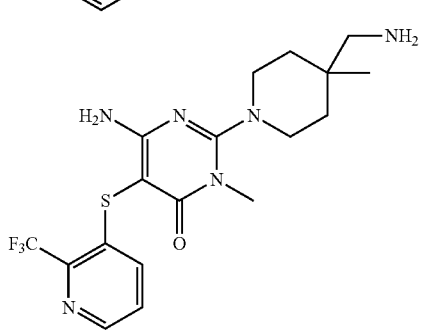

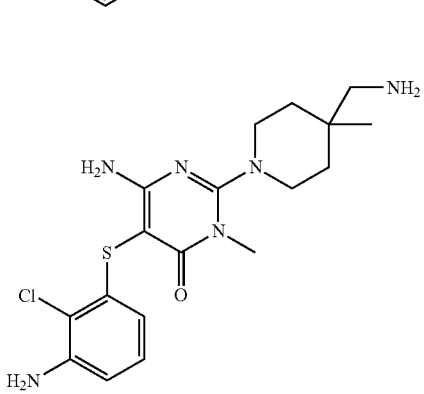

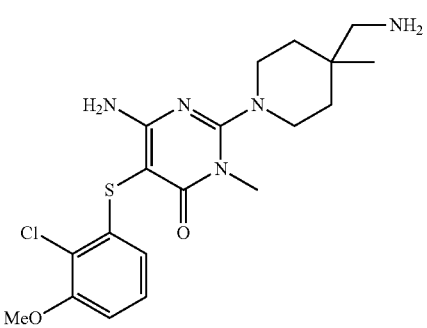

-continued
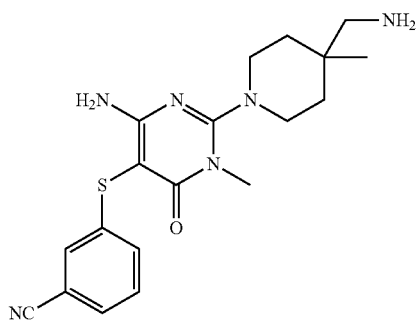
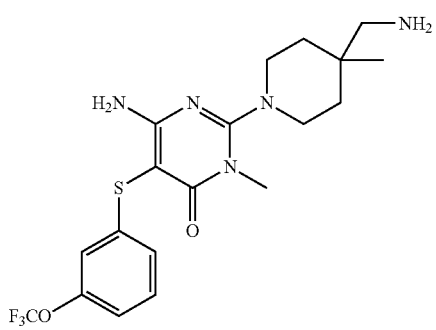
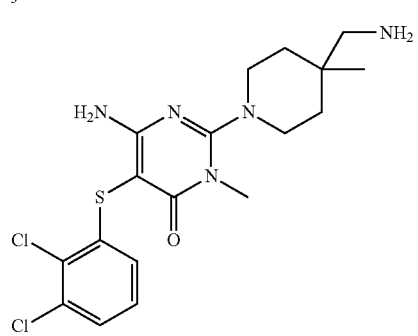
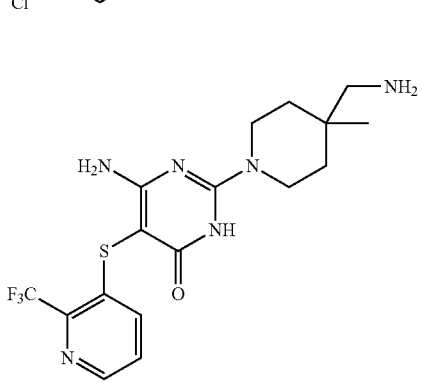
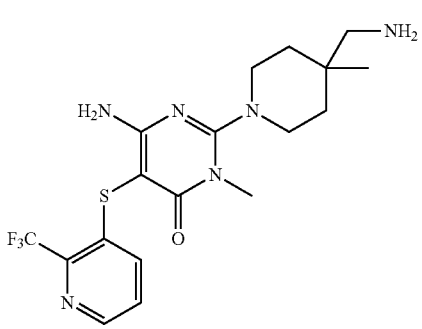
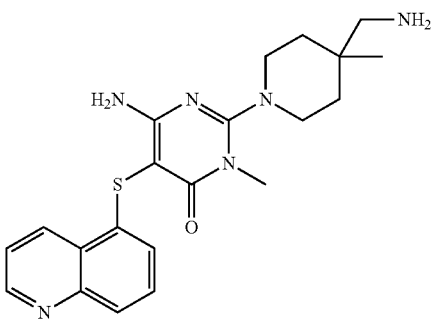
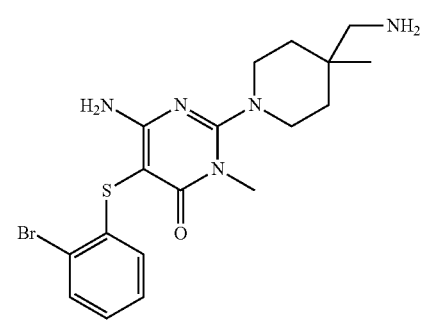
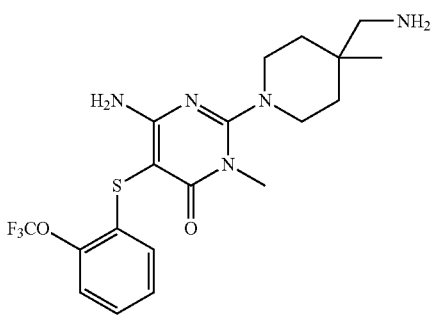
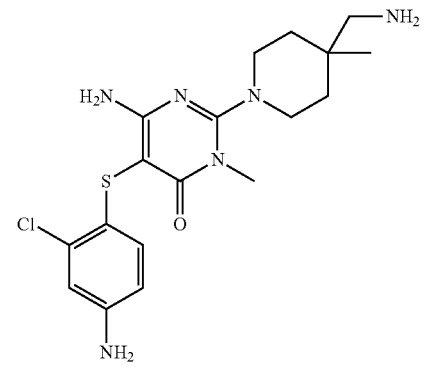
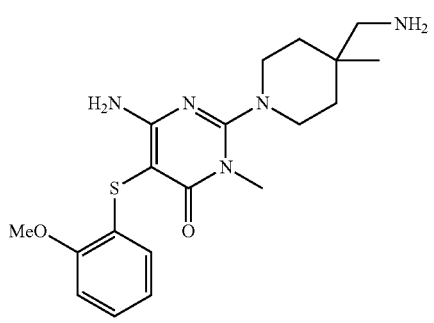

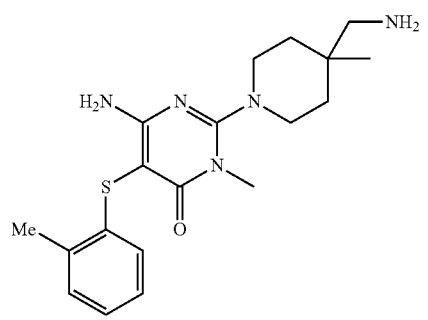
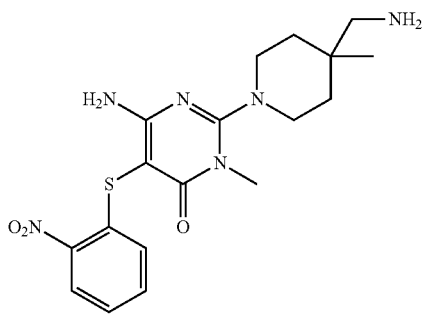
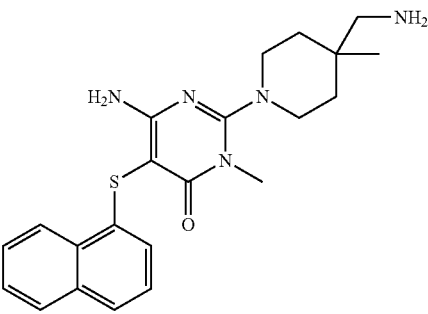
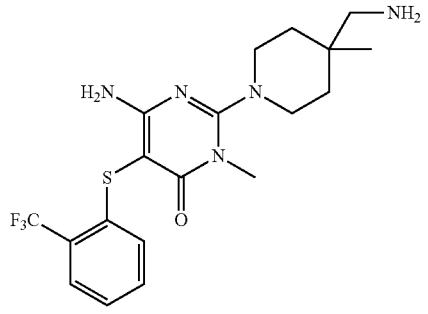
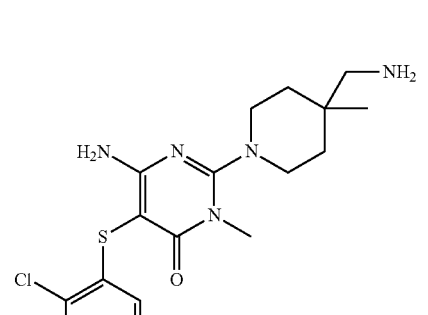
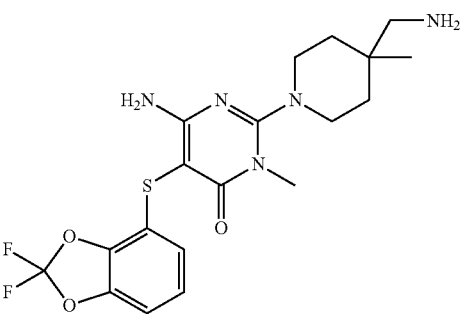
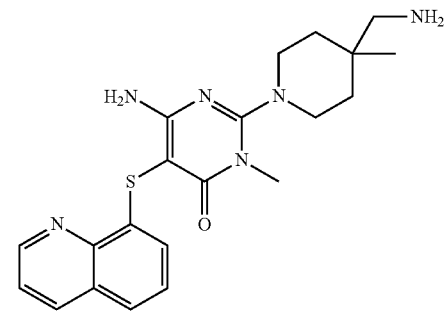
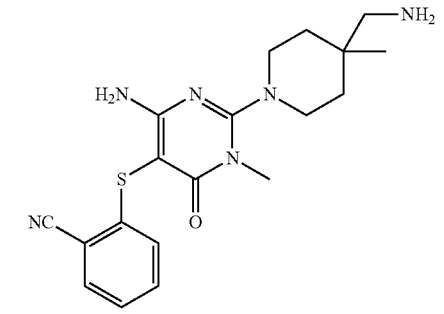
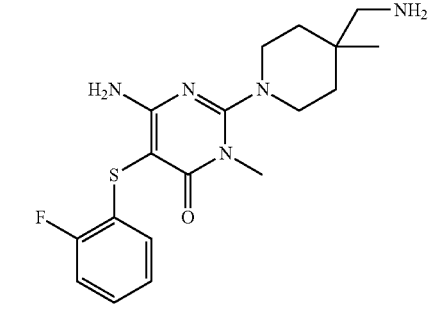
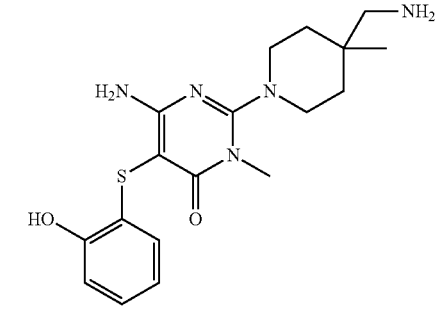
In another aspect of the invention are compounds of formula Ib:

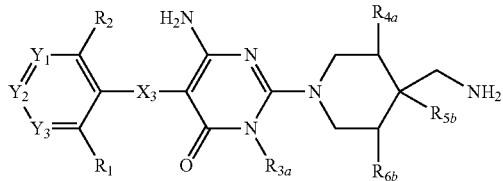

Ib

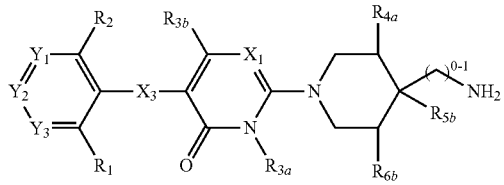

Ic in which: $X_3$ is selected from a bond; $Y_1$ is $CR_7$; wherein $R_7$ is selected from hydrogen, chloro and fluoro; $Y_2$ is $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_6$aryl and $C_6$aryl-$C_{0-1}$alkoxy; $Y_3$ is selected from $CR_9$; wherein $R_9$ is selected from hydrogen, chloro, fluoro and methyl; $R_1$ is selected from hydrogen, chloro, fluoro; $R_2$ is selected from hydrogen; $R_{4a}$ is selected from hydrogen, hydroxy and fluoro; $R_{5b}$ is selected from $C_{1-6}$alkyl; $R_{6b}$ is selected from hydrogen, hydroxy and fluoro; or the pharmaceutically acceptable salts thereof.

In a further aspect of the invention are compounds, or a pharmaceutically acceptable salt thereof, selected from:

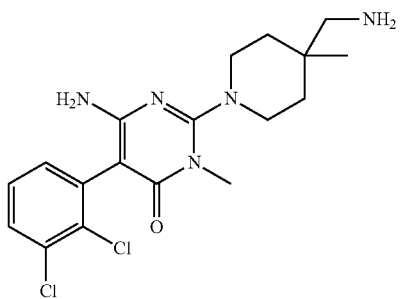

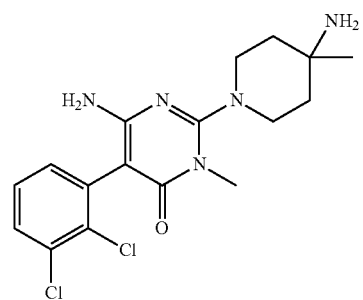

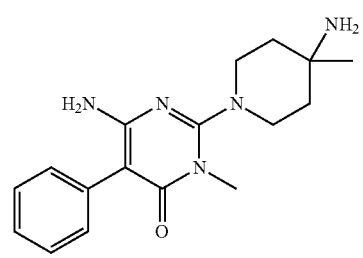

In another aspect of the invention are compounds of formula Ic:

in which: $X_1$ is selected from N and CH; $X_3$ is selected from S; $Y_1$ is selected from N and $CR_7$; wherein $R_7$ is selected from hydrogen, amino, halo, $C_{1-3}$alkyl, $C_{1-3}$alkoxy; $Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole; $Y_3$ is selected from N and $CR_9$; wherein $R_9$ is selected from hydrogen, amino, halo, $C_{1-3}$alkyl, $C_{1-3}$alkoxy and hydroxy; $R_1$ is selected from hydrogen, halo, halo-substituted-$C_{1-2}$alkyl; $R_2$ is selected from hydrogen and halo; $R_{3a}$ is selected from hydrogen and methyl; $R_{3b}$ is selected from hydrogen and methyl; $R_{4a}$ is selected from hydrogen, hydroxy and fluoro; $R_{5b}$ is selected from $C_{1-6}$alkyl; $R_{6b}$ is selected from hydrogen, hydroxy and fluoro.

In a further aspect of the invention are compounds in which: $Y_1$ is selected from N and $CR_7$; wherein $R_7$ is selected from hydrogen, halo and amino; $Y_2$ is selected from N and $CR_8$; wherein $R_8$ is selected from hydrogen, halo, amino, cyano, halo-substituted-$C_{1-2}$alkyl, $C_{1-2}$alkoxy and halo-substituted-$C_{1-2}$alkoxy; $Y_3$ is selected from N and $CR_9$; wherein $R_9$ is selected from hydrogen, amino, halo, $C_{1-2}$alkoxy and hydroxy; $R_1$ is selected from halo, trifluoromethyl, $C_{1-2}$alkyl and cyano; $R_2$ is selected from hydrogen, fluoro and chloro; $R_3$ is selected from hydrogen and methyl; $R_{4a}$ is hydrogen; $R_{6b}$ is hydrogen; or the pharmaceutically acceptable salts thereof.

In a further aspect of the invention are compounds, or a pharmaceutically acceptable salt thereof, selected from:

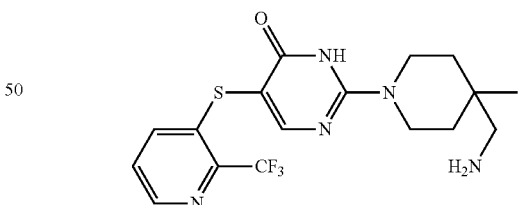

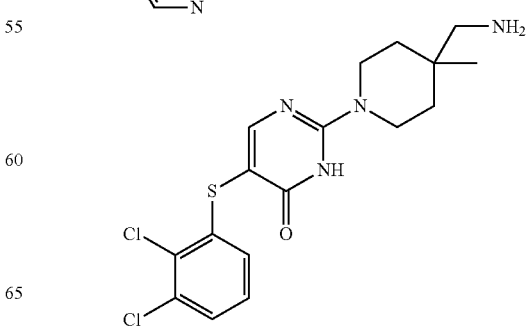

31

-continued

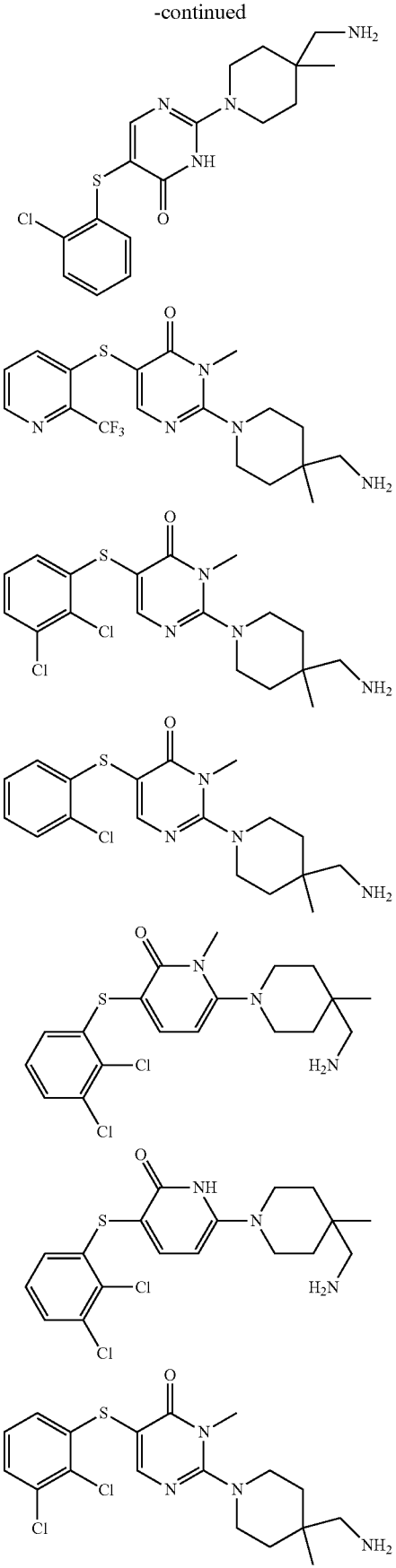

32

-continued

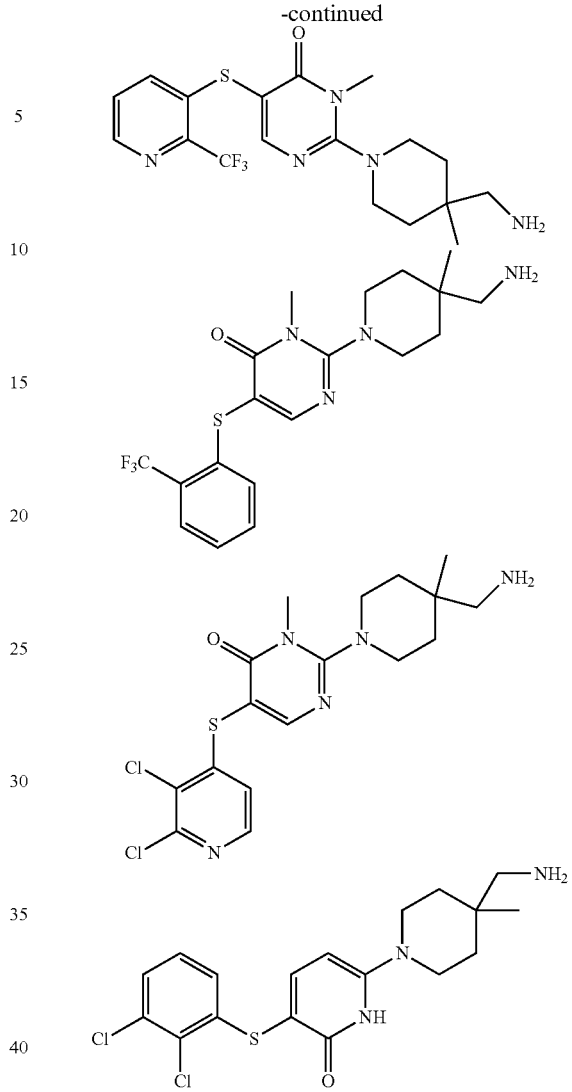

In another aspect of the invention are compounds of formula Id:

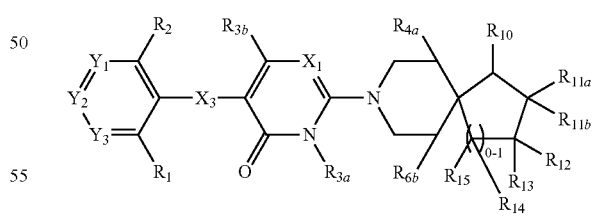

in which: $X_1$ is selected from N and CH; $X_3$ is selected from S; $Y_1$ is selected from N and $CR_7$; wherein $R_7$ is selected from hydrogen, amino, halo, $C_{1-3}$alkyl, $C_{1-3}$alkoxy; $Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole; $Y_3$ is selected from N and $CR_9$; wherein $R_9$ is selected from hydrogen, amino, halo, $C_{1-3}$alkyl, $C_{1-3}$alkoxy and hydroxy; $R_1$ is selected from hydrogen, halo, halo-substituted-$C_{1-2}$alkyl, halo-substituted-$C_{1-2}$alkoxy and cyano; $R_2$ is selected from hydrogen and halo; $R_{3a}$ is selected from hydrogen, methyl and halo-substituted-$C_{1-2}$alkyl; $R_{3b}$ is selected from hydrogen, methyl and amino; $R_{4a}$ is selected from hydrogen, hydroxy and fluoro; $R_{6b}$ is selected from hydrogen, hydroxy and fluoro; $R_{10}$ is amino; $R_{11a}$ is selected from hydrogen, hydroxy, fluoro, $C_{1-3}$alkyl and hydroxymethyl; $R_{11b}$ is selected from fluoro, methyl and hydrogen; with proviso that $R_{11a}$ and $R_{11b}$ cannot both be OH and fluoro simultaneously; $R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy; $R_{13}$ is selected from hydrogen, halo and $C_{1-3}$alkyl; with proviso that $R_{12}$ and $R_{13}$ cannot both be OH and fluoro simultaneously; $R_{14}$ is selected from hydrogen and fluoro; $R_{15}$ is selected from hydrogen and fluoro; or the pharmaceutically acceptable salts thereof.

In a further aspect of the invention are compounds, or a pharmaceutically acceptable salt thereof, selected from:

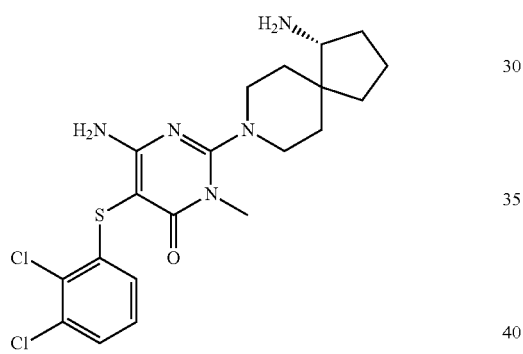

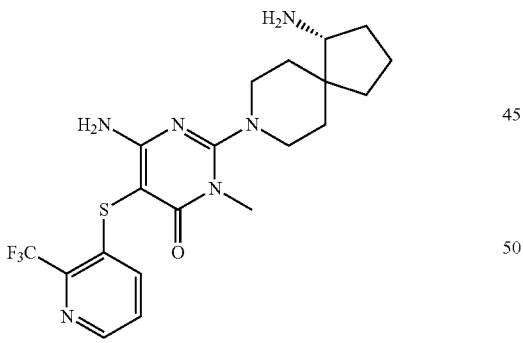

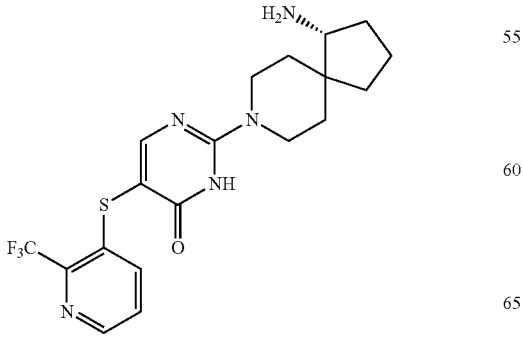

-continued

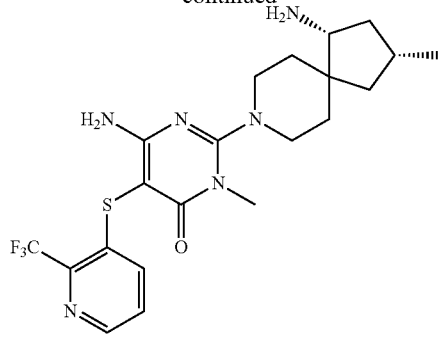

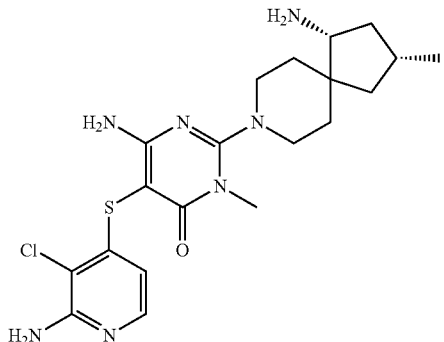

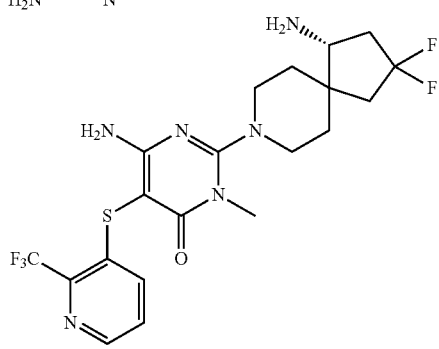

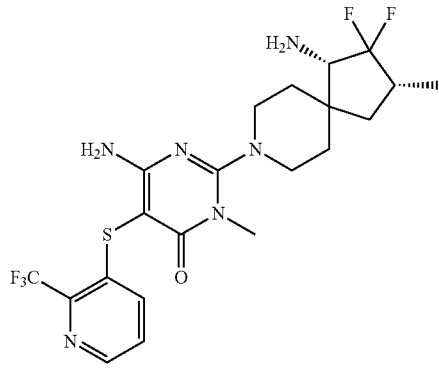

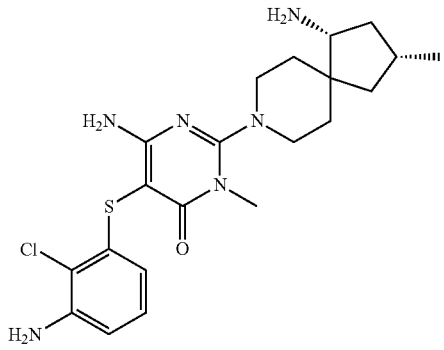

35
-continued
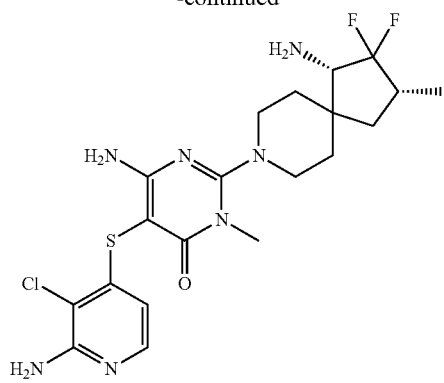
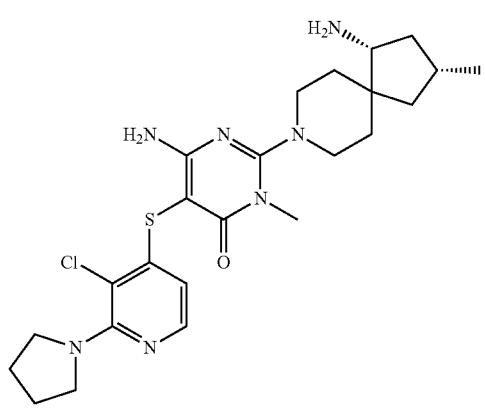
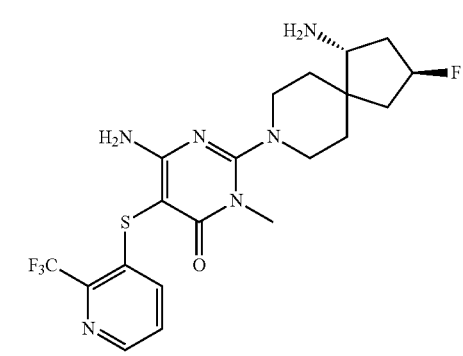
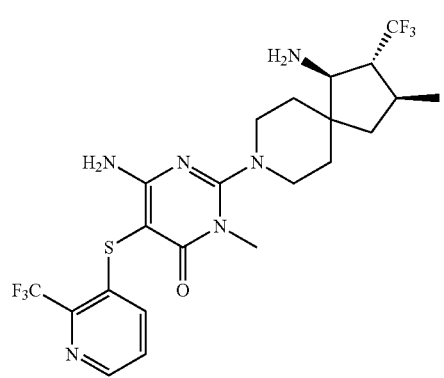
36
-continued
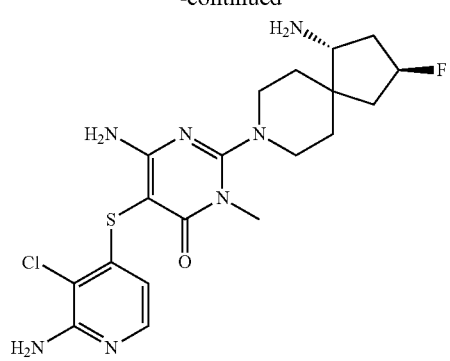
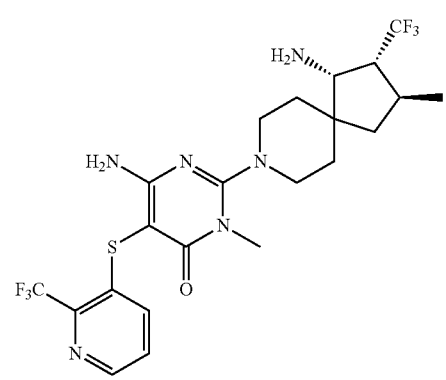
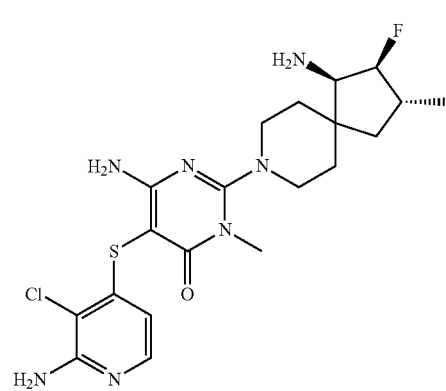
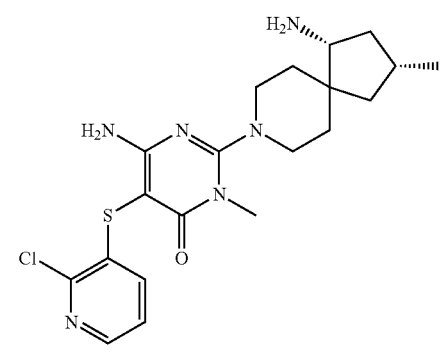

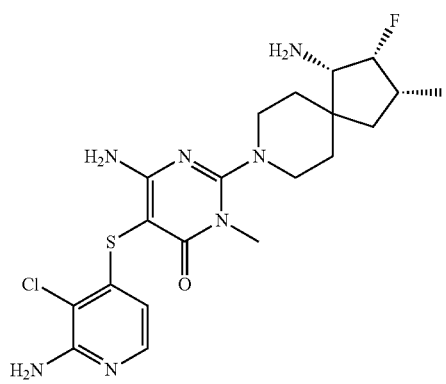
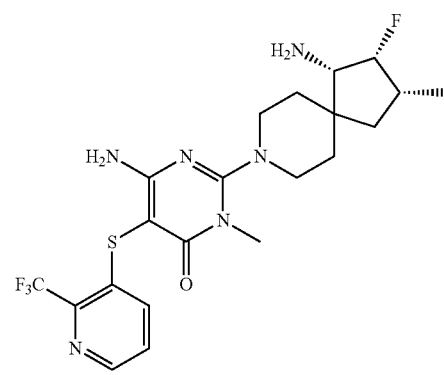
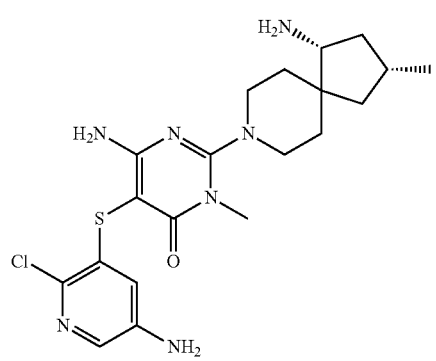
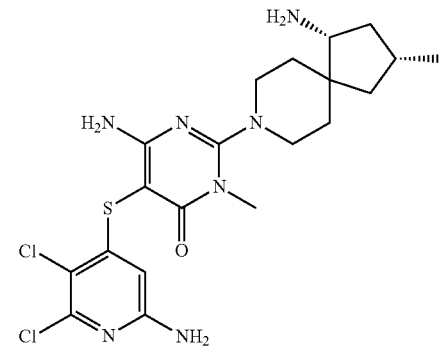
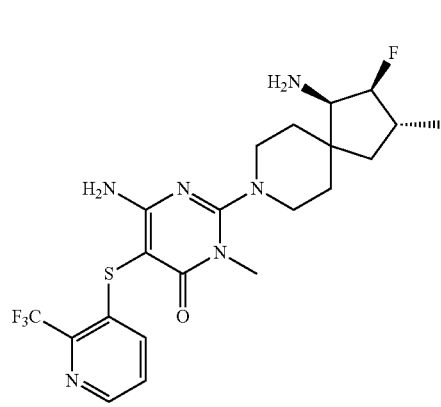
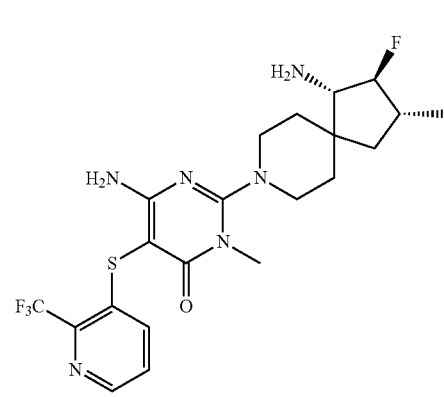
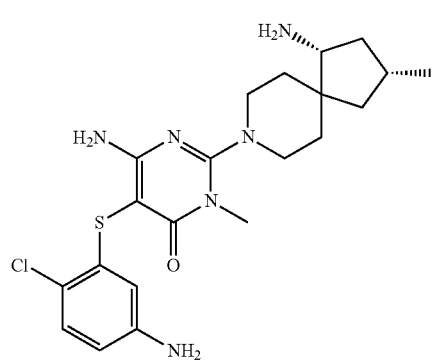
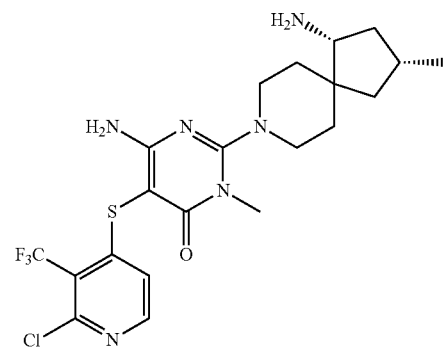

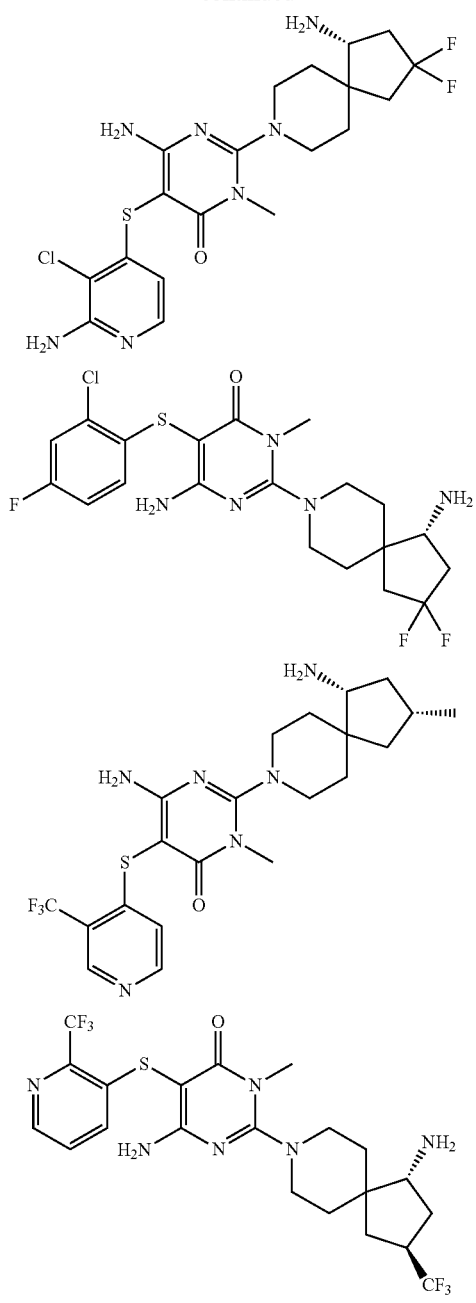
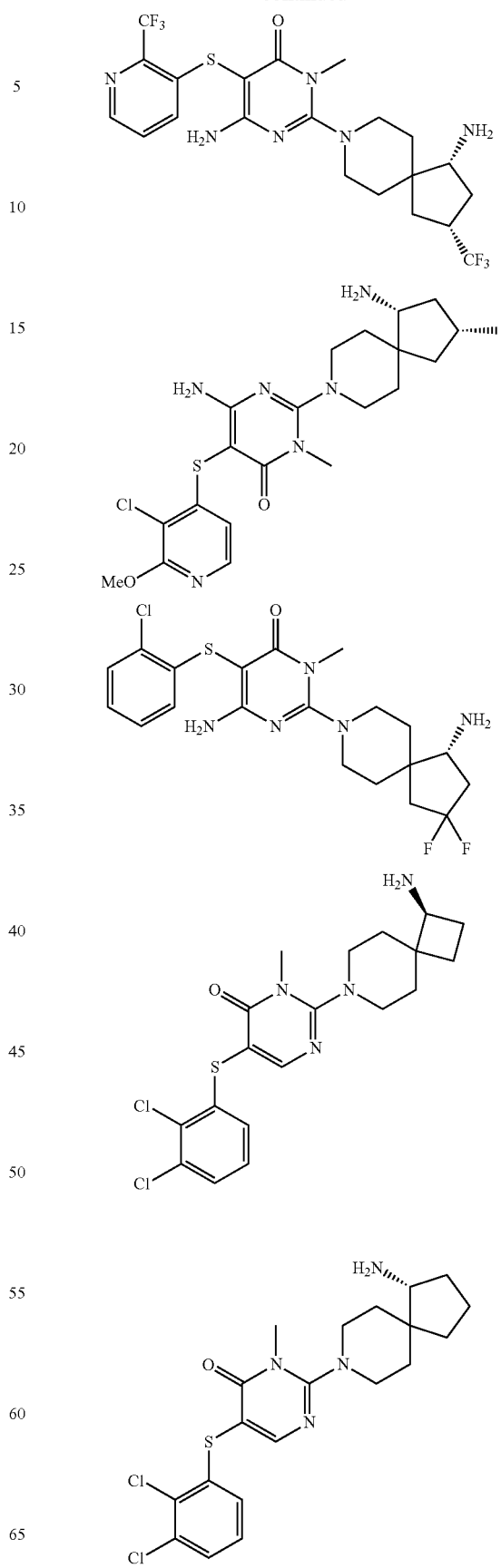

-continued

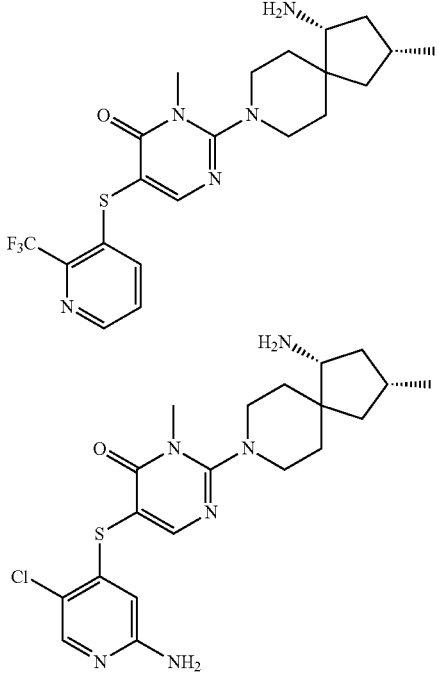

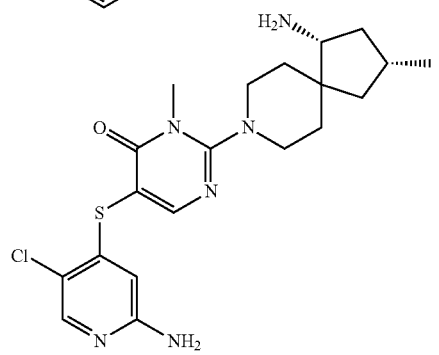

In another aspect of the invention are compounds of formula Id:

Id

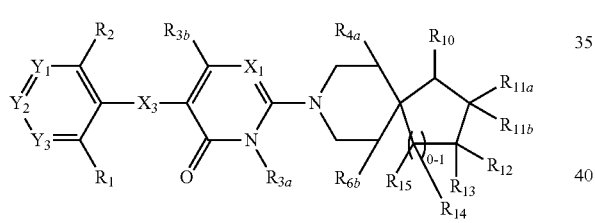

in which: $X_1$ is selected from N and CH; $X_3$ is selected from a bond; $Y_1$ is $CR_7$; wherein $R_7$ is selected from hydrogen, chloro and fluoro; $Y_2$ is $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$ alkoxy, halo-substituted-$C_{1-3}$alkoxy, $C_{1-3}$alkoxy-$C_{1-3}$alkoxy, $C_6$aryl and $C_6$aryl-$C_{0-1}$alkoxy; $Y_3$ is selected from $CR_9$; wherein $R_9$ is selected from hydrogen, chloro, fluoro and methyl; $R_1$ is selected from hydrogen, chloro, fluoro; $R_2$ is selected from hydrogen; $R_{3a}$ is selected from methyl; $R_{3b}$ is selected from amino; $R_{4a}$ is selected from hydrogen, hydroxy and fluoro; $R_{6b}$ is selected from hydrogen, hydroxy and fluoro; $R_{10}$ is amino; $R_{11a}$ is selected from hydrogen, hydroxy, fluoro, $C_{1-3}$alkyl and hydroxy-methyl; $R_{11b}$ is selected from fluoro, methyl and hydrogen; with proviso that $R_{11a}$ and $R_{11b}$ cannot both be OH and fluoro simultaneously; $R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy; $R_{13}$ is selected from hydrogen, halo and $C_{1-3}$alkyl; with proviso that $R_{12}$ and $R_{13}$ cannot both be OH and fluoro simultaneously; $R_{14}$ is selected from hydrogen and fluoro; $R_{15}$ is selected from hydrogen and fluoro; or the pharmaceutically acceptable salts thereof.

In a further aspect of the invention are compounds, or a pharmaceutically acceptable salt thereof, selected from:

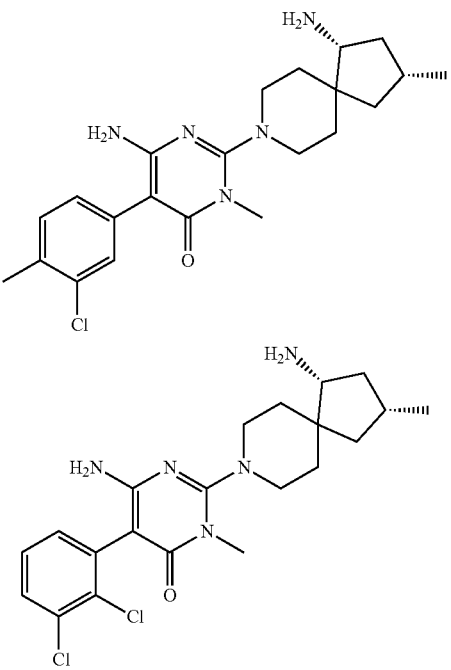

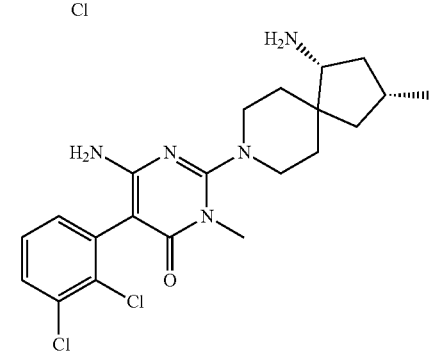

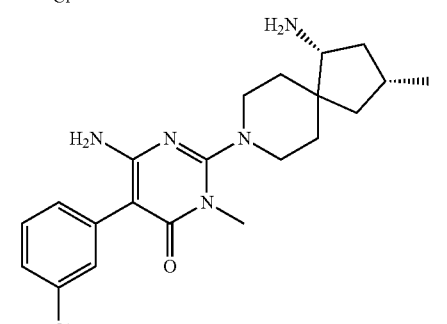

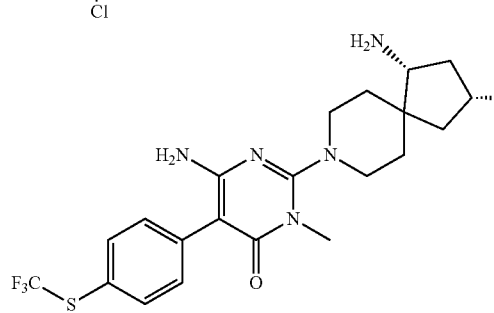

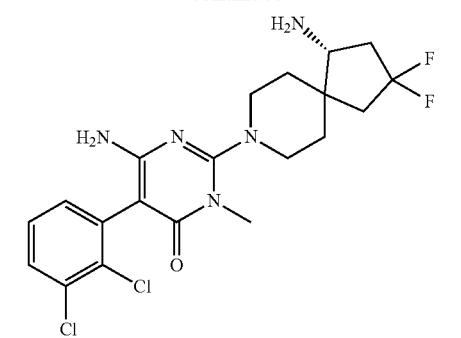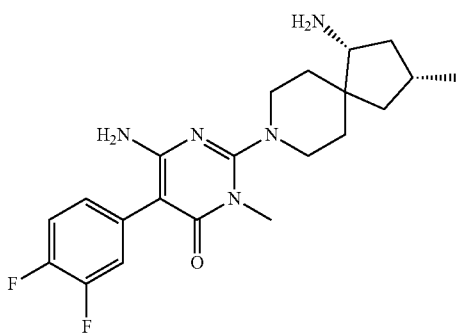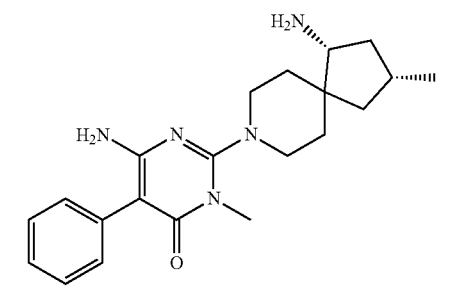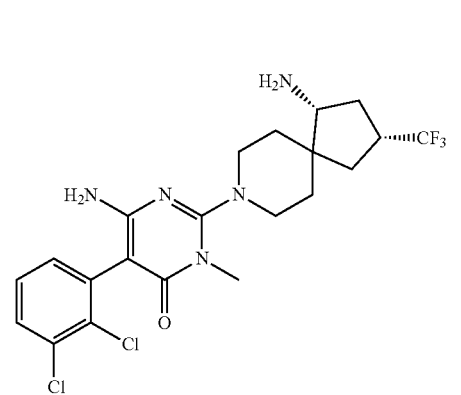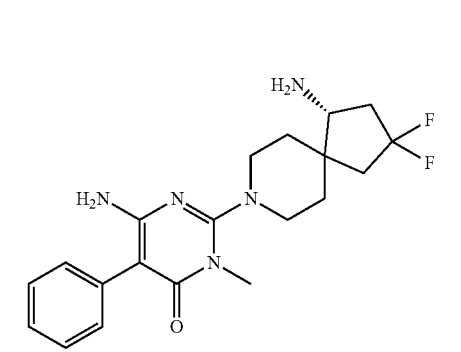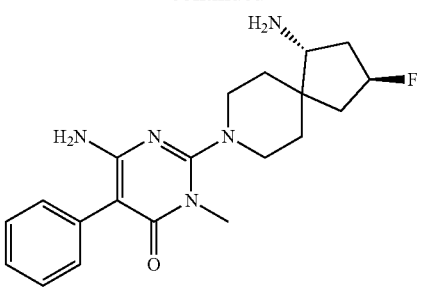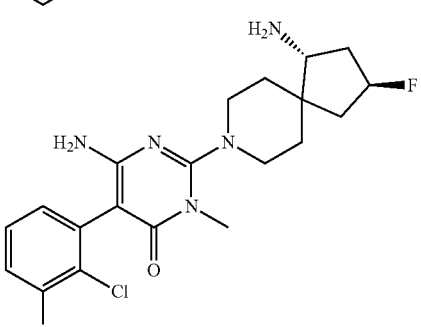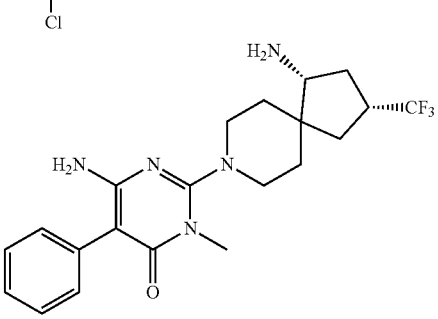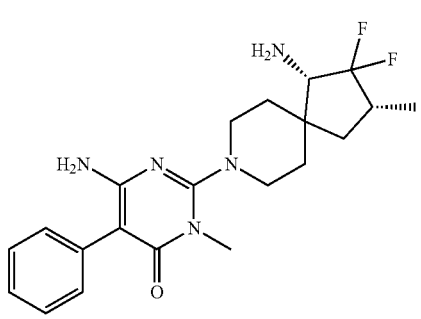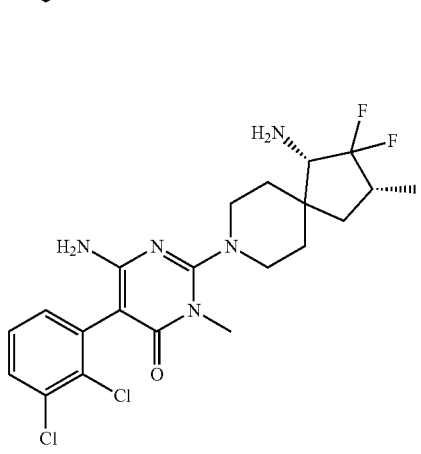

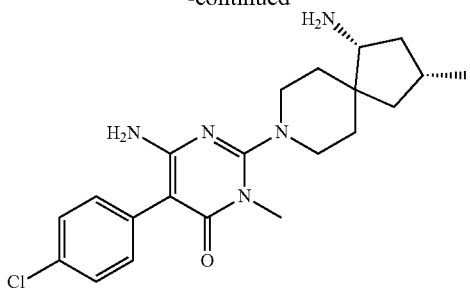

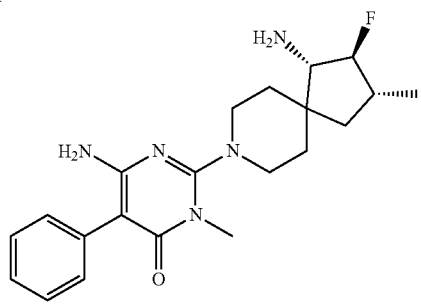

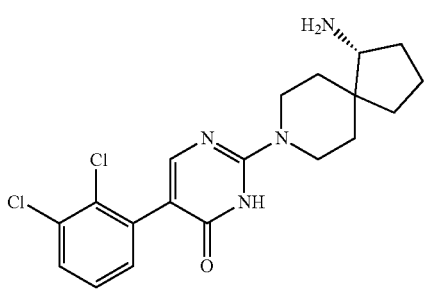

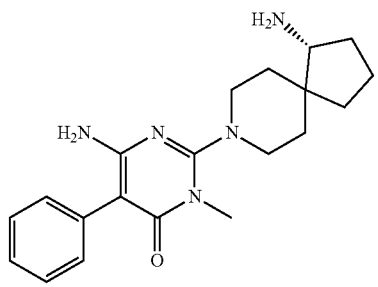

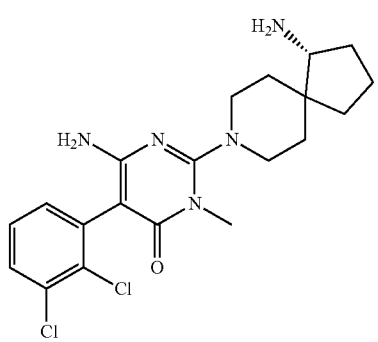

In another aspect of the invention are compounds of formula Ie:

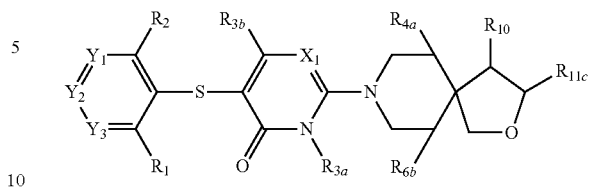

in which: $X_1$ is selected from N and CH; $Y_1$ is selected from N and $CR_7$; wherein $R_7$ is selected from hydrogen, halo and amino; $Y_2$ is selected from N and $CR_8$; wherein $R_8$ is selected from hydrogen, halo, amino, cyano, halo-substituted-$C_{1-3}$alkyl, $C_{1-3}$alkoxy and halo-substituted-$C_{1-3}$alkoxy; $Y_3$ is selected from N and $CR_9$; wherein $R_9$ is selected from hydrogen, amino, halo, $C_{1-3}$alkoxy and hydroxy; $R_1$ is selected from halo, halo-substituted-$C_{1-2}$alkyl, halo-substituted-$C_{1-2}$alkoxy, $C_{1-2}$alkyl and cyano; $R_2$ is selected from hydrogen and halo; $R_{3a}$ is selected from hydrogen, and methyl; $R_{3b}$ is selected from hydrogen and methyl; $R_{4a}$ is selected from hydrogen, hydroxy and fluoro; $R_{6b}$ is selected from hydrogen, hydroxy and fluoro; $R_{10}$ is amino; $R_{11a}$ is selected from hydrogen, hydroxy, fluoro, $C_{1-3}$alkyl and hydroxy-methyl; $R_{11b}$ is selected from fluoro, methyl and hydrogen; $R_{11c}$ is selected from hydrogen, $C_{1-3}$alkyl and hydroxy-methyl; $R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy; $R_{13}$ is selected from hydrogen, halo and $C_{1-3}$alkyl; with proviso that $R_{12}$ and $R_{13}$ cannot both be OH and fluoro simultaneously; or the pharmaceutically acceptable salts thereof.

In a further aspect of the invention are compounds, or a pharmaceutically acceptable salt thereof, selected from:

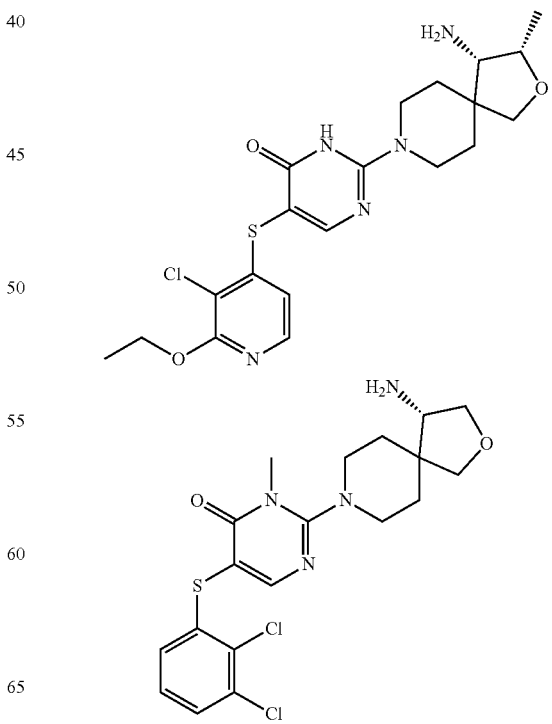

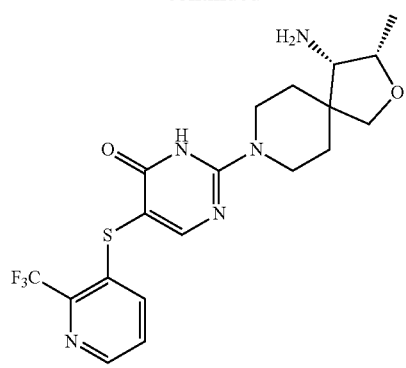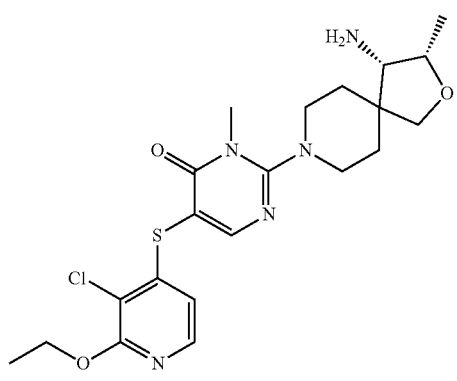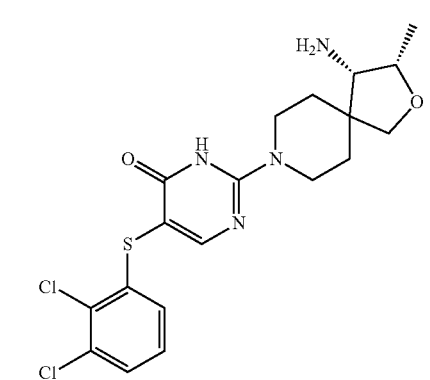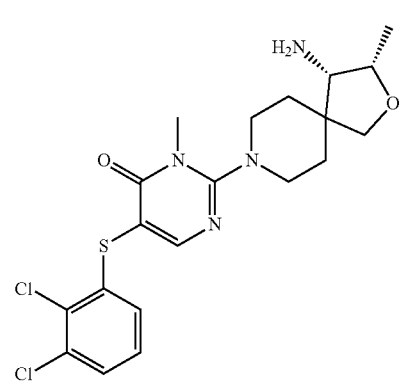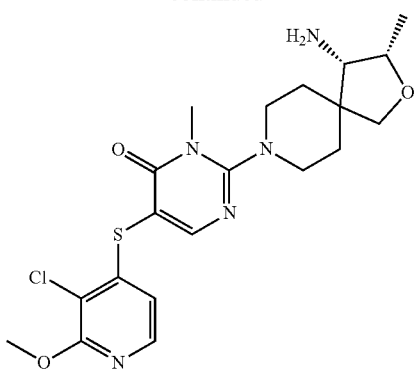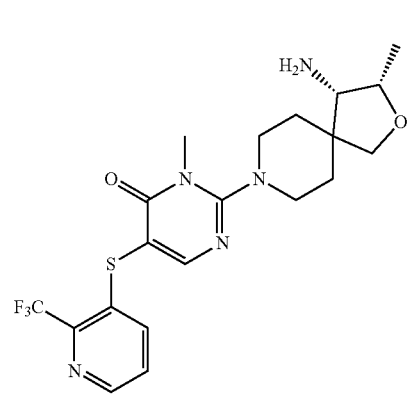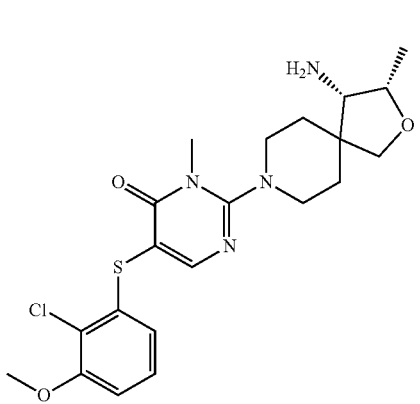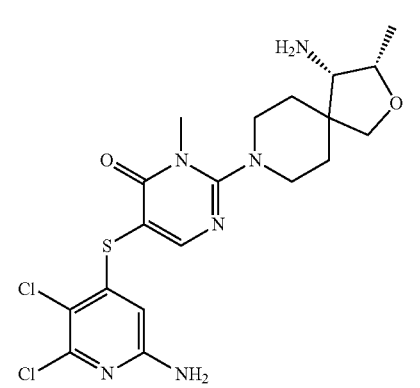

-continued

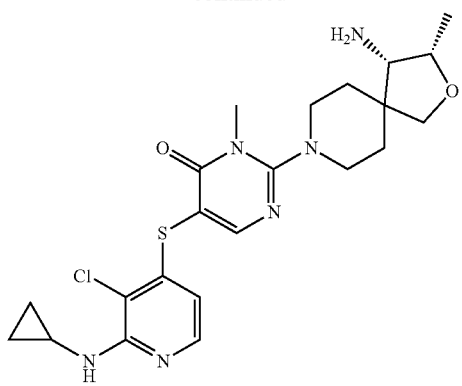

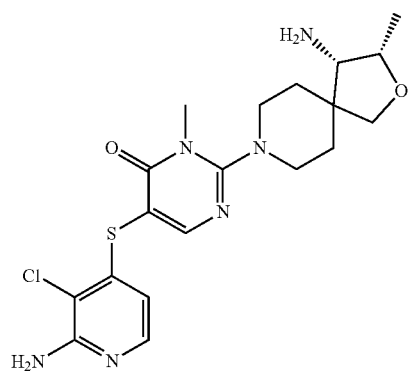

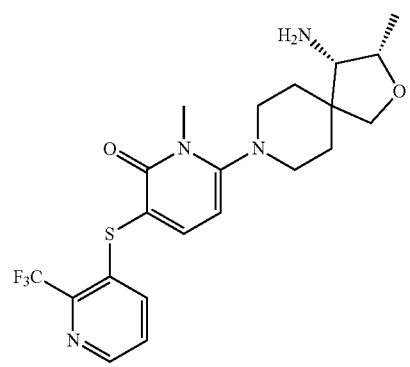

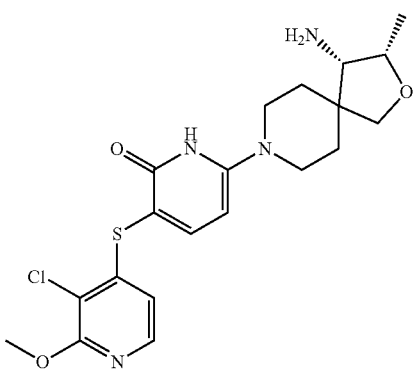

-continued

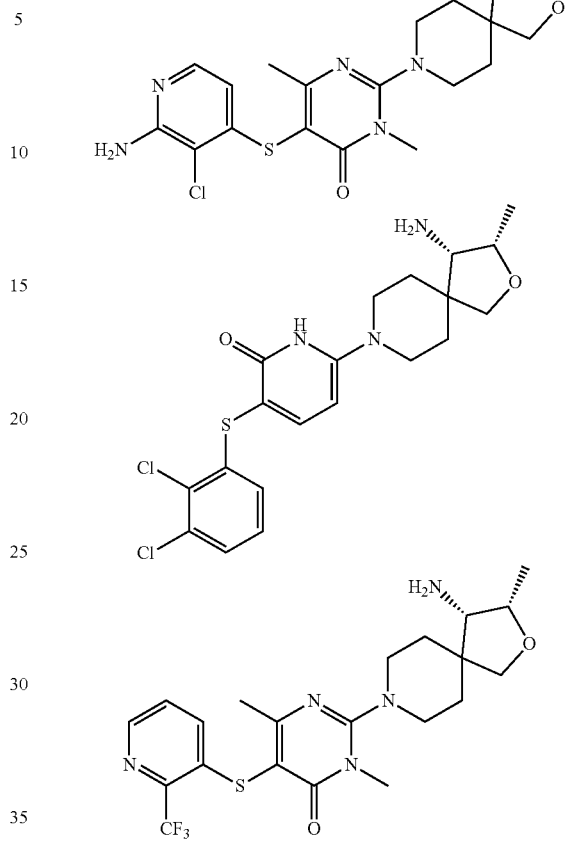

Pharmacology and Utility

The Src Homolgy-2 phosphatase (SHP2) is a protein tyrosine phosphatase encoded by the PTPN11 gene that contributes to multiple cellular functions including proliferation, differentiation, cell cycle maintenance and migration. SHP2 is involved in signaling through the Ras-mitogen-activated protein kinase, the JAK-STAT or the phosphoinositol 3-kinase-AKT pathways. SHP2 mediates activation of Erk1 and Erk2 (Erk1/2, Erk) MAP kinases by receptor tyrosine kinases such as ErbB1, ErbB2 and c-Met.

SHP2 has two N-terminal Src homology 2 domains (N-SH2 and C-SH2), a catalytic domain (PTP), and a C-terminal tail. The two SH2 domains control the subcellular localization and functional regulation of SHP2. The molecule exists in an inactive conformation, inhibiting its own activity via a binding network involving residues from both the N-SH2 and PTP domains. In response to growth factor stimulation, SHP2 binds to specific tyrosine-phosphorylated sites on docking proteins such as Gab1 and Gab2 via its SH2 domains. This induces a conformational change that results in SHP2 activation.

Mutations in PTPN11 have been identified in several human diseases, such as Noonan Syndrome, Leopard Syndrome, juvenile myelomonocytic leukemias, neuroblastoma, melanoma, acute myeloid leukemia and cancers of the breast, lung and colon. SHP2 is an important downstream signaling molecule for a variety of receptor tyrosine kinases, including the receptors of platelet-derived growth factor (PDGF-R), fibroblast growth factor (FGF-R) and epidermal growth factor (EGF-R). SHP2 is also an important downstream signaling molecule for the activation of the mitogen activated protein (MAP) kinase pathway which can lead to cell transformation, a prerequisite for the development of cancer. Knock-down of SHP2 significantly inhibited cell growth of lung cancer cell lines with SHP2 mutation or EML4/ALK translocations as well as EGFR amplified breast cancers and esophageal cancers. SHP2 is also activated downstream of oncogenes in gastric carcinoma, anaplastic large-cell lymphoma and glioblastoma.

Noonan Syndrome (NS) and Leopard Syndrome (LS)—PTPN11 mutations cause LS (multiple lentigenes, electrocardiographic conduction abnormalities, ocular hypertelorism, pulmonic stenosis, abnormal genitalia, retardation of growth, sensorineural deafness) and NS (congenital anomalies including cardiac defects, craniofacial abnormalities and short stature). Both disorders are part of a family of autosomal dominant syndromes caused by germline mutations in components of the RAS/RAF/MEK/ERK mitogen activating protein kinase pathway, required for normal cell growth and differentiation. Aberrant regulation of this pathway has profound effects, particularly on cardiac development, resulting in various abnormalities, including valvuloseptal defects and/or hypertrophic cardiomyopathy (HCM). Perturbations of the MAPK signaling pathway have been established as central to these disorders and several candidate genes along this pathway have been identified in humans, including mutations in KRAS, NRAS, SOS1, RAF1, BRAF, MEK1, MEK2, SHOC2, and CBL. The gene most commonly mutated in NS and LS is PTPN11. Germline mutations in PTPN11 (SHP2) are found in ~50% of the cases with NS and nearly all patients with LS that shares certain features with NS. For NS, Y62D and Y63C substitutions in the protein are largely invariant and are among the most common mutations. Both these mutations affect the catalytically inactive conformation of SHP2 without perturbing the binding of the phosphatase to its phosphorylated signaling partners.

Juvenile Myelomonocytic Leukemias (JMML)—Somatic mutations in PTPN11 (SHP2) occur in about 35% of the patients with JMML, a childhood myeloproliferative disorder (MPD). These gain-of-function mutations are typically point mutations in the N-SH2 domain or in the phosphatase domain, which prevent self-inhibition between the catalytic domain and the N-SH2 domain, resulting in SHP2 activity.

Acute Myeloid Leukemia—PTPN11 mutations have been identified in: ~10% of pediatric acute leukemias, such as myelodysplastic syndrome (MDS); ~7% of B cell acute lymphoblastic leukemia (B-ALL); and ~4% of acute myeloid leukemia (AML).

NS and leukemia mutations cause changes in amino acids located at the interface formed by the N-SH2 and PTP domains in the self-inhibited SHP2 conformation, disrupting the inhibitory intramolecular interaction, leading to hyperactivity of the catalytic domain.

SHP2 acts as a positive regulator in receptor tyrosine kinase (RTK) signaling. Cancers containing RTK alterations (EGFR$^{amp}$, Her2$^{amp}$, FGFR$^{amp}$, Met$^{amp}$, translocated/activated RTK, i.e. ALK, BCR/ABL) include Esophageal, Breast, Lung, Colon, Gastric, Glioma, Head and Neck cancers.

Esophageal cancer (or oesophageal cancer) is a malignancy of the esophagus. There are various subtypes, primarily squamous cell cancer (<50%) and adenocarcinoma. There is a high rate of RTK expression in esophageal adenocarcinoma and squamous cell cancer. A SHP2 inhibitor of the invention can, therefore, be employed for innovative treatment strategies.

Breast cancer is a major type of cancer and a leading cause of death in women, where patients develop resistance to current drugs. There are four major subtypes of breast cancers including luminal A, luminal B, Her2 like, and triple negative/Basal-like. Triple negative breast cancer (TNBC) is an aggressive breast cancer lacking specific targeted therapy. Epidermal growth factor receptor I (EGFR) has emerged as a promising target in TNBC. Inhibition of Her2 as well as EGFR via SHP2 may be a promising therapy in breast cancer.

Lung Cancer—NSCLC is currently a major cause of cancer-related mortality. accounting for about 85% of lung cancers (predominantly adenocarcinomas and squamous cell carcinomas). Although cytotoxic chemotherapy remains an important part of treatment, targeted therapies based on genetic alterations such as EGFR and ALK in the tumor are more likely to benefit from a targeted therapy.

Colon Cancer—Approximately 30% to 50% of colorectal tumors are known to have a mutated (abnormal) KRAS, and BRAF mutations occur in 10 to 15% of colorectal cancers. For a subset of patients whose colorectal tumors have been demonstrated to over express EGFR, these patients exhibit a favorable clinical response to anti-EGFR therapy.

Gastric Cancer is one of the most prevalent cancer types. Aberrant expression of tyrosine kinases, as reflected by the aberrant tyrosine phosphorylation in gastric cancer cells, is known in the art. Three receptor-tyrosine kinases, c-met (HGF receptor), FGF receptor 2, and erbB2/neu are frequently amplified in gastric carcinomas. Thus, subversion of different signal pathways may contribute to the progression of different types of gastric cancers.

Neuroblastoma is a pediatric tumor of the developing sympathetic nervous system, accounting for about 8% of childhood cancers. Genomic alterations of the anaplastic lymphoma kinase (ALK) gene have been postulated to contribute to neuroblastoma pathogenesis.

Squamous-cell carcinoma of the head and neck (SCCHN). High levels of EGFR expression are correlated with poor prognosis and resistance to radiation therapy in a variety of cancers, mostly in squamous-cell carcinoma of the head and neck (SCCHN). Blocking of the EGFR signaling results in inhibition of the stimulation of the receptor, cell proliferation, and reduced invasiveness and metastases. The EGFR is, therefore, a prime target for new anticancer therapy in SCCHN.

The present invention relates to compounds capable of inhibiting the activity of SHP2. The invention further provides a process for the preparation of compounds of the invention and pharmaceutical preparations comprising such compounds. Another aspect of the present invention relates to a method of treating SHP2-mediated disorders comprising the step of administering to a patient in need thereof a therapeutically effective amount of a compound of formula I as defined in the Summary of the Invention.

In certain embodiments, the present invention relates to the aforementioned method, wherein said SHP2-mediated disorders are cancers selected from, but not limited to: JMML; AML; MDS; B-ALL; neuroblastoma; esophageal; breast cancer; lung cancer; colon cancer; Gastric cancer, Head and Neck cancer.

The compounds of the present invention may also be useful in the treatment of other diseases or conditions related to the aberrant activity of SHP2. Thus, as a further aspect, the invention relates to a method of treatment of a disorder selected from: NS; LS; JMML; AML; MDS; B-ALL; neuroblastoma; esophageal; breast cancer; lung cancer; colon cancer; gastric cancer; head and neck cancer.

A SHP2 inhibitor of the present invention may be usefully combined with another pharmacologically active compound, or with two or more other pharmacologically active compounds, particularly in the treatment of cancer. For example, a compound of the formula (I), or a pharmaceutically acceptable salt thereof, as defined above, may be administered simultaneously, sequentially or separately in combination with one or more agents selected from chemotherapy agents, for example, mitotic inhibitors such as a taxane, a vinca alkaloid, paclitaxel, docetaxel, vincristine, vinblastine, vinorelbine or vinflunine, and other anticancer agents, e.g. cisplatin, 5-fluorouracil or 5-fluoro-2-4(1H,3H)-pyrimidinedione (5FU), flutamide or gemcitabine.

Such combinations may offer significant advantages, including synergistic activity, in therapy.

In certain embodiments, the present invention relates to the aforementioned method, wherein said compound is administered parenterally.

In certain embodiments, the present invention relates to the aforementioned method, wherein said compound is administered intramuscularly, intravenously, subcutaneously, orally, pulmonary, intrathecally, topically or intranasally.

In certain embodiments, the present invention relates to the aforementioned method, wherein said compound is administered systemically.

In certain embodiments, the present invention relates to the aforementioned method, wherein said patient is a mammal.

In certain embodiments, the present invention relates to the aforementioned method, wherein said patient is a primate.

In certain embodiments, the present invention relates to the aforementioned method, wherein said patient is a human.

In another aspect, the present invention relates to a method of treating an SHP2-mediated disorder, comprising the step of: administering to a patient in need thereof a therapeutically effective amount of a chemotherapeutic agent in combination with a therapeutically effective amount of a compound of formula I as defined in the Summary of the Invention.

Pharmaceutical Compositions

In another aspect, the present invention provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; (8) nasally; (9) pulmonary; or (10) intrathecally.

The phrase "therapeutically-effective amount" as used herein means that amount of a compound, material, or composition comprising a compound of the present invention which is effective for producing some desired therapeutic effect in at least a sub-population of cells in an animal at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, for example, Berge et al. (1977) "Pharmaceutical Salts", *J. Pharm. Sci.* 66:1-19).

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, for example, Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient, when used for the indicated analgesic effects, will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

The term "treatment" is intended to encompass also prophylaxis, therapy and cure.

The patient receiving this treatment is any animal in need, including primates, in particular humans, and other mammals such as equines, cattle, swine and sheep; and poultry and pets in general.

The compound of the invention can be administered as such or in admixtures with pharmaceutically acceptable carriers and can also be administered in conjunction with antimicrobial agents such as penicillins, cephalosporins, aminoglycosides and glycopeptides. Conjunctive therapy, thus includes sequential, simultaneous and separate administration of the active compound in a way that the therapeutical effects of the first administered one is not entirely disappeared when the subsequent is administered.

Microemulsification technology can improve bioavailability of some lipophilic (water insoluble) pharmaceutical agents. Examples include Trimetrine (Dordunoo, S. K., et al., Drug Development and Industrial Pharmacy, 17(12), 1685-1713, 1991 and REV 5901 (Sheen, P. C., et al., J Pharm Sci 80(7), 712-714, 1991). Among other things, microemulsification provides enhanced bioavailability by preferentially directing absorption to the lymphatic system instead of the circulatory system, which thereby bypasses the liver, and prevents destruction of the compounds in the hepatobiliary circulation.

While all suitable amphiphilic carriers are contemplated, the presently preferred carriers are generally those that have Generally-Recognized-as-Safe (GRAS) status, and that can both solubilize the compound of the present invention and microemulsify it at a later stage when the solution comes into a contact with a complex water phase (such as one found in human gastrointestinal tract). Usually, amphiphilic ingredients that satisfy these requirements have HLB (hydrophilic to lipophilic balance) values of 2-20, and their structures contain straight chain aliphatic radicals in the range of C-6 to C-20. Examples are polyethylene-glycolized fatty glycerides and polyethylene glycols.

Commercially available amphiphilic carriers are particularly contemplated, including Gelucire-series, Labrafil, Labrasol, or Lauroglycol (all manufactured and distributed by Gattefosse Corporation, Saint Priest, France), PEG-mono-oleate, PEG-di-oleate, PEG-mono-laurate and di-laurate, Lecithin, Polysorbate 80, etc (produced and distributed by a number of companies in USA and worldwide).

Hydrophilic polymers suitable for use in the present invention are those which are readily water-soluble, can be covalently attached to a vesicle-forming lipid, and which are tolerated in vivo without toxic effects (i.e., are biocompatible). Suitable polymers include polyethylene glycol (PEG), polylactic (also termed polylactide), polyglycolic acid (also termed polyglycolide), a polylactic-polyglycolic acid copolymer, and polyvinyl alcohol. Preferred polymers are those having a molecular weight of from about 100 or 120 daltons up to about 5,000 or 10,000 daltons, and more preferably from about 300 daltons to about 5,000 daltons. In a particularly preferred embodiment, the polymer is polyethyleneglycol having a molecular weight of from about 100 to about 5,000 daltons, and more preferably having a molecular weight of from about 300 to about 5,000 daltons. In a particularly preferred embodiment, the polymer is polyethyleneglycol of 750 daltons (PEG(750)). Polymers may also be defined by the number of monomers therein; a preferred embodiment of the present invention utilizes polymers of at least about three monomers, such PEG polymers consisting of three monomers (approximately 150 daltons).

Other hydrophilic polymers which may be suitable for use in the present invention include polyvinylpyrrolidone, polymethoxazoline, polyethyloxazoline, polyhydroxypropyl methacrylamide, polymethacrylamide, polydimethylacrylamide, and derivatized celluloses such as hydroxymethylcellulose or hydroxyethylcellulose.

In certain embodiments, a formulation of the present invention comprises a biocompatible polymer selected from the group consisting of polyamides, polycarbonates, polyalkylenes, polymers of acrylic and methacrylic esters, polyvinyl polymers, polyglycolides, polysiloxanes, polyurethanes and co-polymers thereof, celluloses, polypropylene, polyethylenes, polystyrene, polymers of lactic acid and glycolic acid, polyanhydrides, poly(ortho)esters, poly(butic acid), poly(valeric acid), poly(lactide-co-caprolactone), polysaccharides, proteins, polyhyaluronic acids, polycyanoacrylates, and blends, mixtures, or copolymers thereof.

Cyclodextrins are cyclic oligosaccharides, consisting of 6, 7 or 8 glucose units, designated by the Greek letter alpha, beta or gamma, respectively. Cyclodextrins with fewer than six glucose units are not known to exist. The glucose units are linked by alpha-1,4-glucosidic bonds. As a consequence of the chair conformation of the sugar units, all secondary hydroxyl groups (at C-2, C-3) are located on one side of the ring, while all the primary hydroxyl groups at C-6 are situated on the other side. As a result, the external faces are hydrophilic, making the cyclodextrins water-soluble. In contrast, the cavities of the cyclodextrins are hydrophobic, since they are lined by the hydrogen of atoms C-3 and C-5, and by ether-like oxygens. These matrices allow complexation with a variety of relatively hydrophobic compounds, including, for instance, steroid compounds such as 17.beta.-estradiol (see, e.g., van Uden et al. Plant Cell Tiss. Org. Cult. 38:1-3-113 (1994)). The complexation takes place by Van der Waals interactions and by hydrogen bond formation. For a general review of the chemistry of cyclodextrins, see, Wenz, Agnew. Chem. Int. Ed. Engl., 33:803-822 (1994).

The physico-chemical properties of the cyclodextrin derivatives depend strongly on the kind and the degree of substitution. For example, their solubility in water ranges from insoluble (e.g., triacetyl-beta-cyclodextrin) to 147% soluble (w/v) (G-2-beta-cyclodextrin). In addition, they are soluble in many organic solvents. The properties of the cyclodextrins enable the control over solubility of various formulation components by increasing or decreasing their solubility.

Numerous cyclodextrins and methods for their preparation have been described. For example, Parmeter (I), et al. (U.S. Pat. No. 3,453,259) and Gramera, et al. (U.S. Pat. No. 3,459,731) described electroneutral cyclodextrins. Other derivatives include cyclodextrins with cationic properties [Parmeter (II), U.S. Pat. No. 3,453,257], insoluble cross-linked cyclodextrins (Solms, U.S. Pat. No. 3,420,788), and cyclodextrins with anionic properties [Parmeter (III), U.S. Pat. No. 3,426,011]. Among the cyclodextrin derivatives with anionic properties, carboxylic acids, phosphorous acids, phosphinous acids, phosphonic acids, phosphoric acids, thiophosphonic acids, thiosulphinic acids, and sulfonic acids have been appended to the parent cyclodextrin [see, Parmeter (III), supra]. Furthermore, sulfoalkyl ether cyclodextrin derivatives have been described by Stella, et al. (U.S. Pat. No. 5,134,127).

Liposomes consist of at least one lipid bilayer membrane enclosing an aqueous internal compartment. Liposomes may be characterized by membrane type and by size. Small unilamellar vesicles (SUVs) have a single membrane and typically range between 0.02 and 0.05 m in diameter; large unilamellar vesicles (LUVS) are typically larger than 0.05 m Oligolamellar large vesicles and multilamellar vesicles have multiple, usually concentric, membrane layers and are typically larger than 0.1 μm. Liposomes with several nonconcentric membranes, i.e., several smaller vesicles contained within a larger vesicle, are termed multivesicular vesicles.

One aspect of the present invention relates to formulations comprising liposomes containing a compound of the present invention, where the liposome membrane is formulated to provide a liposome with increased carrying capacity. Alternatively or in addition, the compound of the present invention may be contained within, or adsorbed onto, the liposome bilayer of the liposome. The compound of the present invention may be aggregated with a lipid surfactant and carried within the liposome's internal space; in these cases, the liposome membrane is formulated to resist the disruptive effects of the active agent-surfactant aggregate.

According to one embodiment of the present invention, the lipid bilayer of a liposome contains lipids derivatized with polyethylene glycol (PEG), such that the PEG chains extend from the inner surface of the lipid bilayer into the interior space encapsulated by the liposome, and extend from the exterior of the lipid bilayer into the surrounding environment.

Active agents contained within liposomes of the present invention are in solubilized form. Aggregates of surfactant and active agent (such as emulsions or micelles containing the active agent of interest) may be entrapped within the interior space of liposomes according to the present invention. A surfactant acts to disperse and solubilize the active agent, and may be selected from any suitable aliphatic, cycloaliphatic or aromatic surfactant, including but not limited to biocompatible lysophosphatidylcholines (LPCs) of varying chain lengths (for example, from about $C_{14}$ to about $C_{20}$). Polymer-derivatized lipids such as PEG-lipids may also be utilized for micelle formation as they will act to inhibit micelle/membrane fusion, and as the addition of a polymer to surfactant molecules decreases the CMC of the surfactant and aids in micelle formation. Preferred are surfactants with CMCs in the micromolar range; higher CMC surfactants may be utilized to prepare micelles entrapped within liposomes of the present invention, however, micelle surfactant monomers could affect liposome bilayer stability and would be a factor in designing a liposome of a desired stability.

Liposomes according to the present invention may be prepared by any of a variety of techniques that are known in the art. See, e.g., U.S. Pat. No. 4,235,871; Published PCT applications WO 96/14057; New RRC, Liposomes: A practical approach, IRL Press, Oxford (1990), pages 33-104; Lasic D D, Liposomes from physics to applications, Elsevier Science Publishers BV, Amsterdam, 1993.

For example, liposomes of the present invention may be prepared by diffusing a lipid derivatized with a hydrophilic polymer into preformed liposomes, such as by exposing preformed liposomes to micelles composed of lipid-grafted polymers, at lipid concentrations corresponding to the final mole percent of derivatized lipid which is desired in the liposome. Liposomes containing a hydrophilic polymer can also be formed by homogenization, lipid-field hydration, or extrusion techniques, as are known in the art.

In one aspect of the present invention, the liposomes are prepared to have substantially homogeneous sizes in a selected size range. One effective sizing method involves extruding an aqueous suspension of the liposomes through a series of polycarbonate membranes having a selected uniform pore size; the pore size of the membrane will correspond roughly with the largest sizes of liposomes produced by extrusion through that membrane. See e.g., U.S. Pat. No. 4,737,323 (Apr. 12, 1988).

The release characteristics of a formulation of the present invention depend on the encapsulating material, the concentration of encapsulated drug, and the presence of release modifiers. For example, release can be manipulated to be pH dependent, for example, using a pH sensitive coating that releases only at a low pH, as in the stomach, or a higher pH, as in the intestine. An enteric coating can be used to prevent release from occurring until after passage through the stomach. Multiple coatings or mixtures of cyanamide encapsulated in different materials can be used to obtain an initial release in the stomach, followed by later release in the intestine. Release can also be manipulated by inclusion of salts or pore forming agents, which can increase water uptake or release of drug by diffusion from the capsule. Excipients which modify the solubility of the drug can also be used to control the release rate. Agents which enhance degradation of the matrix or release from the matrix can also be incorporated. They can be added to the drug, added as a separate phase (i.e., as particulates), or can be co-dissolved in the polymer phase depending on the compound. In all cases the amount should be between 0.1 and thirty percent (w/w polymer). Types of degradation enhancers include inorganic salts such as ammonium sulfate and ammonium chloride, organic acids such as citric acid, benzoic acid, and ascorbic acid, inorganic bases such as sodium carbonate, potassium carbonate, calcium carbonate, zinc carbonate, and zinc hydroxide, and organic bases such as protamine sulfate, spermine, choline, ethanolamine, diethanolamine, and triethanolamine and surfactants such as Tween® and Pluronic®. Pore forming agents which add microstructure to the matrices (i.e., water soluble compounds such as inorganic salts and sugars) are added as particulates. The range should be between one and thirty percent (w/w polymer).

Uptake can also be manipulated by altering residence time of the particles in the gut. This can be achieved, for example, by coating the particle with, or selecting as the encapsulating material, a mucosal adhesive polymer. Examples include most polymers with free carboxyl groups, such as chitosan, celluloses, and especially polyacrylates (as used herein, polyacrylates refers to polymers including acrylate groups and modified acrylate groups such as cyanoacrylates and methacrylates).

Pharmaceutical Combinations

The invention especially relates to the use of a compound of the formula I (or a pharmaceutical composition comprising a compound of the formula I) in the treatment of one or more of the diseases mentioned herein; wherein the response to treatment is beneficial as demonstrated, for example, by the partial or complete removal of one or more of the symptoms of the disease up to complete cure or remission.

A compound of formula (I) can also be used in combination with the following compounds and antibody-drug conjugates:

BCR-ABL inhibitors: Imatinib (Gleevec®); Inilotinib hydrochloride; Nilotinib (Tasigna®); Dasatinib (BMS-345825); Bosutinib (SKI-606); Ponatinib (AP24534); Bafetinib (INNO406); Danusertib (PHA-739358), AT9283 (CAS 1133385-83-7); Saracatinib (AZD0530); and N-[2-[(1S,4R)-6-[[4-(Cyclobutylamino)-5-(trifluoromethyl)-2-pyrimidinyl]amino]-1,2,3,4-tetrahydronaphthalen-1,4-imin-9-yl]-2-oxoethyl]-acetamide (PF-03814735, CAS 942487-16-3).

ALK inhibitors: PF-2341066 (XALKORI®; crizotinib); 5-chloro-N4-(2-(isopropylsulfonyl)phenyl)-N2-(2-methoxy-4-(4-(4-methylpiperazin-1-yl)piperidin-1-yl)phenyl)pyrimidine-2,4-diamine; GSK1838705A; and CH5424802.

BRAF inhibitors: Vemurafanib (PLX4032); and Dabrafenib.

FLT3 inhibitors—sunitinib malate (sold under the tradename Sutent® by Pfizer); PKC412 (midostaurin); tanutinib, sorafenib, sunitinib, midostaurin, lestaurtinib, KW-2449, quizartinib (AC220) and crenolanib.

MEK Inhibitors—trametinib.

Vascular Endothelial Growth Factor (VEGF) receptor inhibitors: Bevacizumab (sold under the trademark Avastin® by Genentech/Roche), axitinib, (N-methyl-2-[[3-[(E)-2-pyridin-2-ylethenyl]-1H-indazol-6-yl]sulfanyl]benzamide, also known as AG013736, and described in PCT Publication No. WO 01/002369), Brivanib Alaninate ((S)—((R)-1-(4-(4-Fluoro-2-methyl-1H-indol-5-yloxy)-5-methylpyrrolo[2,1-f][1,2,4]triazin-6-yloxy)propan-2-yl)2-aminopropanoate, also known as BMS-582664), motesanib (N-(2,3-dihydro-3,3-dimethyl-1H-indol-6-yl)-2-[(4- pyridinylmethyl)amino]-3-pyridinecarboxamide, and described in PCT Publication No. WO 02/066470), pasireotide (also known as SOM230, and described in PCT Publication No. WO 02/010192), sorafenib (sold under the tradename Nexavar®);

HER2 receptor inhibitors: Trastuzumab (sold under the trademark Herceptin® by Genentech/Roche), neratinib (also known as HKI-272, (2E)-N-[4-[[3-chloro-4-[(pyridin-2-yl)methoxy]phenyl]amino]-3-cyano-7-ethoxyquinolin-6-yl]-4-(dimethylamino)but-2-enamide, and described PCT Publication No. WO 05/028443), lapatinib or lapatinib ditosylate (sold under the trademark Tykerb® by GlaxoSmithKline); Trastuzumab emtansine (in the United States, ado-trastuzumab emtansine, trade name Kadcyla)—an antibody-drug conjugate consisting of the monoclonal antibody trastuzumab (Herceptin) linked to the cytotoxic agent mertansine (DM1);

CD20 antibodies: Rituximab (sold under the trademarks Riuxan® and MabThera® by Genentech/Roche), tositumomab (sold under the trademarks Bexxar® by GlaxoSmithKline), ofatumumab (sold under the trademark Arzerra® by GlaxoSmithKline);

Tyrosine kinase inhibitors: Erlotinib hydrochloride (sold under the trademark Tarceva® by Genentech/Roche), Linifanib (N-[4-(3-amino-1H-indazol-4-yl)phenyl]-N'-(2-fluoro-5-methylphenyl)urea, also known as ABT 869, available from Genentech), sunitinib malate (sold under the tradename Sutent® by Pfizer), bosutinib (4-[(2,4-dichloro-5-methoxyphenyl)amino]-6-methoxy-7-[3-(4-methylpiperazin-1-yl)propoxy]quinoline-3-carbonitrile, also known as SKI-606, and described in U.S. Pat. No. 6,780,996), dasatinib (sold under the tradename Sprycel® by Bristol-Myers Squibb), armala (also known as pazopanib, sold under the tradename Votrient® by GlaxoSmithKline), imatinib and imatinib mesylate (sold under the tradenames Gilvec® and Gleevec® by Novartis);

DNA Synthesis inhibitors: Capecitabine (sold under the trademark Xeloda® by Roche), gemcitabine hydrochloride (sold under the trademark Gemzar® by Eli Lilly and Company), nelarabine ((2R,3S,4R,5R)-2-(2-amino-6-methoxypurin-9-yl)-5-(hydroxymethyl)oxolane-3,4-diol, sold under the tradenames Arranon® and Atriance® by GlaxoSmithKline);

Antineoplastic agents: oxaliplatin (sold under the tradename Eloxatin® ay Sanofi-Aventis and described in U.S. Pat. No. 4,169,846);

Epidermal growth factor receptor (EGFR) inhibitors: Gefitnib (sold under the tradename Iressa®), N-[4-[(3-Chloro-4-fluorophenyl)amino]-7-[[(3"S")-tetrahydro-3-furanyl]oxy]-6-quinazolinyl]-4(dimethylamino)-2-butenamide, sold under the tradename Tovok® by Boehringer Ingelheim), cetuximab (sold under the tradename Erbitux® by Bristol-Myers Squibb), panitumumab (sold under the tradename Vectibix® by Amgen);

HER dimerization inhibitors: Pertuzumab (sold under the trademark Omnitarg®, by Genentech);

Human Granulocyte colony-stimulating factor (G-CSF) modulators: Filgrastim (sold under the tradename Neupogen® by Amgen);

Immunomodulators: Afutuzumab (available from Roche®), pegfilgrastim (sold under the tradename Neulasta® by Amgen), lenalidomide (also known as CC-5013, sold under the tradename Revlimid®), thalidomide (sold under the tradename Thalomid®);

CD40 inhibitors: Dacetuzumab (also known as SGN-40 or huS2C6, available from Seattle Genetics, Inc);

Pro-apoptotic receptor agonists (PARAs): Dulanermin (also known as AMG-951, available from Amgen/Genentech);

Hedgehog antagonists: 2-chloro-N-[4-chloro-3-(2-pyridinyl)phenyl]-4-(methylsulfonyl)-benzamide (also known as GDC-0449, and described in PCT Publication No. WO 06/028958);

PI3K inhibitors: 4-[2-(1H-Indazol-4-yl)-6-[[4-(methylsulfonyl)piperazin-1-yl]methyl]thieno[3,2-d]pyrimidin-4-yl]morpholine (also known as GDC 0941 and described in PCT Publication Nos. WO 09/036082 and WO 09/055730), 2-Methyl-2-[4-[3-methyl-2-oxo-8-(quinolin-3-yl)-2,3-dihydroimidazo[4,5-c]quinolin-1-yl]phenyl]propionitrile (also known as BEZ 235 or NVP-BEZ 235, and described in PCT Publication No. WO 06/122806);

Phospholipase A2 inhibitors: Anagrelide (sold under the tradename Agrylin®);

BCL-2 inhibitors: 4-[4-[[2-(4-chlorophenyl)-5,5-dimethyl-1-cyclohexen-1-yl]methyl]-1-piperazinyl]-N-[[4-[[(1R)-3-(4-morpholinyl)-1-[(phenylthio)methyl]propyl]amino]-3-[(trifluoromethyl)sulfonyl]phenyl]sulfonyl]benzamide (also known as ABT-263 and described in PCT Publication No. WO 09/155386);

Mitogen-activated protein kinase kinase (MEK) inhibitors: XL-518 (Cas No. 1029872-29-4, available from ACC Corp.);

Aromatase inhibitors: Exemestane (sold under the trademark Aromasin® by Pfizer), letrozole (sold under the tradename Femara® by Novartis), anastrozole (sold under the tradename Arimidex®);

Topoisomerase I inhibitors: Irinotecan (sold under the trademark Camptosar® by Pfizer), topotecan hydrochloride (sold under the tradename Hycamtin® by GlaxoSmithKline);

Topoisomerase II inhibitors: etoposide (also known as VP-16 and Etoposide phosphate, sold under the tradenames Toposar®, VePesid® and Etopophos®), teniposide (also known as VM-26, sold under the tradename Vumon®);

mTOR inhibitors: Temsirolimus (sold under the tradename Torisel® by Pfizer), ridaforolimus (formally known as deferolimus, (1R,2R,4S)-4-[(2R)-2 [(1R,9S,12S,15R,16E,18R,19R,21R,23S,24E,26E,28Z,30S,32S,35R)-1,18-dihydroxy-19,30-dimethoxy-15,17,21,23,29,35-hexamethyl-2,3,10,14,20-pentaoxo-11,36-dioxa-4-azatricyclo[30.3.1.0$^{4,9}$] hexatriaconta-16,24,26,28-tetraen-12-yl]propyl]-2-methoxycyclohexyl dimethylphosphinate, also known as AP23573 and MK8669, and described in PCT Publication No. WO 03/064383), everolimus (sold under the tradename Afinitor® by Novartis);

Osteoclastic bone resorption inhibitors: 1-Hydroxy-2-imidazol-1-yl-phosphonoethyl) phosphonic acid monohydrate (sold under the tradename Zometa® by Novartis);

CD33 Antibody Drug Conjugates: Gemtuzumab ozogamicin (sold under the tradename Mylotarg® by Pfizer/Wyeth);

CD22 Antibody Drug Conjugates: Inotuzumab ozogamicin (also referred to as CMC-544 and WAY-207294, available from Hangzhou Sage Chemical Co., Ltd.);

CD20 Antibody Drug Conjugates: Ibritumomab tiuxetan (sold under the tradename Zevalin®);

Somatostain analogs: octreotide (also known as octreotide acetate, sold under the tradenames Sandostatin® and Sandostatin LAR®);

Synthetic Interleukin-11 (IL-11): oprelvekin (sold under the tradename Neumega® by Pfizer/Wyeth);

Synthetic erythropoietin: Darbepoetin alfa (sold under the tradename Aranesp® by Amgen);

Receptor Activator for Nuclear Factor κ B (RANK) inhibitors: Denosumab (sold under the tradename Prolia® by Amgen);

Thrombopoietin mimetic peptibodies: Romiplostim (sold under the tradename Nplate® by Amgen;

Cell growth stimulators: Palifermin (sold under the tradename Kepivance® by Amgen);

Anti-Insulin-like Growth Factor-1 receptor (IGF-1R) antibodies: Figitumumab (also known as CP-751,871, available from ACC Corp), robatumumab (CAS No. 934235-44-6);

Anti-CS1 antibodies: Elotuzumab (HuLuc63, CAS No. 915296-00-3);

CD52 antibodies: Alemtuzumab (sold under the tradename Campath®);

CTLA-4 inhibitors: Tremelimumab (IgG2 monoclonal antibody available from Pfizer, formerly known as ticilimumab, CP-675,206), ipilimumab (CTLA-4 antibody, also known as MDX-010, CAS No. 477202-00-9);

Histone deacetylase inhibitors (HDI): Voninostat (sold under the tradename Zolinza® by Merck);

Alkylating agents: Temozolomide (sold under the tradenames Temodar® and Temodal® by Schering-Plough/Merck), dactinomycin (also known as actinomycin-D and sold under the tradename Cosmegen®), melphalan (also known as L-PAM, L-sarcolysin, and phenylalanine mustard, sold under the tradename Alkeran®), altretamine (also known as hexamethylmelamine (HMM), sold under the tradename Hexalen®), carmustine (sold under the tradename BiCNU®), bendamustine (sold under the tradename Treanda®), busulfan (sold under the tradenames Busulfex® and Myleran®), carboplatin (sold under the tradename Paraplatin®), lomustine (also known as CCNU, sold under the tradename CeeNU®), cisplatin (also known as CDDP, sold under the tradenames Platinol® and Platinol®-AQ), chlorambucil (sold under the tradename Leukeran®), cyclophosphamide (sold under the tradenames Cytoxan® and Neosar®), dacarbazine (also known as DTIC, DIC and imidazole carboxamide, sold under the tradename DTIC-Dome®), altretamine (also known as hexamethylmelamine (HMM) sold under the tradename Hexalen®), ifosfamide (sold under the tradename Ifex®), procarbazine (sold under the tradename Matulane®), mechlorethamine (also known as nitrogen mustard, mustine and mechloroethamine hydrochloride, sold under the tradename Mustargen®), streptozocin (sold under the tradename Zanosar®), thiotepa (also known as thiophosphoamide, TESPA and TSPA, sold under the tradename Thioplex®);

Biologic response modifiers: *bacillus* calmette-guerin (sold under the tradenames theraCys® and TICE® BCG), denileukin diftitox (sold under the tradename Ontak®);

Anti-tumor antibiotics: doxorubicin (sold under the tradenames Adriamycin® and Rubex®), bleomycin (sold under the tradename Lenoxane®), daunorubicin (also known as dauorubicin hydrochloride, daunomycin, and rubidomycin hydrochloride, sold under the tradename Cerubidine®), daunorubicin liposomal (daunorubicin citrate liposome, sold under the tradename DaunoXome®), mitoxantrone (also known as DHAD, sold under the tradename Novantrone®), epirubicin (sold under the tradename Ellence™), idarubicin (sold under the tradenames Idamycin®, Idamycin PFS®), mitomycin C (sold under the tradename Mutamycin®);

Anti-microtubule agents: Estramustine (sold under the tradename Emcyl®);

Cathepsin K inhibitors: Odanacatib (also know as MK-0822, N-(1-cyanocyclopropyl)-4-fluoro-N²-{(1S)-2,2,2-trifluoro-1-[4'-(methylsulfonyl)biphenyl-4-yl]ethyl}-L-leucinamide, available from Lanzhou Chon Chemicals, ACC Corp., and ChemieTek, and described in PCT Publication no. WO 03/075836);

Epothilone B analogs: Ixabepilone (sold under the tradename Lxempra® by Bristol-Myers Squibb);

Heat Shock Protein (HSP) inhibitors: Tanespimycin (17-allylamino-17-demethoxygeldanamycin, also known as KOS-953 and 17-AAG, available from SIGMA, and described in U.S. Pat. No. 4,261,989);

TpoR agonists: Eltrombopag (sold under the tradenames Promacta® and Revolade® by GlaxoSmithKline);

Anti-mitotic agents: Docetaxel (sold under the tradename Taxotere® by Sanofi-Aventis);

Adrenal steroid inhibitors: aminoglutethimide (sold under the tradename Cytadren®);

Anti-androgens: Nilutamide (sold under the tradenames Nilandron® and Anandron®), bicalutamide (sold under tradename Casodex®), flutamide (sold under the tradename Fulexin™);

Androgens: Fluoxymesterone (sold under the tradename Halotestin®);

Proteasome inhibitors: Bortezomib (sold under the tradename Velcade®);

CDK1 inhibitors: Alvocidib (also known as flovopirdol or HMR-1275, 2-(2-chlorophenyl)-5,7-dihydroxy-8-[(3S,4R)-3-hydroxy-1-methyl-4-piperidinyl]-4-chromenone, and described in U.S. Pat. No. 5,621,002);

Gonadotropin-releasing hormone (GnRH) receptor agonists: Leuprolide or leuprolide acetate (sold under the tradenames Viadure® by Bayer AG, Eligard® by Sanofi-Aventis and Lupron® by Abbott Lab);

Taxane anti-neoplastic agents: Cabazitaxel (1-hydroxy-7β,10β-dimethoxy-9-oxo-5β,20-epoxytax-11-ene-2α,4,13α-triyl-4-acetate-2-benzoate-13-[(2R,3S)-3-{[(tert-butoxy)carbonyl]amino}-2-hydroxy-3-phenylpropanoate), larotaxel ((2α,3ξ,4α,5β,7α,10β,13α)-4,10-bis(acetyloxy)-13-({(2R,3S)-3-[(tert-butoxycarbonyl) amino]-2-hydroxy-3-phenylpropanoyl}oxy)-1-hydroxy-9-oxo-5,20-epoxy-7,19-cyclotax-11-en-2-yl benzoate);

5HT1a receptor agonists: Xaliproden (also known as SR57746, 1-[2-(2-naphthyl)ethyl]-4-[3-(trifluoromethyl) phenyl]-1,2,3,6-tetrahydropyridine, and described in U.S. Pat. No. 5,266,573);

HPC vaccines: Cervarix® sold by GlaxoSmithKline, Gardasil® sold by Merck;

Iron Chelating agents: Deferasinox (sold under the tradename Exjade® by Novartis);

Anti-metabolites: Claribine (2-chlorodeoxyadenosine, sold under the tradename Leustatin®), 5-fluorouracil (sold under the tradename Adrucil®), 6-thioguanine (sold under the tradename Purinethol®), pemetrexed (sold under the tradename Alimta®), cytarabine (also known as arabinosylcytosine (Ara-C), sold under the tradename Cytosar-U®), cytarabine liposomal (also known as Liposomal Ara-C, sold under the tradename DepoCyt™), decitabine (sold under the tradename Dacogen®), hydroxyurea (sold under the tradenames Hydrea®, Droxia™ and Mylocel™), fludarabine (sold under the tradename Fludara®), floxuridine (sold under the tradename FUDR®), cladribine (also known as 2-chlorodeoxyadenosine (2-CdA) sold under the tradename Leustatin™), methotrexate (also known as amethopterin, methotrexate sodim (MTX), sold under the tradenames Rheumatrex® and Trexall™), pentostatin (sold under the tradename Nipent®);

Bisphosphonates: Pamidronate (sold under the tradename Aredia®), zoledronic acid (sold under the tradename Zometa®);

Demethylating agents: 5-azacitidine (sold under the tradename Vidaza®), decitabine (sold under the tradename Dacogen®);

Plant Alkaloids: Paclitaxel protein-bound (sold under the tradename Abraxane®), vinblastine (also known as vinblastine sulfate, vincaleukoblastine and VLB, sold under the tradenames Alkaban-AQ® and Velban®), vincristine (also known as vincristine sulfate, LCR, and VCR, sold under the tradenames Oncovin® and Vincasar Pfs®), vinorelbine (sold under the tradename Navelbine®), paclitaxel (sold under the tradenames Taxol and Onxal™);

Retinoids: Alitretinoin (sold under the tradename Panretin®), tretinoin (all-trans retinoic acid, also known as ATRA, sold under the tradename Vesanoid®), Isotretinoin (13-cis-retinoic acid, sold under the tradenames Accutane®, Amnesteem®, Claravis®, Clarus®, Decutan®, Isotane®, Izotech®, Oratane®, Isotret®, and Sotret®), bexarotene (sold under the tradename Targretin®);

Glucocorticosteroids: Hydrocortisone (also known as cortisone, hydrocortisone sodium succinate, hydrocortisone sodium phosphate, and sold under the tradenames Ala-Cort®, Hydrocortisone Phosphate, Solu-Cortef®, Hydrocort Acetate® and Lanacort®), dexamethazone ((8S,9R,10S,11S,13S,14S,16R,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthren-3-one), prednisolone (sold under the tradenames Delta-Cortel®, Orapred®, Pediapred® and Prelone®), prednisone (sold under the tradenames Deltasone®, Liquid Red®, Meticorten® and Orasone®), methylprednisolone (also known as 6-Methylprednisolone, Methylprednisolone Acetate, Methylprednisolone Sodium Succinate, sold under the tradenames Duralone®, Medralone®, Medrol®, M-Prednisol® and Solu-Medrol®);

Cytokines: interleukin-2 (also known as aldesleukin and IL-2, sold under the tradename Proleukin®), interleukin-11 (also known as oprevelkin, sold under the tradename Neumega®), alpha interferon alfa (also known as IFN-alpha, sold under the tradenames Intron® A, and Roferon-A®);

Estrogen receptor downregulators: Fulvestrant (sold under the tradename Faslodex®);

Anti-estrogens: tamoxifen (sold under the tradename Novaldex®);

Toremifene (sold under the tradename Fareston®);

Selective estrogen receptor modulators (SERMs): Raloxifene (sold under the tradename Evista®);

Leutinizing hormone releasing hormone (LHRH) agonists: Goserelin (sold under the tradename Zoladex®);

Progesterones: megestrol (also known as megestrol acetate, sold under the tradename Megace®);

Miscellaneous cytotoxic agents: Arsenic trioxide (sold under the tradename Trisenox®), asparaginase (also known as L-asparaginase, *Erwinia* L-asparaginase, sold under the tradenames Elspar® and Kidrolase®);

A compound of formula (I) can also be used in combination with the following adjunct therapies:

Anti-nausea drugs: NK-1 receptor antagonists: Casopitant (sold under the tradenames Rezonic® and Zunrisa® by GlaxoSmithKline); and Cytoprotective agents: Amifostine (sold under the tradename Ethyol®), leucovorin (also known as calcium leucovorin, citrovorum factor and folinic acid).

None of the quotations of references made within the present disclosure is to be understood as an admission that the references cited are prior art that would negatively affect the patentability of the present invention.

Processes for Making Compounds of the Invention

The present invention also includes processes for the preparation of compounds of the invention. In the reactions described, it can be necessary to protect reactive functional groups, for example hydroxy, amino, imino, thio or carboxy groups, where these are desired in the final product, to avoid their unwanted participation in the reactions. Conventional protecting groups can be used in accordance with standard practice, for example, see T. W. Greene and P. G. M. Wuts in "Protective Groups in Organic Chemistry", John Wiley and Sons, 1991.

Compounds of Formula I, where $X_3$ is S, can be prepared by proceeding as in the following Reaction Scheme I:

Reaction Scheme I:

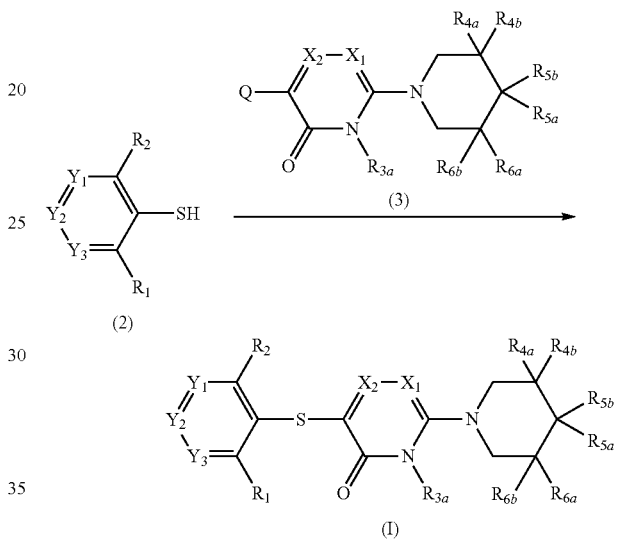

in which $X_1$, $X_2$, $Y_1$, $Y_2$, $Y_3$, $R_1$, $R_2$, $R_{3a}$, $R_{3b}$, $R_{4a}$, $R_{4b}$, $R_{5a}$, $R_{5b}$, $R_{6a}$ and $R_{6b}$ are as defined by the Summary of the Invention and Q is a leaving group such as iodide, or the like. Compounds of formula I can be prepared by reacting a compound of formula 2 with a compound of formula 3 in the presence of a suitable solvent (such as dioxane or the like), a suitable metal ligand (such as TMEDA, or the like), a suitable metal halide (such as Cu(I)I, or the like) and a suitable salt (such as $K_3PO_4$, or the like). The reaction proceeds at a temperature range of about 80° C. to about 140° C. and can take from about 1 hour to about 24 hours to complete.

Alternatively, compounds of formula I can be prepared by reacting a compound of formula 2 with a compound of formula 3 in the presence of a suitable solvent (such as DMF or the like), a suitable coupling agent (such as CuTC, or the like) and a suitable salt (such as potassium carbonate, or the like). The reaction proceeds at a temperature range of about 80° C. to about 140° C. and can take from about 1 hour to about 24 hours to complete.

Alternatively, compounds of formula I, where $X_3$ is S, can be prepared by reacting a compound of formula 2 with a compound of formula 3 in the presence of a suitable solvent (such as dioxane or the like), a suitable metal halide (such as Cu(I)I, or the like), a suitable base (such as cesium carbonate, or the like) and a suitable ligand (such as 1,10-phenanthroline, or the like). The reaction proceeds at a temperature range of about 80° C. to about 140° C. and can take from about 1 hour to about 24 hours to complete.

Reaction Scheme II:

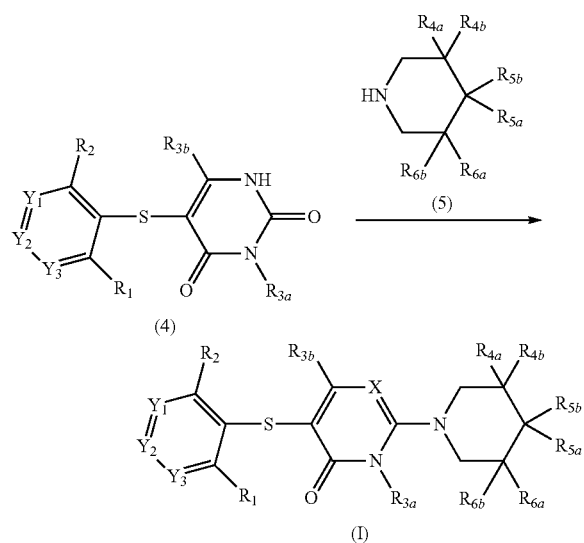

in which $X_1$, $X_2$, $Y_1$, $Y_2$, $Y_3$, $R_1$, $R_2$, $R_{3a}$, $R_{3b}$, $R_{4a}$, $R_{4b}$, $R_{5a}$, $R_{5b}$, $R_{6a}$ and $R_{6b}$ are as defined by the Summary of the Invention and Q is a leaving group such as iodide, or the like. Compounds of formula I can be prepared by reacting a compound of formula 4 with a compound of formula 5 in the presence of a suitable solvent (such as MeCN, DMF, or the like), a suitable coupling agent (such as BOP—Cl, BOP, or the like) and a suitable catalyst (such as DBU, or the like). The reaction proceeds at a temperature range of about 80° C. to about 140° C. and can take from about 1 hour to about 24 hours to complete.

Detailed examples of the synthesis of compounds of Formula I can be found in the Examples, infra.

Additional Processes for Making Compounds of the Invention

A compound of the invention can be prepared as a pharmaceutically acceptable acid addition salt by reacting the free base form of the compound with a pharmaceutically acceptable inorganic or organic acid. Alternatively, a pharmaceutically acceptable base addition salt of a compound of the invention can be prepared by reacting the free acid form of the compound with a pharmaceutically acceptable inorganic or organic base.

Compounds of the formula I can also be modified by appending appropriate functionalities to enhance selective biological properties. Modifications of this kind are known in the art and include those that increase penetration into a given biological system (e.g. blood, lymphatic system, central nervous system, testis), increase bioavailability, increase solubility to allow parenteral administration (e.g. injection, infusion), alter metabolism and/or alter the rate of secretion. Examples of this type of modifications include but are not limited to esterification, e.g. with polyethylene glycols, derivatisation with pivaloyloxy or fatty acid substituents, conversion to carbamates, hydroxylation of aromatic rings and heteroatom substitution in aromatic rings. Wherever compounds of the formula I, and/or N-oxides, tautomers and/or (preferably pharmaceutically acceptable) salts thereof are mentioned, this comprises such modified formulae, while preferably the molecules of the formula I, their N-oxides, their tautomers and/or their salts are meant.

Alternatively, the salt forms of the compounds of the invention can be prepared using salts of the starting materials or intermediates. In view of the close relationship between the novel compounds of the formula I in free form and those in the form of their salts, including those salts that can be used as intermediates, for example in the purification or identification of the novel compounds, any reference to the compounds or a compound of the formula I hereinbefore and hereinafter is to be understood as referring to the compound in free form and/or also to one or more salts thereof, as appropriate and expedient, as well as to one or more solvates, e.g. hydrates.

Salts are formed, for example, as acid addition salts, preferably with organic or inorganic acids, from compounds of formula I with a basic nitrogen atom, especially the pharmaceutically acceptable salts. Suitable inorganic acids are, for example, halogen acids, such as hydrochloric acid, sulfuric acid, or phosphoric acid. Suitable organic acids are, for example, carboxylic, phosphonic, sulfonic or sulfamic acids, for example acetic acid, propionic acid, octanoic acid, decanoic acid, dodecanoic acid, glycolic acid, lactic acid, fumaric acid, succinic acid, malonic acid, adipic acid, pimelic acid, suberic acid, azelaic acid, malic acid, tartaric acid, citric acid, amino acids, such as glutamic acid or aspartic acid, maleic acid, hydroxymaleic acid, methylmaleic acid, cyclohexanecarboxylic acid, adamantanecarboxylic acid, benzoic acid, salicylic acid, 4-aminosalicylic acid, phthalic acid, phenylacetic acid, mandelic acid, cinnamic acid, methane- or ethane-sulfonic acid, 2-hydroxyethanesulfonic acid, ethane-1,2-disulfonic acid, benzenesulfonic acid, 4-toluenesulfonic acid, 2-naphthalenesulfonic acid, 1,5-naphthalene-disulfonic acid, 2- or 3-methylbenzenesulfonic acid, methylsulfuric acid, ethylsulfuric acid, dodecylsulfuric acid, N-cyclohexylsulfamic acid, N-methyl-, N-ethyl- or N-propyl-sulfamic acid, or other organic protonic acids, such as ascorbic acid.

For isolation or purification purposes it is also possible to use pharmaceutically unacceptable salts, for example picrates or perchlorates. For therapeutic use, only pharmaceutically acceptable salts or free compounds are employed (where applicable in the form of pharmaceutical preparations), and these are therefore preferred.

The free acid or free base forms of the compounds of the invention can be prepared from the corresponding base addition salt or acid addition salt from, respectively. For example a compound of the invention in an acid addition salt form can be converted to the corresponding free base by treating with a suitable base (e.g., ammonium hydroxide solution, sodium hydroxide, and the like). A compound of the invention in a base addition salt form can be converted to the corresponding free acid by treating with a suitable acid (e.g., hydrochloric acid, etc.).

Compounds of the invention in unoxidized form can be prepared from N-oxides of compounds of the invention by treating with a reducing agent (e.g., sulfur, sulfur dioxide, triphenyl phosphine, lithium borohydride, sodium borohydride, phosphorus trichloride, tribromide, or the like) in a suitable inert organic solvent (e.g. MeCN, ethanol, aqueous dioxane, or the like) at 0 to 80° C.

Prodrug derivatives of the compounds of the invention can be prepared by methods known to those of ordinary skill in the art (e.g., for further details see Saulnier et al., (1994), Bioorganic and Medicinal Chemistry Letters, Vol. 4, p. 1985). For example, appropriate prodrugs can be prepared by reacting a non-derivatized compound of the invention with a suitable carbamylating agent (e.g., 1,1-acyloxyalkylcarbanochloridate, para-nitrophenyl carbonate, or the like).

Protected derivatives of the compounds of the invention can be made by means known to those of ordinary skill in the art. A detailed description of techniques applicable to the creation of protecting groups and their removal can be found in T. W. Greene, "Protecting Groups in Organic Chemistry", $3^{rd}$ edition, John Wiley and Sons, Inc., 1999.

Compounds of the present invention can be conveniently prepared, or formed during the process of the invention, as solvates (e.g., hydrates). Hydrates of compounds of the present invention can be conveniently prepared by recrystallization from an aqueous/organic solvent mixture, using organic solvents such as dioxin, tetrahydrofuran or methanol.

Compounds of the invention can be prepared as their individual stereoisomers by reacting a racemic mixture of the compound with an optically active resolving agent to form a pair of diastereoisomeric compounds, separating the diastereomers and recovering the optically pure enantiomers. While resolution of enantiomers can be carried out using covalent diastereomeric derivatives of the compounds of the invention, dissociable complexes are preferred (e.g., crystalline diastereomeric salts). Diastereomers have distinct physical properties (e.g., melting points, boiling points, solubilities, reactivity, etc.) and can be readily separated by taking advantage of these dissimilarities. The diastereomers can be separated by chromatography, or preferably, by separation/resolution techniques based upon differences in solubility. The optically pure enantiomer is then recovered, along with the resolving agent, by any practical means that would not result in racemization. A more detailed description of the techniques applicable to the resolution of stereoisomers of compounds from their racemic mixture can be found in Jean Jacques, Andre Collet, Samuel H. Wilen, "Enantiomers, Racemates and Resolutions", John Wiley And Sons, Inc., 1981.

In summary, the compounds of Formula I can be made by a process, which involves:
- (a) that of reaction schemes I and II; and
- (b) optionally converting a compound of the invention into a pharmaceutically acceptable salt;
- (c) optionally converting a salt form of a compound of the invention to a non-salt form;
- (d) optionally converting an unoxidized form of a compound of the invention into a pharmaceutically acceptable N-oxide;
- (e) optionally converting an N-oxide form of a compound of the invention to its unoxidized form;
- (f) optionally resolving an individual isomer of a compound of the invention from a mixture of isomers;
- (g) optionally converting a non-derivatized compound of the invention into a pharmaceutically acceptable prodrug derivative; and
- (h) optionally converting a prodrug derivative of a compound of the invention to its non-derivatized form.

Insofar as the production of the starting materials is not particularly described, the compounds are known or can be prepared analogously to methods known in the art or as disclosed in the Examples hereinafter.

One of skill in the art will appreciate that the above transformations are only representative of methods for preparation of the compounds of the present invention, and that other well known methods can similarly be used.

EXAMPLES

The following examples and intermediates serve to illustrate the invention without limiting the scope thereof. Some abbreviations used in the examples are as follows: acetic acid (AcOH); MeCN (MeCN); triethylamine (TEA); tetrahydrofuran (THF); aqueous (aq); saturated (sat.); atmosphere (atm.); 2,2'-bis-diphenylphosphanyl-[1,1']binaphthalenyl (BINAP); 4-dimethylaminopyridine (DMAP); tert-butoxycarbonyl (Boc); 1,1-carbonyldiimidazole (CDI); di-tert-butyl dicarbonate ($Boc_2O$); benzotriazole-1-yl-oxy-tris-(dimethylamino)-phosphonium hexafluorophosphate (BOP); dichloromethane (DCM); diethyl ether ($Et_2O$); p-toluene sulfonic acid (PTSA); ethyl acetate (EtOAc); ethanol (EtOH); lithium bis(trimethylsilyl)amide (LHMDS); diisopropyl azodicarboxylate (DIAD); N,N-diisopropyl-ethylamine (DIEA or DIPEA); N,N-dimethylformamide (DMF); dimethyl sulfoxide (DMSO); diphenylphosphoryl azide (DPPA); hour(s) (h); 2-(1H-7-azabenzotriazol-1-yl)-1,1,3,3-tetramethyluronium hexafluorophosphate (HATU); High Performance Liquid Chromatography (HPLC); isopropyl alcohol (IPA); lithium aluminium hydride (LAH); liquid chromatography coupled with mass spectrometry (LCMS); lithium diisopropylamide (LDA); methanol (MeOH); milliliter(s) (mL); minute(s) (min); microwave (MW); sodium bis(trimethylsilyl)amide (NHMDS); n-butyllithium (n-BuLi); 1,1-bis(diphenylphosphino)-ferrocenedichloropalladium (II) ($PdCl_2(dppf)$); tris (dibenzylideneacetone)dipalladium (0) ($Pd_2(dba)_3$); dichlorobis(triphenylphosphine)palladium (II) ($PdCl_2(PPh_3)_2$); room temperature (RT); tetra-n-butylammonium fluoride (TBAF); tert-butyldimethylsilyl chloride (TBSCl); trifluoroacetic acid (TFA); tetrahydrofuran (THF); thin layer chromatography (TLC); retention time ($t_R$); (S)-(−)-2,2'-Bis(di-p-tolylphosphino)-1,1'-binaphthyl ((S)-TolBINAP); & 4,5-bis(diphenylphosphino)-9,9-dimethylxanthene (XantPhos).

Intermediate S-1

Sodium 2-amino-3-chloropyridine-4-thiolate

Step a: To a solution of 3-chloro-4-iodopyridin-2-amine (1.0 g, 3.93 mmol), XantPhos (136 mg, 0.236 mmol), and $Pd(OAc)_2$ (44 mg, 0.196 mmol) in dioxane (13 mL) was added methyl 3-mercaptopropanoate (479 µL, 4.32 mmol) followed by the addition of DIPEA (1.37 mL, 7.86 mmol) at RT and under $N_2$ atmosphere. The resulting solution was stirred for 2 h at 100° C. After cooling to RT, the reaction mixture was diluted with EtOAc (20 mL) and filtered through a pad of Celite followed by EtOAc wash (25 mL). The combined filtrates were concentrated under reduced pressure and the residue was purified by silica chromatography (0 to 10% gradient of MeOH/DCM) to give methyl 3-((2-amino-3-chloropyridin-4-yl)thio)propanoate (970 mg, 3.93 mmol). MS m/z 247.1 (M+H)⁺.

Step b: To a solution of methyl 3-((2-amino-3-chloropyridin-4-yl)thio)propanoate (1.04 g, 4.22 mmol) in THF (14 mL) was added at RT and under $N_2$ sodium ethoxide (21% wt. in EtOH, 1.65 mL, 4.43 mmol) at RT and under $N_2$ atmosphere. After stirring vigorously for 40 min at RT, the reaction mixture was diluted with DCM (30 mL) and it was sonicated for 5 min. The resulting solid formed was filtered off followed by DCM wash (5 mL), and dried under reduced pressure to give sodium 2-amino-3-chloropyridine-4-thiolate (770 mg, 4.22 mmol). $^1$H NMR (400 MHz, Methanol-$d_4$) δ ppm 7.23 (d, J=5.56 Hz, 1H), 6.82 (d, J=5.56 Hz, 1H).

The following intermediates of Table 1 were made using the above procedure or modifications to the above procedure using the corresponding aryl iodide or aryl bromide.

TABLE 1

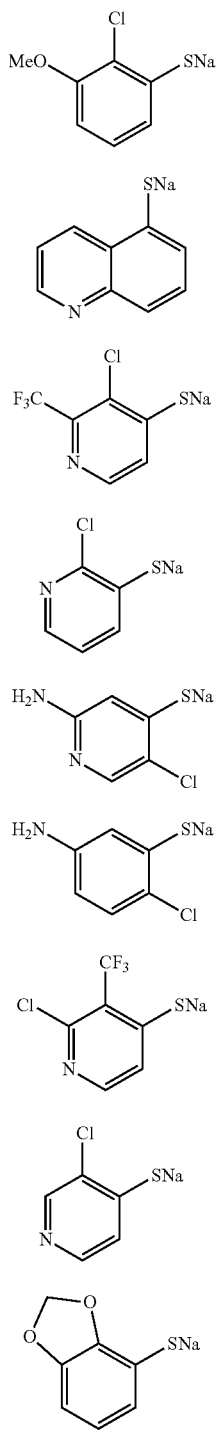

TABLE 1-continued

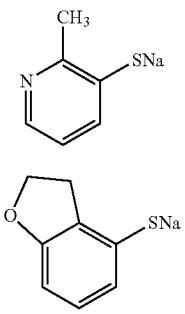

---

Intermediate S-2

2-(trifluoromethoxy)pyridine-3-thiol

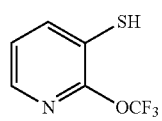

Step a: To a −78° C. solution of 2-(trifluoromethoxy)pyridin-3-ol (0.75 g, 4.19 mmol) and Et$_3$N (1.17 mL, 8.38 mmol) in DCM (15 mL) was added trifluoromethanesulfonic anhydride (1 M in DCM, 6.28 mL, 6.28 mmol). The resulting solution was stirred for 30 min at −78° C. The reaction mixture was diluted carefully with sat. aq. NaHCO$_3$ solution (25 mL) and the resulting mixture was extracted with DCM (2×15 mL). The combined organic phases were dried over MgSO$_4$, filtered, and the volatiles were removed under reduced pressure. The residue was purified by silica chromatography (0 to 40% gradient of EtOAc/heptane) to give 2-(trifluoromethoxy)pyridin-3-yl trifluoromethanesulfonate (1.25 g, 4.02 mmol). MS m/z 312.0 (M+H)$^+$.

Step b: To a solution of 2-(trifluoromethoxy)pyridin-3-yl trifluoromethanesulfonate (1.25 g, 4.02 mmol), XantPhos (139 mg, 0.241 mmol), and Pd(OAc)$_2$ (45 mg, 0.201 mmol) in dioxane (10 mL) was added methyl 3-mercaptopropanoate (489 μL, 4.42 mmol) followed by the addition of DIPEA (1.4 mL, 8.03 mmol) at RT and under N$_2$ atmosphere. The resulting solution was stirred for 2 h at 100° C. After cooling to RT, the reaction mixture was diluted with EtOAc (20 mL) and filtered through a pad of Celite followed by EtOAc wash (25 mL). The combined filtrates were concentrated under reduced pressure and the residue was purified by column chromatography (silica gel, 0 to 25% gradient of EtOAc/heptane) to give methyl 3-((2-(trifluoromethoxy)pyridin-3-yl)thio)propanoate (1.025 g, 3.64 mmol). MS m/z 282.1 (M+H)$^+$.

Step c: To a solution of methyl 3-((2-(trifluoromethoxy)pyridin-3-yl)thio)propanoate (1.025 g, 3.64 mmol) in THF (12 mL) was added at RT and under N$_2$ sodium ethoxide (21% wt. in EtOH, 1.43 mL, 3.83 mmol). After stirring vigorously for 40 min at RT, the reaction mixture was diluted with DCM (40 mL) and sonicated for 5 min. The volatiles were removed under reduced pressure and the residue was suspended in DCM and poured into a separation funnel containing sat. aq. NH$_4$Cl. The organic phase was separated and the aqueous phase was extracted with DCM (2×15 mL). The combined organic phases were dried over MgSO$_4$, filtered, and the volatiles were removed under reduced pressure. The aqueous phase was acidified with aq. 1 N HCl and extracted with DCM (3×10 mL). The combined organic phases were dried over MgSO₄, filtered, and the volatiles were removed under reduced pressure to give crude 2-(trifluoromethoxy)pyridine-3-thiol (711 mg, 3.64 mmol). MS m/z 194.1 (M−H)⁻.

Intermediate S-3

Sodium 3-chloro-2-(pyrrolidin-1-yl)pyridine-4-thiolate

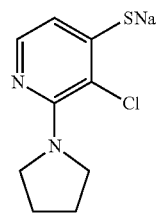

Step a: A solution of 3-chloro-2-fluoro-4-iodopyridine (2.0 g, 7.77 mmol) and pyrrolidine (1.93 mL, 23.31 mmol) in DMSO (10 mL) was stirred at 70° C. for 30 min. After cooling to RT, the resulting mixture was poured into a separation funnel containing sat. aq. NH₄Cl and extracted with Et₂O (5×10 mL). The combined organic phases were dried over MgSO₄, filtered, and the volatiles were removed under reduced pressure to give 3-chloro-4-iodo-2-(pyrrolidin-1-yl)pyridine (1.66 g, 5.38 mmol). MS m/z 309.0 (M+H)⁺.

Step b: To a solution of 3-chloro-4-iodo-2-(pyrrolidin-1-yl)pyridine (1.66 g, 5.38 mmol), XantPhos (187 mg, 0.323 mmol), and Pd(OAc)₂ (60 mg, 0.269 mmol) in dioxane (11 mL) was added methyl 3-mercaptopropanoate (655 μL, 5.92 mmol) followed by addition of DIPEA (1.88 mL, 10.76 mmol) at RT and under N₂ atmosphere. The resulting solution was stirred for 2 h at 100° C. After cooling to RT, the reaction mixture was diluted with EtOAc (20 mL) and filtered through a pad of Celite followed by EtOAc wash (25 mL). The combined filtrates were concentrated under reduced pressure and the residue was purified by column chromatography (silica gel, 0 to 30% gradient of EtOAc/heptane) to give methyl 3-((3-chloro-2-(pyrrolidin-1-yl)pyridin-4-yl)thio)propanoate (1.62 g, 5.38 mmol). MS m/z 301.2 (M+H)⁺.

Step c: To a solution of methyl 3-((3-chloro-2-(pyrrolidin-1-yl)pyridin-4-yl)thio)propanoate (1.62 g, 5.38 mmol) in THF (20 mL) was added sodium ethoxide (21% wt. in EtOH, 2.39 mL, 6.39 mmol at RT and under N₂ atmosphere. After stirring vigorously for 40 min at RT, the reaction was diluted with DCM (40 mL) and it was sonicated for 5 min. The volatiles were removed under reduced pressure and the residue was used without further purification. MS m/z 215.1 (M−H)⁻.

The following intermediates of Table 2 were made using the above procedure or modifications to the above procedure using the corresponding aryl iodide.

TABLE 2

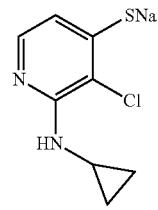

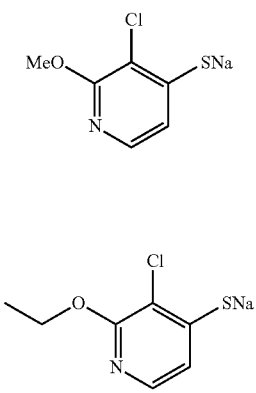

Intermediate S-4

3-amino-2-(trifluoromethyl)benzenethiol

Step a: A mixture of 3-fluoro-2-(trifluoromethyl)aniline (2.21 g, 12.35 mmol), Cs₂CO₃ (12.08 g, 37.1 mmol), and 2-methylpropane-2-thiol (4.18 mL, 37.1 mmol) in DMF (25 mL) was stirred for 18 h at 130° C. After cooling to RT, the reaction mixture was poured into a separation funnel containing H₂O (50 mL) and extracted with EtOAc (100 mL). The organic phase was washed with H₂O (2×25 mL), brine (2×25 mL), dried over MgSO₄, filtered, and the volatiles were removed under reduced pressure to give 3-(tert-butylthio)-2-(trifluoromethyl)aniline (3.08 mg, 12.35 mmol). MS m/z 250.1 (M+H)⁺.

Step b: A solution of 3-(tert-butylthio)-2-(trifluoromethyl)aniline (7.19 g, 31.3 mmol) in conc. HCl (308 mL) was stirred for 2 h at 85° C. After cooling to RT, a stream of N₂ was led through the solution for 16 h. The volatiles were removed under reduced pressure, the resulting solid was filtered off, washed with heptane and dried under vacuum to give 3-amino-2-(trifluoromethyl)benzenethiol (7.19 g, 31.3 mmol). MS m/z 194.0 (M+H)⁺.

Intermediate S-5

Sodium 3-chloro-2-cyclopropylpyridine-4-thiolate

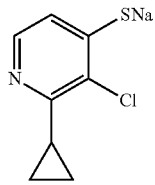

Step a: A mixture of 2,3-dichloro-4-iodopyridine (1.0 g, 3.65 mmol), XantPhos (127 mg, 0.219 mmol), and Pd(OAc)$_2$ (41 mg, 0.183 mmol) in dioxane (7 mL) was added methyl 3-mercaptopropanoate (445 µL, 4.02 mmol) followed by addition of DIPEA (1.28 mL, 7.3 mmol) at RT and under N$_2$ atmosphere. The resulting solution was stirred for 4.5 h at 100° C. After cooling to RT, the reaction mixture was diluted with EtOAc (20 mL) and filtered through a pad of Celite followed by EtOAc wash (25 mL). The combined filtrates were concentrated under reduced pressure and the residue was purified by silica chromatography (10 to 50% gradient of EtOAc/heptane) to give methyl 3-((2,3-dichloropyridin-4-yl)thio)propanoate (965 mg, 5.38 mmol). MS m/z 266.1 (M+H)$^+$.

Step b: A mixture of methyl 3-((2,3-dichloropyridin-4-yl)thio)propanoate (800 mg, 3.19 mmol), n-BuPAd$_2$ (86 mg, 0.240 mmol), Pd(OAc)$_2$ (36 mg, 0.160 mmol), Cs$_2$CO$_3$ (3.12 g, 9.58 mmol), and potassium cyclopropyltrifluoroborate (709 mg, 4.79 mmol) in toluene:H$_2$O (10:1; 13 mL) was stirred for 4.5 h at 100° C. After cooling to RT, the reaction mixture was poured into a separation funnel containing sat. aq. NH$_4$Cl and extracted with EtOAc (3×15 mL). The combined organic phases were dried over MgSO$_4$, filtered, and the volatiles were removed under reduced pressure. The residue was purified by silica chromatography (10 to 40% gradient of EtOAc/heptane) to give methyl 3-((3-chloro-2-cyclopropylpyridin-4-yl)thio)propanoate (380 mg, 1.398 mmol). MS m/z 272.1 (M+H)$^+$.

Step c: To a of solution methyl 3-((3-chloro-2-cyclopropylpyridin-4-yl)thio)propanoate (380 mg, 1.398 mmol) in THF (5 mL) was added sodium ethoxide (21% wt. in EtOH, 0.548 mL, 1.468 mmol) at RT and under N$_2$ atmosphere. After stirring vigorously for 30 min at RT, the volatiles were removed under reduced pressure to give sodium 3-chloro-2-cyclopropylpyridine-4-thiolate (290 mg, 1.398 mmol) which was used without further purification. MS m/z 186.1 (M+H)$^+$.

Intermediate S-6

6-amino-2,3-dichloropyridine-4-thiol

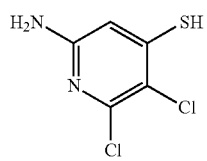

Step a: To a 0° C. solution of 5,6-dichloropyridin-2-amine (2.445 g, 15 mmol) in THF (60 mL) was added LiHMDS (1 M in THF, 33.0 mL, 33.0 mmol) dropwise and the reaction mixture was stirred for 10 min at 0° C. Boc$_2$O (3.60 g, 16.5 mmol) in THF (20 mL) was added and the resulting mixture was stirred for 15 min at this temperature. The reaction mixture was allowed to warm to RT and taken to pH 4 using aq. 1 N HCl. The aqueous layer was separated and extracted with EtOAc (2×20 mL). The combined organic phases were washed with sat. aq. NaHCO$_3$, dried over MgSO$_4$, filtered, and the volatiles were removed under reduced pressure. The residue was purified by silica chromatography (0 to 40% gradient of EtOAc/heptane) to give tert-butyl (5,6-dichloropyridin-2-yl)carbamate (3.12 g, 11.86 mmol). MS m/z 207.8 (M+H-tBu)$^+$.

Step b: To a −78° C. solution of diisopropylamine (3.25 mL, 22.80 mmol) in THF (20 mL) was added n-BuLi (2.5 M in hexanes, 9.12 mL, 22.80 mmol) dropwise and the reaction mixture was stirred for 1 h at −78° C. tert-Butyl (5,6-dichloropyridin-2-yl)carbamate (3.0 g, 11.40 mmol) in THF (20 mL) was added and the resulting mixture was stirred for 2 h at −78° C. I$_2$ (3.04 g, 11.97 mmol) in THF (20 mL) was added and the mixture was stirred for 30 min −78° C. After warming up to RT, the reaction mixture was diluted carefully with H$_2$O and extracted with EtOAc (2×50 mL). The combined organic phases were washed with sat. aq. Na$_2$S$_2$O$_3$, brine, dried over MgSO$_4$, filtered, and the volatiles were removed under reduced pressure. The residue was purified by silica chromatography (0 to 40% gradient of EtOAc/heptane) to give tert-butyl (5,6-dichloro-4-iodopyridin-2-yl)carbamate (3.33 g, 4.792 mmol). MS m/z 332.8 (M+H-tBu)$^+$.

Step c: To a solution of tert-butyl (5,6-dichloro-4-iodopyridin-2-yl)carbamate (1.0 g, 2.57 mmol), XantPhos (89 mg, 0.154 mmol), and Pd(OAc)$_2$ (29 mg, 0.129 mmol) in dioxane (10 mL) was added methyl 3-mercaptopropanoate (313 µL, 2.83 mmol) followed by addition of DIPEA (0.9 mL, 5.14 mmol) at RT and under N$_2$ atmosphere. The resulting solution was stirred for 2 h at 100° C. After cooling to RT, the reaction mixture was diluted with EtOAc (20 mL) and filtered through a pad of Celite followed by EtOAc wash (25 mL). The combined filtrates were concentrated under reduced pressure and the residue was purified by silica chromatography (0 to 25% gradient of EtOAc/heptane) to give methyl 3-((6-((tert-butoxycarbonyl)amino)-2,3-dichloropyridin-4-yl)thio)propanoate (668 mg, 1.752 mmol). MS m/z 325.1 (M+H-tBu)$^+$.

Step d: A solution of methyl 3-((6-((tert-butoxycarbonyl)amino)-2,3-dichloropyridin-4-yl)thio)propanoate (668 mg, 1.75 mmol) and TFA (1.35 mL) in DCM (10 mL) was stirred for 1 h at RT. After this time, the volatiles were removed under reduced pressure to give 6-amino-2,3-dichloropyridine-4-thiol (342 mg, 1.75 mmol), which was used in next step without further purification. MS m/z 194.6 (M+H)$^+$.

Intermediate S-7

Sodium 3-(trifluoromethyl)pyridine-4-thiolate

Step a: A solution of 4-chloro-3-(trifluoromethyl)pyridine (535 mg, 2.95 mmol), potassium carbonate (407 mg, 2.95 mmol), and methyl 3-mercaptopropanoate (0.343 mL, 3.09 mmol) in DMF (8 mL) was stirred for 1 h at RT. The reaction mixture was diluted with EtOAc (60 mL), washed with H₂O (3×60 mL), dried over MgSO₄, filtered, and concentrated under reduced pressure to give methyl 3-((3-(trifluoromethyl)pyridin-4-yl)thio)propanoate (710 mg, 2.68 mmol) as a clear oil. MS m/z 266.1 (M+H)⁺.

Step b: To a solution of methyl 3-((3-(trifluoromethyl)pyridin-4-yl)thio)propanoate (710 mg, 2.68 mmol) in THF (5.4 mL) was added sodium ethoxide (21% wt. in EtOH, 1.01 mL, 2.94 mmol) at RT and under N₂ atmosphere. After stirring vigorously for 1 h at RT additional sodium ethoxide (21% wt. in EtOH, 0.25 mL, 0.44 mmol) was added and the reaction mixture was stirred for 30 min at RT. The volatiles were removed under reduced pressure and the residue was suspended in DCM (3 mL). The suspension was filtered and dried under reduced pressure to give sodium 3-(trifluoromethyl)pyridine-4-thiolate (216 mg, 1.074 mmol) as a tan solid. MS m/z 180.1 (M+2H—Na)⁺.

Intermediate S-8

Sodium 3-chloro-2-methylpyridine-4-thiolate

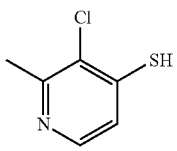

Step a: A solution of 3,4-dichloro-2-methylpyridine (3.05 g, 18.83 mmol), potassium carbonate (2.73 g, 19.77 mmol), and methyl 3-mercaptopropanoate (2.19 mL, 19.8 mmol) in DMF (25 mL) was stirred for 4 h at RT. The reaction mixture was diluted with EtOAc (125 mL), washed with H₂O (3×100 mL), dried over MgSO₄, filtered, and concentrated under reduced pressure. The residue was purified by column chromatography over silica gel (0 to 50% gradient of EtOAc/heptane) providing methyl 3-((3-chloro-2-methylpyridin-4-yl)thio)propanoate (1.07 g). MS m/z 246.0 (M+H)⁺. ¹H NMR (400 MHz, Chloroform-d) δ ppm 8.27 (d, J=5.27 Hz, 1H), 6.97 (d, J=5.27 Hz, 1H), 3.71-3.82 (m, 3H), 3.26 (t, J=7.53 Hz, 2H), 2.78 (t, J=7.53 Hz, 2H), 2.63 (s, 3H).

Step b: To a solution of methyl 3-((3-chloro-2-methylpyridin-4-yl)thio)propanoate (1.07 g, 4.35 mmol) in THF (9 mL) was added sodium ethoxide (21% wt. in EtOH, 1.8 mL, 4.82 mmol) at RT and under N₂ atmosphere. After stirring vigorously for 1 h the volatiles were removed under reduced pressure and the residue was suspended in DCM (20 mL). The precipitate was filtered off and dried under reduced pressure to give sodium 3-chloro-2-methylpyridine-4-thiolate as a white powder (850 mg) as a white solid. MS m/z 160.0 (M+H-Na)⁺. ¹H NMR (400 MHz, DMSO-d₆) δ ppm 7.36 (d, J=5.31 Hz, 1H), 6.97 (d, J=5.31 Hz, 1H), 2.30 (s, 3H).

Intermediate S-9

Sodium 2-methoxy-3-(trifluoromethyl)pyridine-4-thiolate

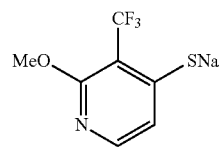

Step a: To a −78° C. solution of diisopropylamine (0.966 mL, 6.77 mmol) in THF (20 mL) was added n-BuLi (1.6 M in hexanes, 4.23 mL, 6.77 mmol) dropwise and the reaction mixture was stirred for 5 min at −78° C. A solution of 2-methoxy-3-(trifluoromethyl)pyridine (1.2 g, 6.77 mmol) in THF (10 mL) was added and the resulting mixture was stirred for 2 h at −78° C. 12 (1.72 g, 6.77 mmol) in THF (5 mL) was added at −78° C. and the resulting mixture was allowed to warm to RT within 30 min and was further stirred at this temperature for 30 min. The volatiles were removed under reduced pressure, the residue was dissolved in Et₂O (200 mL) The organic layer was washed sequentially with sat. aq. Na₂S₂O₃ (200 mL), sat. aq. NH₄Cl (200 mL), and sat. aq. NaHCO₃ (200 mL), dried over MgSO₄, filtered, and the volatiles were removed under reduced pressure. The residue was purified by silica chromatography (0 to 25% gradient of EtOAc/heptane) to give 4-iodo-2-methoxy-3-(trifluoromethyl)pyridine (540 mg, 1.354 mmol). MS m/z 304.0 (M+H)⁺.

Step b: To a solution of 4-iodo-2-methoxy-3-(trifluoromethyl)pyridine (540 mg, 1.354 mmol), XantPhos (63 mg, 0.108 mmol), and Pd(OAc)₂ (12 mg, 0.054 mmol) in dioxane (1.5 mL) was added methyl 3-mercaptopropanoate (158 µL, 1.422 mmol) followed by addition of DIPEA (0.47 mL, 2.71 mmol) at RT and under N₂ atmosphere. The resulting solution was stirred for 30 min at 105° C. After cooling to RT, the reaction mixture was diluted with EtOAc (10 mL) and filtered through a pad of Celite followed by EtOAc wash (15 mL). The combined filtrates were concentrated and the residue was purified by silica chromatography (0 to 50% gradient of EtOAc/heptane) to give methyl 3-((2-methoxy-3-(trifluoromethyl)pyridin-4-yl)thio)propanoate (344 mg, 1.165 mmol). MS m/z 296.1 (M+H)⁺.

Step c: To a solution of methyl 3-((2-methoxy-3-(trifluoromethyl)pyridin-4-yl)thio)propanoate (340 mg, 1.151 mmol) in THF (2.3 mL) was added sodium ethoxide (21% wt. in EtOH, 0.52 mL, 1.382 mmol) at RT and under N₂ atmosphere. After stirring vigorously for 30 min at RT, the volatiles were removed under reduced pressure and the residue was suspended in DCM (10 mL). The resulting suspension was filtered and dried under reduced pressure to give 3-chloro-2-methylpyridine-4-thiolate (850 mg, 4.31 mmol) as a white solid. MS m/z 210.0 (M+H)⁺.

Intermediate S-10

2-(trifluoromethyl)pyridine-3-thiol

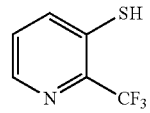 [SMILES: FC(F)(F)c1ncccc1S]

Step a: To a solution of 3-bromo-2-(trifluoromethyl)pyridine (1.0 g, 4.42 mmol), XantPhos (256 mg, 0.442 mmol), Pd$_2$(dba)$_3$ (203 mg, 0.221 mmol) in dioxane (12 mL) under nitrogen atm. was added 2-ethylhexyl-3-mercaptopropanoate (1.1 mL, 4.87 mmol) at RT followed by addition of DIPEA (1.55 mL, 8.85 mmol). The resulting mixture was radiated in a MW reactor for 1 h at 110° C. After cooling to RT, the reaction mixture was filtered through a pad of Celite followed by EtOAc (25 mL) wash. The combined filtrates were concentrated under reduced pressure and the resulting residue was purified by silica chromatography (0 to 30% gradient of EtOAc/heptane) to give 2-ethylhexyl 3-((2-(trifluoromethyl)pyridin-3-yl)thio)propanoate (1.41 g, 3.88 mmol). MS m/z 364.0 (M+H)$^+$.

Step b: To a solution of 2-ethylhexyl 3-((2-(trifluoromethyl)pyridin-3-yl)thio)propanoate (1.0 g, 2.75 mmol) in THF (8 mL) was added at −78° C. and under N$_2$ atm. potassium tert-butoxide (1 M in THF, 8.25 mL, 8.25 mmol). After stirring vigorously at −78° C. for 20 min, the reaction was quenched with K$_2$CO$_3$ (2 M in H$_2$O, 0.5 mL) and the volatiles were removed under reduced pressure. The residue was poured into a separation funnel containing K$_2$CO$_3$ (2 M in H$_2$O, 30 mL). The mixture was extracted with Et$_2$O (2×20 mL), the aq. phase was acidified with 6 N HCl until pH 4 and the resulting cloudy suspension was extracted with CHCl$_3$/IPA (9/1; 3×20 mL) to give 2-(trifluoromethyl)pyridine-3-thiol (380 mg, 2.12 mmol). MS m/z 180.0 (M+H)$^+$.

Intermediate S-11

3-amino-2-chlorobenzenethiol

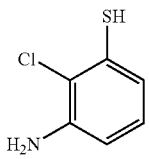

Step a: A suspension of 2-methylpropane-2-thiol (137 mL, 1216 mmol), 2-chloro-3-fluoroaniline (63.2 g, 437 mmol), and cesium carbonate (283 g, 868 mmol) in DMF (650 mL) was stirred for 16 h at 120° C. After cooling to RT, the reaction mixture was diluted with EtOAc (500 mL), washed with H$_2$O, brine, dried over Na$_2$SO$_4$, filtered, and concentrated under reduced pressure to give 3-(tert-butylthio)-2-chloroaniline (111.2 g, 423 mmol). MS m/z 216.1 (M+H)$^+$.

Step b: A suspension of 3-(tert-butylthio)-2-chloroaniline (53 g, 246 mmol) and conc. HCl (700 mL) was vigorously stirred for 8 h at 45° C. and for 16 h at RT. After cooling to 0° C., the suspension was filtered, the solids were washed with conc. HCl (100 mL) and hexane (3×100 mL), and dried under reduced pressure to give 3-amino-2-chlorobenzenethiol hydrogen chloride salt (42 g, 214 mmol). MS m/z 159.6 (M+H)$^+$.

Intermediate B-1

4-phenylpiperidin-4-amine

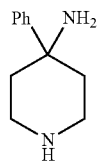

Step a: A suspension of N-(1-benzyl-4-phenylpiperidin-4-yl)acetamide (400 mg, 1.3 mmol) and Pd/C (10% wt., 138 mg) in MeOH was vigorously stirred for 16 h under hydrogen atmosphere. The reaction mixture was filtered through a pad of Celite and the volatiles were removed under reduced pressure. The resulting residue was dissolved in EtOAc and it was washed with sat. aq. NaHCO$_3$, brine, dried over MgSO$_4$, filtered, and concentrated under reduced pressure to give N-(4-phenylpiperidin-4-yl)acetamide which was carried into the next step without any further purification.

Step b: A suspension of N-(4-phenylpiperidin-4-yl)acetamide (150 mg, 0.69 mmol) and 4 N LiOH (2.1 mL, 8.40 mmol) in MeOH/dioxane (1/1, 4 mL) was stirred for 16 h at 100° C. After cooling to RT, the volatiles were removed under reduced pressure and the remaining aq. phase was extracted with EtOAc (3×5 mL). The combined organic phases were washed with brine, dried over MgSO$_4$, filtered, and concentrated under reduced pressure to give 4-phenylpiperidin-4-amine as a colorless oil which was used without further purification.

Intermediate B-2

Tert-butyl ((4-(pyrazin-2-yl)piperidin-4-yl)methyl) carbamate

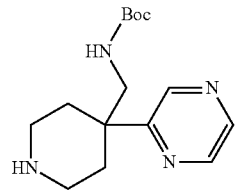 [SMILES: CC(C)(C)OC(=O)NCC1(c2cnccn2)CCNCC1]

Step a: To a suspension of sodium hydride (60% in mineral oil, 1.90 g, 47.7 mmol) in DMF (30 mL) was added at 0° C. 2-(pyrazin-2-yl)acetonitrile (1.90 g, 15.90 mmol) in DMF (5 mL) dropwise within 10 min. The resulting mixture was stirred 30 min at 0° C. N-benzyl-2-chloro-N-(2-chloroethyl)ethanamine (4.7 g, 17.5 mmol) in DMF (5 mL) was added at 0° C., the resulting mixture was stirred for 15 min at 0° C. and for 16 h at 90° C. After cooling to RT, the reaction mixture was diluted with sat. aq. NaHCO$_3$ and extracted with EtOAc (3×25 mL). The combined organic phases were dried over Na$_2$SO$_4$, filtered, concentrated under reduced pressure, and the resulting residue was purified by trituration with hexane to give 1-benzyl-4-(pyrazin-2-yl)piperidine-4-carbonitrile (1.60 g, 5.76 mmol).

Step b: To a solution of 1-benzyl-4-(pyrazin-2-yl)piperidine-4-carbonitrile (1.50 g, 5.39 mmol) in NH$_3$ (7 N in MeOH, 50 mL) was added Raney nickel (50% in water, 750 mg) at RT. The resulting suspension was vigorously stirred under hydrogen atm. (60 psi) at RT until the starting material was consumed (~16 h). The reaction mixture was filtered through a pad of Celite followed by MeOH (50 mL) wash. The volatiles were removed under reduced pressure to give (1-benzyl-4-(pyrazin-2-yl)piperidin-4-yl)methanamine (1.20 g, 4.25 mmol), which was used in next step without further purification. MS m/z 319 (M+H)$^+$.

Step c: A solution of (1-benzyl-4-(pyrazin-2-yl)piperidin-4-yl)methanamine (1.20 g, 4.25 mmol), Et$_3$N (1.17 mL, 8.51 mmol), and Boc$_2$O (1.95 mL, 8.51 mmol) in DCM (50 mL) was stirred for 2 h at RT. The reaction was diluted with H$_2$O and it was extracted with DCM (3×25 mL). The combined organic phases were washed with brine, dried over Na₂SO₄, filtered, and the volatiles were removed under reduced pressure. The resulting residue was purified by silica chromatography (0 to 100% gradient of EtOAc/heptane) to give tert-butyl ((1-benzyl-4-(pyrazin-2-yl)piperidin-4-yl)methyl) carbamate (1.30 g, 3.40 mmol). MS m/z 383 (M+H)⁺.

Step d: A suspension of tert-butyl ((1-benzyl-4-(pyrazin-2-yl)piperidin-4-yl)methyl)carbamate (1.50 g, 3.93 mmol) and Pd(OH)₂ (20% on carbon, 600 mg, 50% moisture) in MeOH (20 mL) was vigorously stirred under hydrogen atm. (50 psi) for 3 h at RT. The reaction mixture was filtered through a pad of Celite followed by MeOH (50 mL) wash. The volatiles were removed under reduced pressure and to give tert-butyl ((4-(pyrazin-2-yl)piperidin-4-yl)methyl)carbamate (1.10 g, 3.76 mmol), which was used without further purification. MS m/z 283 (M+H)⁺.

The following intermediates of Table 3 were made using the above procedure or modifications to the above procedure using the corresponding commercial available heteroaromatic acetonitriles.

TABLE 3

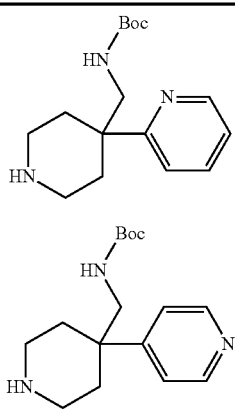

Intermediate B-3

Tert-butyl ((4-isobutylpiperidin-4-yl)methyl)carbamate

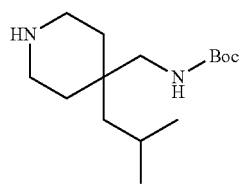

Step a: To solution of LHMDS (1 M in THF, 16.45 mL, 16.45 mmol) was added a solution of 1-benzylpiperidine-4-carbonitrile (1.50 g, 7.49 mmol) in THF (37.4 mL) at −78° C. The resulting yellow solution was stirred for 1 h at −78° C. 1-Iodo-2-methylpropane (5.60 mL, 48.7 mmol) was added and the reaction mixture was allowed to warm up to RT and stirring was continued for 3 days. Saturated aq. NH₄Cl (~30 mL) was added at 0° C. and the mixture was extracted with EtOAc. The organic phase was washed with water (50 mL) and brine (50 mL). Each aq. layer was extracted with EtOAc and the combined organic phases were dried over Na₂SO₄, filtered, and concentrated under reduced pressure to give crude 1-benzyl-4-isobutylpiperidine-4-carbonitrile (2.54 g) as a yellow oil, which was directly used without further purification. MS m/z 257.3 (M+H)⁺.

Step b: A solution of crude 1-benzyl-4-isobutylpiperidine-4-carbonitrile (2.48 g), Boc₂O (6.33 g, 29.0 mmol), and nickel(II)chloride hydrate (1.15 g, 4.84 mmol) in MeOH (38.7 mL) was stirred for 15 min at RT. Sodium borohydride (2.56 g, 67.7 mmol) was added at 0° C. portionwise and stirring was continued for 18 h at RT. Additional sodium borohydride (2.56 g, 67.7 mmol) was added at 0° C. and the resulting mixture was stirred for 18 h at 35° C. After cooling to RT, the volatiles were removed under reduced pressure, the resulting residue was suspended in DCM (100 mL) and filtered through a pad of Celite. The filtrate was concentrated under reduced pressure and the resulting residue was purified by silica chromatography (0 to 50% gradient of EtOAc/heptane) to give tert-butyl ((1-benzyl-4-isobutylpiperidin-4-yl)methyl)carbamate (482 mg, 1.34 mmol) as colorless oil. MS m/z 361.4 (M+H)⁺.

Step c: A suspension of tert-butyl ((1-benzyl-4-isobutylpiperidin-4-yl)methyl)carbamate (482 mg, 1.34 mmol) and Pd/C (10 wt. %, 142 mg) in MeOH (6.7 mL) was vigorously stirred for 18 h under hydrogen atmosphere. The mixture was filtered through a pad of Celite followed by MeOH wash and the volatiles were removed under reduced pressure to give tert-butyl ((4-isobutylpiperidin-4-yl)methyl)carbamate (338 mg, 1.25 mmol) which was directly used without further purification. MS m/z 271.3 (M+H)⁺.

The following compounds were synthesized using the above procedure or modifications to the above procedure using the corresponding iodoalkane.

TABLE 4

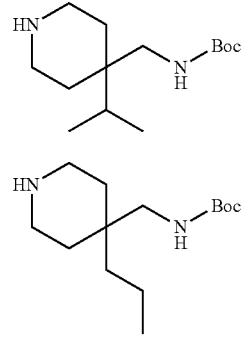

Intermediate B-4

Racemic tert-butyl trans-((3-hydroxy-4-methylpiperidin-4-yl)methyl)carbamate

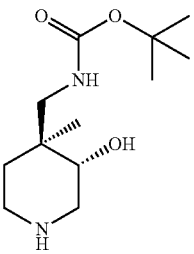 [SMILES: CC(C)(C)OC(=O)NC[C@]1(C)CCNC[C@H]1O]

Step a: A solution of lithium hydride (0.118 g, 14.8 mmol) in THF (20 mL) was added acetone cyanohydrin (1.4 mL, 14.8 mmol) at 0° C. The resulting reaction mixture was stirred for 2 h at RT. The volatiles were removed under reduced pressure to give a white solid. To a solution of this solid in THF (60 mL) was added 3-benzyl-6-methyl-7-oxa-3-azabicyclo[4.1.0]heptane (2.0 g, 9.85 mmol) dropwise at RT. The solution was heated for 14 h to reflux. After cooling to RT, water (10 mL) was added and the resulting mixture was extracted with EtOAc (3×100 mL). The combined organic phases were washed with brine, dried over $Na_2SO_4$, filtered and concentrated under reduced pressure. The resulting residue was purified by silica chromatography (0 to 20% gradient of EtOAc/heptane) to obtain racemic trans-1-benzyl-3-hydroxy-4-methylpiperidine-4-carbonitrile (0.70 g, 3.0 mmol). $^1$H NMR (400 MHz, DMSO-$d_6$) δ ppm 7.36-7.22 (m, 5H), 5.25 (d, J=6.0 Hz, 1H), 3.70-3.67 (m, 1H), 3.49 (dd, J=13.2, 10.4 Hz, 2H), 2.37 (m, 3H), 1.88-1.74 (m, 2H), 1.25 (s, 3H). MS m/z 231.2 $(M+H)^+$.

Step b: A suspension of racemic trans-1-benzyl-3-hydroxy-4-methyl piperidine-4-carbonitrile (1.3 g, 5.6 mmol) and Raney nickel (50% in water, 600 mg) in ammonia (7 N in EtOH; 80 mL) was vigorously stirred under hydrogen atm. (balloon) for 6 h at RT. The mixture was filtered through Celite under $N_2$ and washed with MeOH. The volatiles were removed under reduced pressure to give trans-4-(aminomethyl)-1-benzyl-4-methylpiperidin-3-ol (1.6 g, 4.79 mmol) which was used in next step without further purification. MS m/z 235.2 $(M+H)^+$.

Step c: A solution of trans-4-(aminomethyl)-1-benzyl-4-methylpiperidin-3-ol (1.6 g, 4.79 mmol), $Boc_2O$ (2.84 mL, 12.4 mmol), and $NaHCO_3$ (0.935 g, 11.1 mmol) in $CHCl_3$ (70 mL) was stirred for 14 h at RT. The mixture was diluted with DCM and washed with ice water and brine, dried over $Na_2SO_4$, filtered, and concentrated under reduced pressure. The resulting residue was purified by silica chromatography (0 to 5% gradient of MeOH/DCM) to give racemic tert-butyl trans-(1-benzyl-3-hydroxy-4-methylpiperidin-4-yl)methyl)carbamate (1.1 g, 3.3 mmol). MS m/z 335.3 $(M+H)^+$.

Step d: A suspension of racemic tert-butyl trans-((1-benzyl-3-hydroxy-4-methylpiperidin-4-yl)methyl)carbamate (1.1 g, 3.3 mmol) and $Pd(OH)_2$ (20% on charcoal; 0.250 g) in MeOH (60 mL) was vigorously stirred under hydrogen atm. (balloon) for 6 h at RT. The resulting mixture was filtered through Celite, washed with MeOH and concentrated under reduced pressure. The residue was triturated from hexane (10 mL) and diethyl ether (2 mL) to give racemic tert-butyl trans-((3-hydroxy-4-methylpiperidin-4-yl)methyl)carbamate (0.70 g, 2.87 mmol) as a white powder. $^1$H NMR (400 MHz, Methanol-$d_4$) δ ppm 3.42 (dd, J=9.9, 4.4 Hz, 1H), 3.12 (d, J=13.9 Hz, 1H), 2.94-2.84 (m, 2H), 2.82-2.68 (m, 2H), 2.62 (dd, J=12.5, 10.0 Hz, 1H), 1.44 (s, 9H), 1.41-1.30 (m, 2H), 0.91 (s, 3H). MS m/z 245.1 $(M+H)^+$.

Intermediate B-5

Racemic tert-butyl cis-((3-hydroxy-4-methylpiperidin-4-yl)methyl)carbamate

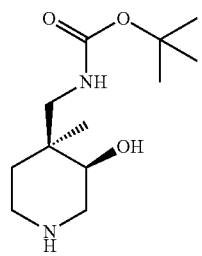 [SMILES: CC(C)(C)OC(=O)NC[C@]1(C)CCNC[C@@H]1O]

Step a: A solution of racemic trans-1-benzyl-3-hydroxy-4-methyl piperidine-4-carbonitrile (2.0 g, 8.70 mmol), triphenylphosphine (3.41 g, 13.0 mmol), and DIAD (2.63 g, 13.0 mmol) in THF (30 mL) was stirred for 10 min at 0° C. 4-Nitrobenzoic acid (2.18 g, 13.0 mmol) was added portionwise and the resulting mixture was stirred for 16 h at RT. The mixture was diluted with water and extracted with EtOAc. The combined organic phases were washed with brine, dried over $Na_2SO_4$, filtered, and concentrated under reduced pressure. The resulting residue was triturated with MeOH to give racemic cis-1-benzyl-4-cyano-4-methylpiperidin-3-yl 4-nitrobenzoate (1.5 g, 3.96 mmol) which was used without further purification. MS m/z 380 $(M+H)^+$.

Step b: A solution of racemic cis-1-benzyl-4-cyano-4-methylpiperidin-3-yl 4-nitrobenzoate (1.5 g, 3.96 mmol) and potassium carbonate (1.07 g, 7.92 mmol) in MeOH (20 mL) was vigorously stirred for 10 min at 0° C. and for 1 h at RT. The volatiles were removed under reduced pressure. The resulting residue was diluted with water and extracted with EtOAc (3×). The combined organic phases were washed with brine, dried over $Na_2SO_4$, filtered, and concentrated under reduced pressure. The resulting residue was purified by silica chromatography (0 to 15% gradient of EtOAc/heptane) to give racemic cis-1-benzyl-3-hydroxy-4-methylpiperidine-4-carbonitrile (0.8 g, 3.5 mmol). $^1$H NMR (400 MHz, $CDCl_3$) δ ppm 7.36-7.26 (m, 5H), 3.99 (d, J=12.4 Hz, 1H), 3.67 (d, J=12.8, 1H), 3.60-3.51 (m, 2H), 3.11-3.07 (m, 2H), 2.76-2.69 (m, 2H), 2.24 (dd, J=12.8, 6.0 Hz, 1H), 1.87-1.80 (m, 1H), 1.54 (s, 3H). MS m/z 231 $(M+H)^+$.

Step c: A suspension of cis-1-benzyl-3-hydroxy-4-methylpiperidine-4-carbonitrile (800 mg, 3.5 mmol) and Raney nickel (50% in water, 700 mg) in ammonia (7 N in EtOH; 20 mL) was vigorously stirred under hydrogen atm. (balloon) for 16 h at RT. The mixture was filtered through Celite under $N_2$ atm. and rinsed with MeOH. The volatiles were removed under reduced pressure to give racemic cis-4-(aminomethyl)-1-benzyl-4-methylpiperidin-3-ol (700 mg, 3.0 mmol) which was used in next step without further purification. MS m/z 235.2 $(M+H)^+$.

Step d: A solution of cis-4-(aminomethyl)-1-benzyl-4-methylpiperidin-3-ol (700 mg, 3.0 mmol), $Boc_2O$ (1.1 mL, 2.99 mmol), and $Et_3N$ (860 µL, 5.98 mmol) in DCM (10 mL) was stirred for 2 h at RT. The mixture was diluted with DCM and washed with ice water and brine, dried over $Na_2SO_4$, filtered, and concentrated under reduced pressure. The resulting residue was purified by silica chromatography (0 to 50% gradient of EtOAc/heptane) to give racemic tert-butyl cis-(1-benzyl-3-hydroxy-4-methylpiperidin-4-yl)methyl)carbamate (700 mg, 2.10 mmol) which was used in next step without further purification. MS m/z 335 $(M+H)^+$.

Step e: A suspension of racemic tert-butyl cis-(1-benzyl-3-hydroxy-4-methylpiperidin-4-yl)methyl)carbamate (700 mg, 2.1 mmol) and Pd (10% on charcoal; 300 mg) in MeOH (20 mL) was vigorously stirred under hydrogen atm. (balloon) for 5 h at RT. The resulting mixture was filtered through Celite, washed with MeOH and concentrated under reduced pressure. The resulting residue was purified by silica chromatography (0 to 10% gradient of MeOH/DCM) to give racemic tert-butyl cis-((3-hydroxy-4-methylpiperidin-4-yl)methyl)carbamate (200 mg, 0.8 mmol) as a white powder. $^1$H NMR (400 MHz, Methanol-$d_4$) δ ppm 3.73-3.67 (m, 1H), 3.59 (dd, J=11.1, 7.7 Hz, 1H), 3.15-2.99 (m, 4H), 1.90 (m, 1H), 1.62 (m, 1H), 1.47 (m, 1H), 1.44 (s, 9H), 0.96 (s, 3H). MS m/z 245 $(M+H)^+$.

Intermediates B-6

Racemic tert-butyl 1-(1,1-dimethylethylsulfinamino)-2,2-difluoro-8-azaspiro[4.5]decane-8-carboxylate

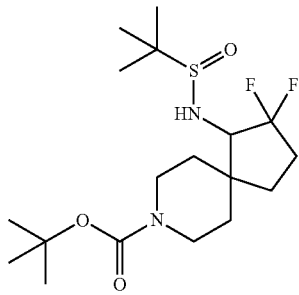 [SMILES: CC(C)(C)OC(=O)N1CCC2(CC1)CCC(F)(F)C2NS(=O)C(C)(C)C]

Step a: To a solution of NHMDS (1 M in THF, 8.68 mL, 8.68 mmol) was added a solution of tert-butyl 1-oxo-8-azaspiro[4.5]decane-8-carboxylate (2.0 g, 7.89 mmol) in THF (5 mL) at −78° C. After stirring for 30 min at this temperature, a solution of N-fluorobenzenesulfonamide (2.49 g, 7.89 mmol) in THF (10 mL) was added. After stirring for 3 h at −78° C., the mixture was diluted with sat. aq. NaHCO$_3$ (100 mL) and extracted with DCM (3×100 mL). The combined organic phases were washed with brine, dried over Na$_2$SO$_4$, filtered, and concentrated under reduced pressure. The resulting residue was purified by silica chromatography (0 to 25% gradient of EtOAc/heptane) to give racemic tert-butyl 2-fluoro-1-oxo-8-azaspiro[4.5]decane-8-carboxylate (351 mg, 1.29 mmol), MS m/z 272.1 (M+H)$^+$, and tert-butyl 2,2-difluoro-1-oxo-8-azaspiro[4.5]decane-8-carboxylate which coeluted with starting material. The combined difluoro ketone containing fractions were purified by silica chromatography (0 to 5% gradient of MeOH/DCM) to give tert-butyl 2,2-difluoro-1-oxo-8-azaspiro[4.5]decane-8-carboxylate (573 mg, 1.98 mmol). MS m/z 290.1 (M+H)$^+$.

Step b: A solution of tert-butyl 2,2-difluoro-1-oxo-8-azaspiro [4.5]decane-8-carboxylate (220 mg, 0.76 mmol), racemic 2-methylpropane-2-sulfinamide (184 mg, 1.52 mmol), and titanium(IV)ethoxide (0.640 mL, 3.0 mmol) in THF (4 mL) was stirred for 30 min at 90° C. After cooling to 0° C., lithium borohydride (33 mg, 1.5 mmol) was added in one portion. After stirring for 30 min, the reaction mixture was quenched by addition of MeOH. The volatiles were removed under reduce pressure. The resulting residue was diluted with brine and extracted with EtOAc (4×10 mL). The combined organic phases were dried over Na$_2$SO$_4$, filtered, and concentrated under reduced pressure. The resulting residue was purified by silica chromatography (10 to 50% gradient of EtOAc/heptane) to give racemic tert-butyl 1-(1,1-dimethylethylsulfinamino)-2,2-difluoro-8-azaspiro[4.5]decane-8-carboxylate as white powder (190 mg, 0.48 mmol). MS m/z 395.2 (M+H)$^+$.

Intermediates B-7

Tert-butyl 1-((R)-1,1-dimethylethylsulfinamino)-2-fluoro-8-azaspiro[4.5]decane-8-carboxylate

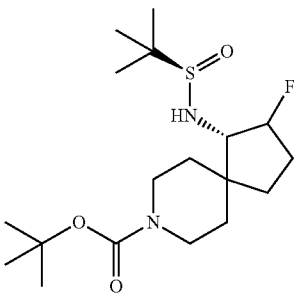 [SMILES: CC(C)(C)OC(=O)N1CCC2(CCC(F)[C@H]2N[S@](=O)C(C)(C)C)CC1]

A solution of racemic tert-butyl 2-fluoro-1-oxo-8-azaspiro[4.5]decane-8-carboxylate (78 mg, 0.28 mmol), titanium(IV)ethoxide (235 µL, 1.1 mmol), and (R)-2-methylpropane-2-sulfinamide (68 mg, 0.56 mmol) in THF (1.5 mL) was stirred for 1 h at 90° C. After cooling to 0° C., lithium borohydride (12 mg, 0.56 mmol) was added in one portion. After stirring for 30 min, the reaction mixture was quenched by addition of MeOH. The volatiles were removed under reduce pressure. The resulting residue was diluted with brine and extracted with EtOAc (4×10 mL), the combined organic phases were dried over Na$_2$SO$_4$, filtered, and concentrated under reduced pressure. The resulting residue was purified by silica chromatography (0 to 50% gradient of EtOAc/heptane) to give tert-butyl 1-((R)-1,1-dimethylethylsulfinamino)-2-fluoro-8-azaspiro[4.5]decane-8-carboxylate (mixture of isomers, 64 mg, 0.17 mmol). MS m/z 377.3 (M+H)$^+$.

Intermediates B-8

Tert-butyl 1-oxo-8-azaspiro[4.5]dec-2-ene-8-carboxylate

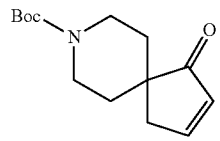

Step a: A mixture of tert-butyl 4-formylpiperidine-1-carboxylate (35.0 g, 164 mmol), lithium tert-butoxide (15.77 g, 197 mmol), and allylbromide (11.54 mL, 189 mmol) in DMF (328 mL) was stirred for 1 h at 0° C. The mixture was poured into a separation funnel containing sat. aq. NH$_4$Cl/H$_2$O (1/1, 500 mL) and it was extracted with Et$_2$O (5×50 mL). The combined organic phases were dried over MgSO$_4$, filtered, and the volatiles were removed under reduced pressure. The resulting residue was purified by silica chromatography (0 to 25% gradient of EtOAc/heptane) to give tert-butyl 4-allyl-4-formylpiperidine-1-carboxylate (24 g, 95 mmol) as a colorless oil. $^1$H NMR (400 MHz, Chloroform-d) δ ppm 9.52 (s, 1H), 5.53-5.76 (m, 1H), 4.96-5.19 (m, 2H), 3.80 (br. s, 2H), 2.97 (t, J=11.49 Hz, 2H), 2.26 (d, J=7.33 Hz, 2H), 1.95 (dt, J=13.71, 3.13 Hz, 2H), 1.38-1.58 (m, 11H).

Step b: To a solution of tert-butyl 4-allyl-4-formylpiperidine-1-carboxylate (24 g, 95 mmol) in THF (300 mL) under $N_2$ atm. was added vinyl magnesium bromide (1 M in THF, 118 mL, 118 mmol) at −78° C. The resulting mixture was allowed to warm up to RT within 1 h. The mixture was poured into a separation funnel containing sat. aq. $NH_4Cl$ (250 mL) and it was extracted with EtOAc (4×50 mL). The combined organic phases were dried over $MgSO_4$, filtered and the volatiles were removed under reduced pressure to give tert-butyl 4-allyl-4-(1-hydroxyallyl)piperidine-1-carboxylate (26.7 g, 95 mmol) as a colorless oil which was used in next reaction without further purification. $^1$H NMR (400 MHz, Chloroform-d) δ ppm 9.52 (s, 1H), 5.56-5.75 (m, 1H), 5.05-5.18 (m, 2H), 3.80 (br. s., 2H), 2.97 (t, J=11.49 Hz, 2H), 2.26 (d, J=7.33 Hz, 2H), 1.96 (dt, J=13.83, 3.06 Hz, 2H), 1.49-1.60 (m, 2H), 1.41-1.49 (m, 9H).

Step c: A mixture of tert-butyl 4-allyl-4-(1-hydroxyallyl) piperidine-1-carboxylate (26.7 g, 95 mmol) and Dess-Martin periodinane (44.3 g, 105 mmol) in DCM (380 mL) was stirred for 1 h at RT. The mixture was poured into a separation funnel containing sat. aq. $NaHCO_3/Na_2SO_3$ (1/1, 300 mL) and it was extracted with DCM (4×50 mL). The combined organic phases were dried over $MgSO_4$, filtered and the volatiles were removed under reduced pressure to provide a white solid. This solid was suspended in heptane (250 mL) and sonicated for 5 min. The white suspension was filtered through a pad of Celite and the volatiles were removed under reduced pressure to give tert-butyl 4-acryloyl-4-allylpiperidine-1-carboxylate (26.5 g, 95 mmol) as a yellow oil which was used in next reaction without further purification. $^1$H NMR (400 MHz, Chloroform-d) δ ppm 6.81 (dd, J=16.93, 10.36 Hz, 1H), 6.40 (dd, J=16.80, 1.89 Hz, 1H), 5.71 (dd, J=10.36, 2.02 Hz, 1H), 5.46-5.66 (m, 1H), 4.91-5.14 (m, 2H), 3.78 (br. s., 2H), 2.96 (br. s, 2H), 2.25-2.39 (m, 2H), 1.97-2.15 (m, 2H), 1.37-1.57 (m, 11H).

Step d: To a solution of tert-butyl 4-acryloyl-4-allylpiperidine-1-carboxylate (26.5 g, 95 mmol) in toluene (degassed, 850 mL) was added Grubbs II catalyst (2.02 g, 2.38 mmol) in toluene (degassed, 100 mL). The resulting mixture was stirred for 45 min at 85° C. The solvent was removed under reduced pressure and the resulting residue was purified by silica chromatography (0 to 40% gradient of EtOAc/heptane) to give tert-butyl 1-oxo-8-azaspiro[4.5]dec-2-ene-8-carboxylate (20.76 g, 83 mmol) as a brown solid. A solution of this compound and DDQ (565 mg, 2.49 mmol) in toluene (540 mL) was stirred for 15 min at RT. The resulting bright red solution was filtered through a pad of Celite. Charcoal (200 g) was added to the filtrate and the resulting suspension was stirred for 2 h at RT. The mixture was filtered through a pad of Celite and the filtrate was concentrated under reduce pressure. The resulting residue was purified by silica chromatography (0 to 40% gradient of EtOAc/heptane) to give tert-butyl-1-oxo-8-azaspiro[4.5] dec-2-ene-8-carboxylate (15.6 g, 62.3 mmol) as a white solid. $^1$H NMR (400 MHz, Chloroform-d) δ ppm 7.63-7.74 (m, 1H), 6.20 (dt, J=5.81, 2.15 Hz, 1H), 3.99-4.25 (m, 2H), 2.92 (t, J=11.62 Hz, 2H), 2.63 (s, 2H), 1.72-1.86 (m, 2H), 1.49 (s, 9H), 1.29 (d, J=12.88 Hz, 2H).

Intermediate B-9

(1R,3R)-benzyl 1-((R)-1,1-dimethylethylsulfinamino)-3-methyl-8-azaspiro[4.5]decane-8-carboxylate

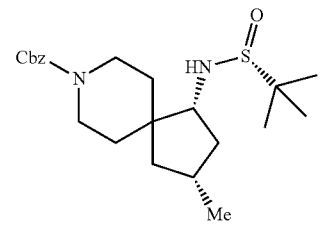 [SMILES: C[C@H]1C[C@@H](N[S@](=O)C(C)(C)C)C2(CCN(C(=O)OCc3ccccc3)CC2)C1]

Step a: To a suspension of tert-butyl 1-oxo-8-azaspiro [4.5]dec-2-ene-8-carboxylate (4.2 g, 16.71 mmol) and CuI (6.37 g, 33.4 mmol) in $Et_2O$ (100 mL) under $N_2$ atm. was added MeLi (1.6 M in THF, 31.3 mL, 50.1 mmol) at 0° C. After stirring for 90 min at 0° C., the mixture was poured into a separation funnel containing sat. aq. $NH_4Cl$ and extracted with EtOAc (3×15 mL). The combined organic phases were dried over $MgSO_4$, filtered and the volatiles were removed under reduced pressure. The resulting residue was purified by silica chromatography (0 to 50% gradient of EtOAc/heptane) to give tert-butyl 3-methyl-1-oxo-8-azaspiro[4.5]dec-2-ene-8-carboxylate (4.23 g, 15.82 mmol) as colorless oil. $^1$H NMR (400 MHz, Chloroform-d) δ ppm 3.89-4.00 (m, 1H), 3.83 (d, J=13.39 Hz, 1H), 3.11 (ddd, J=13.64, 10.36, 3.28 Hz, 1H), 2.99 (ddd, J=13.58, 10.42, 3.54 Hz, 1H), 2.47-2.59 (m, 1H), 2.19-2.36 (m, 2H), 1.74-1.97 (m, 2H), 1.50-1.65 (m, 2H), 1.48 (s, 9H), 1.33-1.44 (m, 2H), 1.17 (d, J=6.32 Hz, 3H).

Step b: A mixture of tert-butyl 3-methyl-1-oxo-8-azaspiro [4.5]dec-2-ene-8-carboxylate (4.23 g, 15.82 mmol) and TFA (17 mL) in DCM (80 mL) was stirred for 30 min at RT. The volatiles were removed under reduced pressure. A mixture of the resulting residue, DIPEA (13.82 mL, 79 mmol), and benzyl chloroformate (3.39 mL, 23.73 mmol) was stirred for 16 h at RT. The mixture was poured into a separation funnel containing sat. aq. $NH_4Cl$ and it was extracted with DCM (3×25 mL). The combined organic phases were dried over $MgSO_4$, filtered, and the volatiles were removed under reduced pressure. The resulting residue was purified by silica chromatography (0 to 40% gradient of EtOAc/heptane) to give benzyl 3-methyl-1-oxo-8-azaspiro[4.5]decane-8-carboxylate (4.58 g, 15.20 mmol) as a light yellow oil. MS m/z 302.2 (M+H)$^+$.

Step c: Benzyl 3-methyl-1-oxo-8-azaspiro[4.5]decane-8-carboxylate (4.58 g, 15.20 mmol) was further purified by chiral SFC as follows: column: IA 21×250 mm, flow rate: 70 g per minute, mobile phase: 45% (9/1 EtOH/MeCN) in $CO_2$, detection: 220 nm UV to give (R)-benzyl 3-methyl-1-oxo-8-azaspiro[4.5]decane-8-carboxylate (2.02 g, 6.70 mmol), $T_R$: 2.0 min; and (S)-benzyl 3-methyl-1-oxo-8-azaspiro[4.5] decane-8-carboxylate (2.11 g, 7.0 mmol), $T_R$: 3.6 min.

Step d: A solution of (R)-benzyl 3-methyl-1-oxo-8-azaspiro[4.5]decane-8-carboxylate (2.02 g, 6.70 mmol), titanium(IV)ethoxide (5.62 mL, 26.8 mmol), and (R)-2-methylpropane-2-sulfinamide (1.625 g, 13.4 mmol) in THF (67 mL) was stirred for 16 h at 65° C. The mixture was cooled to −78° C., MeOH (12 mL) was added followed by lithium borohydride (0.438 g, 20.11 mmol). The resulting mixture was stirred for 16 h at −78° C. to RT. Saturated aq. $NH_4Cl$ was slowly added to quench excess of borohydride followed by addition of EtOAc (100 mL). The resulting mixture was vigorously stirred for 15 min and then filtered through a pad of Celite. The volatiles were removed under reduced pressure and the resulting residue was purified by silica chromatography (5 to 90% gradient of EtOAc/heptane) to give (1R,3R)-benzyl 1-((R)-1,1-dimethylethylsulfinamino)-3-methyl-8-azaspiro[4.5]decane-8-carboxylate (1.94 g, 4.77 mmol) as a white solid. MS m/z 407.3 (M+H)+.

(1R,3S)-Benzyl 1-((R)-1,1-dimethylethylsulfinamino)-3-methyl-8-azaspiro[4.5]decane-8-carboxylate was synthesized using the above procedure or modifications to the above procedure using (S)-benzyl 3-methyl-1-oxo-8-azaspiro[4.5]decane-8-carboxylate as starting material.

Intermediate B-10

(1R,3R)-tert-butyl 3-((tert-butyldimethylsilyl)oxy)-1-((R)-1,1-dimethylethylsulfinamino)-8-azaspiro[4.5]decane-8-carboxylate)

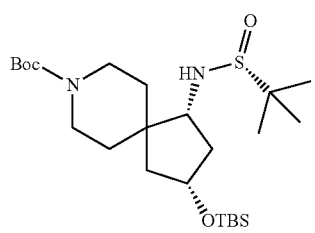 [SMILES: CC(C)(C)OC(=O)N1CCC2(CC1)C[C@@H](O[Si](C)(C)C(C)(C)C)C[C@H]2N[S@](=O)C(C)(C)C]

Step a: A mixture of CuCl (142 mg, 1.432 mmol), (S)-TolBINAP (972 mg, 1.432 mmol), and sodium tert-butoxide (138 mg, 1.432 mmol) in THF (60 mL) was stirred for 30 min at RT. Bis(pinacolato)diboran (13.34 g, 52.5 mmol) in THF (20 mL) was added and the resulting mixture was stirred for 10 min at RT. tert-Butyl 1-oxo-8-azaspiro[4.5]dec-2-ene-8-carboxylate (12.0 g, 47.7 mmol) in THF (50 mL) was added followed by MeOH (3.9 mL, 95 mmol). The resulting mixture was stirred for 16 h at RT. $H_2O$ (150 mL) was added followed by sodium perborate (36.7 g, 239 mmol) and the resulting mixture was vigorously stirred at RT for 1 h. The resulting green suspension was filtered through a pad of Celite, poured into a separation funnel containing sat. aq. $NaHCO_3/Na_2SO_3$ (1/1, 300 mL) and extracted with EtOAc (4×40 mL). The combined organic phases were dried over $MgSO_4$, filtered and the volatiles were removed under reduced pressure to give crude (R)-tert-butyl 3-hydroxy-1-oxo-8-azaspiro[4.5]decane-8-carboxylate. Enantiomeric determination of this mixture show 90% ee ($R_t$(S): 1.59 min, $R_t$(R): 1.80 min; chiral SFC; column: IA 4.6×100 mm, flow rate: 70 g per minute, mobile phase: 5-55% MeOH in $CO_2$, detection: 220 nm UV). A mixture of (R)-tert-butyl 3-hydroxy-1-oxo-8-azaspiro[4.5]decane-8-carboxylate crude (47.7 mmol), imidazole (4.87 g, 71.6 mmol), and TBSCl (8.99 g, 59.6 mmol) in DMF (120 mL) was stirred for 16 h at RT. The reaction mixture was poured into a separation funnel containing sat. aq. $NH_4Cl/H_2O$ (1/1, 250 mL) and it was extracted with $Et_2O$ (5×50 mL). The combined organic phases were dried over $MgSO_4$, filtered and the volatiles were removed under reduced pressure. The resulting residue was purified by silica chromatography (0 to 30% gradient of EtOAc/heptane) to give (R)-tert-butyl 3-((tert-butyldimethylsilyl)oxy)-1-oxo-8-azaspiro[4.5]decane-8-carboxylate (13.115 g, 34.2 mmol) as a colorless oil that solidified upon standing.

Step b: A solution of (R)-tert-butyl 3-((tert-butyldimethylsilyl)oxy)-1-oxo-8-azaspiro[4.5]decane-8-carboxylate (8.0 g, 20.86 mmol), titanium(IV)ethoxide (17.49 mL, 83.0 mmol), and (R)-2-methylpropane-2-sulfinamide (5.06 g, 41.7 mmol) in THF (100 mL) was stirred for 16 h at 65° C. After cooling to −78° C., MeOH (15 mL) was added followed by lithium borohydride (1.363 g, 62.6 mmol). The resulting mixture was stirred for 16 h at −78° C. Saturated aq. $NH_4Cl$ was slowly added to quench excess of borohydride followed by addition of EtOAc (100 mL). The resulting mixture was vigorously stirred for 15 min and then filtered through a pad of Celite. The volatiles were removed under reduced pressure and the resulting residue was purified by silica chromatography (0 to 50% gradient of EtOAc/heptane) to give (1R,3R)-tert-butyl 3-((tert-butyldimethylsilyl)oxy)-1-((R)-1,1-dimethylethylsulfinamino)-8-azaspiro[4.5]decane-8-carboxylate (5.3 g, 10.84 mmol) as a white solid. MS m/z 489.3 (M+H)+ and 389.3 (M+H-Boc)+.

Intermediate B-11

(1R,3R)-tert-butyl 1-((R)-1,1-dimethylethylsulfinamino)-3-hydroxy-8-azaspiro[4.5]decane-8-carboxylate

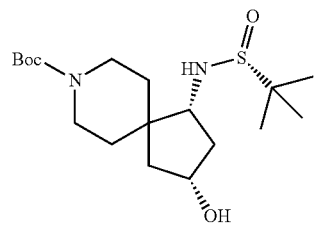 [SMILES: CC(C)(C)OC(=O)N1CCC2(CC1)C[C@@H](O)C[C@H]2N[S@](=O)C(C)(C)C]

A mixture of (1R,3R)-tert-butyl 3-((tert-butyldimethylsilyl)oxy)-1-((R)-1,1-dimethylethylsulfinamino)-8-azaspiro[4.5]decane-8-carboxylate (3.84 g, 7.86 mmol) and TBAF (1 M in THF; 8.64 mL, 8.64 mmol) in THF (40 mL) was stirred for 30 min at RT. The volatiles were removed under reduced pressure and the resulting residue was purified by silica chromatography (0 to 10% gradient of MeOH/DCM) to give (1R,3R)-tert-butyl 1-((R)-1,1-dimethylethylsulfinamino)-3-hydroxy-8-azaspiro[4.5]decane-8-carboxylate (2.94 g, 7.86 mmol). MS m/z 375.3 (M+H)+.

Intermediate B-12

(1R,3S)-tert-butyl 1-((R)-1,1-dimethylethylsulfinamino)-3-hydroxy-8-azaspiro[4.5]decane-8-carboxylate

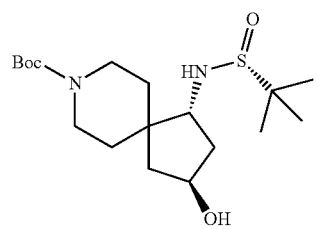 [SMILES: CC(C)(C)OC(=O)N1CCC2(CC1)C[C@H](O)C[C@H]2N[S@](=O)C(C)(C)C]

Step a: To a solution of (1R,3R)-tert-butyl 1-((R)-1,1-dimethylethylsulfinamino)-3-hydroxy-8-azaspiro[4.5]decane-8-carboxylate (3.0 g, 8.01 mmol), triphenylphosphine (4.2 g, 16.02 mmol), and isoquinoline-1-carboxylic acid (4.16 g, 24.03 mmol) in THF (80 mL) was added DIAD (3.1 mL, 16.02 mmol). The resulting mixture was stirred for 1 h at RT. The reaction was diluted with EtOAc (50 mL), filtered through a pad of Celite, poured into a separation funnel containing sat. aq. NaHCO₃ and extracted with EtOAc (3×25 mL). The combined organic phases were dried over MgSO₄, filtered, and the volatiles were removed under reduced pressure. The resulting residue was purified by silica chromatography (0 to 4% gradient of MeOH/DCM) to give (2S,4R)-8-(tert-butoxycarbonyl)-4-((R)-1,1-dimethylethylsulfinamino)-8-azaspiro[4.5]decan-2-yl isoquinoline-1-carboxylate (3.65 g, 6.89 mmol) as an orange solid. MS m/z 530.3 (M+H)⁺.

Step b: A mixture of (2S,4R)-8-(tert-butoxycarbonyl)-4-((R)-1,1-dimethylethylsulfinamino)-8-azaspiro[4.5]decan-2-yl isoquinoline-1-carboxylate (3.65 g, 6.89 mmol) and lithium hydroxide (2.95 g, 68.9 mmol) in THF/H₂O (1/1, 70 mL) was stirred for 2 h at RT. The mixture was poured into a separation funnel containing sat. aq. NH₄Cl and it was extracted with EtOAc (3×15 mL). The combined organic phases were dried over MgSO₄, filtered, and the volatiles were removed under reduced pressure. The resulting residue was purified by silica chromatography (0 to 10% gradient of MeOH/DCM) to give (1R,3S)-tert-butyl 1-((R)-1,1-dimethylethylsulfinamino)-3-hydroxy-8-azaspiro[4.5]decane-8-carboxylate (2.35 g, 6.27 mmol) as a white solid. MS m/z 275.2 (M+H-Boc)⁺.

Intermediate B-13

(1R,3S)-tert-butyl 1-((R)-1,1-dimethylethylsulfinamino)-3-methoxy-8-azaspiro[4.5]decane-8-carboxylate

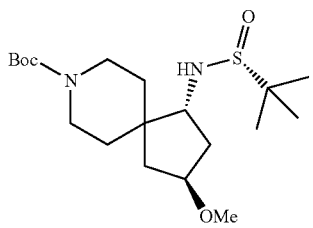 [SMILES: CO[C@@H]1C[C@@H](N[S@](=O)C(C)(C)C)C2(CCN(C(=O)OC(C)(C)C)CC2)C1]

A mixture of (1R,3S)-tert-butyl 1-((R)-1,1-dimethylethylsulfinamino)-3-hydroxy-8-azaspiro[4.5]decane-8-carboxylate (500 mg, 1.335 mmol), silver(I)oxide (340 mg, 1.468 mmol), and iodomethane (0.25 mL, 4.0 mmol) in DCM (5 mL) was stirred (protected from the light) for 24 h at RT and 24 h at 45° C. After cooling to RT, the mixture was filtered through a pad of Celite, the volatiles were removed under reduced pressure, and the resulting residue was purified by silica chromatography (0 to 5% gradient of MeOH/DCM) to give (1R,3S)-tert-butyl 1-((R)-1,1-dimethylethylsulfinamino)-3-methoxy-8-azaspiro[4.5]decane-8-carboxylate (248 mg, 0.638 mmol). MS m/z 289.2 (M+H-Boc)⁺.

(1R,3R)-tert-Butyl 1-((R)-1,1-dimethylethylsulfinamino)-3-methoxy-8-azaspiro[4.5]decane-8-carboxylate was synthesized using the above procedure or modifications to the above procedure using (1R,3R)-tert-butyl 1-((R)-1,1-dimethylethylsulfinamino)-3-hydroxy-8-azaspiro[4.5]decane-8-carboxylate as starting material.

Intermediate B-14

Racemic tert-butyl 1-((tert-butoxycarbonyl)amino)-3,3-difluoro-8-azaspiro[4.5]decane-8-carboxylate

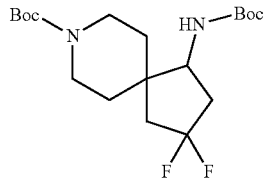 [SMILES: CC(C)(C)OC(=O)NC1CC(F)(F)CC12CCN(C(=O)OC(C)(C)C)CC2]

Step a: A mixture of tert-butyl 3-((tert-butyldimethylsilyl)oxy)-1-(1,1-dimethylethylsulfinamino)-8-azaspiro[4.5]decane-8-carboxylate (365 mg, 0.746 mmol) and HCl (4 M in dioxane, 1.86 mL, 7.46 mmol) in MeOH (4 mL) was stirred for 1 h at 40° C. After cooling to RT, the volatiles were removed under reduced pressure to give crude 4-amino-8-azaspiro[4.5]decan-2-ol as a white solid. MS m/z 171.1 (M+H)⁺.

Step b: A mixture of crude 4-amino-8-azaspiro[4.5]decan-2-ol, DIPEA (2.6 mL, 14.92 mmol), and Boc₂O (407 mg, 1.865 mmol) in THF (15 mL) was stirred for 16 h at RT. The mixture was poured into a separation funnel containing sat. aq. NH₄Cl and it was extracted with Et₂O (5×10 mL). The combined organic phases were dried over MgSO₄, filtered and the volatiles were removed under reduced pressure. The resulting residue was purified by silica chromatography (10 to 80% gradient of EtOAc/heptane) to give tert-butyl 1-((tert-butoxycarbonyl)amino)-3-hydroxy-8-azaspiro[4.5]decane-8-carboxylate (275 mg, 0.742 mmol). MS m/z 271.3 (M+H-Boc)⁺.

Step c: A mixture of tert-butyl 1-((tert-butoxycarbonyl)amino)-3-hydroxy-8-azaspiro[4.5]decane-8-carboxylate (275 mg, 0.742 mmol) and Dess-Martin periodinane (472 mg, 1.113 mmol) in DCM (7.5 mL) was stirred for 2 h at 0° C. The mixture was poured into a separation funnel containing sat. aq. NaHCO₃ and it was extracted with DCM (3×10 mL). The combined organic phases were dried over MgSO₄, filtered, and the volatiles were removed under reduced pressure. The resulting residue was purified by silica chromatography (5 to 75% gradient of EtOAc/heptane) to give tert-butyl 1-((tert-butoxycarbonyl)amino)-3-oxo-8-azaspiro[4.5]decane-8-carboxylate (135 mg, 0.366 mmol). ¹H NMR (400 MHz, Chloroform-d) δ ppm 4.57 (d, J=9.09 Hz, 1H), 4.16 (d, J=8.08 Hz, 1H), 3.89-4.08 (m, 2H), 2.77-2.93 (m, 2H), 2.71 (dd, J=18.95, 8.08 Hz, 1H), 2.50 (d, J=18.19 Hz, 1H), 2.07-2.24 (m, 2H), 1.76 (td, J=12.82, 4.67 Hz, 1H), 1.58-1.70 (m, 1H), 1.42-1.53 (m, 18H), 1.25-1.38 (m, 1H).

Step d: A mixture of tert-butyl 1-((tert-butoxycarbonyl)amino)-3-oxo-8-azaspiro[4.5]decane-8-carboxylate (95 mg, 0.258 mmol) and DeoxoFluor (190 μL, 1.031 mmol) in DCM (1 mL) was stirred for 48 h at 50° C. The mixture was poured into a separation funnel containing sat. aq. NaHCO₃/ice and it was extracted with EtOAc (3×5 mL). The combined organic phases were dried over MgSO₄, filtered, and the volatiles were removed under reduced pressure. The resulting residue was purified by silica chromatography (0 to 30% gradient of EtOAc/heptane) to give tert-butyl 1-((tert-butoxycarbonyl)amino)-3,3-difluoro-8-azaspiro[4.5]decane-8-carboxylate (52 mg, 0.133 mmol). $^1$H NMR (400 MHz, Chloroform-d) δ ppm 4.55 (d, J=9.35 Hz, 1H), 3.78-4.02 (m, 3H), 2.64-2.86 (m, 2H), 2.38-2.59 (m, 1H), 2.10-2.32 (m, 1H), 1.79-2.10 (m, 2H), 1.58 (qd, J=12.72, 3.79 Hz, 1H), 1.27-1.52 (m, 21H).

(R)-tert-Butyl 1-((tert-butoxycarbonyl)amino)-3,3-difluoro-8-azaspiro[4.5]decane-8-carboxylate was synthesized using the above procedure or modifications to the above procedure using the chirally pure (1R,3R)-tert-butyl 3-((tert-butyldimethylsilyl)oxy)-1-((R)-1,1-dimethylethylsulfinamino)-8-azaspiro[4.5]decane-8-carboxylate as starting material.

Intermediate B-15

(1R,3S)-tert-butyl 1-((R)-1,1-dimethylethylsulfinamino)-3-fluoro-8-azaspiro[4.5]decane-8-carboxylate

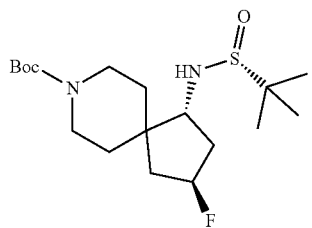 [SMILES: CC(C)(C)OC(=O)N1CCC2(CC1)C[C@H](F)C[C@H]2N[S@](=O)C(C)(C)C]

A mixture (1R,3R)-tert-butyl 1-((R)-1,1-dimethylethylsulfinamino)-3-hydroxy-8-azaspiro[4.5]decane-8-carboxylate (400 mg, 1.068 mmol) and DAST (1 M in DCM, 1.87 mL, 1.87 mmol) in DCM (8.5 mL) was stirred for 90 min at 0° C. The reaction mixture was quenched by addition of sat. aq. NaHCO$_3$ (5 mL). After stirring for 10 min at 0° C., the phases were separated and the aq. layer was extracted with DCM (2×5 mL). The combined organic phases were dried over MgSO$_4$, filtered, and the volatiles were removed under reduced pressure to give (1R,3S)-tert-butyl 1-((R)-1,1-dimethylethylsulfinamino)-3-fluoro-8-azaspiro[4.5]decane-8-carboxylate which was used in next step without further purification. MS m/z 277.2 (M+H-Boc)$^+$.

Intermediate B-16

(1R,3R)-tert-butyl 1-((R)-1,1-dimethylethylsulfinamino)-3-fluoro-8-azaspiro[4.5]decane-8-carboxylate

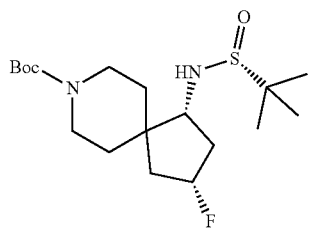 [SMILES: CC(C)(C)OC(=O)N1CCC2(CC1)C[C@@H](F)C[C@H]2N[S@](=O)C(C)(C)C]

A mixture (1R,3S)-tert-butyl 1-((R)-1,1-dimethylethylsulfinamino)-3-hydroxy-8-azaspiro[4.5]decane-8-carboxylate (200 mg, 0.534 mmol) and DAST (1 M in DCM, 934 μL, 0.934 mmol) in DCM (5 mL) was stirred for 90 min at 0° C. The reaction mixture was quenched by addition of sat. aq. NaHCO$_3$ (5 mL). After stirring for 10 min at RT, the phases were separated and the aq. layer was extracted with DCM (2×5 mL). The combined organic phases were dried over MgSO$_4$, filtered, and the volatiles were removed under reduced pressure to give (1R,3R)-tert-butyl 1-((R)-1,1-dimethylethylsulfinamino)-3-fluoro-8-azaspiro[4.5]decane-8-carboxylate which was used in next step without further purification. MS m/z 277.2 (M+H-Boc)$^+$.

Intermediate B-17

Tert-butyl 4-oxo-2-oxa-8-azaspiro[4.5]decane-8-carboxylate

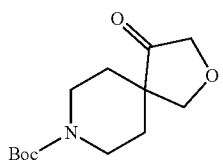 [SMILES: CC(C)(C)OC(=O)N1CCC2(CC1)COCC2=O]

Following procedures of Dirat et al., WO2004/078750, 16 Sep. 2004, tert-butyl 4-hydroxy-2-oxa-8-azaspiro[4.5]decane-8-carboxylate was prepared from 1-tert-butyl 4-ethyl piperidine-1,4-dicarboxylate in four steps. $^1$H NMR (400 MHz, Chloroform-d) δ ppm 4.13 (dd, J=10.1, 4.6 Hz, 1H), 4.03 (dd, J=4.6, 2.0 Hz, 1H), 3.78-3.71 (m, 2H), 3.69 (d, J=8.6 Hz, 1H), 3.67-3.58 (m, 2H), 3.29 (m, 1H), 3.16 (m, 1H), 1.78 (m, 2H), 1.58 (m, 1H), 1.50 (m, 2H), 1.47 (s, 9H). MS m/z 258.1 (M-H)$^+$.

A solution of tert-butyl 4-hydroxy-2-oxa-8-azaspiro[4.5]decane-8-carboxylate (544 mg, 2.11 mmol) and Dess-Martin periodinane (1.39 g, 3.17 mmol) in DCM (10 mL) was stirred for 2 h at 0° C. Saturated aq. NaHCO$_3$/Na$_2$S$_2$O$_3$ (1/1, 10 mL) was added, the organic phase was separated and the aq. phase was extracted with DCM (3×10 mL). The combined organic phases were dried over Na$_2$SO$_4$, filtered, and the volatiles were removed under reduced pressure. The resulting residue was purified by silica chromatography (0 to 50% gradient of EtOAc/heptane) to give tert-butyl 4-oxo-2-oxa-8-azaspiro[4.5]decane-8-carboxylate (470 mg, 1.84 mmol) as a colorless oil which crystallized upon standing. $^1$H NMR (400 MHz, Chloroform-d) δ ppm 4.08 (s, 2H), 4.05 (s, 2H), 3.88 (dt, J=13.7, 4.9 Hz, 2H), 3.12 (ddd, J=13.6, 9.8, 3.6 Hz, 2H), 1.75 (ddd, J=13.9, 9.7, 4.2 Hz, 2H), 1.58-1.51 (m, 2H), 1.48 (s, 9H). MS m/z 256.2 (M+H)$^+$.

Intermediate B-18

(S)-tert-butyl 4-((R)-1,1-dimethylethylsulfinamino)-2-oxa-8-azaspiro[4.5]decane-8-carboxylate

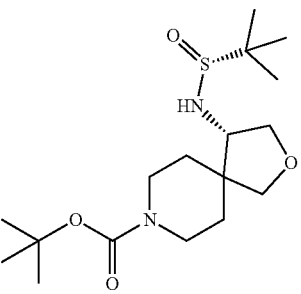 [SMILES: CC(C)(C)OC(=O)N1CCC2(CC1)COC[C@H]2N[S@](=O)C(C)(C)C]

A solution of tert-butyl 4-oxo-2-oxa-8-azaspiro[4.5]decane-8-carboxylate (220 mg, 0.86 mmol), titanium(IV) ethoxide (725 µL, 3.45 mmol), and (R)-2-methylpropane-2-sulfinamide (209 mg, 1.72 mmol) in THF (4 mL) was stirred for 1 h at 90° C. After cooling to 0° C., lithium borohydride (23 mg, 1.06 mmol) was added. After stirring for 30 min, the reaction mixture was quenched by addition of MeOH. The volatiles were removed under reduce pressure. The resulting residue was diluted with brine and it was extracted with EtOAc (4×10 mL). The combined organic phases were dried over Na$_2$SO$_4$, filtered, the volatiles were removed under reduced pressure, and the resulting residue was purified by silica chromatography (0 to 100% gradient of EtOAc/heptane) to give (S)-tert-butyl 4-((R)-1,1-dimethylethylsulfinamino)-2-oxa-8-azaspiro[4.5]decane-8-carboxylate (170 mg, 0.47 mmol). MS m/z 361.1 (M+H)$^+$.

The following compounds of Table 5 were synthesized using the above procedure or modifications to the above procedure using the corresponding ketone and sulfonamide.

TABLE 5

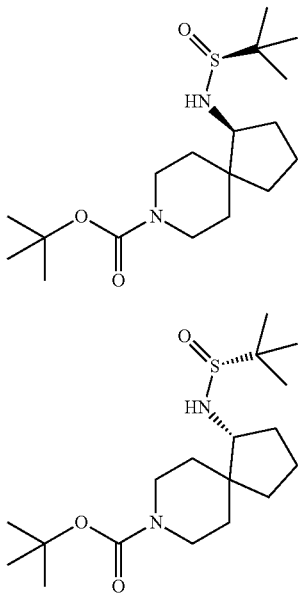

Intermediate B-19 & B-20

(3S,4S)-tert-butyl 4-((R)-1,1-dimethylethylsulfinamino)-3-methyl-2-oxa-8-azaspiro[4.5]decane-8-carboxylate & (3R,4S)-tert-butyl 4-((R)-1,1-dimethylethylsulfinamino)-3-methyl-2-oxa-8-azaspiro[4.5]decane-8-carboxylate

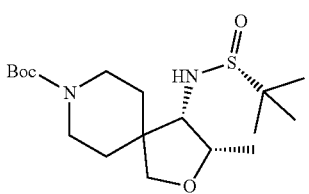

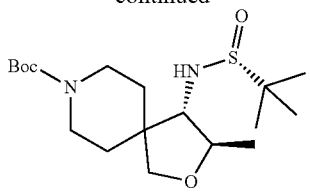

Step a: To a solution of tert-butyl 4-oxo-2-oxa-8-azaspiro[4.5]decane-8-(2.47 g, 9.67 mmol) in THF (24 mL) was added LHMDS (1 M in THF, 9.67 mL, 9.67 mmol) at −78° C. After stirring the mixture for 30 minutes at this temperature, iodomethane (0.605 mL, 9.67 mmol) in THF (10 mL) was added. The resulting mixture was allowed to warm to RT and stirred for 1 h. The reaction mixture was diluted with EtOAc and sat. aq. NaHCO$_3$. The organic layer was washed with brine, dried over Na$_2$SO$_4$, filtered and concentrated under reduced pressure. The resulting brown oil was purified by silica chromatography (0 to 20% gradient of EtOAc/heptane) to give tert-butyl 3-methyl-4-oxo-2-oxa-8-azaspiro[4.5]decane-8-carboxylate (318 mg, 1.18 mmol). MS m/z 270.2 (M+H)$^+$.

Step b: A solution of tert-butyl 3-methyl-4-oxo-2-azaspiro[4.5]decane-8-carboxylate (318 mg, 1.18 mmol), titanium(IV)ethoxide (990 µL, 4.72 mmol), and (R)-2-methylpropane-2-sulfinamide (286 mg, 2.361 mmol) in THF (4 mL) was stirred for 90 min at 90° C. After cooling to 0° C., lithium borohydride (65.3 mg, 3.00 mmol) was added in one portion and the resulting mixture was stirred for 16 h at RT. Saturated aq. NH$_4$Cl was slowly added to quench the excess of borohydride followed by addition of EtOAc (25 mL). The resulting mixture was vigorously stirred for 15 min and then filtered through a pad of Celite. The organic phase was washed with sat. aq. NaHCO$_3$ and brine, dried over Na$_2$SO$_4$, filtered, and the volatiles were removed under reduced pressure. The resulting residue was purified by silica chromatography (0 to 100% gradient of EtOAc/heptane) to give (4S)-tert-butyl 4-((R)-1,1-dimethylethylsulfinamino)-3-methyl-2-oxa-8-azaspiro[4.5]decane-8-carboxylate (88 mg, 0.235 mmol). MS m/z 375.2 (M+H)$^+$.

Step c: The diastereomers were separated by chiral SFC. Column: LUXC4 30×250 mm, flow rate: 80 g per minute, mobile phase: 20% MeOH in CO$_2$, detection: 210 nm to give (3R,4S)-tert-butyl 4-((R)-1,1-dimethylethylsulfinamino)-3-methyl-2-oxa-8-azaspiro[4.5]decane-8-carboxylate R$_t$=4.0 min; and (3S,4S)-tert-butyl 4-((R)-1,1-dimethylethylsulfinamino)-3-methyl-2-oxa-8-azaspiro[4.5]decane-8-carboxylate T$_R$=4.55 min.

Alternative preparation of (3S,4S)-tert-butyl 4-((R)-1,1-dimethylethylsulfinamino)-3-methyl-2-oxa-8-azaspiro[4.5]decane-8-carboxylate:

Step a: To a −10° C. solution of diisopropylamine (23.4 mL, 166 mmol) in THF (220 mL) was added n-BuLi (2.5 M in hexane, 64.1 mL, 160 mmol) dropwise. After stirring for 30 min at this temperature, 1-tert-butyl 4-ethyl piperidine-1,4-dicarboxylate (27.5 g, 107 mmol) in THF (50 mL) was added dropwise and the resulting mixture was stirred for 30 min at 0° C. (S)-2-((tert-butyldimethylsilyl)oxy)propanal (20.47 mL, 102 mmol) was added and the mixture was stirred for 1 h at 0° C. and 1 h at RT. The reaction was diluted with sat. aq. NaHCO$_3$/H$_2$O (1:4, 125 mL), EtOAc (50 mL) was added, and the phases were separated. The aq. phase was further extracted with EtOAc (3×100 mL). The combined organic phases were dried over Na$_2$SO$_4$, filtered, and the solvent was removed under reduced pressure. The resulting residue was used in next step without further purification. MS m/z 346.4 (M+H-Boc)⁺.

Step b: To a solution of crude 1-tert-butyl 4-ethyl 4-((2S)-2-((tert-butyldimethylsilyl)oxy)-1-hydroxypropyl)piperidine-1,4-dicarboxylate (95 g, 214 mmol) in THF (600 mL) was added portionwise lithium borohydride (7.0 g, 321 mmol) and the resulting mixture was stirred for 16 h at RT. After cooling to 0° C., sat. aq. NaHCO₃/H₂O (1/2, 150 mL) was added and the resulting mixture was vigorously stirred until no gas development was observed. EtOAc (100 mL) was added, the mixture was filtered, the phases were separated, and the aq. phase was further extracted with EtOAc (3×50 mL). The combined organic phases were washed with brine, dried over Na₂SO₄, filtered, and the volatiles were removed under reduced pressure to give tert-butyl 4-((2S)-2-((tert-butyldimethylsilyl)oxy)-1-hydroxypropyl)-4-(2-hydroxyethyl)piperidine-1-carboxylate (64.8 g, 161 mmol) which was used in next step without further purification.

Step c: A solution of tert-butyl 4-((2S)-2-((tert-butyldimethylsilyl)oxy)-1-hydroxypropyl)-4-(2-hydroxyethyl)piperidine-1-carboxylate (64.8 g, 161 mmol) and TBAF (1 M in THF, 242 mL, 242 mmol) in THF (500 mL) was stirred for 2 h at RT. Saturated aq. NaHCO₃/H₂O (1:2, 150 mL) were added, the phases were separated, and the aq. phase was further extracted with EtOAc (3×100 mL). The combined organic phases were washed with brine, dried over Na₂SO₄, filtered, and the volatiles were removed under reduced pressure. The resulting residue was purified by silica chromatography (20 to 100% gradient of EtOAc/heptane) to give tert-butyl 4-((2S)-1,2-dihydroxypropyl)-4-(2-hydroxyethyl)piperidine-1-carboxylate (39.25 g, 136 mmol) as a semi-solid colorless oil.

Step d: To a 0° C. suspension of NaH (10.60 g, 424 mmol) in THF (600 mL) was added dropwise a solution of tert-butyl 4-((2S)-1,2-dihydroxypropyl)-4-(2-hydroxyethyl)piperidine-1-carboxylate (35.06 g, 121 mmol) and 4-toluenesulfonyl chloride (23.1 g, 121 mmol) in THF (200 mL). The resulting mixture was stirred for 1 h at 0° C. Saturated aq. NH₄Cl (~5 mL) was added slowly at -20° C. and the reaction was vigorously stirred until no gas development was observed. At this point, sat. aq. NH₄Cl (100 mL) was added followed by brine (100 mL) and the mixture was extracted with EtOAc (3×100 mL). The combined organic phases were dried over Na₂SO₄, filtered, and the solvent was removed under reduced pressure to give (3S)-tert-butyl 4-hydroxy-3-methyl-2-oxa-8-azaspiro[4.5]decane-8-carboxylate (32.19 g, 119 mmol) which was used in next step without further purification. MS m/z 171.1 (M-Boc)⁻.

Step e: A solution of (3S)-tert-butyl 4-hydroxy-3-methyl-2-oxa-8-azaspiro[4.5]decane-8-carboxylate (32.19 g, 119 mmol) and Dess-Martin periodinane (67.4 g, 154 mmol) in DCM (300 mL) was stirred for 2 h at 0° C. The mixture was warmed up to RT and the volatiles were removed under reduced pressure. The resulting residue was purified by silica chromatography (0 to 40% gradient of EtOAc/heptane) to give (3S)-tert-butyl 3-methyl-4-oxo-2-oxa-8-azaspiro[4.5]decane-8-carboxylate (27.68 g, 92 mmol) as a pale yellow oil. ¹H NMR (400 MHz, Chloroform-d) δ ppm 4.09 (d, J=9.60 Hz, 1H), 3.66-3.86 (m, 4H), 3.03 (ddd, J=13.77, 9.73, 3.79 Hz, 1H), 2.90 (ddd, J=13.64, 10.23, 3.41 Hz, 1H), 1.68 (ddd, J=13.83, 9.92, 4.29 Hz, 1H), 1.41-1.59 (m, 2H), 1.30-1.40 (m, 10H), 1.20-1.25 (m, 3H).

Step f: A solution of (3S)-tert-butyl 3-methyl-4-oxo-2-oxa-8-azaspiro[4.5]decane-8-carboxylate (22.52 g mg, 84 mmol), titanium(IV)ethoxide (70.1 mL, 334 mmol), and (R)-2-methylpropane-2-sulfinamide (21 g, 173 mmol) in THF (300 mL) was stirred for 21 h at 90° C. After cooling to -4° C., MeOH (30 mL) was added, followed by dropwise addition (maintaining reaction temperature below 2° C.) of lithium borohydride (1.82 g, 84 mmol) and the resulting mixture was stirred for 1 h at -4° C. Saturated aq. NH₄Cl was slowly added to quench excess of borohydride (semi-solid) followed by addition of EtOAc (500 mL). The resulting mixture was vigorously stirred for 15 min at RT and then filtered through a pad of Celite followed by EtOAc (500 mL) wash. The volatiles were removed under reduced pressure and the resulting residue was purified by silica chromatography (0 to 100% gradient of EtOAc/heptane) to give (3S,4S)-tert-butyl 4-((R)-1,1-dimethylethylsulfinamino)-3-methyl-2-oxa-8-azaspiro[4.5]decane-8-carboxylate as a 95:5 diastereomeric mixture (minor diastereomer (3R,4S)-tert-butyl 4-((R)-1,1-dimethylethylsulfinamino)-3-methyl-2-oxa-8-azaspiro[4.5]decane-8-carboxylate).

Step g: The diastereomers were separated by chiral SFC. Column: LC-4 30×250 mm, flow rate: 100 g per minute, mobile phase: 30% MeOH in CO₂, detection: 225 nm, $T_R$: 0.95 min (minor diastereomer $T_R$: 0.55 min) to give (3S,4S)-tert-butyl 4-((R)-1,1-dimethylethylsulfinamino)-3-methyl-2-oxa-8-azaspiro[4.5]decane-8-carboxylate (19 g, 50.68 mmol). MS m/z 375.2. ¹H NMR (400 MHz, Chloroform-d) δ ppm 4.24-4.16 (m, 1H), 4.03-3.94 (m, 1H), 3.91-3.85 (m, 1H), 3.84-3.78 (m, 1H), 3.64 (d, J=9.1 Hz, 1H), 3.50-3.42 (m, 1H), 3.32 (d, J=10.1 Hz, 1H), 2.99-2.85 (m, 2H), 1.82 (td, J=18.1, 15.1, 7.7 Hz, 2H), 1.62-1.53 (m, 1H), 1.53-1.47 (m, 1H), 1.46 (s, 9H), 1.22 (d, J=6.4 Hz, 3H).

The following compounds of Table 6 were synthesized using the above procedure or modifications to the above procedure using the corresponding iodoalkanes.

TABLE 6

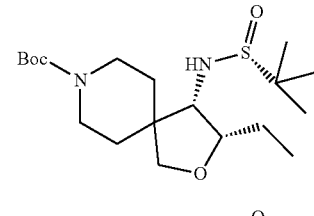

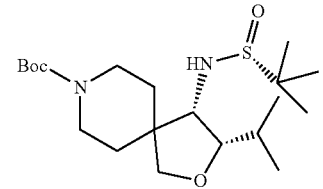 [SMILES: CC(C)[C@@H]1OCC2(CCN(C(=O)OC(C)(C)C)CC2)[C@@H]1N[S@](=O)C(C)(C)C]

Intermediate B-21

(1R)-tert-butyl 1-((R)-1,1-dimethylethylsulfinamino)-2-methyl-8-azaspiro[4.5]decane-8-carboxylate

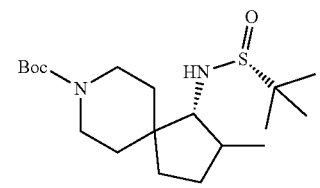 [SMILES: CC1CCC2(CCN(C(=O)OC(C)(C)C)CC2)[C@@H]1N[S@](=O)C(C)(C)C]

Step a: To a solution of tert-butyl 1-oxo-8-azaspiro[4.5]decane-8-carboxylate (2.2 g, 8.68 mmol) in THF (24 mL) was added LHMDS (1 M in THF, 8.68 mL, 8.68 mmol) at 0-5° C. After stirring the mixture for 30 min at this temperature, iodomethane (0.543 mL, 8.68 mmol) was added. The resulting mixture was allowed to warm to RT and stirred for additional 2 h. The reaction mixture was diluted with EtOAc and sat. aq. NaHCO$_3$. The organic phase was washed with brine, dried over Na$_2$SO$_4$, filtered and concentrated under reduced pressure. The resulting brown oil was purified by silica chromatography (0 to 25% gradient of EtOAc/heptane) to give racemic tert-butyl 2-methyl-1-oxo-8-azaspiro[4.5]decane-8-carboxylate (1.3 g, 4.86 mmol). MS m/z 268.1. (M+H)$^+$.

Step b: A solution of racemic tert-butyl 2-methyl-1-oxo-8-azaspiro[4.5]decane-8-carboxylate (267 mg, 0.999 mmol), titanium(IV)ethoxide (837 μL, 3.99 mmol), and (R)-2-methylpropane-2-sulfinamide (242 mg, 1.997 mmol) in THF (10 mL) was stirred for 24 h at 85° C. After cooling to −78° C., MeOH (12 mL) was added followed by lithium borohydride (65.3 mg, 3.00 mmol). The resulting mixture was stirred at −78° C. to RT for 16 h. Saturated aq. NH$_4$Cl was slowly added to quench the excess of borohydride followed by addition of EtOAc (100 mL). The resulting mixture was vigorously stirred for 15 min and then filtered through a pad of Celite. The volatiles were removed under reduced pressure and the resulting residue was purified by silica chromatography (0 to 60% gradient of EtOAc/heptane (containing 0.25% of Et$_3$N)) to give (1R)-tert-butyl 1-((R)-1,1-dimethylethylsulfinamino)-2-methyl-8-azaspiro[4.5]decane-8-carboxylate (92 mg, 0.247 mmol). MS m/z 373.1 (M+H)$^+$.

Intermediate B-22

Racemic (1S,2S,3S)-tert-butyl 1-((tert-butoxycarbonyl)amino)-2,3-dihydroxy-8-azaspiro[4.5]decane-8-carboxylate

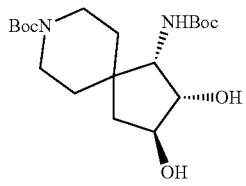 [SMILES: CC(C)(C)OC(=O)N[C@@H]1[C@H](O)[C@@H](O)CC12CCN(C(=O)OC(C)(C)C)CC2]

Step a: To a mixture of tert-butyl 1-oxo-8-azaspiro[4.5]dec-2-ene-8-carboxylate (2 g, 7.96 mmol) and cerium(III) chloride heptahydrate (3.26 g, 8.75 mmol) was added MeOH (60 mL) and THF (20 mL) under N$_2$ atmosphere. The resulting mixture was stirred at RT for 1 h and cooled to 0° C., sodium borohydride (0.60 g, 15.9 mmol) was added. The reaction mixture was stirred at 0° C. for 1 h and then poured into 1 N NaOH (75 mL). The mixture was extracted with Et$_2$O (3×50 mL), the combined extracts were dried over Na$_2$SO$_4$, filtered, and concentrated under reduced pressure. The residue was purified by silica chromatography (10 to 60% gradient of EtOAc/heptane containing 0.25% NEt$_3$) to give racemic tert-butyl 1-hydroxy-8-azaspiro[4.5]dec-2-ene-8-carboxylate (2.01 g, 7.93 mmol) as an orange oil. $^1$H NMR (400 MHz, Chloroform-d) δ ppm 5.99-5.94 (m, 1H), 5.89-5.83 (m, 1H), 4.32 (s, 1H), 3.79-3.65 (m, 2H), 3.29-3.12 (m, 2H), 2.36-2.27 (m, 1H), 2.26-2.15 (m, 1H), 1.81-1.71 (m, 1H), 1.55-1.50 (m, 2H), 1.49 (s, 9H), 1.43-1.36 (m, 1H). MS m/z 276.2 (M+Na)$^+$.

Step b: To a solution of racemic tert-butyl 1-hydroxy-8-azaspiro[4.5]dec-2-ene-8-carboxylate (1.63 g, 6.43 mmol) in DCM (64 mL) was added sequentially tert-butylhydroperoxide (5.5 M solution in decane, 1.4 mL, 7.72 mmol) and vanadyl acetylacetonate (156 mg, 0.643 mmol) at 0° C. under N$_2$ atmosphere. The reaction mixture was stirred for 20 min at 0° C. and for 15 h at RT. The reaction mixture was poured into sat. aq. Na$_2$SO$_3$ (50 mL) and extracted with DCM (3×25 mL). The combined extracts were dried over Na$_2$SO$_4$, filtered, and concentrated under reduced pressure. The residue was purified by silica chromatography (10 to 60% gradient of EtOAc/heptane containing 0.25% NEt$_3$) to give racemic (1R,2R,5S)-tert-butyl 2-hydroxy-6-oxaspiro[bicyclo[3.1.0]hexane-3,4'-piperidine]-1'-carboxylate (805 mg, single diastereomer). $^1$H NMR (400 MHz, Chloroform-d) δ ppm 3.92-3.78 (m, 3H), 3.65 (t, J=2.27 Hz, 1H), 3.56 (t, J=2.27 Hz, 1H), 2.99-2.82 (m, 2H), 2.22 (d, J=14.65 Hz, 1H), 1.78 (br. s., 1H), 1.70-1.58 (m, 3H), 1.47-1.40 (m, 10H). MS m/z 170.1 (M+H-Boc)$^+$.

Step c: To a solution of racemic (1R,2R,5S)-tert-butyl 2-hydroxy-6-oxaspiro[bicyclo[3.1.0]hexane-3,4'-piperidine]-1'-carboxylate (805 mg, 2.99 mmol), triphenyl phosphine (1.57 g, 5.98 mmol) and di-tert-butyl-iminodicarboxylate (1.30 g, 5.98 mmol) in THF (15 mL) under nitrogen atmosphere was slowly added DIAD (1.16 mL, 5.98 mmol) at 0° C. The resulting mixture was stirred at 0° C. for 5 min, stirred at RT for 10 min and then heated to 40° C. for 15 h. The reaction mixture was diluted with EtOAc (25 mL), poured into sat. aq. NH$_4$Cl, and extracted with EtOAc (3×10 mL). The combined extracts were dried over Na$_2$SO$_4$, filtered, and concentrated under reduced pressure. The residue was purified by silica chromatography (0 to 40% gradient of EtOAc containing 0.25% NEt$_3$/heptane containing 0.25% NEt$_3$) to give racemic (1R,2S,5S)-tert-butyl 2-((di-tert-butoxycarbonyl)amino)-6-oxaspiro[bicyclo[3.1.0]hexane-3,4'-piperidine]-1'-carboxylate (480 mg; single diastereomer). MS m/z 491.3 (M+Na)$^+$.

Step d: To a solution of racemic (1R,2S,5S)-tert-butyl 2-((di-tert-butoxycarbonyl)amino)-6-oxaspiro[bicyclo[3.1.0]hexane-3,4'-piperidine]-1'-carboxylate (346 mg) in CHCl$_3$ (4 mL) was added HOAc (0.2 mL). The reaction mixture was stirred for 5 h at RT, concentrated under reduced pressure to give crude racemic (3aS,6S,6aS)—N,N'-bis-(tert-butylcarbonyl)-6-hydroxytetrahydrospiro[cyclopenta[d]oxazole-4,4'-piperidin]-2(5H)-one (295 mg; single diastereomer) as a clear oil. $^1$H NMR (400 MHz, Chloroform-d) δ ppm 4.74 (dd, J=7.45, 1.39 Hz, 1H), 4.48 (br. s, 1H), 4.42 (d, J=7.33 Hz, 1H), 4.04 (br. s., 2H), 2.78 (br. s., 2H), 2.03-1.99 (m, 2H), 1.93-1.79 (m, 3H), 1.66-1.58 (m, 1H), 1.56 (s, 9H), 1.46 (s, 9H). MS m/z 435.2 (M+Na)$^+$.

Step e: To a solution of crude racemic (3aS,6S,6aS)—N,N'-bis-(tert-butylcarbonyl)-6-hydroxytetrahydrospiro[cyclopenta[d]oxazole-4,4'-piperidin]-2(5H)-one (125 mg) in MeOH (1.5 mL) was added Cs$_2$CO$_3$ (20 mg, 0.06 mmol) and the reaction mixture was stirred for 5 h at RT. The mixture was diluted with EtOAc (10 mL) and sat. aq. NH$_4$Cl/water (1:1, 10 mL). The separated aq. layer was extracted with EtOAc (2×10 mL). The combined extracts were dried over MgSO$_4$, filtered, and concentrated under reduced pressure. The residue was purified by SFC (Princetone 2-EP 20×150 mm 5 um, CO$_2$/MeOH 80 g/min 120 bar) to give racemic (1S,2S,3S)-tert-butyl 1-((tert-butoxycarbonyl)amino)-2,3-dihydroxy-8-azaspiro[4.5]decane-8-carboxylate (44 mg, single diastereomer) as a clear oil. $^1$H NMR (400 MHz, Chloroform-d) δ ppm 5.02 (d, J=9.35 Hz, 1H), 4.17-4.10 (m, 1H), 4.04 (br. s, 1H), 3.96 (br. s, 3H), 2.83 (d, J=12.13 Hz, 2H), 2.22-2.10 (m, 1H), 1.98 (br. s, 2H), 1.76 (td, J=12.88, 4.55 Hz, 1H), 1.64-1.52 (m, 1H), 1.46 (s, 9H), 1.45 (s, 9H). MS m/z 409.3 (M+Na)+.

Intermediates B-23

Tert-butyl ((1R,3R)-3-(trifluoromethyl)-8-azaspiro[4.5]decan-1-yl)carbamate

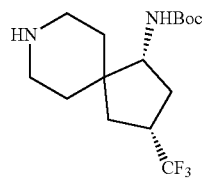

Step a: To a solution of benzyl 1-oxo-8-azaspiro[4.5]dec-2-ene-8-carboxylate (3.05 g, 10.7 mmol) in THF (40 mL) was added trimethyl(trifluoromethyl)silane (2 M in THF, 6.41 mL) and TBAF (1 M in THF, 0.214 mL) at 0° C., and the resulting mixture was stirred at 0° C. for 1.5 h. The reaction mixture was carefully diluted with 2 M aq. HCl (10 mL) and stirred at 0° C. for 1 h. The solution was further diluted with sat. aq. NH₄Cl (50 mL) and extracted with EtOAc (3×50 mL). The combined organic layers were dried over Na₂SO₄, filtered, and the volatiles were removed under reduced pressure. The residue was purified by silica chromatography (0 to 50% gradient of EtOAc/heptane) to give benzyl 1-oxo-3-(trifluoromethyl)-8-azaspiro[4.5]decane-8-carboxylate as a colorless oil (2.22 g, 6.25 mmol). ¹H NMR (400 MHz, Chloroform-d) δ ppm 7.45-7.31 (m, 5H), 5.16 (s, 2H), 3.84 (dd, J=8.9, 5.1 Hz, 1H), 3.30 (ddd, J=13.5, 9.5, 3.4 Hz, 1H), 3.21 (ddd, J=13.5, 9.8, 3.6 Hz, 1H), 3.03-2.87 (m, 1H), 2.66 (ddd, J=18.8, 8.4, 1.5 Hz, 1H), 2.46 (dd, J=18.9, 10.7 Hz, 1H), 2.38-2.25 (m, 1H), 1.97-1.79 (m, 2H), 1.70-1.58 (m, 1H), 1.54 (m, 3H). ¹⁹F NMR (376 MHz, Chloroform-d) δ ppm −72.08 (d, J=8.0 Hz). ¹³C NMR (101 MHz, Chloroform-d) δ ppm 215.93, 155.18, 136.67, 128.53, 128.07, 127.93, 125.74 (q, J=263 Hz), 67.24, 47.96, 40.35, 39.86, 37.30, 32.77 (q, J=29 Hz), 33.77 (q, J=3 Hz), 31.89, 31.10.

Step b: A mixture of benzyl 1-oxo-3-(trifluoromethyl)-8-azaspiro[4.5]decane-8-carboxylate (2.22 g, 6.25 mmol), (R)-tert-butanesulfinamide (1.514 g, 12.50 mmol), and tetraethoxytitanium (5.70 g, 5.24 mL, 25 mmol) in THF (50 mL) was heated to 80° C. for 16 h. The reaction mixture was cooled to −78° C., then MeOH (10 mL) and lithium borohydride (0.408 g, 18.74 mmol) were added. The reaction mixture was allowed to warm to RT over 3 h. The reaction mixture was carefully diluted sat. aq. NH₄Cl (50 mL). The resulting heterogeneous mixture was filtered through Celite, washed with EtOAc. The layers of the filtrate were separated and the aqueous layer was extracted with EtOAc (2×25 mL). The combined organic layers were dried over Na₂SO₄, filtered, and the volatiles were removed under reduced pressure providing crude benzyl (1R)-1-(((R)-tert-butylsulfinyl)amino)-3-(trifluoromethyl)-8-azaspiro[4.5]decane-8-carboxylate as a white solid which was used in the next step without further purification. MS: m/z 461.3 (M+H)+.

Step c: To a solution of crude benzyl (1R)-1-(((R)-tert-butylsulfinyl)amino)-3-(trifluoromethyl)-8-azaspiro[4.5]decane-8-carboxylate (2.88 g, 6.25 mmol) in MeOH (25 mL) was added HCl (4 M in dioxane, 3.13 mL). The resulting solution was stirred at ambient temperature for 1 h. Volatiles were removed under reduced pressure and the resulting residue was dried under reduced pressure for 2 h. The residue was dissolved in CH₂Cl₂ and DIPEA (5.57 mL, 31.3 mmol) and di-tert-butyldicarbonate (2.05 g, 9.4 mmol) were added. The resulting mixture was stirred at ambient temperature for 72 h. The reaction mixture was diluted with sat. aq. NH₄Cl (50 mL) and extracted with CH₂Cl₂ (3×25 mL). The combined organic layers were dried over Na₂SO₄, filtered, and the volatiles were removed under reduced pressure. The resulting residue was purified by silica chromatography (0 to 100% gradient of EtOAc/heptane) to give benzyl (1R,3R)-1-((tert-butoxycarbonyl)amino)-3-(trifluoromethyl)-8-azaspiro[4.5]decane-8-carboxylate (0.90 g, 1.97 mmol) as a white solid, along with 1.47 g of a mixture of benzyl (1R,3R)-1-((tert-butoxycarbonyl)amino)-3-(trifluoromethyl)-8-azaspiro[4.5]decane-8-carboxylate and benzyl (1R,3S)-1-((tert-butoxycarbonyl)amino)-3-(trifluoromethyl)-8-azaspiro[4.5]decane-8-carboxylate. The mixture was further purified by preparative SFC (Column: IB 21×250 mm, 10% IPA co-solvent) to afford benzyl (1R,3R)-1-((tert-butoxycarbonyl)amino)-3-(trifluoromethyl)-8-azaspiro[4.5]decane-8-carboxylate (0.60 g, 1.32 mmol) [¹H NMR (400 MHz, Chloroform-d) δ ppm 7.34-7.20 (m, 5H), 5.06 (s, 2H), 4.39 (d, J=9.6 Hz, 1H), 3.96-3.75 (m, 3H), 2.99 (t, J=11.0 Hz, 2H), 2.65 (dq, J=18.3, 9.1 Hz, 1H), 2.24 (dt, J=15.3, 8.3 Hz, 1H), 1.77 (dd, J=13.9, 9.7 Hz, 1H), 1.66 (dd, J=13.9, 8.4 Hz, 1H), 1.60-1.41 (m, 3H), 1.39 (s, 9H), 1.31-1.16 (m, 2H)] and benzyl (1R,3S)-1-((tert-butoxycarbonyl)amino)-3-(trifluoromethyl)-8-azaspiro[4.5]decane-8-carboxylate (0.50 g, 1.09 mmol) [¹H NMR (400 MHz, Chloroform-d) δ ppm 7.44-7.30 (m, 5H), 5.15 (s, 2H), 4.36 (d, J=9.1 Hz, 1H), 4.24-4.01 (m, 2H), 3.88 (q, J=8.7 Hz, 1H), 2.91 (dd, J=29.7, 16.1 Hz, 2H), 2.72 (ddt, J=14.6, 9.7, 5.0 Hz, 1H), 2.30-2.11 (m, 2H), 1.77-1.60 (m, 2H), 1.46 (m, 12H), 1.27-1.15 (m, 1H)].

Step d: A mixture of benzyl (1R,3R)-1-((tert-butoxycarbonyl)amino)-3-(trifluoromethyl)-8-azaspiro[4.5]decane-8-carboxylate (0.90 g, 1.97 mmol) and Pd/C (10% wt., 200 mg) in EtOH (40 mL) was hydrogenated for 2 h under H₂ atmosphere (balloon). The mixture was sparged with nitrogen for 5 min., then filtered through Celite, rinsed with EtOH. The filtrate was concentrated under reduced pressure and dried under reduced pressure to give crude tert-butyl ((1R,3R)-3-(trifluoromethyl)-8-azaspiro[4.5]decan-1-yl)carbamate (625 mg, 1.94 mmol) as a white foam, which was directly used without purification. ¹H NMR (400 MHz, Chloroform-d) δ ppm 4.54 (d, J=9.7 Hz, 1H), 3.84 (q, J=8.8 Hz, 1H), 3.00 (tt, J=12.1, 4.0 Hz, 2H), 2.79-2.63 (m, 3H), 2.28 (ddd, J=13.5, 8.8, 6.8 Hz, 1H), 2.19 (d, J=8.5 Hz, 1H), 1.80 (qd, J=14.0, 9.1 Hz, 2H), 1.63 (qd, J=9.0, 3.4 Hz, 2H), 1.47 (m, 12H). ¹⁹F NMR (376 MHz, Chloroform-d) δ ppm −71.42 (d, J=9.6 Hz).

tert-Butyl ((1R,3S)-3-(trifluoromethyl)-8-azaspiro[4.5]decan-1-yl)carbamate (355 mg, 1.09 mmol) was prepared from benzyl (1R,3S)-1-((tert-butoxycarbonyl)amino)-3-(trifluoromethyl)-8-azaspiro[4.5]decane-8-carboxylate (0.50 g, 1.09 mmol) following the above procedure. ¹H NMR (400 MHz, Chloroform-d) δ ppm 4.45 (d, J=9.3 Hz, 1H), 3.80 (q, J=9.2 Hz, 1H), 3.15-2.96 (m, 2H), 2.79 (t, J=11.9 Hz, 1H), 2.67 (tt, J=13.8, 6.9 Hz, 2H), 2.17 (dd, J=13.7, 9.1 Hz, 2H), 1.73 (td, J=13.2, 4.3 Hz, 1H), 1.68-1.56 (m, 1H), 1.54-1.31 (m, 12H), 1.26-1.13 (m, 1H), 0.84 (d, J=4.6 Hz, 1H).

Intermediate B-24

Tert-butyl ((1S,3R)-2,2-difluoro-3-methyl-8-azaspiro[4.5]decan-1-yl)carbamate

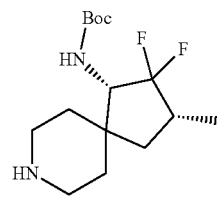

Step a: To a −78° C. solution of LiHMDS (1 M in THF, 3.7 mL, 3.7 mmol) in THF (15 mL) was added dropwise benzyl (R)-3-methyl-1-oxo-8-azaspiro[4.5]decane-8-carboxylate (1.0 g, 3.32 mmol) in THF (5 mL). After stirring for 30 min at −78° C., N-fluoro-N-(phenylsulfonyl)benzenesulfonamide (1.15 g, 3.65 mmol) in THF (5 mL) was added and the resulting mixture was stirred for 30 min at this temperature. After warming to RT, the reaction mixture was poured into a separation funnel containing sat. aq. NaHCO$_3$ (25 mL) and it was extracted with EtOAc (3×30 mL). The combined organic phases were dried over MgSO$_4$, filtered, and the volatiles were removed under reduced pressure. The residue was purified by silica chromatography (0 to 40% gradient of EtOAc/heptane) to give benzyl (3R)-2-fluoro-3-methyl-1-oxo-8-azaspiro[4.5]decane-8-carboxylate (1.05 g, 3.32 mmol). MS m/z 320.2 (M+H)$^+$.

Step b: To a −78° C. solution of LiHMDS (1 M in THF, 3.45 mL, 3.45 mmol) in THF (15 mL) was added benzyl (3R)-2-fluoro-3-methyl-1-oxo-8-azaspiro[4.5]decane-8-carboxylate (1.0 g, 3.13 mmol) in THF (5 mL). After stirring for 30 min at −78° C., N-fluoro-N-(phenylsulfonyl)benzenesulfonamide (1.086 g, 3.44 mmol) in THF (5 mL) was added and the resulting mixture was stirred for 1 h at this temperature. After warming to RT, the reaction mixture was poured into a separation funnel containing sat. aq. NaHCO$_3$ (25 mL) and was extracted with EtOAc (3×30 mL). The combined organic phases were dried over MgSO$_4$, filtered, and the volatiles were removed under reduced pressure. The residue was purified by silica chromatography (0 to 40% gradient of EtOAc/heptane) to give benzyl (R)-2,2-difluoro-3-methyl-1-oxo-8-azaspiro[4.5]decane-8-carboxylate (1.17 g, 3.32 mmol). $^1$H NMR (400 MHz, Chloroform-d) δ ppm 7.30-7.48 (m, 5H), 5.16 (s, 2H), 3.75-3.99 (m, 2H), 3.32-3.44 (m, 1H), 3.28 (ddd, J=13.52, 9.47, 3.54 Hz, 1H), 2.25-2.47 (m, 1H), 2.17 (ddd, J=13.20, 7.52, 2.78 Hz, 1H), 1.72-1.92 (m, 2H), 1.42-1.62 (m, 2H), 1.24 (dd, J=7.33, 0.76 Hz, 3H). $^{19}$F NMR (376 MHz, Chloroform-d) δ ppm −119.79 (br. d, J=277.64 Hz, 1F), −123.89 (d, J=271.90 Hz, 1F).

Step c: A solution of benzyl (R)-2,2-difluoro-3-methyl-1-oxo-8-azaspiro[4.5]decane-8-carboxylate (1.17 g, 3.32 mmol), titanium(IV) ethoxide (2.91 mL, 13.87 mmol), and (R)-2-methylpropane-2-sulfinamide (841 mg, 6.94 mmol) in THF (35 mL) was stirred for 4 h at 60° C. After cooling to −78° C., MeOH (3.5 mL) was added followed by lithium borohydride (0.227 g, 10.40 mmol). The resulting mixture was stirred for 2 h at −78° C. to RT. Sat. aq. NH$_4$Cl was slowly added followed by addition of EtOAc (100 mL). The resulting mixture was vigorously stirred for 5 min and then filtered through a pad of Celite. The volatiles were removed under reduced pressure and the residue was purified by silica chromatography (0 to 50% gradient of EtOAc/heptane) to give benzyl (1S,3R)-1-(((R)-tert-butylsulfinyl)amino)-2,2-difluoro-3-methyl-8-azaspiro[4.5]decane-8-carboxylate (700 mg, 1.582 mmol) as a single diastereomer. MS m/z 443.3 (M+H)$^+$.

Step d: To a solution of benzyl (1S,3R)-1-(((R)-tert-butylsulfinyl)amino)-2,2-difluoro-3-methyl-8-azaspiro[4.5]decane-8-carboxylate (700 mg, 1.582 mmol) in MeOH (10 mL) was added HCl (4 M in dioxane, 3.95 mL, 15.82 mmol). The resulting mixture was stirred for 30 min at 45° C. After cooling to RT, the volatiles were removed under reduced pressure. A solution of this residue, Boc$_2$O (432 mg, 1.977 mmol), and DIPEA (2.76 mL, 15.82 mmol) in THF (20 mL) was stirred for 16 h at RT. The mixture was poured into a separation funnel containing sat. aq. NH$_4$Cl and was extracted with EtOAc (3×10 mL). The combined organic phases were dried over MgSO$_4$, filtered, the volatiles were removed under reduced pressure, and the residue was purified by silica chromatography (0 to 50% gradient of EtOAc/heptane) to give benzyl (1S,3R)-1-((tert-butoxycarbonyl)amino)-2,2-difluoro-3-methyl-8-azaspiro[4.5]decane-8-carboxylate (645 mg, 1.471 mmol). MS m/z 383.3 (M+H-tBu)$^+$.

Step e: A suspension Pd/C (10% wt, 78 mg) in MeOH (10 mL) was stirred vigorously under H$_2$ atmosphere (balloon) for 5 min. Benzyl (1S,3R)-1-((tert-butoxycarbonyl)amino)-2,2-difluoro-3-methyl-8-azaspiro[4.5]decane-8-carboxylate (645 mg, 1.471 mmol) in MeOH (10 mL) was added and the resulting suspension was vigorously stirred under H$_2$ atmosphere for 16 h. The reaction mixture was filtered through a pad of Celite, the pad was washed with DCM and the volatiles were removed under reduced pressure to give tert-butyl ((1S,3R)-2,2-difluoro-3-methyl-8-azaspiro[4.5]decan-1-yl)carbamate (448 mg, 1.471 mmol) which was used without further purification. MS m/z 305.3 (M+H)$^+$.

Intermediate B-25

Tert-butyl ((1R,2S,3R)-2-fluoro-3-methyl-8-azaspiro[4.5]decan-1-yl)carbamate (A) and tert-butyl ((1S,2R,3R)-2-fluoro-3-methyl-8-azaspiro[4.5]decan-1-yl)carbamate (B); (Mixture of A:B=4:1)

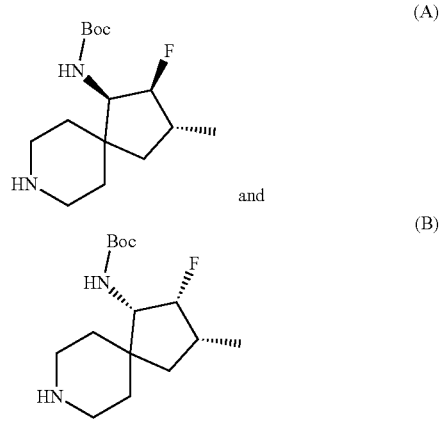

Step a: To a −78° C. solution of LiHMDS (1 M in THF, 7.31 mL, 7.31 mmol) in THF (30 mL) was added dropwise benzyl (R)-3-methyl-1-oxo-8-azaspiro[4.5]decane-8-carboxylate (2.0 g, 6.64 mmol) in THF (10 mL). After stirring for 30 min at −78° C., N-fluoro-N-(phenylsulfonyl)benzenesulfonamide (2.3 g, 7.30 mmol) in THF (10 mL) was added and the resulting mixture was stirred for 30 min at this temperature. After warming to RT, the reaction mixture was poured into a separation funnel containing sat. aq. NaHCO₃ (25 mL) and was extracted with EtOAc (3×30 mL). The combined organic phases were dried over MgSO₄, filtered, and the volatiles were removed under reduced pressure. The residue was purified by silica chromatography (0 to 40% gradient of EtOAc/heptane) to give a 4:1 mixture of diastereomers benzyl (2S,3R)-2-fluoro-3-methyl-1-oxo-8-azaspiro[4.5]decane-8-carboxylate (major) and benzyl (2R,3R)-2-fluoro-3-methyl-1-oxo-8-azaspiro[4.5]decane-8-carboxylate (minor) (1.81 g, 5.67 mmol). This diastereomeric mixture was used in next step without further purification. MS m/z 320.2 (M+H)⁺.

Step b: A mixture of the 4:1 mixture of diastereomers benzyl (2S,3R)-2-fluoro-3-methyl-1-oxo-8-azaspiro[4.5]decane-8-carboxylate (major) and benzyl (2R,3R)-2-fluoro-3-methyl-1-oxo-8-azaspiro[4.5]decane-8-carboxylate (minor) (1.95 g, 6.11 mmol), titanium(IV)ethoxide (5.12 mL, 24.42 mmol), and (R)-2-methylpropane-2-sulfinamide (1.48 g, 12.21 mmol) in THF (35 mL) was stirred for 4 h at 60° C. After cooling to −78° C., MeOH (3.5 mL) was added followed by lithium borohydride (0.399 g, 18.32 mmol). The resulting mixture was stirred for 2 h at −78° C. to RT. Sat. aq. NH₄Cl was slowly added to quench the excess of borohydride followed by addition of EtOAc (100 mL). The resulting mixture was vigorously stirred for 5 min and then filtered through a pad of Celite. The volatiles were removed under reduced pressure and the residue was purified by silica chromatography (0 to 50% gradient of EtOAc/heptane) to give a 4:1 mixture of benzyl (1R,2S,3R)-1-(((R)-tert-butylsulfinyl)amino)-2-fluoro-3-methyl-8-azaspiro[4.5]decane-8-carboxylate and benzyl (1S,2R,3R)-1-(((R)-tert-butylsulfinyl)amino)-2-fluoro-3-methyl-8-azaspiro[4.5]decane-8-carboxylate (2.05 g, 4.83 mmol). This diastereomeric mixture was used in next step without further purification. MS m/z 443.3 (M+H)⁺.

Step c: To a solution of a 4:1 mixture of benzyl (1R,2S,3R)-1-(((R)-tert-butylsulfinyl)amino)-2-fluoro-3-methyl-8-azaspiro[4.5]decane-8-carboxylate and benzyl (1S,2R,3R)-1-(((R)-tert-butylsulfinyl)amino)-2-fluoro-3-methyl-8-azaspiro[4.5]decane-8-carboxylate (2.05 mg, 4.83 mmol) in MeOH (20 mL) was added HCl (4 M in dioxane, 12 mL, 48.0 mmol). The resulting mixture was stirred for 30 min at 45° C. After cooling to RT, the volatiles were removed under reduced pressure. A mixture of this residue, Boc₂O (1.32 g, 6.04 mmol), and DIPEA (8.43 mL, 48.3 mmol) in THF (40 mL) was stirred for 1 h at RT. The reaction mixture was poured into a separation funnel containing sat. aq. NH₄Cl and was extracted with EtOAc (3×25 mL). The combined organic phases were dried over MgSO₄, filtered, the volatiles were removed under reduced pressure, and the residue was purified by silica chromatography (0 to 50% gradient of EtOAc/heptane) to give a 4:1 mixture of benzyl (1R,2S,3R)-1-((tert-butoxycarbonyl)amino)-2-fluoro-3-methyl-8-azaspiro[4.5]decane-8-carboxylate and benzyl (1S,2R,3R)-1-((tert-butoxycarbonyl)amino)-2-fluoro-3-methyl-8-azaspiro[4.5]decane-8-carboxylate (1.51 g, 3.59 mmol). This diastereomeric mixture was used in next step without further purification. MS m/z 383.3 (M+H-tBu)⁺.

Step d: A suspension of Pd/C (10% wt., 78 mg) in MeOH (10 mL) was stirred vigorously under H₂ atmosphere (balloon) for 5 min. The 4:1 mixture of benzyl (1R,2S,3R)-1-((tert-butoxycarbonyl)amino)-2-fluoro-3-methyl-8-azaspiro[4.5]decane-8-carboxylate and benzyl (1S,2R,3R)-1-((tert-butoxycarbonyl)amino)-2-fluoro-3-methyl-8-azaspiro[4.5]decane-8-carboxylate (1.50 g, 3.57 mmol) in MeOH (10 mL) was added and the resulting suspension was vigorously stirred under H₂ atmosphere for 16 h. The reaction mixture was filtered through a pad of Celite, the pad was washed with DCM and the volatiles were removed under reduced pressure to give a 4:1 mixture of tert-butyl ((1R,2S,3R)-2-fluoro-3-methyl-8-azaspiro[4.5]decan-1-yl)carbamate and tert-butyl ((1S,2R,3R)-2-fluoro-3-methyl-8-azaspiro[4.5]decan-1-yl)carbamate (1.07 g, 3.74 mmol). This diastereomeric mixture was used in next step without further purification. MS m/z 305.3 (M+H)⁺.

Intermediate B-26

2-((1S,2S,3R)-2-fluoro-3-methyl-8-azaspiro[4.5]decan-1-yl)isoindoline-1,3-dione

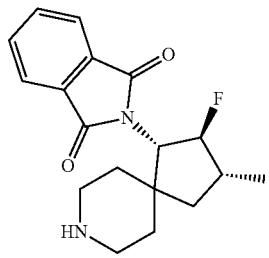 [SMILES: C[C@@H]1CC2(CCNCC2)[C@H](N2C(=O)c3ccccc3C2=O)[C@H]1F]

Step a: To a solution of (2S,3R)-benzyl 2-fluoro-3-methyl-1-oxo-8-azaspiro[4.5]decane-8-carboxylate (1.89 g, 5.92 mmol; contain 40% of (2R,3R)-2-fluoro-3-methyl-1-oxo-8-azaspiro[4.5]decane-8-carboxylate) in THF/MeOH (9:1 20 mL) was added LiBH₄ (2 M in THF, 11.84 mL, 23.67 mmol) at −78° C. The resulting mixture was stirred at −78° C. for 30 min. To the solution was slowly added sat. aq NH₄Cl and the mixture was allowed to warm up to RT. The mixture was extracted with EtOAc (3×), the combined organic phases were washed with brine, dried over MgSO₄, filtered, and the volatiles were removed under reduced pressure. The resulting residue was purified by silica chromatography (0 to 50% gradient of EtOAc/heptane) to give (1R,2S,3R)-benzyl 2-fluoro-1-hydroxy-3-methyl-8-azaspiro[4.5]decane-8-carboxylate (970 mg, 3.02 mmol). MS m/z 322.2 (M+H)⁺. ¹H NMR (400 MHz, Methanol-d₄) δ 7.37-7.28 (m, 5H), 5.10 (s, 2H), 4.47 (dt, J=54.4, 4.7 Hz, 1H), 3.86 (d, J=12.9 Hz, 2H), 3.65 (dd, J=18.0, 4.7 Hz, 1H), 3.20-3.03 (m, 2H), 2.39-2.21 (m, 1H), 2.20-2.10 (m, 1H), 1.75-1.60 (m, 2H), 1.45 (d, J=13.4 Hz, 1H), 1.29 (d, J=13.1 Hz, 1H), 1.08 (d, J=7.1 Hz, 3H), 0.96 (dd, J=13.3, 8.5 Hz, 1H).

Step b: To a solution of benzyl (1R,2S,3R)-2-fluoro-1-hydroxy-3-methyl-8-azaspiro[4.5]decane-8-carboxylate (1.03 g, 3.20 mmol), triphenylphosphine (1.68 g, 6.41 mmol), and phthalimide (0.943 g, 6.41 mmol) in THF (20 mL) was added DIAD (1.25 mL, 6.41 mmol) dropwise. The resulting mixture was stirred for 16 h at 55° C. After cooling to RT, the reaction mixture was poured into a separation funnel containing sat. aq. NH₄Cl and was extracted with EtOAc (5×10 mL). The combined organic phases were dried over MgSO₄, filtered, and the volatiles were removed under reduced pressure. The residue was purified by silica chromatography (0 to 50% gradient of EtOAc/heptane) to give benzyl (1S,2S,3R)-1-(1,3-dioxoisoindolin-2-yl)-2-fluoro-3-methyl-8-azaspiro[4.5]decane-8-carboxylate (2.3 g, ~50% pure based on UV-absorption). This material was used in next step without further purification. MS m/z 451.2 (M+H)⁺.

Step c: A suspension of Pd/C (10% wt., 170 mg) in MeOH (15 mL) was stirred vigorously under H$_2$ atmosphere (balloon) for 5 min. Then, benzyl (1S,2S,3R)-1-(1,3-dioxoisoindolin-2-yl)-2-fluoro-3-methyl-8-azaspiro[4.5]decane-8-carboxylate (50% pure based on UV absorption, 3.20 mmol) in MeOH (15 mL) was added and the resulting suspension was vigorously stirred under H$_2$ atmosphere for 2.5 h. The reaction mixture was filtered through a pad of Celite, the pad was washed with DCM and the volatiles were removed under reduced pressure to give 2-((1S,2S,3R)-2-fluoro-3-methyl-8-azaspiro[4.5]decan-1-yl)isoindoline-1,3-dione (294 mg, 0.929 mmol). MS m/z 317.2 (M+H)⁺.

Intermediate B-27

Tert-butyl 1-((R)-1,1-dimethylethylsulfinamido)-2-(hydroxymethyl)-8-azaspiro[4.5]decane-8-carboxylate

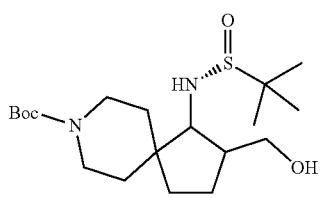

Step a: Following the procedure in "Suna, E. et al., (J. Org. Chem. 2014, 79, 3715-3724), THF (8 mL), MeOH (0.811 mL, 20 mmol) and paraformaldehyde (660 mg, 22 mmol) were added to a heavy-walled pressure vessel and the reaction mixture was heated at 100° C. for 70 min. The reaction mixture was allowed to cool to RT. Upon cooling to RT, a precipitate formed at the bottom of the vessel. Additional THF (1.2 mL) was added to adjust the concentration of the methoxymethanol to a 2 M solution in THF. Quantitative yield, on the basis of MeOH being the limiting reagent, was assumed.

Step b: A flask containing tert-butyl 1-oxo-8-azaspiro[4.5]decane-8-carboxylate (238 g, 939 mmol) was charged with (R)-(+)-2-methyl-2-propanesulfinamide (171 g, 1409 mmol) under N$_2$ atmosphere. Titanium(IV)ethoxide (985 mL, 4.70 mol) was added and the mixture was then heated to 105° C. for 4 h. The heating mantle was removed and the mixture was vacuum transferred, under a stream of N$_2$, with EtOAc (6 L) via a FEP tubing cannula to a 10 L, 4-necked flask equipped with a mechanical overhead stirrer and a 250 mL addition funnel with an N$_2$ inlet adapter that was cooled in a cold water bath. Water (288 mL) was added dropwise via the addition funnel over 30-45 min, resulting in the precipitation of a large volume of light yellow salts. The suspension was aged for 15 minutes with the bath removed before filtering the entire mixture through Celite, washing with EtOAc (2×1 L). The filtrate was then washed with water (3×1 L) and concentrated under reduced pressure. Upon concentration and back-addition of heptane (2 L), the water was azeotroped off, which led to the precipitation of a cloudy, white film of salts on the interior wall of the flask. The light brown mixture was filtered through a medium sintered glass funnel (rinsed with EtOAc and heptane). The filtrate was further concentrated until most of the EtOAc was removed, and additional heptane was added (1 L). The mixture was concentrated further under reduced pressure to produce a precipitate, and additional heptane (500 mL) was added to keep the mixture mobile. The mixture was stirred at RT, then cooled with an ice bath before isolating the solids by vacuum filtration. The solid was washed three times with ice-cold heptane. The solid was dried under reduced pressure to give (R,E)-tert-butyl 1-((tert-butylsulfinyl)imino)-8-azaspiro[4.5]decane-8-carboxylate as a cream solid (408.9 g, 66.7% yield). ¹H NMR (400 MHz, Chloroform-d) δ ppm 3.93 (m, 2H), 3.05 (m, 3H), 2.71 (dt, J=19.6, 7.2 Hz, 1H), 1.96-1.71 (m, 6H), 1.49 (s, 9H), 1.42 (m, 2H), 1.27 (s, 9H).

Step c: To a solution of (R,E)-tert-butyl 1-((tert-butylsulfinyl)imino)-8-azaspiro[4.5]decane-8-carboxylate (1.95 g, 5.47 mmol) in THF (27.3 mL) was slowly added LiHMDS (1 M in THF, 6.02 mL) under N$_2$ atmosphere at −78° C. and the reaction mixture was stirred at −78° C. for 10 min. Methoxymethanol (2 M in THF, 9.57 mL) was added dropwise over ~10 min, the reaction mixture was allowed to warm up to 0° C. and stirring was continued at this temperature for 1 h. The reaction mixture was carefully diluted with sat. aq. NH$_4$Cl (20 mL) and extracted with EtOAc. The combined organic layers were washed with brine, dried over MgSO$_4$ and concentrated under reduced pressure. The residue was purified by column chromatography (silica gel, 0 to 100% of EtOAc/heptane) providing (E)-tert-butyl 1-(((R)-tert-butylsulfinyl)imino)-2-(hydroxymethyl)-8-azaspiro [4.5]decane-8-carboxylate (1.14 g) as a white solid. ¹H NMR (400 MHz, DMSO-d$_6$) δ ppm 4.90 (t, J=5.1 Hz, 1H), 3.83 (dd, J=14.1, 8.5 Hz, 2H), 3.67 (dt, J=9.5, 4.5 Hz, 1H), 3.39 (td, J=9.7, 4.7 Hz, 1H), 3.16 (dt, J=9.0, 5.8 Hz, 1H), 2.84 (d, J=60.4 Hz, 2H), 2.08-1.85 (m, 2H), 1.84-1.62 (m, 2H), 1.62-1.49 (m, 1H), 1.39 (s, 12H), 1.13 (s, 9H).

Step d: To a solution of (E)-tert-butyl 1-(((R)-tert-butylsulfinyl)imino)-2-(hydroxymethyl)-8-azaspiro[4.5]decane-8-carboxylate (1.025 g, 2.65 mmol) in THF (12 mL) and MeOH (1.2 mL) was added LiBH$_4$ (87 mg, 3.98 mmol) under N$_2$ atmosphere and at −78° C. The reaction mixture was stirred at −78° C. for 5 min and then allowed to warm up to room temperature. The reaction mixture was carefully diluted with sat. aq. NaHCO$_3$ (5 mL) and extracted with EtOAc. The combined organic layers were washed with brine, dried over MgSO$_4$ and concentrated under reduced pressure. The residue was purified by column chromatography (silica gel, 0 to 20% gradient of MeOH/DCM) providing tert-butyl 1-((R)-1,1-dimethylethylsulfinamido)-2-(hydroxymethyl)-8-azaspiro[4.5]decane-8-carboxylate (778 mg) as a white solid. ¹H NMR (400 MHz, DMSO-d$_6$) indicated the presence of diagnostic NH signal of the amine at 4.98 ppm (d, J=10.4 Hz, 1H).

Intermediate B-28

(2R,3S)-3-methyl-2-(trifluoromethyl)-8-azaspiro [4.5]decan-1-amine

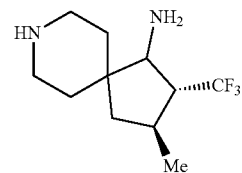 [SMILES: C[C@H]1CC2(CCNCC2)C(N)[C@@H]1C(F)(F)F]

Step a: To a −78° C. solution of (S)-benzyl 3-methyl-1-oxo-8-azaspiro[4.5]decane-8-carboxylate (2.1 g, 6.97 mmol) in THF (30 mL) was added LiHMDS (1 M in THF, 8.36 mL, 8.36 mmol), and the reaction mixture was stirred for 30 min at −78° C. Chlorotriethylsilane (1.23 mL, 7.32 mmol) was added and the reaction mixture was allowed to warm to RT and was stirred for 18 h at this temperature. The reaction mixture was poured into a separation funnel containing sat. aq. NH$_4$Cl (125 mL) and was extracted with heptane (3×125 mL). The combined organic extracts were dried over MgSO$_4$, filtered, and concentrated under reduced pressure. The residue was purified by silica chromatography (0 to 30% gradient of EtOAc/heptane) to give (S)-benzyl 3-methyl-1-((triethylsilyl)oxy)-8-azaspiro[4.5]dec-1-ene-8-carboxylate (2.78 g, 6.69 mmol) as a clear oil. MS m/z 416.3 (M+H)$^+$.

Step b: A mixture of (S)-benzyl 3-methyl-1-((triethylsilyl)oxy)-8-azaspiro[4.5]dec-1-ene-8-carboxylate (2.14 g, 5.15 mmol), 1-trifluoromethyl-1,2-benziodoxol-3-(1H)-one 60% wt., contains 40% wt. Celatom® FW-80 as additive (Togni's II, 4.07 g, 7.72 mmol), and Cu(I)SCN (63 mg, 0.515 mmol) in DMF (43 mL) was stirred for 3 days at 50° C. After cooling to RT, the reaction mixture was diluted with Et$_2$O, filtered, and the filter pad was washed with Et$_2$O (150 mL). The organic layer was washed with sat. aq. NaHCO$_3$ (2×150 mL), dried over MgSO4, filtered, and the volatiles were removed under reduced pressure. The residue was purified by silica chromatography (0 to 30% gradient of EtOAc/heptane) to give (2R,3S)-benzyl 3-methyl-1-oxo-2-(trifluoromethyl)-8-azaspiro[4.5]decane-8-carboxylate (1.52 g, 4.12 mmol) as a clear oil. $^1$H NMR (400 MHz, chloroform-d) δ ppm 7.30-7.45 (m, 5H), 5.15 (s, 2H), 4.00 (dt, J=13.36, 4.99 Hz, 1H), 3.79 (dt, J=13.49, 4.93 Hz, 1H), 3.26-3.39 (m, 1H), 3.20 (ddd, J=13.49, 9.72, 3.64 Hz, 1H), 2.55-2.70 (m, 1H), 2.42-2.55 (m, 1H), 2.29 (dd, J=13.30, 6.53 Hz, 1H), 1.81-1.92 (m, 1H), 1.65 (ddd, J=13.49, 9.47, 3.89 Hz, 1H), 1.45-1.58 (m, 1H), 1.38 (br. d, J=12.30 Hz, 2H), 1.32 (d, J=6.27 Hz, 3H). $^{19}$F NMR (376 MHz) δ ppm −66.32 (br. d, J=7.76 Hz). MS m/z 370.2 (M+H)$^+$.

Step c: A mixture of O-methylhydroxylamine hydrochloride (2.896 g, 34.7 mmol), (2R,3S)-benzyl 3-methyl-1-oxo-2-(trifluoromethyl)-8-azaspiro[4.5]decane-8-carboxylate (854 mg, 2.312 mmol), and pyridine (3.74 mL, 46.2 mmol) in EtOH (7.5 mL) was stirred for 18 h at 90° C. After cooling to RT, the reaction mixture was poured into a separation funnel containing H$_2$O (60 mL) and sat. aq. CuSO$_4$ (60 mL) and it was extracted with Et$_2$O (3×120 mL). The combined organic phases were dried over MgSO4, filtered, and the volatiles were removed under reduced pressure. The residue was purified by silica chromatography (0 to 30% gradient of EtOAc/heptane) to give a mixture of the two E/Z stereoisomers of (2R,3S)-benzyl 1-(methoxyimino)-3-methyl-2-(trifluoromethyl)-8-azaspiro[4.5]decane-8-carboxylate (750 mg, 1.882 mmol) as a clear oil. MS m/z 399.1 (M+H)$^+$.

Step d: A suspension of Pd/C (10% wt., 68.8 mg) in MeOH (2 mL) was vigorously stirred at RT under H$_2$ atmosphere (balloon) for 5 min. To this suspension was added a solution of the E/Z isomers of (2R,3S)-benzyl 1-(methoxyimino)-3-methyl-2-(trifluoromethyl)-8-azaspiro[4.5]decane-8-carboxylate (515 mg, 1.293 mmol) in MeOH (4 mL), and the resulting mixture was vigorously stirred under H$_2$ atmosphere for 30 min. The reaction mixture was filtered through a pad of Celite, washed with DCM (70 mL). The filtrate was concentrated under reduced pressure to give a mixture of the E/Z isomers of (2R,3S)-3-methyl-2-(trifluoromethyl)-8-azaspiro[4.5]decan-1-one O-methyl oxime (351 mg, 1.275 mmol) as a clear oil. MS m/z 265.1 (M+H)$^+$.

Step e: A solution of a mixture of the E/Z isomers of (2R,3S)-3-methyl-2-(trifluoromethyl)-8-azaspiro[4.5]decan-1-one O-methyl oxime (210 mg, 0.795 mmol), Et$_3$N (0.886 mL, 6.36 mmol), and BnBr (0.378 mL, 3.18 mmol) in MeCN (1.5 mL) was stirred for 1.5 h at RT. The reaction mixture was poured into a separation funnel containing H$_2$O (25 mL) and sat. aq. NH$_4$Cl (25 mL) and was extracted with DCM (3×50 mL). The combined organic extracts were dried over MgSO$_4$, filtered, and the volatiles were removed under reduced pressure. The residue was purified by silica chromatography (0 to 50% gradient of EtOAc/heptane) to give a mixture of the E/Z isomers of (2R,3S)-8-benzyl-3-methyl-2-(trifluoromethyl)-8-azaspiro[4.5]decan-1-one O-methyl oxime (219 mg, 0.618 mmol) as a clear oil. MS m/z 355.2 (M+H)$^+$.

Step f: To a 0° C. solution of E/Z isomers of (2R,3S)-8-benzyl-3-methyl-2-(trifluoromethyl)-8-azaspiro[4.5]decan-1-one O-methyl oxime (150 mg, 0.423 mmol) in THF (1 mL) was added BH$_3$-THF complex (1 M in THF, 6.35 mL, 6.35 mmol) dropwise and the reaction mixture was allowed to warm to RT over 10 min, heated to 80° C., and stirred for 24 h at this temperature. After cooling to 0° C., the reaction mixture was carefully diluted with H$_2$O (5 mL). After the evolution of gas had stopped (5 min), the reaction mixture was allowed to warm to RT, aq. NaOH (2 M, 3 mL, 6 mmol) was added, and the reaction mixture was stirred for 2 h at 80° C. The reaction mixture was poured into a separation funnel containing aq. NaOH (1 M, 20 mL) and was extracted with DCM (3×20 mL). The combined organic extracts were dried over MgSO$_4$, filtered, and the volatiles were removed under reduced pressure. The residue was purified by HPLC (gradient elution 45-70% acetonitrile in water, 5 mM NH$_4$OH modifier) to give a mixture of the epimers of (2R,3S)-8-benzyl-3-methyl-2-(trifluoromethyl)-8-azaspiro[4.5]decan-1-amine (81 mg, 0.248 mmol) as an orange oil. MS m/z 327.1 (M+H)$^+$.

Step g: To a solution of the epimers of (2R,3S)-8-benzyl-3-methyl-2-(trifluoromethyl)-8-azaspiro[4.5]decan-1-amine (90.6 mg, 0.278 mmol) in MeOH (2 mL) under nitrogen atmosphere was added Pd/C (10% wt., 59.1 mg, 0.056 mmol). The reaction mixture was stirred vigorously under H$_2$ atmosphere (balloon) for 26 h. The reaction mixture was diluted with DCM, filtered over Celite, and the pad was washed with DCM (100 mL). The volatiles were removed under reduced pressure to give a mixture of epimers of (2R,3S)-3-methyl-2-(trifluoromethyl)-8-azaspiro[4.5]decan-1-amine (68 mg, 0.276 mmol) as a brown oil. MS m/z 237.2 (M+H)$^+$.

Intermediate B-29

2,8-diazaspiro[4.5]dec-1-en-1-amine Hydrochloride

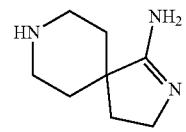

Step a: To a solution of tert-butyl 2-oxo-1,8-diazaspiro[4.5]decane-8-carboxylate (300 mg, 1.180 mmol) in DCM (3 mL) at RT was added phosphorus pentasulfide (110 mg, 0.495 mmol) followed by hexamethyldisiloxane (2.26 mL, 10.6 mmol). The reaction was stirred for 3 h at RT then diluted with EtOAc and filtered through Celite. The filtrate was concentrated under reduced pressure. Crude product was purified by silica chromatography (0 to 80% gradient of EtOAc/heptane) giving tert-butyl 1-thioxo-2,8-diazaspiro[4.5]decane-8-carboxylate (0.290 g, 1.07 mmol) as a white solid. $^1$H NMR (400 MHz, DMSO-d$_6$) δ ppm 10.39 (s, 1H), 3.66 (dt, J=13.6, 4.9 Hz, 2H), 3.09 (s, 2H), 2.78 (t, J=7.8 Hz, 2H), 1.95 (t, J=7.8 Hz, 2H), 1.57 (dd, J=6.6, 4.8 Hz, 4H), 1.39 (s, 9H). MS m/z 271 (M+H)$^+$.

Step b: To a solution of 1-thioxo-2,8-diazaspiro[4.5]decane-8-carboxylate (100 mg, 0.370 mmol) in THF (3 mL) was added dropwise iodomethane (0.231 mL, 3.70 mmol). The resulting solution was stirred for 16 h at RT. The reaction the mixture slowly became more yellow in color and resulted in a light yellow precipitate after stirring the allotted reaction time. The reaction mixture was concentrated and dried under vacuum giving a yellow solid. The yellow solid was taken up in MeOH (2 mL), treated with ammonia (7 M solution in MeOH, 3 mL) and heated in a sealed tube for 8 h to 100° C. The reaction was cooled to RT and concentrated under reduced pressure providing a solid that was sonicated with MeCN and filtered. The filtrate was concentrated under reduced pressure and the residue was purified by silica chromatography (0 to 30% gradient of MeOH/DCM) providing tert-butyl 1-amino-2,8-diazaspiro[4.5]dec-1-ene-8-carboxylate (87 mg, 0.343 mmol). $^1$H NMR (400 MHz, DMSO-d$_6$) δ ppm 9.38 (s, 1H), 8.81 (d, J=25.2 Hz, 2H), 3.98 (s, 2H), 3.55 (t, J=7.0 Hz, 2H), 2.82 (s, 2H), 2.12 (t, J=7.1 Hz, 2H), 1.74 (td, J=12.9, 4.7 Hz, 2H), 1.57 (d, J=12.7 Hz, 2H), 1.41 (s, 9H). MS m/z 254 (M+H)$^+$.

Step c: To a solution of tert-butyl 1-amino-2,8-diazaspiro[4.5]dec-1-ene-8-carboxylate (86 mg, 0.339 mmol) in DCM (3 mL) was added HCl (4 M solution in dioxane, 0.5 mL, 2.0 mmol) at RT and the reaction stirred for 16 h. The reaction mixture was concentrated and residue was triturated from MeCN and filtered giving 2,8-diazaspiro[4.5]dec-1-en-1-amine (57.7 mg, 0.254 mmol) as a tan solid. $^1$H NMR (400 MHz, DMSO-d$_6$) δ ppm 9.64 (s, 1H), 9.39-9.23 (m, 1H), 9.15 (s, 1H), 9.07 (s, 1H), 8.70 (d, J=12.5 Hz, 1H), 3.54 (t, J=6.9 Hz, 2H), 3.32 (d, J=13.3 Hz, 2H), 3.05-2.88 (m, 2H), 2.18 (t, J=6.9 Hz, 2H), 2.01 (td, J=13.7, 4.3 Hz, 2H), 1.80 (d, J=13.8 Hz, 2H). MS m/z 154 (M+H)$^+$.

Intermediate B-30

(4R)-4-amino-2-methyl-8-azaspiro[4.5]decan-2-ol

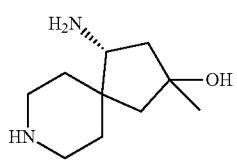

Step a: A mixture of (2R,4R)-4-amino-8-azaspiro[4.5]decan-2-ol dihydrochloride salt (623 mg, 2.56 mmol), Na$_2$CO$_3$ (1.36 g, 12.80 mmol), and benzyl chloroformate (1.05 g, 6.14 mmol) in H$_2$O (5 mL) was stirred vigorously for 30 min at RT. THF (0.5 mL) was added and the resulting mixture was stirred for 18 h at RT. The mixture was diluted with water and DCM. The separated aq. layer was extracted with DCM (2×10 mL). The combined organic phases were dried over Na$_2$SO$_4$, filtered, and concentrated under reduced pressure. The resulting residue was purified by silica chromatography (0 to 100% gradient of EtOAc/heptane) to give (1R,3R)-benzyl 1-(((benzyloxy)carbonyl)amino)-3-hydroxy-8-azaspiro[4.5]decane-8-carboxylate (940 mg, 2.14 mmol) as a white foam. MS m/z 439.3 (M+H)$^+$.

Step b: A mixture of (1R,3R)-benzyl 1-(((benzyloxy)carbonyl)amino)-3-hydroxy-8-azaspiro[4.5]decane-8-carboxylate (440 mg, 1.003 mmol) and Dess-Martin periodinane (638 mg, 1.505 mmol) in DCM (6 mL) was stirred for 1 h at 0° C. and for 18 h at RT. The reaction mixture was diluted with sat. aq. NaHCO$_3$/Na$_2$S$_2$O$_3$ (1:1, 25 mL). The separated aq. phase was extracted with DCM (3×15 mL). The combined organic phases were washed with brine, dried over MgSO$_4$, filtered, and concentrated under reduced pressure. The resulting residue was purified by silica chromatography (0 to 70% gradient of EtOAc/heptane) to give (R)-benzyl 1-(((benzyloxy)carbonyl)amino)-3-oxo-8-azaspiro[4.5]decane-8-carboxylate (415 mg, 0.951 mmol) as a white foam. MS m/z 437.2 (M+H)$^+$.

Step c: To a solution of MeLi (1.2 M in THF, 2.61 mL, 3.13 mmol) in THF (15 mL) was added dropwise (R)-benzyl 1-(((benzyloxy)carbonyl)amino)-3-oxo-8-azaspiro[4.5]decane-8-carboxylate (415 mg, 0.951 mmol) in THF (5 mL) at −30 to −40° C. The resulting mixture was stirred for 20 min at −30 to −40° C. The mixture was diluted with NaHSO$_4$ (10% solution in H$_2$O) and EtOAc, and allowed to warm up to RT under vigorously stirring. The mixture was poured into a separation funnel containing sat. aq. NaHCO$_3$ and the phases were separated. The aq. phase was further extracted with EtOAc (15 mL), the combined organic phases were dried over Na$_2$SO$_4$, filtered, and concentrated under reduced pressure. A solution of the resulting residue (313 mg), Na$_2$CO$_3$ (498 mg, 4.70 mmol), and benzyl chloroformate (295 mg, 1.729 mmol) in water (10 mL) and THF (1 mL) was vigorously stirred for 3 days at RT. The mixture was diluted with EtOAc and the separated aq. phase was extracted with EtOAc (3×15 mL). The combined organic phases were concentrated under reduced pressure. The resulting residue was purified by silica chromatography (0 to 50% gradient of EtOAc/heptane) to give two diastereomers: diastereomer A (112 mg, 0.25 mmol) as a colorless semi-solid, MS m/z 453.3 (M+H)$^+$, and diastereomer B (45 mg, 0.010 mmol) as white foam, MS m/z 453.3 (M+H)$^+$.

Step d: A mixture of diastereomer A (50 mg, 0.11 mmol) and Pd/C (10 wt. %; 12 mg, 0.011 mmol) in MeOH (8 mL) was stirred vigorously under hydrogen atmosphere for 2 h. Celite was added and the mixture was filtered through a pad of Celite, followed by DCM wash. The filtrate was concentrated under reduced pressure to give (4R)-4-amino-2-methyl-8-azaspiro[4.5]decan-2-ol as a colorless solid which was used without further purification. MS m/z 185.2 (M+H)$^+$.

The corresponding stereoisomer was synthesized using the above procedure or modifications to the above procedure using diastereomer B as starting material.

Intermediate B-31

2-((1S,2S,3R)-2-fluoro-3-methyl-8-azaspiro[4.5]decan-1-yl)isoindoline-1,3-dione

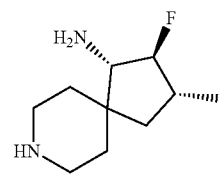

Step a: To a solution of benzyl (1R,2S,3R)-2-fluoro-1-hydroxy-3-methyl-8-azaspiro[4.5]decane-8-carboxylate (760 mg, 2.365 mmol) in THF (16.5 mL) was added triphenylphosphine (744 mg, 2.85 mmol) and DIAD (0.557 mL, 2.84 mmol). The resulting mixture was stirred at 0° C. for 20 min and diphenyl phosphorazidate (0.787 mL, 3.55 mmol) was added. The reaction mixture was warmed up to RT and stirred for 18 h at this temperature. The reaction mixture was poured into a separation funnel containing EtOAc (30 mL) and the organic phase was washed with sat. aq NH$_4$Cl and brine. The combined organic phases were dried over MgSO$_4$, filtered, and the volatiles were removed under reduced pressure. The resulting residue was purified by silica chromatography (0 to 50% gradient of EtOAc/heptane) to give benzyl (1S,2S,3R)-1-azido-2-fluoro-3-methyl-8-azaspiro[4.5]decane-8-carboxylate (432 mg, 1.247 mmol). MS m/z 347.2 (M+H)$^+$. $^1$H NMR (400 MHz, Chloroform-d) δ ppm 7.43-7.31 (m, 5H), 5.15 (s, 2H), 4.48 (dt, J=54.4, 7.5 Hz, 1H), 3.93 (s, 2H), 3.61 (dd, J=16.1, 6.9 Hz, 1H), 3.13-2.95 (m, 2H), 2.31-2.13 (m, 1H), 1.96 (dd, J=13.1, 9.3 Hz, 1H), 1.81-1.64 (m, 2H), 1.47 (s, 1H), 1.32-1.19 (m, 2H), 1.16 (d, J=6.7 Hz, 3H).

Step b: A suspension of Pd/C (10% wt., 65 mg) and benzyl (1S,2S,3R)-1-azido-2-fluoro-3-methyl-8-azaspiro[4.5]decane-8-carboxylate (423 mg, 1.221 mmol) in EtOH (12.2 mL) was stirred vigorously under H$_2$ atmosphere (balloon) for 16 h. The reaction mixture was filtered through a pad of Celite and the volatiles were removed under reduced pressure to give crude (1 S,2S,3R)-2-fluoro-3-methyl-8-azaspiro[4.5]decan-1-amine (235 mg, 0.966 mmol) which was used without further purification. MS m/z 317.2 (M+H)$^+$. $^1$H NMR (400 MHz, Chloroform-d) δ ppm 4.15 (dt, J=55.5, 8.1 Hz, 1H), 2.95 (dt, J=12.5, 3.7 Hz, 2H), 2.87 (dd, J=16.6, 8.0 Hz, 1H), 2.74 (tdd, J=12.4, 7.3, 2.8 Hz, 2H), 2.19-2.02 (m, 1H), 1.95 (dd, J=13.4, 8.4 Hz, 1H), 1.71-1.48 (m, 4H), 1.34-1.23 (m, 3H), 1.18-1.09 (m, 4H).

Intermediate B-32

Racemic (1S,2S,3S)-1-amino-8-azaspiro[4.5]decane-2,3-diol Trifluoroacetic Acid Salt

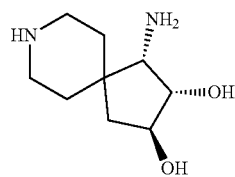 [SMILES: N[C@@H]1[C@H](O)[C@@H](O)CC12CCNCC2]

To a solution of racemic (1S,2S,3S)-tert-butyl 1-((tert-butoxycarbonyl)amino)-2,3-dihydroxy-8-azaspiro[4.5]decane-8-carboxylate (21 mg, 0.054 mmol) in DCM (1 mL) was added trifluoroacetic acid (0.1 mL, 1.298 mmol) and the mixture was stirred for 30 min at 30° C. The volatiles were removed under reduced pressure to afford crude racemic (1S,2S,3S)-1-amino-8-azaspiro[4.5]decane-2,3-diol trifluoroacetic acid salt (single diastereomer) as a clear oil which was directly used without further purification. MS m/z 187.1 (M+H)$^+$.

Intermediate B-33

(3S,4S)-3-methyl-2-oxa-8-azaspiro[4.5]decan-4-amine

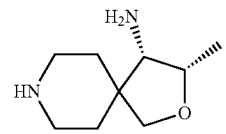

To (3S,4S)-tert-butyl 4-((R)-1,1-dimethyl ethylsulfinamino)-3-methyl-2-oxa-8-azaspiro[4.5]decane-8-carboxylate (9.4 g, 25.1 mmol) in MeOH (200 mL) under N$_2$ atm. was slowly added HCl (4 M solution in dioxane, 35 mL, 140 mmol). The reaction mixture was heated for 40 min at 50° C. and stirring was continued under flow of N$_2$ for 18 h. The reaction mixture was concentrated under reduced pressure. The residue was diluted with MeOH and MeCN, and concentrated under reduced pressure. The residue was triturated from MeCN under sonication. Filtration of solids and drying in high vacuo provided (3S,4S)-3-methyl-2-oxa-8-azaspiro[4.5]decan-4-amine hydrochloride salt as a white powder.

(3R,4R)-3-methyl-2-oxa-8-azaspiro[4.5]decan-4-amine hydrochloride salt was prepared following the procedures as described for (3S,4S)-3-methyl-2-oxa-8-azaspiro[4.5]decan-4-amine hydrochloride salt starting with (R)-2-((tert-butyldimethylsilyl)oxy)propanal and using (S)-tert-butylsulfinamide.

Intermediate B-34

(R)-2-methyl-N—((R)-8-azaspiro[4.5]decan-1-yl)propane-2-sulfinamide

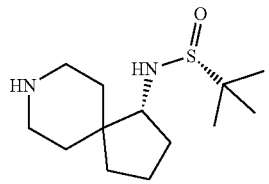 [SMILES: CC(C)(C)[S@@](=O)N[C@@H]1CCCC12CCNCC2]

To a stirring solution of (R)-tert-butyl 1-((R)-1,1-dimethylethylsulfinamino)-8-azaspiro[4.5]decane-8-carboxylate (1 g, 2.79 mmol) in dioxane (14 mL) under ice bath cooling was slowly added sulfuric acid (0.623 mL, 11.2 mmol). The reaction mixture was stirred for 1 h at RT and diluted with aq. NaOH until pH=12. The mixture was extracted with DCM (3×30 mL). The combined organic layers were passed through a phase separator for the removal of residual water and concentrated under reduced pressure providing crude (R)-2-methyl-N—((R)-8-azaspiro[4.5]decan-1-yl)propane-2-sulfinamide (642 mg) which was directly used without further purification.

Intermediate B-35

(1R,3R)-3-methyl-8-azaspiro[4.5]decan-1-amine

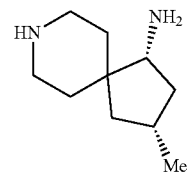 [SMILES: C[C@H]1C[C@@H](N)C2(CCNCC2)C1]

A mixture of (1R,3R)-benzyl 1-((R)-1,1-dimethylethylsulfinamino)-3-methyl-8-azaspiro[4.5]decane-8-carboxylate (182 mg, 0.448 mmol) and HCl (4 M solution in dioxane, 6.7 mL) in MeOH (2.5 mL) under nitrogen atm. was radiated for 23 h at 140° C. in the MW. The mixture was concentrated under reduced pressure. The residue was suspended in Et$_2$O (10 mL). The clear solution was removed and the remaining solids were dried under reduced pressure providing crude (1R,3R)-3-methyl-8-azaspiro[4.5]decan-1-amine hydrochloride salt (126 mg) as a grey cream solid.

(1R,3S)-3-methyl-8-azaspiro[4.5]decan-1-amine dihydrochloride was synthesized using the above procedure or modifications to the above procedure using (1R,3S)-benzyl 1-((R)-1,1-dimethylethylsulfinamino)-3-methyl-8-azaspiro[4.5]decane-8-carboxylate as starting material.

Intermediate B-36

(R)-8-azaspiro[4.5]decan-1-amine

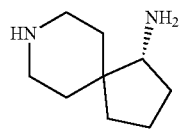

To a solution of (1R)-tert-butyl 1-(1,1-dimethylethylsulfinamino)-8-azaspiro[4.5]decane-8-carboxylate (4.66 g, 13 mmol) in MeOH (10 mL) was added HCl (4 M in dioxane, 32.5 mL, 130 mmol). The mixture was stirred for 1 h at 50° C. The volatiles were removed under reduced pressure, the residue was suspended in toluene (5 mL) and Et$_2$O (10 mL) and the mixture was concentrated under reduced pressure providing crude (R)-8-azaspiro[4.5]decan-1-amine hydrochloride salt which was directly used without further purification. MS m/z 155.1 (M+H)$^+$.

The following compounds of Table 7 were synthesized using the above procedure or modifications to the above procedure using the corresponding protected amines.

TABLE 7

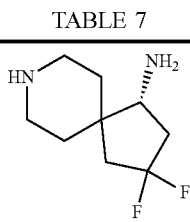

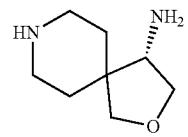 [SMILES: N[C@@H]1COCC12CCNCC2]

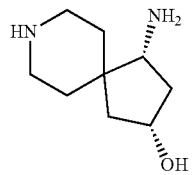 [SMILES: N[C@@H]1C[C@H](O)CC12CCNCC2]

TABLE 7-continued

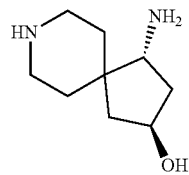 [SMILES: N[C@@H]1C[C@@H](O)CC12CCNCC2]

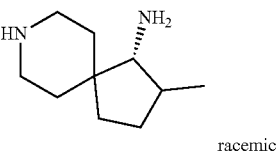

racemic

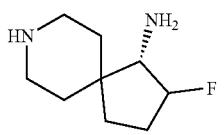

racemic

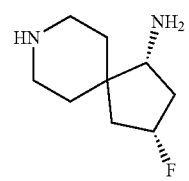 [SMILES: N[C@@H]1C[C@H](F)CC12CCNCC2]

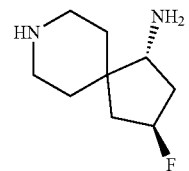 [SMILES: N[C@@H]1C[C@@H](F)CC12CCNCC2]

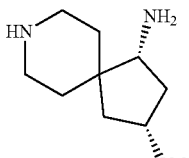

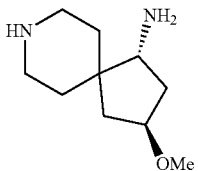 [SMILES: CO[C@@H]1C[C@@H](N)C2(CCNCC2)C1]

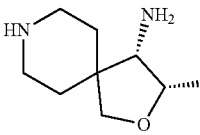

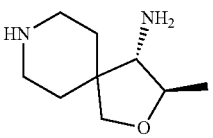

TABLE 7-continued

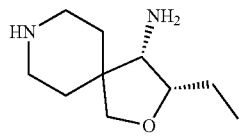

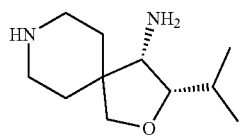

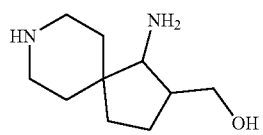

Intermediate R-1

Tert-butyl ((1-(4-amino-5-iodo-1-methyl-6-oxo-1,6-dihydropyrimidin-2-yl)-4-methylpiperidin-4-yl)methyl)carbamate

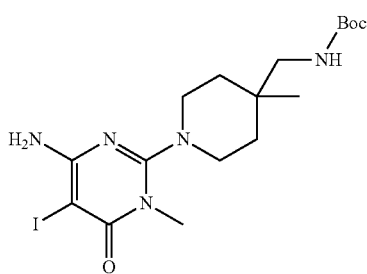 [SMILES: Cn1c(N2CCC(C)(CNC(=O)OC(C)(C)C)CC2)nc(N)c(I)c1=O]

Step a: A mixture of 6-amino-3-methylpyrimidine-2,4 (1H,3H)-dione (1.0 g, 7.09 mmol), tert-butyl ((4-methylpiperidin-4-yl)methyl)carbamate (1.78 g, 7.79 mmol), BOP (6.27 g, 14.17 mmol), and DBU (5.34 mL, 35.4 mmol) in DMF (15 mL) was stirred for 2 h at RT. The resulting mixture was poured into a separation funnel containing sat. aq. NH$_4$Cl (25 mL), water (25 mL) and was extracted with Et$_2$O (3×15 mL) and DCM (3×15 mL). The combined organic phases were dried over MgSO$_4$, filtered, the volatiles were removed under reduced pressure, and the residue was purified by silica chromatography (0 to 10% gradient of MeOH/DCM) to give tert-butyl ((1-(4-amino-1-methyl-6-oxo-1,6-dihydropyrimidin-2-yl)-4-methylpiperidin-4-yl)methyl)carbamate (3.6 g; impure) as a light yellow solid. MS m/z 351.9 (M+H)$^+$. This compound was used in next step without further purification.

Step b: A mixture of crude tert-butyl ((1-(4-amino-1-methyl-6-oxo-1,6-dihydropyrimidin-2-yl)-4-methylpiperidin-4-yl)methyl)carbamate (theoric 7.09 mmol) and NIS (1.76 g, 7.80 mmol) in DMF (14 mL) was stirred for 1 h at RT. The resulting mixture was poured into a separation funnel containing sat. aq. Na$_2$S$_2$O$_3$ (25 mL), sat. aq. NH$_4$Cl (25 mL), and water (25 mL) and was extracted with EtOAc (3×15 mL). The combined organic phases were dried over MgSO$_4$, filtered, the volatiles were removed under reduced pressure, and the residue was purified by silica chromatography (0 to 10% gradient of MeOH/DCM) to give tert-butyl ((1-(4-amino-5-iodo-1-methyl-6-oxo-1,6-dihydropyrimidin-2-yl)-4-methylpiperidin-4-yl)methyl)carbamate impure (2.54 g). MS m/z 478.2 (M+H)$^+$. This compound was used in next step without further purification.

Intermediate R-2

Tert-butyl ((3S,4S)-8-(4-amino-5-iodo-1-methyl-6-oxo-1,6-dihydropyrimidin-2-yl)-3-methyl-2-oxa-8-azaspiro[4.5]decan-4-yl)carbamate

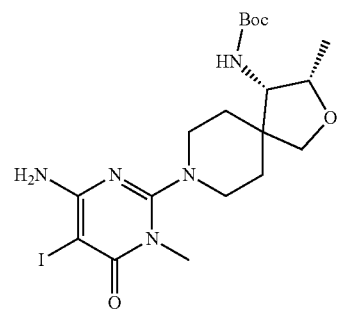

Step a: A mixture of 6-amino-3-methylpyrimidine-2,4 (1H,3H)-dione (1 g, 7.09 mmol), (3S,4S)-3-methyl-2-oxa-8-azaspiro[4.5]decan-4-amine (1.81 g, 7.44 mmol), BOP (6.27 g, 14.17 mmol), and DBU (7.48 mL, 49.6 mmol) in DMF (15 mL) was stirred for 60 h at RT. The resulting mixture was purified by HPLC (gradient elution 2-12% MeCN in water, 5 mM NH$_4$OH modifier) to give 6-amino-2-((3S,4S)-4-amino-3-methyl-2-oxa-8-azaspiro[4.5]decan-8-yl)-3-methylpyrimidin-4(3H)-one (2.08 g, 7.09 mmol). MS m/z 294.3 (M+H)$^+$.

Step b: A mixture 6-amino-2-((3S,4S)-4-amino-3-methyl-2-oxa-8-azaspiro[4.5]decan-8-yl)-3-methylpyrimidin-4 (3H)-one (2.08 g, 7.09 mmol), Boc$_2$O (1.55 g, 7.09 mmol), and DIPEA (2.5 mL, 14.18 mmol) in DMF (14 mL) was stirred for 1 h at RT. The resulting mixture was poured into a separation funnel containing sat. aq. NH$_4$Cl (75 mL) and it was extracted with DCM (3×15 mL). The combined organic phases were dried over MgSO$_4$, filtered, and the volatiles were removed under reduced pressure to give tert-butyl ((3S,4S)-8-(4-amino-1-methyl-6-oxo-1,6-dihydropyrimidin-2-yl)-3-methyl-2-oxa-8-azaspiro[4.5]decan-4-yl)carbamate (2.79 g, 7.09 mmol). MS m/z 394.4 (M+H)$^+$. This compound was used in next step without further purification.

Step c: A mixture of tert-butyl ((3S,4S)-8-(4-amino-1-methyl-6-oxo-1,6-dihydropyrimidin-2-yl)-3-methyl-2-oxa-8-azaspiro[4.5]decan-4-yl)carbamate (2.79 g, 7.09 mmol) and NIS (1.76 g, 7.80 mmol) in DMF (14 mL) was stirred for 1 h at RT. The resulting mixture was poured into a separation funnel containing sat. aq. Na$_2$S$_2$O$_3$ (25 mL), sat. aq. NH$_4$Cl (25 mL), and water (25 mL) and was extracted with DCM (3×20 mL). The combined organic phases were dried over MgSO$_4$, filtered, the volatiles were removed under reduced pressure, and the residue was purified by silica chromatography (0 to 5% gradient of MeOH/DCM) to give tert-butyl ((3S,4S)-8-(4-amino-5-iodo-1-methyl-6-oxo-1,6-dihydropyrimidin-2-yl)-3-methyl-2-oxa-8-azaspiro[4.5]decan-4-yl)carbamate (1.51 g, 2.91 mmol). MS m/z 521.0 (M+H)$^+$.

The following compounds of Table 8 were synthesized using the above procedure or modifications to the above procedure using the corresponding starting materials and intermediates:
TABLE 8
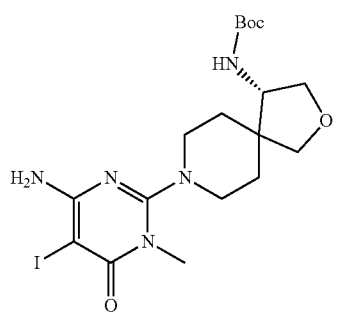 [SMILES: Cn1c(N2CCC3(CC2)COC[C@H]3NC(=O)OC(C)(C)C)nc(N)c(I)c1=O]
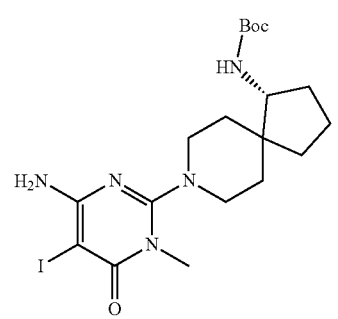 [SMILES: Cn1c(N2CCC3(CCC[C@H]3NC(=O)OC(C)(C)C)CC2)nc(N)c(I)c1=O]
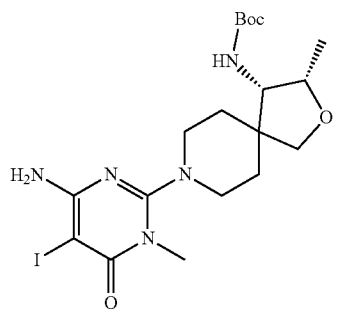 [SMILES: C[C@@H]1OCC2(CCN(c3nc(N)c(I)c(=O)n3C)CC2)[C@@H]1NC(=O)OC(C)(C)C]
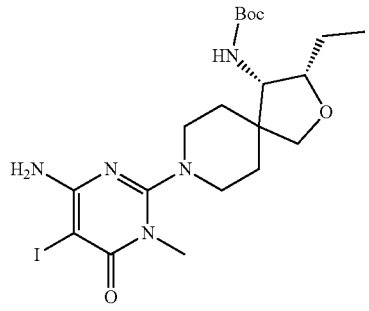 [SMILES: CC[C@@H]1OCC2(CCN(c3nc(N)c(I)c(=O)n3C)CC2)[C@@H]1NC(=O)OC(C)(C)C]
TABLE 8-continued
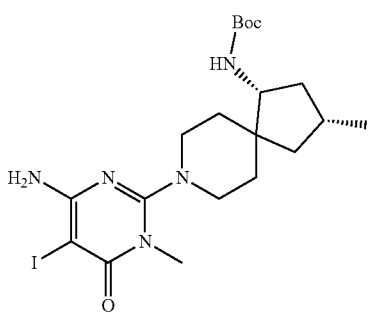 [SMILES: C[C@H]1C[C@@H](NC(=O)OC(C)(C)C)C2(CCN(c3nc(N)c(I)c(=O)n3C)CC2)C1]
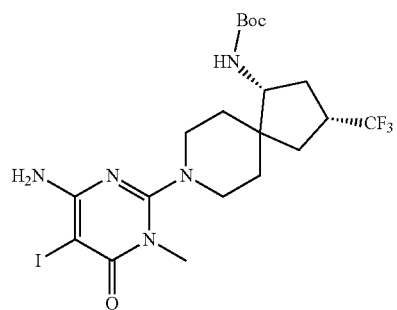 [SMILES: Cn1c(N2CCC3(CC2)C[C@@H](C(F)(F)F)C[C@H]3NC(=O)OC(C)(C)C)nc(N)c(I)c1=O]
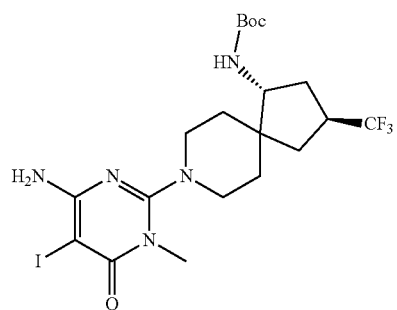 [SMILES: Cn1c(N2CCC3(CC2)C[C@H](C(F)(F)F)C[C@H]3NC(=O)OC(C)(C)C)nc(N)c(I)c1=O]
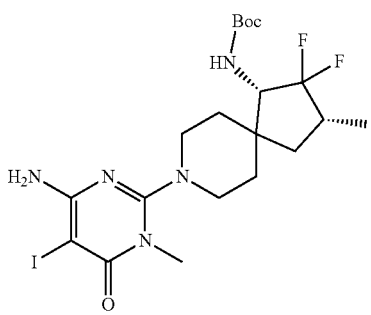 [SMILES: C[C@@H]1CC2(CCN(c3nc(N)c(I)c(=O)n3C)CC2)[C@H](NC(=O)OC(C)(C)C)C1(F)F]
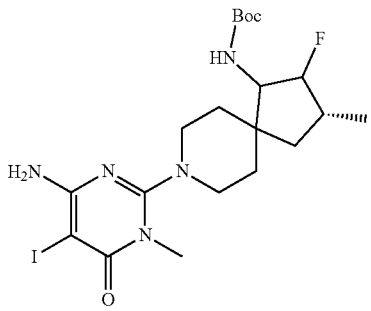 [SMILES: C[C@@H]1CC2(CCN(c3nc(N)c(I)c(=O)n3C)CC2)C(NC(=O)OC(C)(C)C)C1F]

TABLE 8-continued

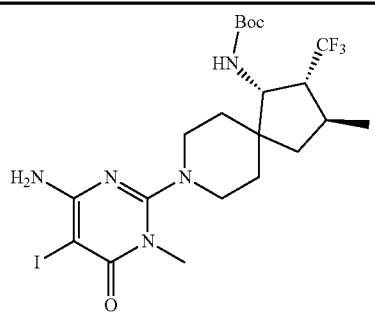

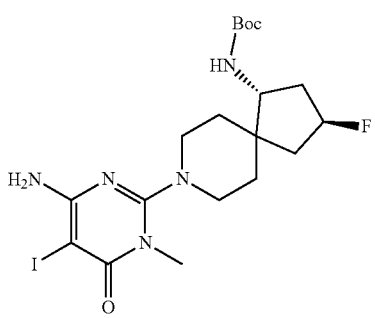 [SMILES: Cn1c(N2CCC3(CC2)C[C@H](F)C[C@H]3NC(=O)OC(C)(C)C)nc(N)c(I)c1=O]

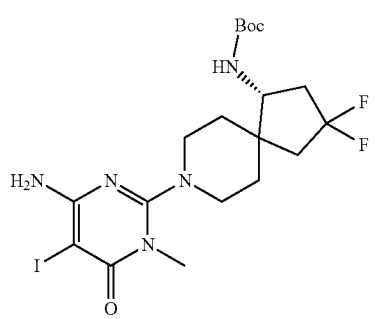 [SMILES: Cn1c(N2CCC3(CC2)CC(F)(F)C[C@H]3NC(=O)OC(C)(C)C)nc(N)c(I)c1=O]

Intermediate R-3

Tert-butyl ((1-(5-iodo-1-methyl-6-oxo-1,6-dihydropyrimidin-2-yl)-4-methylpiperidin-4-yl)methyl)carbamate

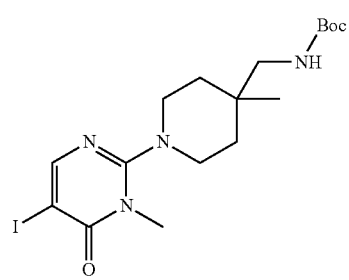 [SMILES: Cn1c(N2CCC(C)(CNC(=O)OC(C)(C)C)CC2)ncc(I)c1=O]

Step a: A mixture of 2,4-dichloro-5-iodopyrimidine (1 g, 3.64 mmol) and aq. NaOH (2 M, 2.73 mL, 5.46 mmol) in THF (4 mL) was stirred for 90 h at RT. The mixture was acidified to pH 1 using aq. HCl (1 M). The aqeuous layer was extracted with EtOAc (2×). The combined organic layer was treated with MgSO₄, filtered, and the volatiles were removed under reduced pressure. The residue was purified by silica chromatography (0% to 10% gradient of MeOH/DCM) to give 2-chloro-5-iodopyrimidin-4(3H)-one (195 mg, 0.760 mmol) as light yellow solid. $^1$H NMR (400 MHz, Methanol-d₄) δ ppm 8.46 (s, 1H). MS m/z 256.7 (M+H)⁺.

Step b: To a solution of 2-chloro-5-iodopyrimidin-4(3H)-one (1 g, 3.90 mmol) in DMF (39 mL) was added dropwise LDA (2.5 M in THF/heptane/ethylbenzene, 2.92 mL, 5.85 mmol) at 0° C. The mixture was stirred at 0° C. for 5 min. Methyl iodide (364 μL, 5.85 mmol) was added and the mixture was allowed to warm up to RT and stirred at this temperature for 18 h. The mixture was carefully diluted with water (20 mL). The aqueous layer was extracted with EtOAc (2×). The combined organic layer was washed with sat. aq. NH₄Cl solution (2×) followed by brine. The organic layer was treated with MgSO₄, filtered, and the volatiles were removed under reduced pressure. The residue material was purified by silica chromatography (20 to 70% gradient of EtOAc/heptane) to give 2-chloro-5-iodo-3-methylpyrimidin-4(3H)-one (663 mg) as a light brown solid. $^1$H NMR (400 MHz, DMSO-d₆) δ ppm 8.33 (s, 1H), 3.58 (s, 3H). MS m/z 270.8 (M+H)⁺.

Step c: A mixture of 2-chloro-5-iodo-3-methylpyrimidin-4(3H)-one (77.1 mg, 0.285 mmol), tert-butyl((4-methylpiperidin-4-yl)methyl)carbamate (78 mg, 0.342 mmol), and DIPEA (0.149 mL, 0.855 mmol) in DMF (1 mL) was radiated in the microwave reactor for 2 h at 120° C. After cooling to RT, the reaction mixture was diluted with EtOAc and it was washed with sat. aq. NH₄Cl solution (2×) followed by brine. The organic layer was dried over MgSO₄, filtered, and removed under reduced pressure. The residue was purified by silica chromatography (0 to 100% gradient of EtOAc/heptane) to give tert-butyl ((1-(5-iodo-1-methyl-6-oxo-1,6-dihydropyrimidin-2-yl)-4-methylpiperidin-4-yl)methyl)carbamate (76.9 mg) as a white solid. $^1$H NMR (400 MHz, Chloroform-d) δ ppm 8.17 (s, 1H), 4.68 (s, 1H), 3.54 (s, 3H), 3.48-3.39 (m, 2H), 3.35-3.22 (m, 2H), 1.71-1.57 (m, 2H), 1.57-1.39 (m, 11H), 1.34-1.21 (m, 2H), 1.03 (s, 3H). MS m/z 463.0 (M+H)⁺.

Intermediate R-4

Tert-butyl ((1-(5-bromo-4-methoxypyrimidin-2-yl)-4-methylpiperidin-4-yl)methyl)carbamate

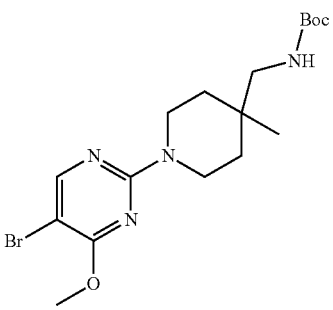 [SMILES: COc1nc(N2CCC(C)(CNC(=O)OC(C)(C)C)CC2)ncc1Br]

A mixture of 5-bromo-2-chloro-4-methoxypyrimidine (200 mg, 0.895 mmol) and tert-butyl ((4-methylpiperidin-4-yl)methyl)carbamate (225 mg, 0.985 mmol) in DMSO (3 mL) and DIPEA (1.49 mL) under N₂ atmosphere was heated to 120° C. for 2 h. The reaction mixture was allowed to cool to RT, diluted with EtOAc (50 mL), and washed with brine (50 mL). The separated aqueous layer was extracted with EtOAc (50 mL). The combined organic layers were dried over Na₂SO₄, filtered and concentrated under reduced pressure providing crude tert-butyl ((1-(5-bromo-4-methoxypyrimidin-2-yl)-4-methylpiperidin-4-yl)methyl)carbamate (424 mg) as a brown-orange solid, which was directly used without further purification. MS m/z 417.2 (M+H)$^+$.

Intermediate R-5

Tert-butyl ((1-(5-iodo-1-methyl-6-oxo-1,6-dihydropyridin-2-yl)-4-methylpiperidin-4-yl)methyl)carbamate

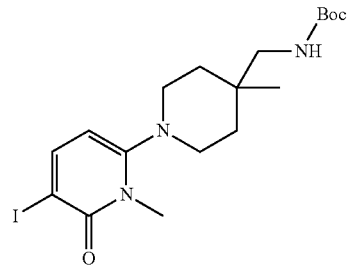 [SMILES: Cn1c(N2CCC(C)(CNC(=O)OC(C)(C)C)CC2)ccc(I)c1=O]

Step a: A mixture of 6-chloropyridin-2(1H)-one (500 mg, 3.86 mmol), K$_2$CO$_3$ (800 mg, 5.79 mmol), and methyl iodide (0.360 mL, 5.79 mmol) in EtOH (11.6 mL) was stirred for 18 h at 70° C. The reaction mixture was allowed to cool to RT, the volatiles were removed under reduced pressure and the residue was suspended in water. The aq. layer was extracted with EtOAc (2×). The combined organic layers were dried over MgSO$_4$, filtered, and the volatiles were removed under reduced pressure. The residue was purified by silica chromatography (0 to 10% gradient of MeOH/DCM) to give 6-chloro-1-methylpyridin-2(1H)-one (472 mg, 3.29 mmol). $^1$H NMR (400 MHz, DMSO-d$_6$) δ ppm 7.39 (dd, J=9.2, 7.3 Hz, 1H), 6.49 (dd, J=7.3, 1.2 Hz, 1H), 6.41 (dd, J=9.2, 1.1 Hz, 1H), 3.55 (s, 3H). MS m/z 144.0 (M+H)$^+$.

Step b: To a solution of 6-chloro-1-methylpyridin-2(1H)-one (55 mg, 0.383 mmol), DIPEA (200 µL, 1.15 mmol), and tert-butyl ((4-methylpiperidin-4-yl)methyl)carbamate (96 mg, 0.421 mmol) in DMF (1 mL) was radiated in a microwave reactor for 2 h at 140° C. After cooling to RT, the reaction mixture was diluted with EtOAc. The organic layer was washed with sat. aq. NH$_4$Cl (2×) followed by brine. The organic layer was dried over MgSO$_4$, filtered, and the volatiles were removed under reduced pressure. The residue was purified by silica chromatography (0 to 100% gradient of EtOAc/heptane) to give tert-butyl ((4-methyl-1-(1-methyl-6-oxo-1,6-dihydropyridin-2-yl)piperidin-4-yl)methyl)carbamate (53 mg, 0.158 mmol). $^1$H NMR (400 MHz, DMSO-d$_6$) δ ppm 7.33 (dd, J=8.9, 7.4 Hz, 1H), 6.94 (t, J=6.3 Hz, 1H), 6.10-6.04 (m, 1H), 3.35 (s, 3H), 2.95-2.85 (m, 4H), 2.77 (s, 2H), 1.56-1.47 (m, 2H), 1.42-1.30 (m, 11H), 0.89 (s, 3H). MS m/z 336.6 (M+H)$^+$ Step c: To a solution of tert-butyl ((4-methyl-1-(1-methyl-6-oxo-1,6-dihydropyridin-2-yl)piperidin-4-yl)methyl)carbamate (53 mg, 0.158 mmol) and NIS (41.2 mg, 0.174 mmol) in THF (2 mL) was stirred for 18 h at RT. The mixture was diluted with EtOAc. The organic layer was washed with twice with sat. aq. Na$_2$S$_2$O$_3$: sat. aq. NH$_4$Cl (1:1) followed by brine. The organic layer was dried over MgSO$_4$, filtered, and the volatiles were removed under reduced pressure. The residue was purified by silica chromatography (0 to 100% gradient of EtOAc/heptane) to give tert-butyl ((1-(5-iodo-1-methyl-6-oxo-1,6-dihydropyridin-2-yl)-4-methylpiperidin-4-yl)methyl)carbamate (34.4 mg, 0.075 mmol). $^1$H NMR (400 MHz, Chloroform-d) δ ppm 7.79 (d, J=7.8 Hz, 1H), 5.57 (d, J=7.9 Hz, 1H), 4.64 (s, 1H), 3.50 (s, 3H), 3.42 (s, 1H), 3.09-2.97 (m, 2H), 2.96-2.85 (m, 2H), 2.84-2.70 (m, 2H), 1.62-1.50 (m, 2H), 1.46-1.30 (m, 11H), 0.92 (s, 3H). MS m/z 462.0 (M+H)$^+$.

Intermediate R-6

Tert-butyl ((1-(5-iodo-4-((4-methoxybenzyl)oxy)pyrimidin-2-yl)-4-methylpiperidin-4-yl)methyl)carbamate

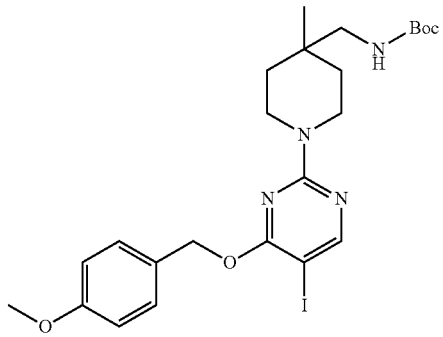 [SMILES: COc1ccc(COc2nc(N3CCC(C)(CNC(=O)OC(C)(C)C)CC3)ncc2I)cc1]

Step a: To a solution of 2-chloro-4-((4-methoxybenzyl)oxy)pyrimidine (118 mg, 0.519 mmol), prepared according to the methods in WO2011022440, in DMF (50 mL) was added tert-butyl ((4-methylpiperidin-4-yl)methyl)carbamate (130 mg, 0.519 mmol). The reaction stirred for 48 h and was diluted in EtOAc:water (1:1, 100 mL). The mixture was extracted with EtOAc (3×) and the combined organic extracts were washed with brine (3×), dried over MgSO$_4$, filtered, and concentrated under reduced pressure to afford crude tert-butyl ((1-(4-((4-methoxybenzyl)oxy)pyrimidin-2-yl)-4-methylpiperidin-4-yl)methyl)carbamate, as a yellow oil (202 mg) which was used without further purification. MS m/z 443 (M+H)$^+$.

Step b: To a solution of crude tert-butyl ((1-(4-((4-methoxybenzyl)oxy)pyrimidin-2-yl)-4-methylpiperidin-4-yl)methyl)carbamate (718 mg) in MeCN (50 mL) was added NIS (365 mg, 1.62 mmol) in one portion at RT. The reaction appeared orange in color, sat. aq. Na$_2$S$_2$O$_3$ (5 mL) was added and the reaction was concentrated to a clear solution. The mixture was diluted with DCM (100 mL) and sat. aq. Na$_2$S$_2$O$_3$ (100 mL). The separated aq. layer was extracted with DCM (3×). The combined organic extracts were washed with brine, dried over MgSO$_4$, filtered, and concentrated under reduced pressure to give tert-butyl ((1-(5-iodo-4-((4-methoxybenzyl)oxy)pyrimidin-2-yl)-4-methylpiperidin-4-yl)methyl)carbamate (800 mg, 1.41 mmol) as a white foam. MS m/z 569 (M+H)$^+$.

Intermediate R-7

Tert-butyl ((3S,4S)-8-(5-bromo-1,4-dimethyl-6-oxo-1,6-dihydropyrimidin-2-yl)-3-methyl-2-oxa-8-azaspiro[4.5]decan-4-yl)carbamate

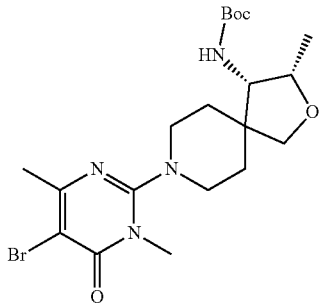 [SMILES: Cc1nc(N2CCC3(CC2)CO[C@@H](C)[C@H]3NC(=O)OC(C)(C)C)n(C)c(=O)c1Br]

Step a: To a mixture of 3,6-dimethylpyrimidine-2,4(1H,3H)-dione (0.5 g, 3.57 mmol) in AcOH (15 mL) was added dropwise bromine (0.230 mL, 4.46 mmol). The mixture was stirred for 1 h at RT. The reaction mixture was diluted with sat. aq. NaS$_2$O$_3$(5 mL), vigorously stirred for 5 min and further diluted with 0.1 M aq. NaOH (10 mL) and stirred for 15 min. The mixture was extracted with DCM (4×) and the combined organic layers were dried over Na$_2$SO$_4$, filtered off, and concentrated under reduced pressure. The residue was suspended in toluene (3 mL) and the mixture was concentrated and dried under reduced pressure providing crude 5-bromo-3,6-dimethylpyrimidine-2,4(1H,3H)-dione (720 mg) as a white solid which was directly used without further purification. MS m/z 221.0 (M+H)$^+$.

Step b: A mixture of 5-bromo-3,6-dimethylpyrimidine-2,4(1H,3H)-dione (0.3 g, 1.37 mmol), (3S,4S)-3-methyl-2-oxa-8-azaspiro[4.5]decan-4-amine bis-hydrochloride salt (0.350 g, 1.438 mmol), and BOP (1.212 g, 2.74 mmol) in DMF (3 mL) was stirred for ~10 min under N$_2$ atmosphere. DBU (1.445 mL, 9.59 mmol) was added and the reaction mixture was stirred overnight. The reaction mixture was diluted with water (3 mL) and ~3/4 of volatile components were removed under reduced pressure. The residue was diluted with brine and EtOAc and the separated aq. layer was extracted with EtOAc. The combined organic layers were washed with water and brine, dried over Na$_2$SO$_4$, filtered off, and concentrated under reduced pressure providing crude 2-((3S,4S)-4-amino-3-methyl-2-oxa-8-azaspiro[4.5]decan-8-yl)-5-bromo-3,6-dimethylpyrimidin-4(3H)-one (1.0 g) which was directly used without further purification. MS m/z 373.2 (M+H)$^+$.

Step c: To a solution of crude 2-((3S,4S)-4-amino-3-methyl-2-oxa-8-azaspiro[4.5]decan-8-yl)-5-bromo-3,6-dimethylpyrimidin-4(3H)-one (509 mg, 1.37 mmol) in DMF (5 mL) was added Boc$_2$O (0.35 mL, 1.51 mmol) and DIPEA (0.526 mL, 3.01 mmol). The mixture was stirred at RT and under N$_2$ atmosphere overnight. The reaction mixture was diluted with sat. aq. NaHCO$_3$ and EtOAc. The separated aq. layer was extracted with EtOAc. The combined organic layers were washed with water and brine, dried over Na$_2$SO$_4$, filtered, and concentrated under reduced pressure. The residue was purified by column chromatography (silica gel, 10 to 100% gradient of EtOAc/heptane) providing tert-butyl ((3S,4S)-8-(5-bromo-1,4-dimethyl-6-oxo-1,6-dihydropyrimidin-2-yl)-3-methyl-2-oxa-8-azaspiro[4.5]decan-4-yl)carbamate (200 mg) as a white fluffy solid. MS m/z 473.2 (M+H)$^+$.

Intermediate L-1

6-amino-5-((2,3-dichlorophenyl)thio)-3-methylpyrimidine-2,4(1H,3H)-dione

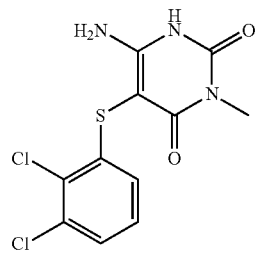 [SMILES: Cn1c(=O)[nH]c(N)c(Sc2cccc(Cl)c2Cl)c1=O]

Step a: A mixture of 6-amino-3-methylpyrimidine-2,4(1H,3H)-dione (1.0 g, 7.09 mmol) and NBS (1.58 g, 8.86 mmol) in DMF (5 mL) was stirred for 16 h at RT. The resulting mixture was diluted with water (20 mL) and the solid formed was filtered followed by water (2×5 mL) wash, to give 6-amino-5-bromo-3-methylpyrimidine-2,4(1H,3H)-dione (1.1 g, 5.0 mmol) as an off white solid. MS m/z 222.1 (M+H)$^+$.

Step b: A mixture of 6-amino-5-bromo-3-methylpyrimidine-2,4(1H,3H)-dione (200 mg, 0.909 mmol), 2,3-dichlorobenzenethiol (326 mg, 1.818 mmol), Cu(I)I (34.6 mg, 0.182 mmol), TMEDA (55 μL, 0.364 mmol), and K$_3$PO$_4$ (579 mg, 2.73 mmol) in dioxane (2 mL) was stirred for 20 h at 100° C. After cooling to RT, the reaction mixture was purified by HPLC (gradient elution 5-20% MeCN in water, 5 mM NH$_4$OH modifier) to give 6-amino-5-((2,3-dichlorophenyl)thio)-3-methylpyrimidine-2,4(1H,3H)-dione (120.0 mg, 0.377 mmol) as a white solid. MS m/z 318.2 (M+H)$^+$.

The following intermediate of Table 9 was made using the above procedure or modifications to the above procedure using the corresponding thiol:

TABLE 9

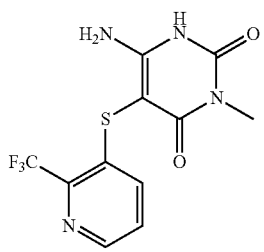 [SMILES: Cn1c(=O)[nH]c(N)c(Sc2cccnc2C(F)(F)F)c1=O]

Intermediate L-2

6-amino-5-((2-(trifluoromethyl)pyridin-3-yl)thio)-3-((2-(trimethylsilyl)ethoxy)methyl)pyrimidine-2,4(1H,3H)-dione

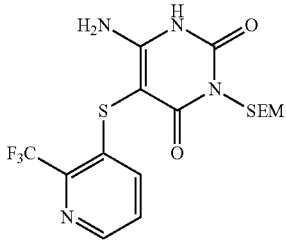 [SMILES: C[Si](C)(C)CCOCn1c(=O)[nH]c(N)c(Sc2cccnc2C(F)(F)F)c1=O]

Step a: A mixture of 6-aminouracil (1.0 g, 7.87 mmol) and ammonium sulfate (52 mg, 0.393 mmol) in hexamethyldisilazane (5 mL) was stirred for 16 h at 130° C. The reaction mixture was allowed to cool to RT, the precipitate was filtered off and the volatiles were removed under reduced pressure. The residue was dissolved in toluene (10 mL) and SEMCl (2.1 mL, 11.80 mmol) was added. The resulting mixture was stirred for 90 min at RT. The volatiles were removed under reduced pressure and the residue was purified by silica chromatography (0 to 15% gradient of MeOH/DCM) to give 6-amino-3-((2-(trimethylsilyl)ethoxy)methyl)pyrimidine-2,4(1H,3H)-dione (720 mg, 2.80 mmol). $^1$H NMR (400 MHz, DMSO-$d_6$) δ ppm 10.44 (s, 1H), 6.32 (br. s, 2H), 5.10 (s, 2H), 4.57 (d, J=2.02 Hz, 1H), 3.42-3.60 (m, 2H), 0.79-0.91 (m, 2H), 0.00 (m, 9H).

Step b: A mixture of 6-amino-3-((2-(trimethylsilyl)ethoxy)methyl)pyrimidine-2,4(1H,3H)-dione (720 mg, 2.80 mmol) and NBS (747 mg, 4.20 mmol) in DMF (5 mL) was stirred for 16 h at RT. The resulting mixture was diluted with water (20 mL) and the solid formed was filtered off followed by water (2×10 mL) wash, to give 6-amino-5-bromo-3-((2-(trimethylsilyl)ethoxy)methyl)pyrimidine-2,4(1H,3H)-dione (941 mg, 2.80 mmol). MS m/z 336.1 (M+H)$^+$.

Step c: A mixture of 6-amino-5-bromo-3-((2-(trimethylsilyl)ethoxy)methyl)-pyrimidine-2,4(1H,3H)-dione (941 mg, 2.80 mmol), Cu(I)I (57 mg, 0.297 mmol), TMEDA (90 μL, 0.595 mmol), and K$_3$PO$_4$ (947 mg, 4.46 mmol) in dioxane (5 mL) was stirred for 14 h at 100° C. After cooling to RT, the reaction mixture was purified by silica chromatography (0 to 10% gradient of MeOH/DCM) to give 6-amino-5-((2-(trifluoromethyl)pyridin-3-yl)thio)-3-((2-(trimethylsilyl)ethoxy)methyl)pyrimidine-2,4(1H,3H)-dione (400 mg, 0.921 mmol). $^1$H NMR (400 MHz, DMSO-$d_6$) δ ppm 10.98 (s, 1H), 8.47 (dd, J=4.29, 1.01 Hz, 1H), 7.45-7.65 (m, 2H), 6.91 (br. s, 2H), 5.18 (s, 2H), 3.42-3.71 (m, 2H), 0.75-1.01 (m, 2H), −0.02-0.02 (m, 9H). $^{19}$F NMR (376 MHz, DMSO-$d_6$) δ ppm −63.48.

Intermediate L-3

2-chloro-5-((2,3-dichlorophenyl)thio)-4-methoxypyrimidine

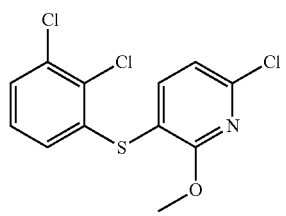 [SMILES: COc1nc(Cl)ccc1Sc1cccc(Cl)c1Cl]

Step a: A mixture of 6-chloro-3-iodo-2-methoxypyridine (100 mg, 0.371 mmol), 2,3-dichlorobenzenethiol (100 mg, 0.557 mmol), 1,10-phenanthroline (26.7 mg, 0.148 mmol), Cu(I)I (14.1 mg, 0.074 mmol), and Cs$_2$CO$_3$ (242 mg, 0.742 mmol) in dioxane (3 mL) was stirred for 1 h at 100° C. The reaction mixture was allowed to cool to RT and diluted with EtOAc and filtered through a pad of Celite. The organic layer was washed with sat. aq. NH$_4$Cl. The organic layer was dried over MgSO$_4$, filtered, and the volatiles were removed under reduced pressure. The residue was purified by silica chromatography (0 to 100% gradient of EtOAc/heptane) to give 2-chloro-5-((2,3-dichlorophenyl)thio)-4-methoxypyrimidine (81.6 mg, 0.255 mmol). $^1$H NMR (400 MHz, DMSO-$d_6$) δ ppm 7.75 (d, J=7.9 Hz, 1H), 7.56 (dd, J=8.0, 1.4 Hz, 1H), 7.30 (t, J=8.0 Hz, 1H), 7.22 (s, 1H), 6.94 (dd, J=8.0, 1.2 Hz, 1H), 3.89 (s, 3H). MS m/z 322.0 (M+H)$^+$.

Intermediate L-4

4-amino-6-fluoro-3-((2-(trifluoromethyl)pyridin-3-yl)thio)pyridin-2(1H)-one

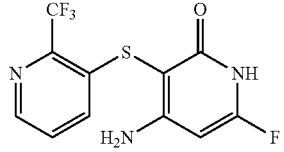 [SMILES: Nc1cc(F)[nH]c(=O)c1Sc1cccnc1C(F)(F)F]

Step a: To a 0° C. solution of 4-amino-6-fluoropyridin-2(1H)-one (490 mg, 3.83 mmol) in AcOH (19 mL) was added NIS (818 mg, 3.63 mmol). The reaction mixture solidated, was allowed to warm to RT, and stirred for 1 h. The volatiles were removed under reduced pressure. The residue was transferred to a separation funnel containing sat. aq. Na$_2$S$_2$O$_3$ (15 mL), sat. aq. NH$_4$Cl (15 mL), and water (15 mL). The mixture was extracted with Et$_2$O (4×50 mL) and the combined organic extracts were dried over MgSO$_4$, filtered, and the volatiles were removed under reduced pressure. The residue was purified by silica chromatography (0 to 5% gradient of MeOH/DCM) to give 4-amino-6-fluoro-3-iodopyridin-2(1H)-one (54 mg, 0.213 mmol) as a white solid. MS m/z 255.0 (M+H)$^+$.

Step b: A mixture of 4-amino-6-fluoro-3-iodopyridin-2(1H)-one (40 mg, 0.157 mmol), 2-(trifluoromethyl)pyridine-3-thiol (33.9 mg, 0.189 mmol), TMEDA (9.51 μL, 0.063 mmol), K$_3$PO$_4$ (66.9 mg, 0.315 mmol), and Cu(I)I (6.00 mg, 0.031 mmol) in dioxane (0.5 mL) was stirred for 90 min at 100° C. After cooling to RT, the mixture was diluted with EtOAc (2 mL), stirred 5 min, and filtered through a pad of Celite. The volatiles were removed under reduced pressure and the residue was purified by silica chromatography (0 to 70% gradient of EtOAc/heptane followed by 0 to 10% gradient of MeOH/DCM) to give 4-amino-6-fluoro-3-((2-(trifluoromethyl)pyridin-3-yl)thio)pyridin-2(1H)-one (22 mg, 0.072 mmol) as a yellow solid. MS m/z 306.0 (M+H)$^+$.

Intermediate L-5

4-amino-6-fluoro-1-methyl-3-((2-(trifluoromethyl)pyridin-3-yl)thio)pyridin-2(1H)-one

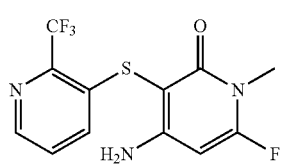 [SMILES: Cn1c(F)cc(N)c(Sc2cccnc2C(F)(F)F)c1=O]

Step a: A suspension of 4-amino-6-fluoropyridin-2(1H)-one (570 mg, 4.45 mmol), K$_2$CO$_3$ (922 mg, 6.67 mmol), and MeI (278 μL, 4.45 mmol) in EtOH (15 mL) was stirred for 15 h at 70° C. After cooling to RT, the reaction mixture was filtered and rinsed with EtOH. The filtrate was suspended in water (40 mL) and extracted with EtOAc (2×40 mL) and trifluoroethanol (10% in DCM, 8×40 mL). The combined organic extracts were dried over MgSO$_4$, filtered, and the volatiles were removed under reduced pressure. The residue was purified by silica chromatography (0 to 10% gradient of MeOH/DCM) to give 4-amino-6-fluoro-1-methylpyridin-2(1H)-one (356 mg, 2.51 mmol) as a white solid. MS m/z 142.8 (M+H)$^+$.

Step b: To a solution of 4-amino-6-fluoro-1-methylpyridin-2(1H)-one (356 mg, 2.505 mmol) in AcOH (8 mL) was added a solution of NIS (552 mg, 2.455) in DMF (2 mL) over 30 min via syringe pump, and the resulting mixture was stirred at RT for an additional 20 min. The volatiles were removed under reduced pressure, the residue was dissolved in Et$_2$O, and poured into a separation funnel containing sat. aq. Na$_2$S$_2$O$_3$ (15 mL), sat. aq. NH$_4$Cl (15 mL), and water (15 mL), and it was extracted with Et$_2$O (8×50 mL). The combined organic extracts were dried over MgSO$_4$, filtered, and concentrated under reduced pressure. The residue was purified by silica chromatography (20 to 70% gradient of EtOAc/heptane) to give 4-amino-6-fluoro-3-iodo-1-methylpyridin-2(1H)-one (80% pure, 345 mg). MS m/z 268.8 (M+H)$^+$.

Step c: A mixture of 4-amino-6-fluoro-3-iodo-1-methylpyridin-2(1H)-one (340 mg, see above), 2-(trifluoromethyl)pyridine-3-thiol (227 mg, 1.269 mmol), TMEDA (0.061 mL, 0.406 mmol), K$_3$PO$_4$ (431 mg, 2.03 mmol), and Cu(I)I (38.7 mg, 0.203 mmol) in dioxane (3.4 mL) was stirred for 1.5 h at 100° C. Additional Cu(I)I (38.7 mg, 0.203 mmol) and TMEDA (61 μL, 0.406 mmol) were added and the reaction mixture was stirred for 2.5 h at 100° C. After cooling to RT, the reaction mixture was diluted with EtOAc (10 mL), stirred 5 min, filtered through a pad of Celite, and washed with EtOAc. The volatiles were removed under reduced pressure and the residue was purified by silica chromatography (0 to 80% EtOAc/heptane) to give 4-amino-6-fluoro-1-methyl-3-((2-(trifluoromethyl)pyridin-3-yl)thio)pyridin-2(1H)-one (81 mg, 0.254 mmol) as a white solid. MS m/z 320.1 (M+H)$^+$.

Intermediate L-6

2-chloro-5-(2,3-dichlorophenyl)-4-methoxypyrimidine

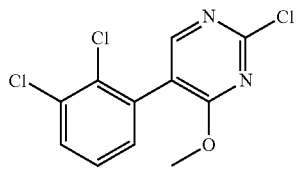 [SMILES: COc1nc(Cl)ncc1-c1cccc(Cl)c1Cl]

A suspension of 5-bromo-2-chloro-4-methoxypyrimidine (200 mg, 0.895 mmol), (2,3-dichlorophenyl)boronic acid (171 mg, 0.895 mmol), PdCl$_2$(dppf) CH$_2$Cl$_2$ adduct (73.1 mg, 0.090 mmol) and K$_2$CO$_3$ (495 mg, 3.58 mmol) in THF (7.46 mL) and water (1.49 mL) was degassed with a stream of N$_2$ for 5 min., heated to 50° C. for 1.5 h. The reaction mixture was partioned between EtOAc (100 mL) and water (50 mL). The separated organic layer was washed with brine (50 mL), dried over Na$_2$SO$_4$, filtered and concentrated under reduced pressure. The residue was purified by column chromatography (silica gel, 0 to 30% gradient of EtOAc/heptane) providing 2-chloro-5-(2,3-dichlorophenyl)-4-methoxypyrimidine (17 mg) as a white solid. MS m/z 289.1 (M+H)$^+$.

Example 1

6-amino-2-((3S,4S)-4-amino-3-methyl-2-oxa-8-azaspiro[4.5]decan-8-yl)-3-methyl-5-((2-(trifluoromethyl)pyridin-3-yl)thio)pyrimidin-4(3H)-one

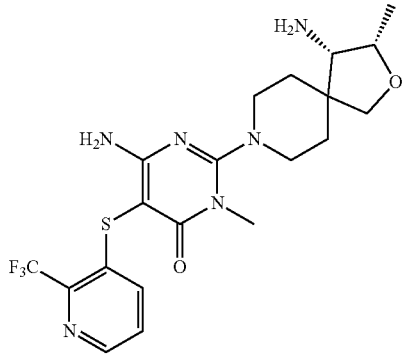 [SMILES: C[C@@H]1OCC2(CCN(c3nc(N)c(Sc4cccnc4C(F)(F)F)c(=O)n3C)CC2)[C@@H]1N]

A mixture of tert-butyl ((3S,4S)-8-(4-amino-5-iodo-1-methyl-6-oxo-1,6-dihydropyrimidin-2-yl)-3-methyl-2-oxa-8-azaspiro[4.5]decan-4-yl)carbamate (42 mg, 0.081 mmol), 2-(trifluoromethyl)pyridine-3-thiol (22 mg, 0.121 mmol), Cu(I)I (3.1 mg, 0.016 mmol), TMEDA (5 μL, 0.032 mmol), and K$_3$PO$_4$ (51 mg, 0.243 mmol) in dioxane (0.5 mL) was stirred for 90 min at 100° C. After cooling to RT, the reaction mixture was poured into a separation funnel containing aq. K$_2$CO$_3$ (2 M, 2 mL) and extracted with DCM (3×5 mL). The combined organic phases were dried over MgSO$_4$, filtered, and the volatiles were removed under reduced pressure. The residue was dissolved in DCM (5 mL) and TFA (1 mL) was added. After stirring for 20 min at RT, the volatiles were removed under reduced pressure and the residue was purified by HPLC (gradient elution 15-40% MeCN in water, 5 mM NH$_4$OH modifier) to give 6-amino-2-((3S,4S)-4-amino-3-methyl-2-oxa-8-azaspiro[4.5]decan-8-yl)-3-methyl-5-((2-(trifluoromethyl)pyridin-3-yl)thio)pyrimidin-4(3H)-one (20.0 mg) as a white solid.

Example 2

6-amino-2-(4-(aminomethyl)-4-methylpiperidin-1-yl)-5-((2,3-dichlorophenyl)thio)-3-methylpyrimidin-4(3H)-one

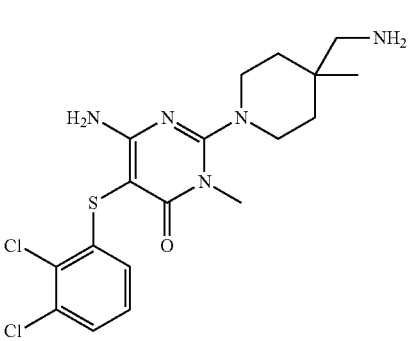 [SMILES: Cn1c(N2CCC(C)(CN)CC2)nc(N)c(Sc2cccc(Cl)c2Cl)c1=O]

A mixture of 6-amino-5-((2,3-dichlorophenyl)thio)-3-methylpyrimidine-2,4(1H,3H)-dione (60 mg, 0.189 mmol), tert-butyl ((4-methylpiperidin-4-yl)methyl)carbamate (64.6 mg, 0.283 mmol), BOP (250 mg, 0.566 mmol), and DBU (142 μL, 0.943 mmol) in DMF (2 mL) was stirred for 2 h at RT. The resulting mixture was poured into a separation funnel containing water and it was extracted with EtOAc (3×5 mL). The combined organic phases were dried over MgSO$_4$, filtered, and the volatiles were removed under reduced pressure. The residue was dissolved in DCM (5 mL) and TFA (1 mL) was added. After stirring for 10 min at RT, the volatiles were removed under reduced pressure and the residue was purified by HPLC (gradient elution 35-60% MeCN in water, 5 mM NH$_4$OH modifier) to give 6-amino-2-(4-(aminomethyl)-4-methylpiperidin-1-yl)-5-((2,3-dichlorophenyl)thio)-3-methylpyrimidin-4(3H)-one (20.0 mg) as a white solid.

The following compounds of Table 10 were synthesized using the above procedure or modifications to the above procedure using the corresponding thiol and iodo-pyrimidinone intermediate:

TABLE 10

| Example | Compound | Characterization | IC$_{50}$ (μM) |
| --- | --- | --- | --- |
| 1 | 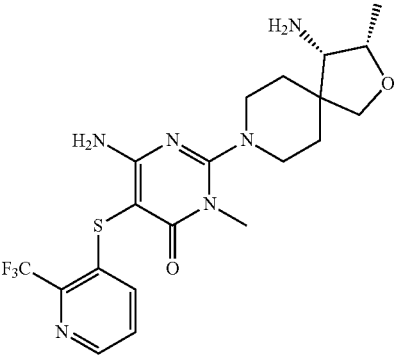 | $^1$H NMR (400 MHz, Methanol-d$_4$) δ ppm 8.24-8.41 (m, 1 H), 7.51 (d, J = 7.58 Hz, 1 H), 7.41 (dd, J = 8.34, 4.55 Hz, 1 H), 4.22 (dd, J = 6.32, 5.05 Hz, 1 H), 3.84 (d, J = 8.84 Hz, 1 H), 3.69 (d, J = 8.59 Hz, 1 H), 3.47-3.61 (m, 2 H), 3.36-3.47 (m, 3 H), 3.04-3.26 (m, 2 H), 3.03 (d, J = 5.05 Hz, 1 H), 1.79-2.02 (m, 2 H), 1.60-1.78 (m, 2 H), 1.13-1.28 (m, 3 H). $^{19}$F NMR (376 MHz, Methanol-d$_4$) δ ppm −66.36. HRMS calcd for C$_{20}$H$_{26}$F$_3$N$_6$O$_2$S (M + H)$^+$ 471.1790, found 471.1809. | 0.053 |
| 2 | 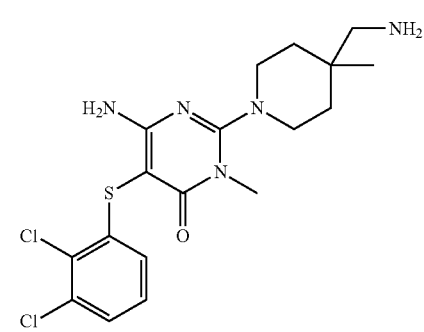 [SMILES: Cn1c(N2CCC(C)(CN)CC2)nc(N)c(Sc2cccc(Cl)c2Cl)c1=O] | $^1$H NMR (400 MHz, Methanol-d$_4$) δ ppm 7.23 (dd, J = 7.96, 1.39 Hz, 1 H), 7.09 (t, J = 8.08 Hz, 1 H), 6.71-6.79 (m, 1 H), 3.44 (dt, J = 13.52, 4.74 Hz, 2 H), 3.40 (s, 3 H), 3.22 (ddd, J = 13.33, 10.17, 3.03 Hz, 2 H), 2.56 (s, 2 H), 1.64 (ddd, J = 13.52, 9.98, 3.79 Hz, 2 H), 1.36-1.55 (m, 2 H), 1.05 (s, 3 H). HRMS calcd for C$_{18}$H$_{24}$Cl$_2$N$_5$OS (M + H)$^+$ 428.1079, found 428.1078. | 0.021 |
| 3 | 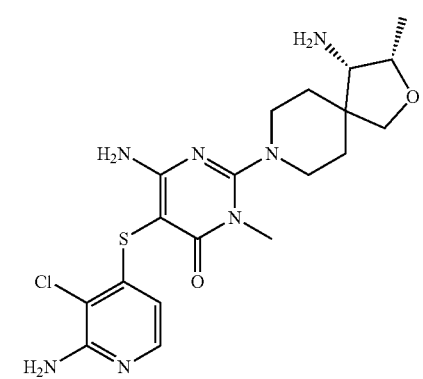 [SMILES: C[C@@H]1OCC2(CCN(c3nc(N)c(Sc4ccnc(N)c4Cl)c(=O)n3C)CC2)[C@@H]1N] | $^1$H NMR (400 MHz, Methanol-d$_4$) δ ppm 7.58 (d, J = 5.56 Hz, 1 H), 6.15 (d, J = 5.56 Hz, 1 H), 4.22 (dd, J = 6.57, 5.05 Hz, 1 H), 3.84 (d, J = 8.59 Hz, 1 H), 3.70 (d, J = 8.59 Hz, 1 H), 3.46-3.58 (m, 2 H), 3.37-3.44 (s, 3 H), 3.05-3.23 (m, 2 H), 2.99-3.05 (m, 1 H), 1.78-2.03 (m, 2 H), 1.62-1.78 (m, 2 H), 1.22 (d, J = 6.57 Hz, 3 H). HRMS calcd for C$_{19}$H$_{27}$ClN$_7$O$_2$S (M + H)$^+$ 452.1635, found 452.1635. | 0.044 |

TABLE 10-continued

| Example | Compound | Characterization | IC$_{50}$ (μM) |
|---|---|---|---|
| 4 | (structure) | $^1$H NMR (400 MHz, Methanol-d$_4$) δ ppm 7.58 (d, J = 5.56 Hz, 1 H), 6.15 (d, J = 5.56 Hz, 1 H), 3.41-3.50 (m, 2 H), 3.40 (s, 3 H), 3.18-3.27 (m, 2 H), 2.60 (s, 2 H), 1.65 (ddd, J = 13.45, 9.92, 4.17 Hz, 2 H), 1.49 (d, J = 14.65 Hz, 2 H), 1.06 (s, 3 H). HRMS calcd for C$_{17}$H$_{25}$ClN$_7$OS (M + H)$^+$ 410.1530, found 410.1470. | 0.053 |
| 5 | (structure) | $^1$H NMR (400 MHz, Methanol-d$_4$) δ ppm 7.14-7.24 (m, 1 H), 6.97-7.11 (m, 3 H), 3.38-3.52 (m, 5 H), 3.21 (ddd, J = 13.26, 10.11, 2.91 Hz, 2 H), 2.57 (s, 2 H), 1.64 (ddd, J = 13.52, 9.85, 3.66 Hz, 2 H), 1.41-1.55 (m, 2 H), 0.99-1.11 (m, 3 H). HRMS calcd for C$_{18}$H$_{25}$ClN$_5$OS (M + H)$^+$ 394.1468, found 394.1465. | 2.214 |
| 6 | (structure) | $^1$H NMR (400 MHz, Methanol-d$_4$) δ ppm 7.32 (dd, J = 7.78, 1.51 Hz, 1 H), 7.12 (td, J = 7.59, 1.38 Hz, 1 H), 7.05 (td, J = 7.59, 1.63 Hz, 1 H), 6.82 (dd, J = 7.78, 1.51 Hz, 1 H), 3.36-3.51 (m, 5 H), 3.22 (ddd, J = 13.30, 10.16, 2.89 Hz, 2 H), 2.58 (s, 2 H), 1.65 (ddd, J = 13.61, 9.98, 3.76 Hz, 2 H), 1.49 (dt, J = 13.80, 3.64 Hz, 2 H), 1.02-1.11 (m, 3 H). HRMS calcd for C$_{18}$H$_{25}$ClN$_5$OS (M + H)$^+$ 394.1468, found 394.1483. | 0.286 |
| 7 | (structure) | $^1$H NMR (400 MHz, Methanol-d$_4$) δ ppm 8.33 (dd, J = 4.55, 1.01 Hz, 1 H), 7.46-7.57 (m, 1 H), 7.41 (dd, J = 8.34, 4.55 Hz, 1 H), 3.42-3.53 (m, 2 H), 3.40 (s, 3 H), 3.23 (ddd, J = 13.39, 10.11, 3.03 Hz, 2 H), 2.57 (s, 2 H), 1.64 (ddd, J = 13.52, 9.85, 3.92 Hz, 2 H), 1.41-1.56 (m, 2 H), 0.98-1.11 (m, 3 H). HRMS calcd for C$_{18}$H$_{24}$F$_3$N$_6$OS (M + H)$^+$ 429.1684, found 429.1724. | 0.109 |
| 8 | (structure) | $^1$H NMR (400 MHz, Methanol-d$_4$) δ ppm 6.84 (t, J = 7.83 Hz, 1 H), 6.57 (dd, J = 7.96, 1.39 Hz, 1 H), 6.14 (dd, J = 7.96, 1.39 Hz, 1 H), 3.37-3.51 (m, 5 H), 3.21 (ddd, J = 13.26, 9.98, 3.03 Hz, 2 H), 2.57 (s, 2 H), 1.64 (ddd, J = 13.52, 9.85, 3.92 Hz, 2 H), 1.49 (dd, J = 13.64, 3.79 Hz, 2 H), 0.98-1.12 (m, 3 H). HRMS calcd for C$_{18}$H$_{26}$ClN$_6$OS (M + H)$^+$ 409.1577, found 409.1253. | 0.232 |

TABLE 10-continued

| Example | Compound | Characterization | IC$_{50}$ (µM) |
|---|---|---|---|
| 9 | | $^1$H NMR (400 MHz, Methanol-d$_4$) δ ppm 7.06 (t, J = 8.08 Hz, 1 H), 6.79 (dd, J = 8.21, 1.14 Hz, 1 H), 6.42 (dd, J = 7.96, 1.14 Hz, 1 H), 3.41-3.47 (m, 2 H), 3.85 (s, 3 H), 3.40 (s, 3 H), 3.21 (ddd, J = 13.33, 10.17, 3.03 Hz, 2 H), 2.58 (s, 2 H), 1.64 (ddd, J = 13.52, 9.98, 3.79 Hz, 2 H), 1.44-1.52 (m, 2 H), 1.05 (s, 3 H). HRMS calcd for C$_{19}$H$_{27}$ClN$_5$O$_2$S (M + H)$^+$ 424.1574, found 424.1530. | 0.047 |
| 10 | | $^1$H NMR (400 MHz, Methanol-d$_4$) d ppm 7.35-7.45 (m, 5 H), 3.42-3.49 (m, 2 H), 3.41 (s, 3 H), 3.22 (ddd, J = 13.45, 10.17, 3.16 Hz, 2 H), 2.58 (s, 2 H), 1.64 (ddd, J = 13.58, 9.92, 3.79 Hz, 2 H), 1.45-1.52 (m, 2 H), 1.05 (s, 3 H). HRMS calcd for C$_{19}$H$_{25}$N$_6$OS (M + H)$^+$ 385.1811, found 385.1764. | 5.633 |
| 11 | | $^1$H NMR (400 MHz, Methanol-d$_4$) δ ppm 7.26-7.32 (m, 1 H), 7.09-7.12 (m, 1 H), 6.94-6.99 (m, 2 H), 3.38-3.47 (m, 5 H), 3.21 (ddd, J = 13.20, 10.17, 2.91 Hz, 2 H), 2.59 (br. s, 2 H), 1.60-1.69 (m, 2 H), 1.48 (d, J = 13.89 Hz, 2 H), 1.05 (s, 3 H). HRMS calcd for C$_{19}$H$_{25}$F$_3$N$_5$O$_2$S (M + H)$^+$ 444.1681, found 444.1391. | 0.441 |
| 12 | | $^1$H NMR (400 MHz, Methanol-d$_4$) δ ppm 7.24 (dd, J = 7.91, 1.38 Hz, 1 H), 7.09 (t, J = 7.91 Hz, 1 H), 6.75 (dd, J = 8.03, 1.51 Hz, 1 H), 4.17-4.30 (m, 1 H), 3.85 (d, J = 8.53 Hz, 1 H), 3.71 (d, J = 8.78 Hz, 1 H), 3.49-3.59 (m, 2 H), 3.39-3.46 (m, 3 H), 3.01-3.21 (m, 3 H), 1.80-2.00 (m, 2 H), 1.62-1.80 (m, 2 H), 1.22 (d, J = 6.53 Hz, 3 H). HRMS calcd for C$_{20}$H$_{26}$Cl$_2$N$_5$O$_2$S (M + H)$^+$ 470.1184, found 470.0880. | 0.033 |

TABLE 10-continued

| Example | Compound | Characterization | IC$_{50}$ (µM) |
|---|---|---|---|
| 13 | | $^1$H NMR (400 MHz, Methanol-d$_4$) δ ppm 7.24 (dd, J = 7.91, 1.38 Hz, 1 H), 7.10 (t, J = 8.03 Hz, 1 H), 6.75 (dd, J = 8.03, 1.25 Hz, 1 H), 3.52-3.73 (m, 2 H), 3.37-3.45 (m, 3 H), 2.97-3.17 (m, 2 H), 2.87 (t, J = 7.40 Hz, 1 H), 1.95-2.15 (m, 1 H), 1.64-1.90 (m, 5 H), 1.53-1.62 (m, 1 H), 1.41-1.52 (m, 2 H), 1.37 (d, J = 13.05 Hz, 1 H). HRMS calcd for C$_{20}$H$_{26}$Cl$_2$N$_5$OS (M + H)$^+$ 454.1235, found 454.1213. | 0.039 |
| 14 | | $^1$H NMR (400 MHz, Methanol-d$_4$) δ ppm 8.25-8.42 (m, 1 H), 7.51 (d, J = 7.58 Hz, 1 H), 7.41 (dd, J = 8.46, 4.42 Hz, 1 H), 3.62 (t, J = 12.51 Hz, 2 H), 3.36-3.46 (m, 3 H), 2.97-3.17 (m, 2 H), 2.85 (t, J = 7.33 Hz, 1 H), 1.96-2.13 (m, 1 H), 1.64-1.89 (m, 5 H), 1.41-1.62 (m, 3 H), 1.36 (d, J = 13.89 Hz, 1 H). HRMS calcd for C$_{20}$H$_{26}$F$_3$N$_6$OS (M + H)$^+$ 455.1841, found 455.1760. | 0.098 |
| 15 | | $^1$H NMR (400 MHz, Methanol-d$_4$) δ ppm 1.54-1.71 (m, 2 H) 1.78-1.96 (m, 2 H) 2.99-3.15 (m, 2 H) 3.18 (t, J = 5.81 Hz, 1 H) 3.43 (s, 3 H) 3.47-3.66 (m, 3 H) 3.78 (d, J = 8.84 Hz, 1 H) 3.84 (d, J = 8.84 Hz, 1 H) 4.12 (dd, J = 9.09, 6.57 Hz, 1 H) 6.76 (dd, J = 8.08, 1.26 Hz, 1 H) 7.10 (t, J = 8.08 Hz, 1 H) 7.24 (dd, J = 7.96, 1.39 Hz, 1 H). HRMS calcd for C$_{19}$H$_{24}$Cl$_2$N$_5$O$_2$S (M + H)$^+$ 456.1028, found 456.1017. | 0.033 |
| 16 | | $^1$H NMR (400 MHz, Methanol-d$_4$) δ ppm 1.56-1.71 (m, 2 H) 1.73-1.93 (m, 2 H) 3.03-3.14 (m, 2 H) 3.15-3.20 (m, 1 H) 3.42 (s, 3 H) 3.46-3.65 (m, 3 H) 3.77 (d, J = 8.84 Hz, 1 H) 3.83 (d, J = 8.59 Hz, 1 H) 4.12 (dd, J = 9.09, 6.57 Hz, 1 H) 6.15 (d, J = 5.56 Hz, 1 H) 7.58 (d, J = 5.56 Hz, 1 H). HRMS calcd for C$_{18}$H$_{25}$ClN$_7$O$_2$S (M + H)$^+$ 438.1479, found 438.1463. | 0.022 |
| 17 | | $^1$H NMR (400 MHz, Methanol-d$_4$) δ ppm 1.62 (t, J = 15.28 Hz, 2 H) 1.75-1.97 (m, 2 H) 3.01-3.22 (m, 3 H) 3.42 (s, 3 H) 3.46-3.67 (m, 3 H) 3.76 (d, J = 8.59 Hz, 1 H) 3.83 (d, J = 8.84 Hz, 1 H) 4.12 (dd, J = 9.09, 6.57 Hz, 1 H) 7.41 (dd, J = 8.34, 4.55 Hz, 1 H) 7.51 (d, J = 7.83 Hz, 1 H) 8.34 (d, J = 3.79 Hz, 1 H). HRMS calcd for C$_{19}$H$_{24}$F$_3$N$_6$O$_2$S (M + H)$^+$ 457.1634, found 457.1617. | 0.034 |

TABLE 10-continued

| Example | Compound | Characterization | IC$_{50}$ (µM) |
|---|---|---|---|
| 18 | | $^1$H NMR (400 MHz, Methanol-d$_4$) δ ppm 8.33 (dd, J = 4.42, 0.88 Hz, 1 H), 7.46-7.57 (m, 1 H), 7.41 (dd, J = 8.34, 4.55 Hz, 1 H), 3.53-3.69 (m, 2 H), 3.41 (s, 3 H), 2.99-3.14 (m, 2 H), 2.83 (dd, J = 9.60, 6.32 Hz, 1 H), 2.14 (dt, J = 12.32, 6.35 Hz, 1 H), 1.98-2.08 (m, 1 H), 1.92 (dd, J = 12.88, 8.34 Hz, 1 H), 1.80 (td, J = 12.38, 3.54 Hz, 2 H), 1.34-1.47 (m, 2 H), 1.29 (dd, J = 12.76, 9.22 Hz, 1 H), 1.09-1.20 (m, 1 H), 1.06 (d, J = 6.57 Hz, 3 H).<br>HRMS calcd for C$_{21}$H$_{28}$F$_3$N$_6$OS (M + H)$^+$ 469.1997, found 469.1887. | 0.023 |
| 19 | | $^1$H NMR (400 MHz, Methanol-d$_4$) δ ppm 5.88 (s, 1 H), 4.13 (dd, J = 6.32, 5.05 Hz, 1 H), 3.75 (d, J = 8.59 Hz, 1 H), 3.60 (d, J = 8.84 Hz, 1 H), 3.37-3.51 (m, 2 H), 3.32 (s, 3 H), 2.85-3.12 (m, 3 H), 1.69-1.91 (m, 2 H), 1.49-1.69 (m, 2 H), 1.12 (d, J = 6.32 Hz, 3 H).<br>HRMS calcd for C$_{19}$H$_{26}$Cl$_2$N$_7$O$_2$S (M + H)$^+$ 486.1246, found 486.1258. | 0.014 |
| 20 | | $^1$H NMR (400 MHz, Methanol-d$_4$) δ ppm 7.00-7.13 (m, 1 H), 6.79 (dd, J = 8.28, 1.25 Hz, 1 H), 6.42 (dd, J = 8.03, 1.25 Hz, 1 H), 4.16-4.29 (m, 1 H), 3.79-3.89 (m, 4 H), 3.70 (d, J = 8.53 Hz, 1 H), 3.46-3.60 (m, 2 H), 3.42 (s, 3 H), 2.91-3.21 (m, 3 H), 1.80-1.99 (m, 2 H), 1.60-1.78 (m, 2 H), 1.22 (d, J = 6.53 Hz, 3 H).<br>HRMS calcd for C$_{21}$H$_{29}$ClN$_5$O$_3$S (M + H)$^+$ 466.1680, found 486.1685. | 0.017 |
| 21 | | $^1$H NMR (400 MHz, Methanol-d$_4$) δ ppm 7.58 (d, J = 5.56 Hz, 1 H), 6.14 (d, J = 5.56 Hz, 1 H), 3.52-3.69 (m, 2 H), 3.41 (s, 3 H), 3.00-3.11 (m, 2 H), 2.86 (dd, J = 9.60, 6.32 Hz, 1 H), 2.11-2.19 (m, 1 H), 1.99-2.10 (m, 1 H), 1.91-1.99 (m, 1 H), 1.80 (td, J = 12.57, 3.66 Hz, 2 H), 1.37-1.45 (m, 2 H), 1.22-1.33 (m, 1 H), 1.14 (dt, J = 12.38, 9.85 Hz, 1 H), 1.07 (d, J = 6.57 Hz, 3 H).<br>HRMS calcd for C$_{20}$H$_{29}$ClN$_7$OS (M + H)$^+$ 450.1843, found 450.1858. | 0.028 |

TABLE 10-continued

| Example | Compound | Characterization | IC$_{50}$ (μM) |
|---|---|---|---|
| 22 | | $^1$H NMR (400 MHz, Methanol-d$_4$) δ ppm 7.96 (dd, J = 4.67, 1.64 Hz, 1 H), 7.31 (dd, J = 7.83, 1.77 Hz, 1 H), 7.15 (dd, J = 7.83, 4.80 Hz, 1 H), 4.22 (dd, J = 6.44, 5.18 Hz, 1 H), 3.84 (d, J = 8.84 Hz, 1 H), 3.69 (d, J = 8.59 Hz, 1 H), 3.46-3.61 (m, 2 H), 3.41 (s, 3 H), 3.12-3.22 (m, 1 H), 3.07 (ddd, J = 13.14, 10.36, 2.53 Hz, 1 H), 3.02 (d, J = 4.80 Hz, 1 H), 1.79-2.00 (m, 2 H), 1.61-1.79 (m, 2 H), 1.22 (d, J = 6.32 Hz, 3 H). $^{19}$F NMR (376 MHz, Methanol-d$_4$) δ ppm −57.31. HRMS calcd for C$_{20}$H$_{26}$F$_3$N$_6$O$_3$S (M + H)$^+$ 487.1739, found 487.1765. | 0.108 |
| 23 | | $^1$H NMR (400 MHz, Methanol-d$_4$) δ ppm 7.76 (d, J = 5.52 Hz, 1 H), 6.43 (d, J = 5.52 Hz, 1 H), 4.15-4.33 (m, 1 H), 3.95 (s, 3 H), 3.85 (d, J = 8.78 Hz, 1 H), 3.71 (d, J = 8.78 Hz, 1 H), 3.49-3.60 (m, 2 H), 3.41 (s, 3 H), 3.06-3.21 (m, 2 H), 3.04 (d, J = 5.02 Hz, 1 H), 1.81-1.99 (m, 2 H), 1.62-1.79 (m, 2 H), 1.22 (d, J = 6.27 Hz, 3 H). HRMS calcd for C$_{20}$H$_{29}$ClN$_6$O$_3$S (M + H)$^+$ 467.1632, found 467.1636. | 0.023 |
| 24 | | $^1$H NMR (400 MHz, Methanol-d$_4$) δ ppm 8.63 (d, J = 5.81 Hz, 1 H), 8.50 (d, J = 7.83 Hz, 1 H), 8.10 (d, J = 8.08 Hz, 1 H), 8.02 (ddd, J = 1.26, 7.14, 8.53 Hz, 1 H), 7.85 (ddd, J = 1.01, 7.01, 8.40 Hz, 1 H), 7.30 (d, J = 5.81 Hz, 1 H), 3.50-3.59 (m, 2 H), 3.44 (s, 3 H), 3.21-3.29 (m, 2 H overlapped with residual MeOH), 2.94 (s, 2 H), 1.67-1.78 (m, 2 H), 1.57-1.66 (m, 2 H), 1.14-1.22 (m, 3 H). HRMS calcd for C$_{21}$H$_{27}$N$_6$OS (M + H)$^+$ 411.1967, found 411.1951. | 0.299 |
| 25 | | $^1$H NMR (400 MHz, Methanol-d$_4$) δ ppm 6.84 (t, J = 7.93 Hz, 1 H), 6.57 (dd, J = 1.39, 7.96 Hz, 1 H), 6.14 (dd, J = 1.40, 7.93 Hz, 1 H), 4.19-4.25 (m, 1 H), 3.81-3.87 (m, 1 H), 3.67-3.73 (m, 1 H), 3.46-3.59 (m, 2 H), 3.42 (s, 3 H), 2.97-3.21 (m, 3 H), 1.83-2.01 (m, 2 H), 1.62-1.77 (m, 2 H), 1.22 (td, J = 0.93, 6.56 Hz, 3 H). HRMS calcd for C$_{20}$H$_{28}$ClN$_6$O$_2$S (M + H)$^+$ 451.1683, found 451.1685. | 0.038 |

TABLE 10-continued

| Example | Compound | Characterization | IC$_{50}$ (µM) |
|---|---|---|---|
| 26 | | $^1$H NMR (400 MHz, Methanol-d$_4$) δ ppm 7.18-7.22 (m, 2 H), 7.05-7.13 (m, 3 H), 4.19-4.25 (m, 1 H), 3.84 (d, J = 8.59 Hz, 1 H), 3.69 (d, J = 8.59 Hz, 1 H), 3.45-3.55 (m, 2 H), 3.42 (s, 3 H), 3.00-3.17 (m, 3 H), 1.83-1.96 (m, 2 H), 1.65-1.76 (m, 2 H), 1.14-1.28 (m, 3 H). HRMS calcd for C$_{20}$H$_{28}$N$_5$O$_2$S (M + H)$^+$ 402.1964, found 402.1973. | 0.082 |
| 27 | | $^1$H NMR (400 MHz, Methanol-d$_4$) δ ppm 7.32 (dd, J = 7.78, 1.25 Hz, 1 H), 7.09-7.17 (m, 1 H), 7.00-7.09 (m, 1 H), 6.81 (dd, J = 7.78, 1.51 Hz, 1 H), 4.14-4.32 (m, 1 H), 3.85 (d, J = 8.78 Hz, 1 H), 3.70 (d, J = 8.78 Hz, 1 H), 3.47-3.58 (m, 2 H), 3.42 (s, 3 H), 3.10-3.21 (m, 1 H), 2.92-3.10 (m, 2 H), 1.80-2.01 (m, 2 H), 1.61-1.79 (m, 2 H), 1.22 (d, J = 6.27 Hz, 3 H). HRMS calcd for C$_{20}$H$_{27}$ClN$_5$O$_2$S (M + H)$^+$ 436.1574, found 436.1587. | 0.025 |
| 28 | | $^1$H NMR (400 MHz, Methanol-d$_4$) δ ppm 7.68 (d, J = 5.52 Hz, 1 H), 6.20 (d, J = 5.27 Hz, 1 H), 4.18-4.29 (m, 1 H), 3.85 (d, J = 8.78 Hz, 1 H), 3.70 (d, J = 8.53 Hz, 1 H), 3.57-3.65 (m, 4 H), 3.48-3.57 (m, 2 H), 3.42 (s, 3 H), 2.98-3.22 (m, 3 H), 1.80-1.99 (m, 6 H), 1.62-1.77 (m, 2 H), 1.22 (d, J = 6.53 Hz, 3 H). HRMS calcd for C$_{23}$H$_{33}$ClN$_7$O$_2$S (M + H)$^+$ 506.2105, found 506.2117. | 0.028 |
| 29 | | $^1$H NMR (400 MHz, Methanol-d$_4$) δ ppm 7.70 (d, J = 5.56 Hz, 1 H), 6.15 (d, J = 5.56 Hz, 1 H), 4.19-4.26 (m, 1 H), 3.85 (d, J = 8.84 Hz, 1 H), 3.70 (d, J = 8.84 Hz, 1 H), 3.53 (dq, J = 13.33, 4.57 Hz, 2 H), 3.41 (s, 3 H), 3.03-3.29 (m, 3 H), 2.66 (tt, J = 6.95, 3.66 Hz, 1 H), 1.83-1.97 (m, 2 H), 1.64-1.78 (m, 2 H), 1.22 (d, J = 6.32 Hz, 3 H), 0.72-0.85 (m, 2 H), 0.47-0.59 (m, 2 H). HRMS calcd for C$_{22}$H$_{31}$ClN$_7$O$_2$S (M + H)$^+$ 492.1948, found 492.1922. | 0.032 |

TABLE 10-continued

| Example | Compound | Characterization | IC$_{50}$ (μM) |
|---|---|---|---|
| 30 | | $^1$H NMR (400 MHz, Methanol-d$_4$) δ ppm 7.73 (d, J = 5.56 Hz, 1 H), 6.41 (d, J = 5.56 Hz, 1 H), 4.37 (q, J = 6.91 Hz, 2 H), 4.18-4.27 (m, 1 H), 3.84 (d, J = 8.59 Hz, 1 H), 3.69 (d, J = 8.84 Hz, 1 H), 3.47-3.61 (m, 2 H), 3.41 (s, 3 H), 2.96-3.22 (m, 3 H), 1.82-1.99 (m, 2 H), 1.59-1.79 (m, 2 H), 1.38 (t, J = 7.07 Hz, 3 H), 1.08-1.27 (m, 3 H).<br>HRMS calcd for C$_{21}$H$_{30}$ClN$_6$O$_3$S (M + H)$^+$ 481.1789, found 481.1763. | 0.032 |
| 31 | | $^1$H NMR (400 MHz, Methanol-d$_4$) δ ppm 6.97 (t, J = 8.03 Hz, 1 H), 6.54 (d, J = 8.28 Hz, 1 H), 6.28 (d, J = 8.03 Hz, 1 H), 4.15-4.32 (m, 1 H), 3.84 (d, J = 8.78 Hz, 1 H), 3.70 (d, J = 8.53 Hz, 1 H), 3.45-3.55 (m, 2 H), 3.41 (s, 3 H), 2.96-3.21 (m, 3 H), 1.82-2.00 (m, 2 H), 1.63-1.78 (m, 2 H), 1.22 (d, J = 6.53 Hz, 3 H).<br>HRMS calcd for C$_{21}$H$_{28}$F$_3$N$_6$O$_2$S (M + H)$^+$ 485.1947, found 485.1964. | 0.020 |
| 32 | | $^1$H NMR (400 MHz, Methanol-d$_4$) δ ppm 7.96 (d, J = 5.31 Hz, 1 H), 6.59 (d, J = 5.31 Hz, 1 H), 4.12-4.32 (m, 1 H), 3.84 (d, J = 8.59 Hz, 1 H), 3.69 (d, J = 8.59 Hz, 1 H), 3.47-3.61 (m, 2 H), 3.38-3.44 (m, 3 H), 3.04-3.23 (m, 2 H), 3.01-3.04 (m, 1 H), 2.54 (tt, J = 7.93, 5.08 Hz, 1 H), 1.83-2.03 (m, 2 H), 1.62-1.83 (m, 2 H), 1.22 (d, J = 6.57 Hz, 3 H), 0.94-1.07 (m, 4 H).<br>HRMS calcd for C$_{22}$H$_{30}$ClN$_6$O$_2$S (M + H)$^+$ 477.1839, found 477.1841. | 0.017 |
| 33 | | $^1$H NMR (400 MHz, Methanol-d$_4$) δ ppm 8.33 (d, J = 3.54 Hz, 1 H), 7.51 (d, J = 7.83 Hz, 1 H), 7.41 (dd, J = 8.08, 4.55 Hz, 1 H), 3.57-3.70 (m, 2 H), 3.41 (s, 3 H), 2.88-3.15 (m, 3 H), 2.25-2.44 (m, 1 H), 2.05-2.17 (m, 1 H), 1.91-2.04 (m, 1 H), 1.85 (td, J = 12.88, 4.04 Hz, 1 H), 1.49 (br. dd, J = 13.26, 2.15 Hz, 1 H), 1.28-1.42 (m, 2 H), 1.08 (d, J = 6.82 Hz, 3 H).<br>$^{19}$F NMR (376 MHz, Methanol-d$_4$) δ ppm −66.36 (s, 3 F), −115.35 (br. d, J = 224.87 Hz, 1 F), −131.59 (br. d, J = 223.71 Hz, 1 F).<br>HRMS calcd for C$_{21}$H$_{25}$F$_5$N$_6$OS (M + H)$^+$ 505.1809, found 505.1785. | 0.040 |

TABLE 10-continued

| Example | Compound | Characterization | IC$_{50}$ (μM) |
|---|---|---|---|
| 34 | | $^1$H NMR (400 MHz, Methanol-d$_4$) δ ppm 7.58 (d, J = 5.56 Hz, 1 H), 6.15 (d, J = 5.56 Hz, 1 H), 3.56-3.71 (m, 2 H), 3.41 (s, 3 H), 2.86-3.17 (m, 3 H), 2.23-2.45 (m, 1 H), 2.05-2.18 (m, 1 H), 1.92-2.04 (m, 1 H), 1.85 (td, J = 12.82, 3.92 Hz, 1 H), 1.44-1.55 (m, 1 H), 1.25-1.43 (m, 2 H), 1.08 (d, J = 6.82 Hz, 3 H). $^{19}$F NMR (376 MHz, Methanol-d$_4$) δ ppm −115.33 (br. d, J = 223.72 Hz, 1 F), −131.60 (br. d, J = 223.71 Hz, 1 F). HRMS calcd for C$_{20}$H$_{27}$ClF$_2$N$_7$OS (M + H)$^+$ 486.1654, found 486.1670. | 0.057 |
| 35 | | $^1$H NMR (400 MHz, Methanol-d$_4$) δ ppm 8.34 (d, J = 3.79 Hz, 1 H), 7.51 (d, J = 8.34 Hz, 1 H), 7.41 (dd, J = 8.08, 4.55 Hz, 1 H), 5.03-5.24 (m, 1 H), 3.65 (br. dd, J = 13.39, 3.79 Hz, 2 H), 3.42 (s, 3 H), 3.11-3.21 (m, 1 H), 2.96-3.11 (m, 2 H), 2.13-2.35 (m, 2 H), 1.70-2.00 (m, 4 H), 1.50 (br. d, J = 11.37 Hz, 1 H), 1.35 (br. d, J = 12.13 Hz, 1 H). $^{19}$F NMR (376 MHz, Methanol-d$_4$) δ ppm −66.37 (s, 3 F), −166.10 (s, 1 F). HRMS calcd for C$_{20}$H$_{27}$ClF$_2$N$_7$OS (M + H)$^+$ 473.1747, found 473.1761. | 0.024 |
| 36 | | $^1$H NMR (400 MHz, Methanol-d$_4$) δ ppm 7.58 (d, J = 5.56 Hz, 1 H), 6.15 (d, J = 5.56 Hz, 1 H), 4.99-5.26 (m, 1 H), 3.54-3.73 (m, 2 H), 3.37-3.46 (m, 3 H), 3.15 (dd, J = 9.35, 6.82 Hz, 1 H), 2.97-3.10 (m, 2 H), 2.09-2.36 (m, 2 H), 1.71-2.00 (m, 4 H), 1.49 (br. d, J = 11.37 Hz, 1 H), 1.34 (br. d, J = 12.63 Hz, 1 H). $^{19}$F NMR (376 MHz, Methanol-d$_4$) δ ppm −166.07 (s, 1 F). HRMS calcd for C$_{20}$H$_{25}$F$_4$N$_6$OS (M + H)$^+$ 454.1592, found 454.1605. | 0.069 |
| 37 | | Chiral SFC purification performed at the Boc protected stage as follows; column: IB 20 × 250 mm, flow rate: 80 g per minute, mobile phase: 25% MeOH and 10 mM NH$_4$OH in CO$_2$, detection: 220 nm UV to obtain single enantiomer R$_t$ (P1) = 5.0 min. $^1$H NMR (400 MHz, Methanol-d$_4$) δ ppm 7.58 (d, J = 5.52 Hz, 1 H), 6.14 (d, J = 5.52 Hz, 1 H), 4.43-4.64 (m, 1 H), 3.64 (br. d, J = 12.05 Hz, 2 H), 3.41 (s, 3 H), 3.04-3.16 (m, 1 H), 2.94-3.04 (m, 1 H), 2.70-2.89 (m, 1 H), 2.37-2.52 (m, 1 H), 2.20-2.35 (m, 1 H), 2.04 (td, J = 13.05, 4.27 Hz, 1 H), 1.78 (td, J = 13.11, 3.89 Hz, 1 H), 1.53 (br. d, J = 13.30 Hz, 1 H), 1.26-1.40 (m, 1 H), 1.11 (d, J = 7.03 Hz, 3 H), 1.01 (dd, J = 12.55, 8.03 Hz, 1 H). $^{19}$F NMR (376 MHz, Methanol-d$_4$) δ ppm −184.19 (br. s, 1 F). HRMS calcd for C$_{20}$H$_{28}$ClFN$_7$OS (M + H)$^+$ 468.1749, found 468.1748 | 0.047 |

TABLE 10-continued

| Example | Compound | Characterization | IC$_{50}$ (µM) |
|---|---|---|---|
| 38 | 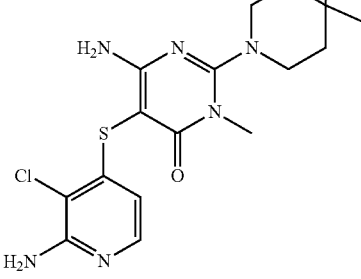 | Chiral SFC purification performed at the Boc protected stage as follows; column: IB 20 × 250 mm, flow rate: 80 g per minute, mobile phase: 25% MeOH and 10 mM NH$_4$OH in CO$_2$, detection: 220 nm UV to obtain single enantiomer R$_t$ (P2) = 6.2 min. $^1$H NMR (400 MHz, Methanol-d$_4$) δ ppm 7.58 (d, J = 5.52 Hz, 1 H), 6.14 (d, J = 5.52 Hz, 1 H), 4.51-4.78 (m, 1 H), 3.65 (br. d, J = 13.30 Hz, 2 H), 3.41 (s, 3 H), 2.92-3.11 (m, 2 H), 2.73-2.89 (m, 1 H), 1.99-2.25 (m, 2 H), 1.79-1.97 (m, 2 H), 1.34-1.49 (m, 3 H), 1.10 (d, J = 6.78 Hz, 3 H). $^{19}$F NMR (376 MHz, Methanol-d$_4$) δ ppm −212.76 (s, 1 F). HRMS calcd for C$_{20}$H$_{28}$ClFN$_7$OS (M + H)$^+$ 468.1749, found 468.1743. | 0.030 |
| 39 | 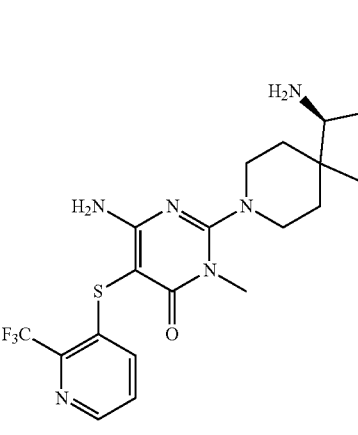 | Chiral SFC purification performed at the Boc protected stage as follows; column: IB 20 × 250 mm, flow rate: 80 g per minute, mobile phase: 25% MeOH and 10 mM NH$_4$OH in CO$_2$, detection: 290 nm UV to obtain single enantiomer R$_t$ (P1) = 2.8 min. $^1$H NMR (400 MHz, Methanol-d$_4$) δ ppm 8.34 (dd, J = 4.52, 0.75 Hz, 1 H), 7.46-7.57 (m, 1 H), 7.42 (dd, J = 8.28, 4.52 Hz, 1 H), 4.40-4.64 (m, 1 H), 3.65 (br. d, J = 13.05 Hz, 2 H), 3.41 (s, 3 H), 3.10 (td, J = 12.74, 1.88 Hz, 1 H), 3.00 (td, J = 13.05, 2.26 Hz, 1 H), 2.72-2.87 (m, 1 H), 2.36-2.47 (m, 1 H), 2.20-2.35 (m, 1 H), 2.04 (td, J = 13.11, 4.14 Hz, 1 H), 1.78 (td, J = 13.05, 3.26 Hz, 1 H), 1.52 (br. d, J = 13.55 Hz, 1 H), 1.24-1.34 (m, 1 H), 1.11 (d, J = 7.03 Hz, 3 H), 1.00 (dd, J = 12.42, 7.91 Hz, 1 H). $^{19}$F NMR (376 MHz, Methanol-d$_4$) δ ppm −66.36, −184.17. HRMS calcd for C$_{21}$H$_{27}$F$_4$N$_6$OS (M + H)$^+$ 487.1903, found 487.1936. | 0.058 |
| 40 | 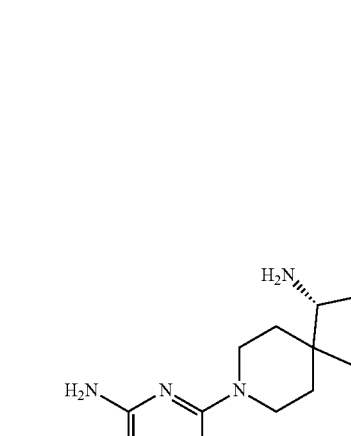 | Chiral SFC purification performed at the Boc protected stage as follows; column: IB 20 × 250 mm, flow rate: 80 g per minute, mobile phase: 25% MeOH and 10 mM NH$_4$OH in CO$_2$, detection: 290 nm UV to obtain single enantiomer R$_t$ (P2) = 3.4 min. $^1$H NMR (400 MHz, Methanol-d$_4$) δ ppm 8.28-8.37 (m, 1 H), 7.46-7.55 (m, 1 H), 7.42 (dd, J = 8.28, 4.52 Hz, 1 H), 4.48-4.76 (m, 1 H), 3.67 (br. d, J = 13.05 Hz, 2 H), 3.41 (s, 3 H), 2.92-3.12 (m, 2 H), 2.72-2.89 (m, 1 H), 2.08-2.25 (m, 1 H), 1.98-2.07 (m, 1 H), 1.73-1.96 (m, 2 H), 1.32-1.52 (m, 3 H), 1.10 (d, J = 6.53 Hz, 3 H). $^{19}$F NMR (376 MHz, Methanol-d$_4$) δ ppm −66.37, −212.75. HRMS calcd for C$_{21}$H$_{27}$F$_4$N$_6$OS (M + H)$^+$ 487.1903, found 487.1916. | 0.051 |

TABLE 10-continued

| Example | Compound | Characterization | IC$_{50}$ (µM) |
|---|---|---|---|
| 41 | | $^1$H NMR (400 MHz, Methanol-d$_4$) δ ppm 8.33 (dd, J = 4.52, 0.75 Hz, 1 H), 7.47-7.56 (m, 1 H), 7.41 (dd, J = 8.03, 4.52 Hz, 1 H), 4.09-4.33 (m, 1 H), 3.52-3.67 (m, 2 H), 3.36-3.45 (m, 3 H), 2.95-3.15 (m, 2 H), 2.87 (br. dd, J = 16.44, 7.91 Hz, 1 H), 1.99-2.26 (m, 2 H), 1.78-2.00 (m, 2 H), 1.37-1.55 (m, 1 H), 1.23-1.35 (m, 1 H), 1.07-1.20 (m, 3 H), 0.81-0.95 (m, 1 H). $^{19}$F NMR (376 MHz, Methanol-d$_4$) δ ppm −66.36, −192.25. HRMS calcd for C$_{21}$H$_{27}$F$_4$N$_6$OS (M + H)$^+$ 487.1903, found 487.1893. | 0.029 |
| 42 | | $^1$H NMR (400 MHz, Methanol-d$_4$) δ ppm 7.58 (d, J = 5.56 Hz, 1 H), 6.15 (d, J = 5.56 Hz, 1 H), 3.54-3.76 (m, 2 H), 3.41 (s, 3 H), 2.93-3.18 (m, 3 H), 2.36-2.61 (m, 2 H), 1.91-2.16 (m, 3 H), 1.84 (td, J = 12.63, 3.54 Hz, 1 H), 1.54 (br. d, J = 11.87 Hz, 1 H), 1.37-1.48 (m, 1 H). $^{19}$F NMR (376 MHz, Methanol-d$_4$) δ ppm −88.84(q). HRMS calcd for C$_{19}$H$_{25}$F$_2$N$_7$OS (M + H)$^+$ 472.1498, found 472.1514. | 0.014 |
| 43 | | $^1$H NMR (400 MHz, Methanol-d$_4$) δ ppm 8.34 (dd, J = 4.42, 0.88 Hz, 1 H), 7.51 (d, J = 8.08 Hz, 1 H), 7.41 (dd, J = 8.34, 4.55 Hz, 1 H), 3.57-3.77 (m, 2 H), 3.41 (s, 3 H), 2.94-3.16 (m, 3 H), 2.35-2.56 (m, 2 H), 1.91-2.17 (m, 3 H), 1.85 (td, J = 12.82, 3.92 Hz, 1 H), 1.55 (br. d, J = 13.14 Hz, 1 H), 1.45 (br. dd, J = 13.39, 2.27 Hz, 1 H). $^{19}$F NMR (376 MHz, Methanol-d$_4$) δ ppm −66.36, −84.86 (q). HRMS calcd for C$_{20}$H$_{24}$F$_5$N$_6$OS (M + H)$^+$ 491.1652, found 491.1630. | 0.018 |
| 45 | | $^1$H NMR (400 MHz, Methanol-d$_4$) δ ppm 7.49 (d, J = 7.83 Hz, 1 H) 7.17 (t, J = 7.58 Hz, 1 H), 6.95-7.01 (m, 1 H), 6.81 (br. d, J = 8.08 Hz, 1 H), 3.41 (m, 5 H), 3.21 (m, 2 H), 2.55 (s, 2 H), 1.60-1.70 (m, 2 H), 1.40-1.52 (m, 2 H), 1.04 (s, 3 H). HRMS calcd for C$_{18}$H$_{25}$BrN$_5$OS (M + H)$^+$ 438.0963, found 438.0972. | 0.137 |

TABLE 10-continued

| Example | Compound | Characterization | IC$_{50}$ (μM) |
|---|---|---|---|
| 46 | (structure) | $^1$H NMR (400 MHz, Methanol-d$_4$) δ ppm 7.22-7.28 (m, 1 H), 7.14-7.20 (m, 2 H), 6.92-6.98 (m, 1 H), 3.41 (m, 5 H), 3.17-3.26 (m, 2 H), 2.55 (s, 2 H), 1.60-1.69 (m, 2 H), 1.48 (br. d, J = 14.1 Hz, 2 H), 1.04 (s, 3 H). HRMS calcd for C$_{19}$H$_{25}$F$_3$N$_5$O$_2$S (M + H)$^+$ 444.1681, found 444.1693. | 0.089 |
| 47 | (structure) | $^1$H NMR (400 MHz, Methanol-d$_4$) δ ppm 7.05-7.10 (m, 1 H), 6.91 (d, J = 8.3 Hz, 1 H), 6.79 (d, J = 4.0 Hz, 2 H), 3.87 (s, 3 H), 3.41 (m, 5 H), 3.15-3.23 (m, 2 H), 2.55 (s, 2 H), 1.60-1.68 (m, 2 H), 1.48 (br. d, J = 14.1 Hz, 2 H), 1.04 (s, 3 H). HRMS calcd for C$_{19}$H$_{28}$N$_5$O$_2$S (M + H)$^+$ 390.1964, found 390.1990. | 0.206 |
| 48 | (structure) | $^1$H NMR (400 MHz, Methanol-d$_4$) δ ppm 8.24 (d, J = 8.3 Hz, 1 H), 7.48 (t, J = 7.5 Hz, 1 H), 7.24-7.31 (m, 1 H), 7.15 (d, J = 8.3 Hz, 1 H), 3.40 (m, 5 H), 3.25 (m, 2 H), 1.63-1.89 (m, 2 H), 1.45-1.63 (m, 2 H), 1.44 (s, 2 H), 1.03 (s, 3 H). HRMS calcd for C$_{18}$H$_{25}$N$_6$O$_3$S (M + H)$^+$ 405.1709, found 405.1748. | 0.300 |
| 49 | (structure) | $^1$H NMR (400 MHz, Methanol-d$_4$) δ ppm 7.63 (d, J = 7.8 Hz, 1 H), 7.36-7.42 (m, 1 H), 7.20-7.26 (m, 1 H), 7.12 (d, J = 7.8 Hz, 1 H), 3.42 (m, 5 H), 3.18-3.27 (m, 2 H), 2.56 (s, 2 H), 1.59-1.74 (m, 2 H), 1.48 (br. d, J = 14.4 Hz, 2 H), 1.05 (s, 3 H). HRMS calcd for C$_{18}$H$_{25}$F$_3$N$_5$OS (M + H)$^+$ 428.1732, found 428.1747. | 0.074 |
| 50 | (structure) | $^1$H NMR (400 MHz, Methanol-d$_4$) δ ppm 6.96-7.03 (m, 1 H), 6.90-6.95 (m, 1 H), 6.74 (dd, J = 8.2, 0.9 Hz, 1 H), 3.38-3.47 (m, 5 H), 3.17-3.26 (m, 2 H), 2.55 (s, 2 H), 1.59-1.69 (m, 2 H), 1.42-1.53 (m, 2 H), 1.04 (s, 3 H). HRMS calcd for C$_{19}$H$_{24}$F$_2$N$_5$O$_3$S (M + H)$^+$ 440.1568, found 440.1563. | 0.152 |

TABLE 10-continued

| Example | Compound | Characterization | IC$_{50}$ (μM) |
|---|---|---|---|
| 51 | | $^1$H NMR (400 MHz, Methanol-d$_4$) δ ppm 7.64 (br. d, J = 7.3 Hz, 1 H), 7.45 (t, J = 7.7 Hz, 1 H), 7.22 (br t, J = 7.6 Hz, 1 H), 7.04 (d, J = 8.1 Hz, 1 H), 3.41 (m, 5 H), 3.20-3.29 (m, 2 H), 2.48 (s, 2 H), 1.70 (br t, J = 10.1 Hz, 2 H), 1.57 (br. d, J = 13.9 Hz, 2 H), 1.15 (s, 3H). HRMS calcd for C$_{19}$H$_{25}$N$_6$OS (M + H)$^+$ 385.1811, found 385.1785. | 0.391 |
| 52 | | $^1$H NMR (400 MHz, Methanol-d$_4$) δ ppm 7.38 (d, J = 7.83 Hz, 1 H), 7.07-7.14 (m, 1 H), 6.81 (d, J = 8.08 Hz, 1 H), 6.71 (t, J = 7.45 Hz, 1 H), 3.40 (m, 5 H), 3.16 (m, 2 H), 2.52 (s, 2 H), 1.55-1.67 (m, 2 H), 1.44 (m, 2 H), 1.01 (s, 3 H). HRMS calcd for C$_{18}$H$_{26}$N$_5$O$_2$S (M + H)$^+$ 376.1807 found 376.0770. | 0.721 |
| 53 | | $^1$H NMR (400 MHz, Methanol-d$_4$) δ ppm 6.76 (d, J = 8.6 Hz, 1 H), 6.72 (d, J = 2.5 Hz, 1 H), 6.51 (dd, J = 8.6, 2.3 Hz, 1 H), 3.40 (m, 5 H), 3.14-3.22 (m, 2 H), 2.53 (s, 2 H), 1.58-1.68 (m, 2 H), 1.47 (br. d, J = 12.4 Hz, 2 H), 1.03 (s, 3 H). HRMS calcd for C$_{18}$H$_{26}$ClN$_6$OS (M + H)$^+$ 409.1578, found 409.0524. | 0.609 |
| 54 | | $^1$H NMR (400 MHz, Methanol-d$_4$) δ ppm 7.11 (br. d, J = 6.57 Hz, 1 H), 6.94-7.03 (m, 2 H), 6.75-6.80 (m, 1 H), 3.41 (m, 5 H), 3.17-3.25 (m, 2 H), 2.56 (s, 2 H), 2.40 (s, 3 H), 1.65 (ddd, J = 13.45, 9.92, 3.66 Hz, 2 H), 1.48 (br. d, J = 13.89 Hz, 2 H) 1.05 (s, 3 H). HRMS calcd for C$_{19}$H$_{28}$N$_5$OS (M + H)$^+$ 374.2015, found 374.2004. | 0.200 |

TABLE 10-continued

| Example | Compound | Characterization | IC$_{50}$ (µM) |
|---|---|---|---|
| 55 | (structure) | $^1$H NMR (400 MHz, Methanol-d$_4$) δ ppm 8.34 (d, J = 8.1 Hz, 1 H), 7.85 (d, J = 7.3 Hz, 1 H), 7.62 (d, J = 8.3 Hz, 1 H), 7.47-7.57 (m, 2 H), 7.30 (t, J = 7.8 Hz, 1 H), 7.05 (d, J = 6.8 Hz, 1 H), 3.43 (m, 5 H), 3.17-3.26 (m, 2 H), 2.55 (s, 2 H), 1.60-1.70 (m, 2 H), 1.49 (br. d, J = 13.9 Hz, 2 H), 1.05 (s, 3 H). HRMS calcd for C$_{22}$H$_{28}$N$_5$OS (M + H)$^+$ 410.2015, found 410.2015. | 0.045 |
| 56 | (structure) | $^1$H NMR (400 MHz, Methanol-d$_4$) δ ppm 7.39 (d, J = 2.3 Hz, 1 H), 7.15 (dd, J = 8.6, 2.3 Hz, 1 H), 6.80 (d, J = 8.6 Hz, 1 H), 3.40 (m, 5 H), 3.18-3.26 (m, 2 H), 2.56 (s, 2 H), 1.60-1.69 (m, 2 H), 1.48 (br. d, J = 13.9 Hz, 2 H), 1.05 (s, 3 H). HRMS calcd for C$_{18}$H$_{25}$Cl$_2$N$_5$OS (M + H)$^+$ 430.1049, found 430.1061. | 0.170 |
| 57 | (structure) | $^1$H NMR (400 MHz, Methanol-d$_4$) δ ppm 8.83-8.90 (m, 1 H), 8.31 (dd, J = 8.1, 1.3 Hz, 1 H), 7.64 (d, J = 8.1 Hz, 1 H), 7.54 (dd, J = 8.3, 4.3 Hz, 1 H), 7.41 (t, J = 7.8 Hz, 1 H), 7.16 (d, J = 7.3 Hz, 1 H), 3.45 (m, 5 H), 3.19-3.29 (m, 2 H), 2.65 (br. s, 2 H), 1.63-1.72 (m, 2 H), 1.52 (br. d, J = 13.6 Hz, 2 H), 1.08 (s, 3 H). HRMS calcd for C$_{21}$H$_{27}$N$_6$OS (M + H)$^+$ 411.1967, found 411.1953. | 0.279 |
| 58 | (structure) | $^1$H NMR (400 MHz, Methanol-d$_4$) δ ppm 7.07-7.14 (m, 1 H), 6.98-7.07 (m, 2 H), 6.89-6.96 (m, 1 H), 3.40 (m, 5 H), 3.15-3.26 (m, 2 H), 2.45-2.61 (m, 2 H), 1.58-1.71 (m, 2 H), 1.42-1.52 (m, 2 H), 1.04 (s, 3 H). HRMS calcd for C$_{18}$H$_{25}$FN$_5$OS (M + H)$^+$ 378.1764, found 378.1763. | 0.429 |

TABLE 10-continued

| Example | Compound | Characterization | IC$_{50}$ (μM) |
|---|---|---|---|
| 59 | | $^1$H NMR (400 MHz, Methanol-d$_4$) δ ppm 8.24 (d, J = 5.31 Hz, 1 H), 7.08 (d, J = 5.31 Hz, 1 H), 4.15-4.27 (m, 1 H), 3.85 (d, J = 8.59 Hz, 1 H), 3.70 (d, J = 8.59 Hz, 1 H), 3.51-3.60 (m, 2 H), 3.42 (s, 3 H), 3.06-3.22 (m, 2 H), 3.03 (d, J = 5.05 Hz, 1 H), 1.82-1.99 (m, 2 H), 1.65-1.77 (m, 2 H), 1.22 (d, J = 6.57 Hz, 3 H). HRMS calcd for C$_{20}$H$_{25}$ClF$_3$N$_6$O$_2$S (M + H)$^+$ 505.1395, found 505.1395. | 0.043 |
| 60 | | $^1$H NMR (400 MHz, Methanol-d$_4$) δ ppm 6.84 (t, J = 7.91 Hz, 1 H), 6.57 (dd, J = 8.03, 1.25 Hz, 1 H), 6.13 (dd, J = 7.91, 1.38 Hz, 1 H), 3.51-3.65 (m, 2 H), 3.41 (s, 3 H), 2.98-3.11 (m, 2 H), 2.81-2.91 (m, 1 H), 2.15 (dt, J = 12.36, 6.49 Hz, 1 H), 1.99-2.10 (m, 1 H), 1.94 (dd, J = 12.80, 8.28 Hz, 1 H), 1.73-1.85 (m, 2 H), 1.35-1.46 (m, 2 H), 1.24-1.32 (m, 1 H), 1.09-1.19 (m, 1 H), 1.07 (d, J = 6.27 Hz, 3 H). HRMS calcd for C$_{21}$H$_{30}$ClN$_6$OS (M + H)$^+$ 449.1885, found 449.1883. | 0.016 |
| 61 | | $^1$H NMR (400 MHz, Methanol-d$_4$) δ ppm 8.64 (s, 1 H), 8.38 (d, J = 5.56 Hz, 1 H), 7.10 (d, J = 5.56 Hz, 1 H), 4.18-4.27 (m, 1 H), 3.85 (d, J = 8.84 Hz, 1 H), 3.70 (d, J = 8.59 Hz, 1 H), 3.56 (br. dd, J = 13.39, 5.05 Hz, 2 H), 3.42 (s, 3 H), 3.08-3.23 (m, 2 H), 3.03 (d, J = 5.05 Hz, 1 H), 1.83-2.00 (m, 2 H), 1.65-1.79 (m, 2 H), 1.22 (d, J = 6.57 Hz, 3 H). HRMS calcd for C$_{20}$H$_{26}$F$_3$N$_6$O$_2$S (M + H)$^+$ 471.1785, found 471.1791. | 0.093 |
| 62 | | $^1$H NMR (400 MHz, Methanol-d$_4$) δ ppm 7.68 (d, J = 5.56 Hz, 1 H), 6.20 (d, J = 5.56 Hz, 1 H), 3.52-3.69 (m, 6 H), 3.41 (s, 3 H), 3.00-3.13 (m, 2 H), 2.86 (br. s, 1 H), 2.10-2.20 (m, 1 H), 1.99-2.07 (m, 1 H), 1.87-1.97 (m, 5 H), 1.74-1.86 (m, 2 H), 1.41 (br t, J = 10.48 Hz, 2 H), 1.29 (br. dd, J = 12.38, 9.35 Hz, 1 H), 1.09-1.19 (m, 1 H), 1.07 (br. d, J = 6.57 Hz, 3 H). HRMS calcd for C$_{24}$H$_{35}$ClN$_7$OS (M + 2H)$^{2+}$ 252.6192, found 252.6190. | 0.025 |

TABLE 10-continued

| Example | Compound | Characterization | IC$_{50}$ (μM) |
|---|---|---|---|
| 63 | 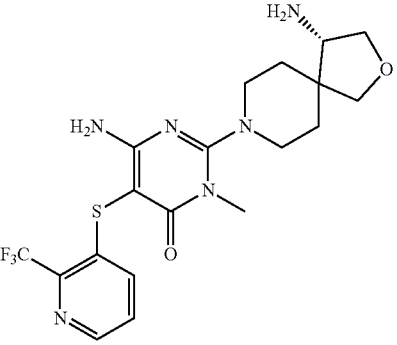 | $^1$H NMR (400 MHz, Methanol-d$_4$) δ ppm 8.34 (d, J = 3.79 Hz, 1 H), 7.51 (d, J = 7.83 Hz, 1 H), 7.41 (dd, J = 8.34, 4.55 Hz, 1 H), 4.12 (dd, J = 9.09, 6.57 Hz, 1 H), 3.83 (d, J = 8.84 Hz, 1 H), 3.76 (d, J = 8.59 Hz, 1 H), 3.46-3.67 (m, 3 H), 3.42 (s, 3 H), 3.01-3.22 (m, 3 H), 1.75-1.97 (m, 2 H), 1.62 (t, J = 15.28 Hz, 2 H). HRMS calcd for C$_{19}$H$_{24}$F$_3$N$_6$O$_2$S (M + H)$^+$ 457.1628, found 457.1617. | 0.034 |
| 64 | 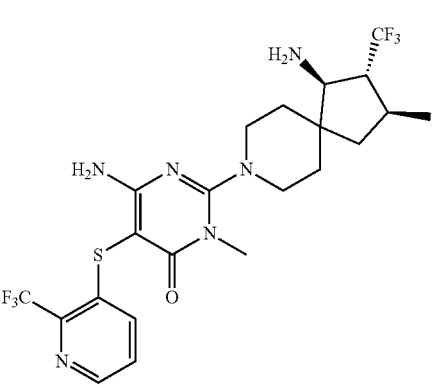 [SMILES: C[C@H]1CC2(CCN(c3nc(N)c(Sc4cccnc4C(F)(F)F)c(=O)n3C)CC2)[C@@H](N)[C@@H]1C(F)(F)F] | Chiral SFC purification performed as follows; column: WHO1 21 × 250 mm, flow rate: 80 g per minute, mobile phase: 35% EtOH and 10 mM NH$_4$OH in CO$_2$, detection: 205 nm UV to obtain single enantiomer R$_t$ (P1) = 9.7 min. $^1$H NMR (400 MHz, Methanol-d$_4$) δ ppm 8.33 (dd, J = 4.55, 1.01 Hz, 1 H), 7.51 (dd, J = 8.08, 0.76 Hz, 1 H), 7.41 (dd, J = 8.08, 4.55 Hz, 1 H), 3.51-3.67 (m, 2 H), 3.38-3.44 (m, 3 H), 3.04-3.18 (m, 2 H), 3.01 (d, J = 7.83 Hz, 1 H), 2.08-2.28 (m, 2 H), 1.76-2.00 (m, 3 H), 1.55 (dd, J = 13.14, 8.08 Hz, 1 H), 1.40-1.50 (m, 2 H), 1.14-1.21 (m, 3 H). HRMS calcd for C$_{22}$H$_{27}$F$_6$N$_6$OS (M + H)$^+$ 537.1866, found 537.1864. | 0.856 |
| 65 | 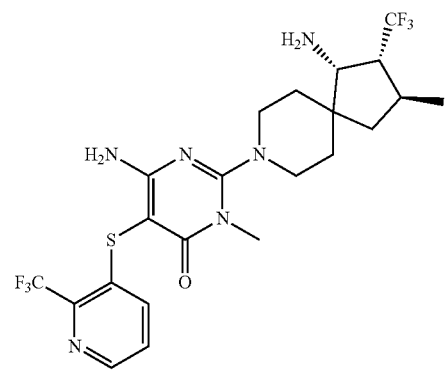 [SMILES: C[C@H]1CC2(CCN(c3nc(N)c(Sc4cccnc4C(F)(F)F)c(=O)n3C)CC2)[C@H](N)[C@@H]1C(F)(F)F] | Chiral SFC purification performed as follows; column: WHO1 21 × 250 mm, flow rate: 80 g per minute, mobile phase: 35% EtOH and 10 mM NH$_4$OH in CO$_2$, detection: 205 nm UV to obtain single enantiomer R$_t$ (P2) = 12.0 min. $^1$H NMR (400 MHz, Methanol-d$_4$) δ ppm 8.33 (dd, J = 4.55, 0.76 Hz, 1 H), 7.47-7.57 (m, 1 H), 7.41 (dd, J = 8.08, 4.55 Hz, 1 H), 3.57 (td, J = 7.96, 3.79 Hz, 2 H), 3.37-3.43 (m, 3 H), 3.25 (d, J = 6.82 Hz, 1 H), 3.05-3.19 (m, 2 H), 2.36-2.64 (m, 2 H), 2.11-2.22 (m, 1 H), 1.75-1.91 (m, 2 H), 1.46-1.64 (m, 2 H), 1.28 (dd, J = 13.26, 8.46 Hz, 1 H), 1.17 (d, J = 6.57 Hz, 3 H). HRMS calcd for C$_{22}$H$_{27}$F$_6$N$_6$OS (M + H)$^+$ 537.1866, found 537.1868. | 0.061 |
| 66 | 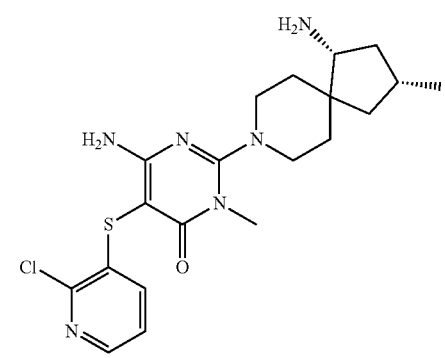 [SMILES: C[C@H]1C[C@@H](N)C2(CCN(c3nc(N)c(Sc4cccnc4Cl)c(=O)n3C)CC2)C1] | $^1$H NMR (400 MHz, Methanol-d$_4$) δ ppm 8.06 (dd, J = 4.29, 2.02 Hz, 1 H), 7.18-7.25 (m, 2 H), 3.54-3.67 (m, 2 H), 3.41 (s, 3 H), 3.01-3.12 (m, 2 H), 2.86 (dd, J = 9.35, 6.32 Hz, 1 H), 2.15 (dt, J = 12.57, 6.47 Hz, 1 H), 1.98-2.09 (m, 1 H), 1.88-1.98 (m, 1 H), 1.80 (td, J = 12.63, 4.04 Hz, 2 H), 1.36-1.48 (m, 2 H), 1.29 (dd, J = 12.88, 9.09 Hz, 1 H), 1.13 (dt, J = 12.19, 9.95 Hz, 1 H), 1.07 (d, J = 6.57 Hz, 3 H). HRMS calcd for C$_{20}$H$_{28}$ClN$_6$OS (M + H)$^+$ 435.1728, found 435.1724. | 0.020 |

Example 67

6-amino-2-((3S,4S)-4-amino-3-methyl-2-oxa-8-azaspiro[4.5]decan-8-yl)-5-((3-chloro-2-methylpyridin-4-yl)thio)-3-methylpyrimidin-4(3H)-one

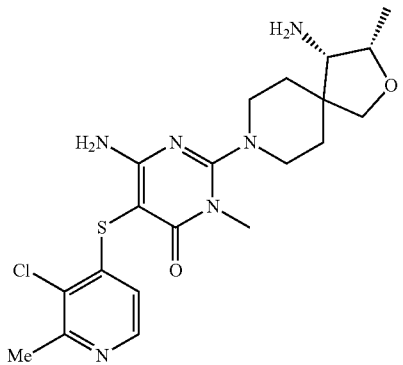 [SMILES: Cc1nccc(Sc2c(N)nc(N3CCC4(CC3)CO[C@@H](C)[C@H]4N)n(C)c2=O)c1Cl]

A mixture of tert-butyl ((3S,4S)-8-(4-amino-5-iodo-1-methyl-6-oxo-1,6-dihydropyrimidin-2-yl)-3-methyl-2-oxa-8-azaspiro[4.5]decan-4-yl)carbamate (145 mg, 0.279 mmol), sodium 3-chloro-2-methylpyridine-4-thiolate (101 mg, 0.558 mmol), Cu(I)I (10.6 mg, 0.056 mmol), TMEDA (17 µL, 0.112 mmol), and $K_3PO_4$ (178 mg, 0.838 mmol) in degassed dioxane (1 mL) under $N_2$ atmosphere was stirred for 90 min at 100° C. After cooling to RT, the reaction mixture was poured into a separation funnel containing aq. $K_2CO_3$ (2 M, 30 mL) and extracted with DCM (3×30 mL). The combined organic phases were dried over $MgSO_4$, filtered, and the volatiles were removed under reduced pressure. The residue was dissolved in DCM (5 mL) and TFA (1 mL) was added. After stirring for 90 min at RT, the volatiles were removed under reduced pressure and the residue was purified by HPLC (gradient elution 10-30% MeCN in water, 5 mM $NH_4OH$ modifier) to give 6-amino-2-((3S,4S)-4-amino-3-methyl-2-oxa-8-azaspiro[4.5]decan-8-yl)-5-((3-chloro-2-methylpyridin-4-yl)thio)-3-methylpyrimidin-4(3H)-one (36.1 mg) as a white solid.

The following compounds of Table 11 were synthesized using the above procedure or modifications to the above procedure using the corresponding thiol and iodo-pyrimidinone intermediate:

TABLE 11

| | | | |
|---|---|---|---|
| 67 | 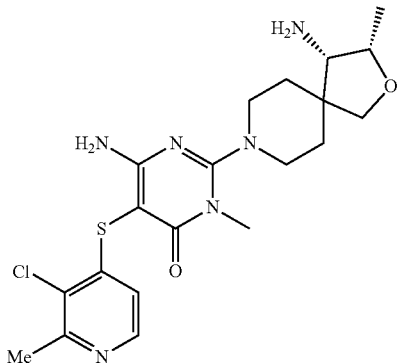 [SMILES: Cc1nccc(Sc2c(N)nc(N3CCC4(CC3)CO[C@@H](C)[C@H]4N)n(C)c2=O)c1Cl] | $^1$H NMR (400 MHz, Methanol-$d_4$) δ ppm 8.02 (d, J = 5.56 Hz, 1 H), 6.73 (d, J = 5.31 Hz, 1 H), 4.15-4.30 (m, 1 H), 3.85 (d, J = 8.84 Hz, 1 H), 3.70 (d, J = 8.59 Hz, 1 H), 3.50-3.62 (m, 2 H), 3.42 (s, 3 H), 3.01-3.23 (m, 3 H), 2.49-2.63 (m, 3 H), 1.83-1.99 (m, 2 H), 1.63-1.78 (m, 2 H), 1.22 (d, J = 6.57 Hz, 3 H). HRMS calcd for $C_{20}H_{28}ClN_6O_2S$ (M + H)$^+$ 451.1677, found 451.1669. | 0.048 |
| 68 | 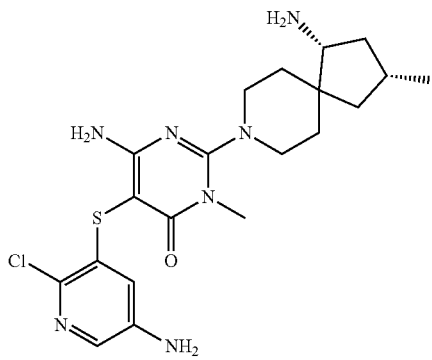 [SMILES: C[C@H]1C[C@@H](N)C2(CCN(c3nc(N)c(Sc4cc(N)cnc4Cl)c(=O)n3C)CC2)C1] | $^1$H NMR (400 MHz, Methanol-$d_4$) δ ppm 7.70 (s, 1 H), 6.06 (s, 1 H), 3.54-3.68 (m, 2 H), 3.40-3.44 (m, 3 H), 2.99-3.11 (m, 2 H), 2.86 (br. d, J = 4.27 Hz, 1 H), 2.15 (dt, J = 12.23, 6.31 Hz, 1 H), 2.04 (dq, J = 15.56, 7.70 Hz, 1 H), 1.88-1.98 (m, 1 H), 1.80 (tt, J = 12.67, 3.89 Hz, 2 H), 1.42 (br t, J = 10.04 Hz, 2 H), 1.29 (dd, J = 12.92, 9.16 Hz, 1 H), 1.09-1.20 (m, 1 H), 1.07 (d, J = 6.53 Hz, 3 H). HRMS calcd for $C_{20}H_{29}ClN_7OS$ (M + H)$^+$ 450.1837, found 450.1824. | 0.010 |

TABLE 11-continued

| # | Structure | Data | Value |
|---|---|---|---|
| 69 | (structure) | ¹H NMR (400 MHz, Methanol-d₄) δ ppm 6.99 (d, J = 8.34 Hz, 1 H), 6.40 (dd, J = 8.46, 2.65 Hz, 1 H), 6.22 (d, J = 2.53 Hz, 1 H), 3.51-3.65 (m, 2 H), 3.42 (s, 3 H), 2.99-3.10 (m, 2 H), 2.87 (br t, J = 7.33 Hz, 1 H), 2.11-2.20 (m, 1 H), 2.04 (br. d, J = 7.58 Hz, 1 H), 1.88-1.98 (m, 1 H), 1.80 (br t, J = 12.00 Hz, 2 H), 1.36-1.47 (m, 2 H), 1.29 (dd, J = 12.88, 9.09 Hz, 1 H), 1.10-1.20 (m, 1 H), 1.07 (d, J = 6.57 Hz, 3 H). HRMS calcd for $C_{21}H_{30}ClN_6OS$ (M + H)⁺ 449.1885, found 449.1874. | 0.010 |
| 70 | (structure) | ¹H NMR (400 MHz, Methanol-d₄) δ ppm 5.97 (s, 1 H), 3.52-3.66 (m, 2 H), 3.41 (s, 3 H), 3.00-3.11 (m, 2 H), 2.84 (br. dd, J = 9.35, 6.57 Hz, 1 H), 2.14 (dt, J = 12.51, 6.38 Hz, 1 H), 1.97-2.09 (m, 1 H), 1.92 (dd, J = 12.88, 8.34 Hz, 1 H), 1.80 (td, J = 12.57, 3.92 Hz, 2 H), 1.40 (br t, J = 10.86 Hz, 2 H), 1.28 (dd, J = 12.88, 9.09 Hz, 1 H), 1.13 (dt, J = 12.13, 9.98 Hz, 1 H), 1.06 (d, J = 6.57 Hz, 3 H). HRMS calcd for $C_{20}H_{28}Cl_2N_7OS$ (M + H)⁺ 484.1448, found 484.1441. | 0.011 |
| 71 | (structure) | NMR (400 MHz, Methanol-d₄) δ ppm 7.58 (d, J = 5.56 Hz, 1 H), 6.15 (d, J = 5.56 Hz, 1 H), 4.12 (dd, J = 9.09, 6.57 Hz, 1 H), 3.83 (d, J = 8.59 Hz, 1 H), 3.77 (d, J = 8.84 Hz, 1 H), 3.46-3.65 (m, 3 H), 3.42 (s, 3 H), 3.15-3.20 (m, 1 H), 3.03-3.14 (m, 2 H), 1.73-1.93 (m, 2 H), 1.56-1.71 (m, 2 H). HRMS calcd for $C_{18}H_{25}ClN_7O_2S$ (M + H)⁺ 438.1473, found 438.1463. | 0.022 |
| 72 | (structure) | 7.24 (dd, J = 7.96, 1.39 Hz, 1 H), 7.10 (t, J = 8.08 Hz, 1 H), 6.76 (dd, J = 8.08, 1.26 Hz, 1 H), 4.12 (dd, J = 9.09, 6.57 Hz, 1 H), 3.84 (d, J = 8.84 Hz, 1 H), 3.78 (d, J = 8.84 Hz, 1 H), 3.47-3.66 (m, 3 H), 3.43 (s, 3 H), 3.18 (t, J = 5.81 Hz, 1 H), 2.99-3.15 (m, 2 H), 1.78-1.96 (m, 2 H), 1.54-1.71 (m, 2 H). HRMS calcd for $C_{19}H_{24}Cl_2N_5O_2S$ (M + H)⁺ 456.1022, found 456.1017. | 0.033 |

TABLE 11-continued

| 73 | (structure) | $^1$H NMR (400 MHz, Methanol-d$_4$) δ ppm 8.12 (d, J = 5.56 Hz, 1 H), 7.04 (d, J = 5.56 Hz, 1 H), 3.57-3.69 (m, 2 H), 3.40 (s, 3 H), 3.02-3.12 (m, 2 H), 2.85 (dd, J = 9.60, 6.32 Hz, 1 H), 2.09-2.20 (m, 1 H), 2.03 (br. s, 1 H), 1.88-1.98 (m, 1 H), 1.74-1.85 (m, 2 H), 1.37-1.48 (m, 2 H), 1.24-1.33 (m, 1 H), 1.11-1.18 (m, 1 H), 1.07 (d, J = 6.57 Hz, 3 H). HRMS calcd for C$_{21}$H$_{27}$ClF$_3$N$_6$OS (M + H)$^+$ 503.1602, found 503.1599. | 0.071 |
| --- | --- | --- | --- |
| 74 | (structure) | $^1$H NMR (400 MHz, Methanol-d$_4$) δ ppm 7.93 (d, J = 5.31 Hz, 1 H), 6.60 (dd, J = 5.56, 0.76 Hz, 1 H), 4.15-4.30 (m, 1 H), 3.95 (s, 3 H), 3.85 (d, J = 8.59 Hz, 1 H), 3.70 (d, J = 8.59 Hz, 1 H), 3.54 (br. dd, J = 13.39, 4.80 Hz, 2 H), 3.41 (s, 3 H), 3.01-3.22 (m, 3 H), 1.82-2.00 (m, 2 H), 1.64-1.77 (m, 2 H), 1.22 (d, J = 6.32 Hz, 3 H). HRMS calcd for C$_{21}$H$_{28}$F$_3$N$_6$O$_3$S (M + H)$^+$ 501.1890, found 501.1894. | 0.017 |
| 75 | (structure) | $^1$H NMR (400 MHz, Methanol-d$_4$) δ ppm 8.63 (s, 1 H), 8.38 (d, J = 5.56 Hz, 1 H), 7.10 (d, J = 5.56 Hz, 1 H), 3.55-3.72 (m, 2 H), 3.42 (s, 3 H), 3.02-3.13 (m, 2 H), 2.85 (dd, J = 9.35, 6.57 Hz, 1 H), 2.15 (dt, J = 12.32, 6.35 Hz, 1 H), 1.98-2.09 (m, 1 H), 1.89-1.97 (m, 1 H), 1.80 (td, J = 12.69, 4.17 Hz, 2 H), 1.41 (br t, J = 10.36 Hz, 2 H), 1.29 (dd, J = 13.01, 8.97 Hz, 1 H), 1.13 (dt, J = 12.19, 9.95 Hz, 1 H), 1.07 (d, J = 6.57 Hz, 3 H). HRMS calcd for C$_{21}$H$_{28}$F$_3$N$_6$OS (M + 2H)$^{2+}$ 235.1033, found 235.1030. | 0.018 |
| 76 | (structure) | $^1$H NMR (400 MHz, Methanol-d$_4$) δ ppm 8.35 (s, 1 H), 8.15 (br. d, J = 5.05 Hz, 1 H), 6.87 (d, J = 5.31 Hz, 1 H), 3.55-3.70 (m, 2 H), 3.42 (s, 3 H), 3.00-3.16 (m, 2 H), 2.87 (br. s, 1 H), 2.15 (dt, J = 12.06, 6.22 Hz, 1 H), 1.98-2.11 (m, 1 H), 1.88-1.98 (m, 1 H), 1.75-1.86 (m, 2 H), 1.42 (br t, J = 10.23 Hz, 2 H), 1.25-1.34 (m, 1 H), 1.10-1.19 (m, 1 H), 1.03-1.09 (m, 3 H). HRMS calcd for C$_{20}$H$_{28}$ClN$_6$OS (M + H)$^+$ 435.1728, found 435.1721. | 0.027 |

| | | | |
|---|---|---|---|
| 77 | 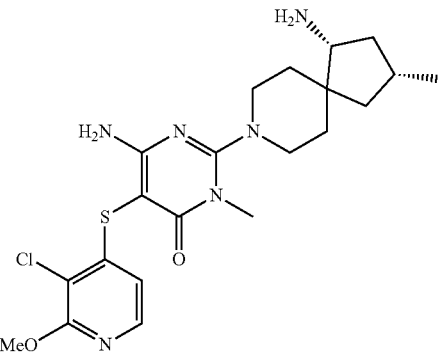 [SMILES: COc1nccc(Sc2c(N)nc(N3CCC4(CC3)C[C@@H](C)C[C@H]4N)n(C)c2=O)c1Cl] | ¹H NMR (400 MHz, Methanol-d₄) δ ppm 7.76 (d, J = 5.31 Hz, 1 H), 6.43 (d, J = 5.56 Hz, 1 H), 3.95 (s, 3 H), 3.53-3.67 (m, 2 H), 3.41 (s, 3 H), 3.00-3.12 (m, 2 H), 2.85 (dd, J = 9.60, 6.32 Hz, 1 H), 2.14 (dt, J = 12.38, 6.44 Hz, 1 H), 1.98-2.10 (m, 1 H), 1.89-1.98 (m, 1 H), 1.80 (td, J = 12.63, 3.79 Hz, 2 H), 1.36-1.47 (m, 2 H), 1.29 (dd, J = 12.88, 9.09 Hz, 1 H), 1.09-1.18 (m, 1 H), 1.06 (d, J = 6.57 Hz, 3 H). HRMS calcd for $C_{21}H_{30}ClN_6O_2S$ (M + H)⁺ 465.1834, found 465.1828. | 0.039 |
| 78 | 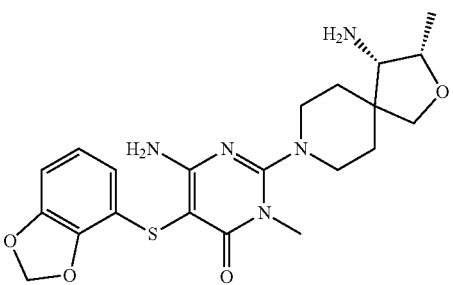 [SMILES: C[C@@H]1OCC2(CCN(c3nc(N)c(Sc4cccc5c4OCO5)c(=O)n3C)CC2)[C@@H]1N] | ¹H NMR (400 MHz, Methanol-d₄) δ ppm 6.68 (t, J = 7.9 Hz, 1 H), 6.61 (dd, J = 7.7, 1.2 Hz, 1 H), 6.52 (dd, J = 8.0, 1.2 Hz, 1 H), 5.94 (s, 2 H), 4.26-4.17 (m, 1 H), 3.83 (d, J = 8.7 Hz, 1 H), 3.68 (d, J = 8.7 Hz, 1 H), 3.53-3.43 (m, 2 H), 3.40 (s, 3 H), 3.17-3.07 (m, 1 H), 3.07-2.97 (m, 2 H), 1.97-1.79 (m, 2 H), 1.77-1.61 (m, 2 H), 1.21 (d, J = 6.5 Hz, 3 H). HRMS calcd for $C_{21}H_{28}N_5O_4S$ (M + H)⁺ 446.1862, found 446.1880. | 0.012 |
| 79 | 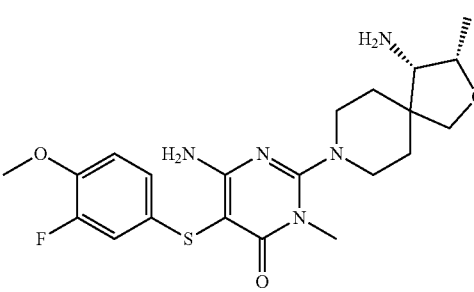 | ¹H NMR (400 MHz, Methanol-d₄) δ ppm 7.00-6.92 (m, 2 H), 6.90 (d, J = 11.7 Hz, 1 H), 4.27-4.18 (m, 1 H), 3.83 (d, J = 8.7 Hz, 1 H), 3.81 (s, 3 H), 3.69 (d, J = 8.8 Hz, 1 H), 3.53-3.44 (m, 2 H), 3.41 (s, 3 H), 3.16-3.08 (m, 1 H), 3.08-2.96 (m, 2 H), 1.97-1.81 (m, 2 H), 1.77-1.60 (m, 2 H), 1.21 (d, J = 6.3 Hz, 3 H). HRMS calcd for $C_{21}H_{29}FN_5O_3S$ (M + H)⁺ 450.1975, found 450.1966. | 0.370 |
| 80 | 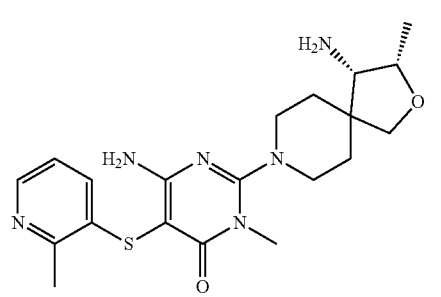 [SMILES: Cc1ncccc1Sc1c(N)nc(N2CCC3(CC2)CO[C@@H](C)[C@H]3N)n(C)c1=O] | ¹H NMR (400 MHz, Methanol-d₄) δ ppm 8.10 (dd, J = 4.9, 1.5 Hz, 1 H), 7.19 (dd, J = 8.0, 1.5 Hz, 1 H), 7.13-7.04 (m, 1 H), 4.26-4.16 (m, 1 H), 3.84 (d, J = 8.7 Hz, 1 H), 3.70 (d, J = 8.7 Hz, 1 H), 3.58-3.46 (m, 2 H), 3.42 (s, 3 H), 3.20-3.11 (m, 1 H), 3.11-2.98 (m, 2 H), 2.59 (s, 3 H), 1.98-1.82 (m, 2 H), 1.78-1.61 (m, 2 H), 1.22 (d, J = 6.5 Hz, 3 H). HRMS calcd for $C_{20}H_{29}N_6O_2S$ (M + H)⁺ 417.2073, found 417.2103. | 0.068 |
| 81 | 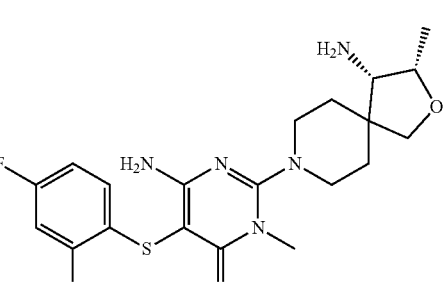 | ¹H NMR (400 MHz, Methanol-d₄) δ ppm 7.19 (dd, J = 8.5, 2.6 Hz, 1 H), 6.97-6.89 (m, 1 H), 6.85 (dd, J = 8.9, 5.8 Hz, 1 H), 4.27-4.17 (m, 1 H), 3.84 (d, J = 8.7 Hz, 1 H), 3.70 (d, J = 8.7 Hz, 1 H), 3.59-3.45 (m, 2 H), 3.41 (s, 3 H), 3.19-3.11 (m, 1 H), 3.10-3.00 (m, 2 H), 1.98-1.82 (m, 2 H), 1.77-1.64 (m, 2 H), 1.22 (d, J = 6.5 Hz, 3 H). HRMS calcd for $C_{20}H_{26}ClFN_5O_2S$ (M + H)⁺ 454.1480, found 454.1474. | 0.015 |

TABLE 11-continued

| | | | |
|---|---|---|---|
| 82 | 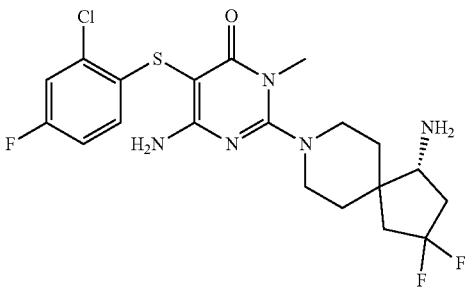 [SMILES: Cn1c(N2CCC3(CC2)CC(F)(F)C[C@H]3N)nc(N)c(Sc2ccc(F)cc2Cl)c1=O] | $^1$H NMR (400 MHz, Chloroform-d) δ ppm 7.01 (dd, J = 8.3, 2.6 Hz, 1 H), 6.90 (dd, J = 8.8, 5.8 Hz, 1 H), 6.80-6.72 (m, 1 H), 3.55-3.41 (m, 2 H), 3.35 (s, 3 H), 3.10 (t, J = 7.7 Hz, 1 H), 2.96-2.77 (m, 2 H), 2.46 (ddt, J = 19.6, 12.5, 7.4 Hz, 1 H), 2.33 (q, J = 14.3 Hz, 1 H), 2.04-1.85 (m, 2 H), 1.77 (qd, J = 13.2, 3.7 Hz, 2 H), 1.43 (dd, J = 37.1, 13.4 Hz, 6 H). HRMS calcd for $C_{20}H_{24}ClF_3N_5OS$ $(M + H)^+$ 474.1342, found 474.1333. | 0.025 |
| 83 | 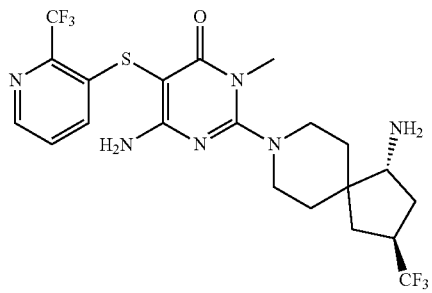 [SMILES: Cn1c(N2CCC3(CC2)C[C@H](C(F)(F)F)C[C@H]3N)nc(N)c(Sc2cccnc2C(F)(F)F)c1=O] | $^1$H NMR (400 MHz, Chloroform d) δ 8.39-8.23 (m, 1 H), 7.58-7.45 (m, 1 H), 7.21 (dd, J = 8.3, 4.7 Hz, 1 H), 3.48 (t, J = 12.5 Hz, 2 H), 3.38 (s, 3 H), 3.03-2.86 (m, 3 H), 2.79 (dq, J = 18.1, 9.8 Hz, 1 H), 2.08 (dd, J = 13.8, 9.4 Hz, 2 H), 1.83-1.24 (m, 10 H). HRMS calcd for $C_{21}H_{25}F_6N_6OS$ $(M + H)^+$ 523.1715, found 523.1711. | 0.056 |
| 84 | 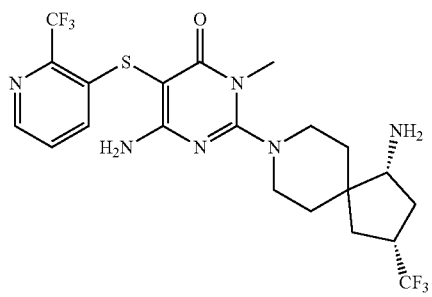 [SMILES: Cn1c(N2CCC3(CC2)C[C@@H](C(F)(F)F)C[C@H]3N)nc(N)c(Sc2cccnc2C(F)(F)F)c1=O] | $^1$H NMR (400 MHz, Chloroform-d) δ ppm 8.32 (dd, J = 4.5, 1.1 Hz, 1 H), 7.51 (d, J = 7.7 Hz, 1 H), 7.31-7.18 (m, 1 H), 3.52-3.40 (m, 2 H), 3.37 (s, 3 H), 2.95 (dt, J = 17.6, 11.4 Hz, 3 H), 2.66 (dq, J = 18.1, 9.1 Hz, 1 H), 2.19 (dt, J = 14.5, 7.3 Hz, 1 H), 1.90-1.80 (m, 1 H), 1.80-1.66 (m, 4 H), 1.66-1.24 (m, 6 H). $^{19}$F NMR (376 MHz, Chloroform-d) δ ppm −64.93, −71.24 (dd, J = 9.4, 3.1 Hz). HRMS calcd for $C_{21}H_{25}F_6N_6OS$ $(M + H)^+$ 523.1715, found 523.1711. | 0.072 |
| 85 | 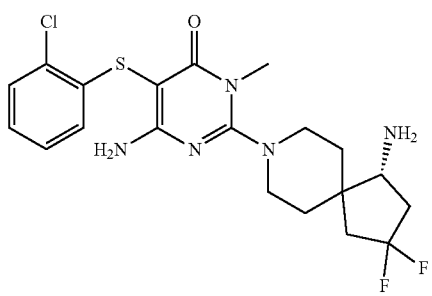 [SMILES: Cn1c(N2CCC3(CC2)CC(F)(F)C[C@H]3N)nc(N)c(Sc2ccccc2Cl)c1=O] | $^1$H NMR (400 MHz, Chloroform-d) δ ppm 7.22 (dd, J = 7.8, 1.4 Hz, 1 H), 6.98 (dtd, J = 26.3, 7.5, 1.5 Hz, 2 H), 6.84 (dd, J = 7.8, 1.5 Hz, 1 H), 6.55-6.30 (m, 2 H), 3.54-3.40 (m, 2 H), 3.36 (s, 3 H), 3.12 (t, J = 7.8 Hz, 1 H), 2.95-2.78 (m, 2 H), 2.54-2.40 (m, 1 H), 2.39-2.23 (m, 1 H), 2.07-1.90 (m, 2 H), 1.84-1.69 (m, 3 H), 1.45-1.19 (m, 3 H). HRMS calcd for $C_{20}H_{25}ClF_2N_5OS$ $(M + H)^+$ 456.1436, found 456.1417. | 0.077 |
| 86 | 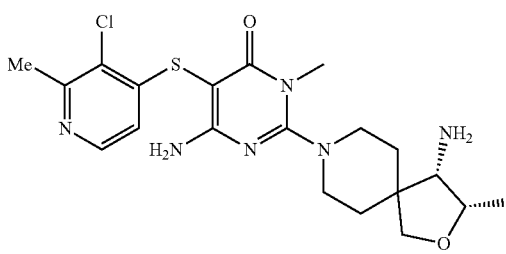 | $^1$H NMR (400 MHz, Methanol-d$_4$) δ ppm 8.02 (d, J = 5.4 Hz, 1 H), 6.74 (d, =5.3 Hz, 1 H), 3.94 (q, J = 6.7, 6.1 Hz, 1 H), 3.84-3.71 (m, 2 H), 3.58-3.49 (m, 2 H), 3.42 (s, 3 H), 3.20 (ddd, J = 13.1, 9.8, 2.9 Hz, 1 H), 3.13-3.03 (m, 2 H), 2.57 (s, 3 H), 1.98-1.82 (m, 2 H), 1.80-1.67 (m, 2 H), 1.59 (p, J = 6.9, 6.3 Hz, 2 H), 1.01 (t, J = 7.4 Hz, 3 H). HRMS calcd for $C_{21}H_{30}ClN_6O_2S$ $(M + H)^+$ 465.1839, found 465.1833. | 0.022 |

| | | |
|---|---|---|
| 87 | 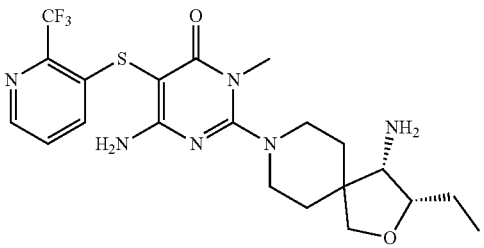 [SMILES: CC[C@@H]1OCC2(CCN(c3nc(N)c(Sc4cccnc4C(F)(F)F)c(=O)n3C)CC2)[C@@H]1N] | ¹H NMR (400 MHz, Methanol-d₄) δ ppm 8.36-8.30 (m, 1 H), 7.53-7.49 (m, 1 H), 7.41 (dd, J = 8.2, 4.5 Hz, 1 H), 3.94 (ddd, J = 7.4, 6.1, 4.7 Hz, 1 H), 3.81 (d, J = 8.7 Hz, 1 H), 3.73 (d, J = 8.7 Hz, 1 H), 3.59-3.49 (m, 2 H), 3.41 (s, 3 H), 3.20 (ddd, J = 13.2, 9.8, 3.0 Hz, 1 H), 3.12-3.04 (m, 2 H), 1.89 (dddd, J = 27.7, 13.4, 10.0, 3.6 Hz, 2 H), 1.79-1.67 (m, 2 H), 1.64-1.54 (m, 2 H), 1.00 (t, J = 7.4 Hz, 3 H). HRMS calcd for C₂₁H₂₈F₃N₆O₂S (M + H)⁺ 485.1947, found 485.1945. | 0.021 |

Example 88

4-amino-6-((3S,4S)-4-amino-3-methyl-2-oxa-8-azaspiro[4.5]decan-8-yl)-3-((2-(trifluoromethyl)pyridin-3-yl)thio)pyridin-2(1H)-one

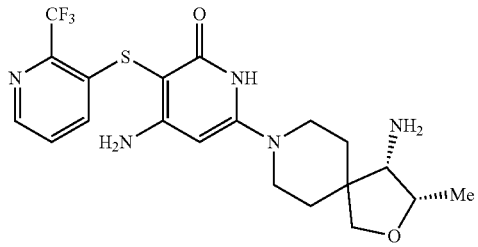 [SMILES: C[C@@H]1OCC2(CCN(c3cc(N)c(Sc4cccnc4C(F)(F)F)c(=O)[nH]3)CC2)[C@@H]1N]

A solution of 4-amino-6-fluoro-3-((2-(trifluoromethyl)pyridin-3-yl)thio)pyridin-2(1H)-one (22 mg, 0.072 mmol) and (3S,4S)-3-methyl-2-oxa-8-azaspiro[4.5]decan-4-amine (21 mg, 0.086 mmol) in DIPEA (0.2 mL) and DMSO (0.1 mL) was stirred for 5 h at 100° C. After cooling to RT, the volatiles were removed under reduced pressure and the residue was purified by HPLC (gradient elution 45-70% MeCN in water, 5 mM NH₄OH modifier) to give 4-amino-6-((3S,4S)-4-amino-3-methyl-2-oxa-8-azaspiro[4.5]decan-8-yl)-3-((2-(trifluoromethyl)pyridin-3-yl)thio)pyridin-2 (1H)-one (6.1 mg) as a white solid. ¹H NMR (400 MHz, Methanol-d₄) δ ppm 8.27-8.37 (m, 1H), 7.48 (d, J=7.58 Hz, 1H), 7.41 (dd, J=8.21, 4.42 Hz, 1H), 5.40 (s, 1H), 4.22 (dd, J=6.44, 4.93 Hz, 1H), 3.83 (d, J=8.84 Hz, 1H), 3.68 (d, J=8.84 Hz, 1H), 3.53 (td, J=11.68, 5.94 Hz, 2H), 3.03-3.20 (m, 2H), 3.01 (d, J=4.80 Hz, 1H), 1.77-1.92 (m, 2H), 1.59-1.74 (m, 2H), 1.22 (d, J=6.32 Hz, 3H). HRMS m/z calcd for C₂₀H₂₅F₃N₅O₂S (M+H)⁺456.1676, found 456.1623. IC₅₀=0.042 µM.

Example 89

4-amino-6-((3S,4S)-4-amino-3-methyl-2-oxa-8-azaspiro[4.5]decan-8-yl)-1-methyl-3-((2-(trifluoromethyl)pyridin-3-yl)thio)pyridin-2(1H)-one

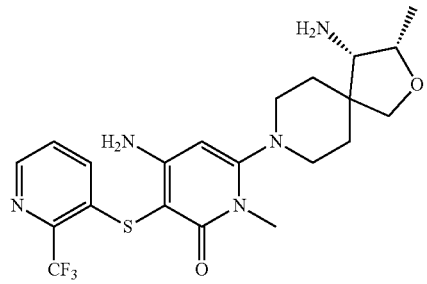 [SMILES: C[C@@H]1OCC2(CCN(c3cc(N)c(Sc4cccnc4C(F)(F)F)c(=O)n3C)CC2)[C@@H]1N]

A solution of 4-amino-6-fluoro-1-methyl-3-((2-(trifluoromethyl)pyridin-3-yl)thio)pyridin-2(1H)-one (80 mg, 0.251 mmol) and (3S,4S)-3-methyl-2-oxa-8-azaspiro[4.5] decan-4-amine (73.1 mg, 0.086 mmol) in DIPEA (0.45 mL) and DMSO (0.15 mL) was stirred for 20 h at 100° C. After cooling to RT, the volatiles were removed under reduced pressure and the residue was purified by HPLC (gradient elution 45-70% MeCN in water, 0.1% TFA modifier) to give the 4-amino-6-((3S,4S)-4-amino-3-methyl-2-oxa-8-azaspiro [4.5]decan-8-yl)-1-methyl-3-((2-(trifluoromethyl)pyridin-3-yl)thio)pyridin-2(1H)-one (84.8 mg) as its TFA salt as an orange oil. ¹H NMR (400 MHz, Methanol-d₄) δ ppm 8.33 (dd, J=4.04, 2.02 Hz, 1H), 7.33-7.43 (m, 2H), 5.71 (s, 1H), 4.23-4.36 (m, 1H), 3.95 (d, J=9.09 Hz, 1H), 3.84 (d, J=9.09 Hz, 1H), 3.47 (br.d, J=2.78 Hz, 1H), 3.46 (s, 3H), 3.15-3.26 (m, 2H), 2.60-2.86 (m, 2H), 1.88-2.02 (m, 3H), 1.76 (br.d, J=12.13 Hz, 1H), 1.32 (d, J=6.57 Hz, 3H). HRMS m/z calcd for C₂₁H₂₇F₃N₅O₂S (M+H)⁺470.1832, found 470.1826. IC₅₀=0.429 µM.

Example 90

6-amino-2-(4-(aminomethyl)-4-methylpiperidin-1-yl)-5-((2-(trifluoromethyl)pyridin-3-yl)thio)pyrimidin-4(3H)-one

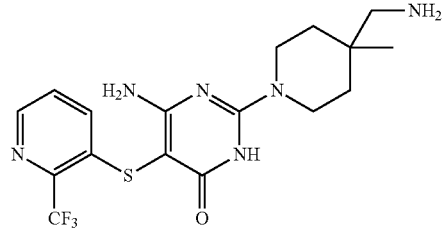 [SMILES: CC1(CN)CCN(c2nc(N)c(Sc3cccnc3C(F)(F)F)c(=O)[nH]2)CC1]

Step a: A mixture of 6-amino-5-((2-(trifluoromethyl)pyridin-3-yl)thio)-3-((2-(trimethylsilyl)ethoxy)methyl)pyrimidine-2,4(1H,3H)-dione (200 mg, 0.460 mmol), BOP—Cl (152 mg, 0.598 mmol), and tert-butyl ((4-methylpiperidin-4-yl)methyl)carbamate (158 mg, 0.690 mmol) in MeCN (5 mL) was added DBU (210 µL). The resulting mixture was stirred for 2 h at 100° C. After cooling to RT, the volatiles were removed under reduced pressure and the residue was purified by silica chromatography (0 to 50% gradient of EtOAc/heptane) to give tert-butyl ((1-(4-amino-6-oxo-5-((2-(trifluoromethyl)pyridin-3-yl)thio)-1-((2-(trimethylsilyl)ethoxy)methyl)-1,6-dihydropyrimidin-2-yl)-4-methylpiperidin-4-yl)methyl)carbamate (32 mg). ¹H NMR (400 MHz, Chloroform-d) δ ppm 8.39 (d, J=4.04 Hz, 1H), 7.58 (d, J=8.08 Hz, 1H), 7.29 (dd, J=8.08, 4.55 Hz, 1H), 5.22 (s, 2H), 4.67 (t, J=6.06 Hz, 1H), 4.12 (q, J=7.16 Hz, 1H), 3.87 (t, J=8.08 Hz, 2H), 3.62-3.77 (m, 2H), 3.37 (t, J=9.98 Hz, 2H), 3.09 (d, J=6.57 Hz, 2H), 2.05 (s, 2H), 1.57 (ddd, J=13.33, 9.54, 3.41 Hz, 2H), 1.37-1.51 (m, 12H), 1.26 (t, J=7.07 Hz, 3H), 1.00 (s, 3H), 0.84-0.97 (m, 3H), 0.02 (br. s, 9H).

Step b: To a solution of tert-butyl ((1-(4-amino-6-oxo-5-((2-(trifluoromethyl)pyridin-3-yl)thio)-1-((2-(trimethylsilyl)ethoxy)methyl)-1,6-dihydropyrimidin-2-yl)-4-methylpiperidin-4-yl)methyl)carbamate (32 mg, 0.050 mmol) in DCM (2 mL) was added TFA (0.5 mL) and the resulting mixture was stirred for 30 min at 50° C. After cooling to RT, the volatiles were removed under reduced pressure and the residue was dissolved in MeOH (2 mL) and ethylenediamine (50 mg, 0.75 mmol) was added. The resulting mixture was stirred for 16 h at RT. The volatiles were removed under reduced pressure and the residue was purified by HPLC (gradient elution 15-40% MeCN in water, 5 mM $NH_4OH$ modifier) to give 6-amino-2-(4-(aminomethyl)-4-methylpiperidin-1-yl)-5-((2-(trifluoromethyl)pyridin-3-yl)thio)pyrimidin-4(3H)-one (4.1 mg, 9.69 μmol) as a white solid. $^1$H NMR (400 MHz, Methanol-$d_4$) δ ppm 8.33 (d, J=3.79 Hz, 1H), 7.56 (d, J=8.08 Hz, 1H), 7.43 (dd, J=8.08, 4.55 Hz, 1H), 3.96 (dt, J=13.77, 4.74 Hz, 2H), 3.39-3.52 (m, 2H), 2.52-2.62 (m, 2H), 1.54 (ddd, J=13.71, 9.92, 4.17 Hz, 2H), 1.39-1.49 (m, 3H), 1.04-1.13 (m, 2H). $^{19}$F NMR (376 MHz, Methanol-$d_4$) δ ppm −66.39. HRMS calcd for $C_{17}H_{22}F_3N_6OS$ $(M+H)^+$ 415.1519, found 415.1528. $IC_{50}$=0.066 μM.

Example 91

Tert-butyl ((1-(4-((4-methoxybenzyl)oxy)pyrimidin-2-yl)-4-methylpiperidin-4-yl)methyl)carbamate

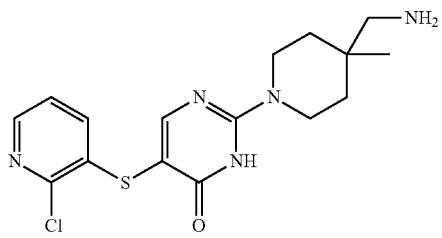 [SMILES: CC1(CN)CCN(c2ncc(Sc3cccnc3Cl)c(=O)[nH]2)CC1]

Step a: To a solution of tert-butyl ((1-(5-iodo-4-((4-methoxybenzyl)oxy)pyrimidin-2-yl)-4-methylpiperidin-4-yl)methyl)carbamate (198 mg, 0.348 mmol) in DMF (2 mL) was added $K_2CO_3$ (96 mg, 0.697 mmol), copper-1-thiophene-2-carboxylate (27 mg, 0.139 mmol), and 2-(trifluoromethyl)pyridine-3-thiol (90 mg, 491 mmol). The mixture was radiated in the microwave reactor for 30 min at 120° C. The reaction was poured into water (100 mL) and the mixture was extracted with DCM (4×). The combined organic extracts were washed with brine, dried over $MgSO_4$, filtered, and concentrated under reduced pressure. The residue was purified by silica chromatography (0 to 50% gradient of EtOAc/heptane) to give tert-butyl ((1-(4-((4-methoxybenzyl)oxy)-5-((2-(trifluoromethyl)pyridin-3-yl)thio)pyrimidin-2-yl)-4-methylpiperidin-4-yl)methyl)carbamate (110 mg) as a clear oil. MS m/z 620 $(M+H)^+$.

Step b: To a solution of tert-butyl ((1-(4-((4-methoxybenzyl)oxy)-5-((2-(trifluoromethyl)pyridin-3-yl)thio)pyrimidin-2-yl)-4-methylpiperidin-4-yl)methyl)carbamate (60 mg, 0.097 mmol) in DCM (2 mL) was added TFA (2 mL). The reaction was stirred at for 30 min at RT and was concentrated under reduced pressure. The residue material was purified by HPLC (gradient elution 10-30% MeCN in water, 0.1% TFA modifier) to give 2-(4-(aminomethyl)-4-methylpiperidin-1-yl)-5-((2-(trifluoromethyl)pyridin-3-yl)thio)pyrimidin-4(3H)-one (50.0 mg, 0.125 mmol).

The following compounds of Table 12 were synthesized using the above procedure or modifications to the above procedure using the corresponding protected amine and thiol intermediate:

TABLE 12

| Example | Compound | Characterization | $IC_{50}$ (μM) |
|---|---|---|---|
| 91 | ![compound 91] | $^1$H NMR (400 MHz, Methanol-$d_4$) δ ppm 8.38 (d, J = 5.5 Hz, 1 H), 8.11 (s, 1 H), 7.60 (d, J = 8.0 Hz, 1 H), 7.45 (dd, J = 4.5, 11.5 Hz, 1 H), 4.11-4.06 (m, 2 H), 3.56-3.49 (m, 2 H), 3.37-3.30 (m, 2 H), 2.92 (s, 2 H), 1.65-1.56 (m, 4 H), 1.20 (s, 3 H). HRMS calcd for $C_{17}H_{21}F_3N_5OS$ $(M + H)^+$ 400.1419, found 400.1418. | 0.181 |
| 92 | ![compound 92] | $^1$H NMR (400 MHz, Methanol-$d_4$) δ ppm 8.38 (d, J = 4.5 Hz, 1 H), 8.11 (s, 1 H), 7.59 (d, J = 8.0, 1 H), 7.44 (dd, J = 4.5, 8.0 Hz, 1 H), 4.42 (d, J = 14 Hz, 1 H), 4.30 (d, J = 14.1 Hz, 1 H), 3.29-3.30 (m, 2 H), 2.28-2.19 (m, 1 H), 1.95-1.23 (m, 10 H). HRMS calcd for $C_{19}H_{23}F_3N_5OS$ $(M + H)^+$ 426.1575, found 426.1557. | 0.092 |

TABLE 12-continued

| Example | Compound | Characterization | IC$_{50}$ (μM) |
|---|---|---|---|
| 93 | 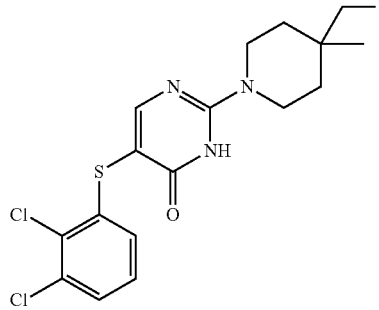 | $^1$H NMR (400 MHz, Methanol-d$_4$) δ ppm 8.38 (d, J = 5.5 Hz, 1 H), 8.11 (s, 1 H), 7.60 (d, J = 8.0 Hz, 1 H), 7.45 (dd, J = 4.5, 11.5 Hz, 1 H), 4.11-4.06 (m, 2 H), 3.56-3.49 (m, 2 H), 2.92 (s, 2 H), 1.65-1.56 (m, 4 H), 1.20 (s, 3 H). HRMS calcd for C$_{17}$H$_{21}$Cl$_2$N$_4$OS (M + H)$^+$ 399.0813, found 399.0804. | 0.065 |
| 94 | 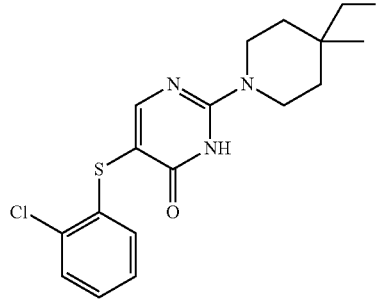 | $^1$H NMR (400 MHz, Methanol-d$_4$) δ ppm 8.03 (s, 1 H), 7.34 (dd, J = 7.65, 1.38 Hz, 1 H), 7.04-7.21 (m, 2 H), 6.91 (dd, J = 7.78, 1.51 Hz, 1 H), 4.07 (dt, J = 14.05, 4.52 Hz, 2 H), 3.43-3.58 (m, 2 H), 2.91 (s, 2 H), 1.50-1.70 (m, 4 H), 1.19 (s, 3 H). HRMS calcd for C$_{17}$H$_{22}$ClN$_4$OS (M + H)$^+$ 365.1203, found 365.1221. | 0.178 |
| 95 | 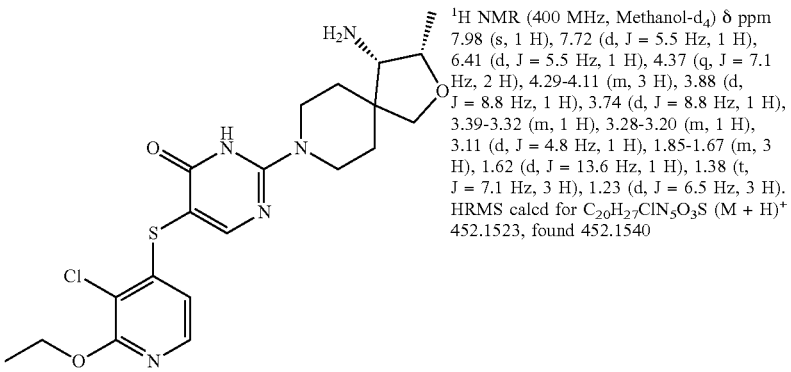 | $^1$H NMR (400 MHz, Methanol-d$_4$) δ ppm 7.98 (s, 1 H), 7.72 (d, J = 5.5 Hz, 1 H), 6.41 (d, J = 5.5 Hz, 1 H), 4.37 (q, J = 7.1 Hz, 2 H), 4.29-4.11 (m, 3 H), 3.88 (d, J = 8.8 Hz, 1 H), 3.74 (d, J = 8.8 Hz, 1 H), 3.39-3.32 (m, 1 H), 3.28-3.20 (m, 1 H), 3.11 (d, J = 4.8 Hz, 1 H), 1.85-1.67 (m, 3 H), 1.62 (d, J = 13.6 Hz, 1 H), 1.38 (t, J = 7.1 Hz, 3 H), 1.23 (d, J = 6.5 Hz, 3 H). HRMS calcd for C$_{20}$H$_{27}$ClN$_5$O$_3$S (M + H)$^+$ 452.1523, found 452.1540 | 0.023 |
| 96 | 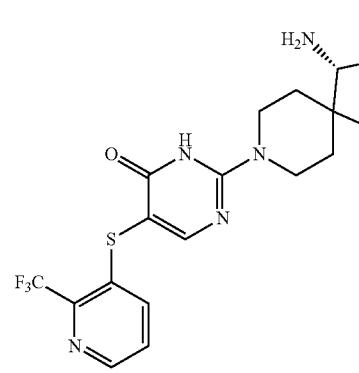 | $^1$H NMR (400 MHz, Methanol-d$_4$) δ ppm 8.33-8.28 (m, 1 H), 8.00 (s, 1 H), 7.56-7.50 (m, 1 H), 7.40 (dd, J = 8.3, 4.5 Hz, 1 H), 4.28-4.11 (m, 3 H), 3.88 (d, J = 8.8 Hz, 1 H), 3.74 (d, J = 8.8 Hz, 1 H), 3.39-3.32 (m, 1 H), 3.27-3.21 (m, 1 H), 3.11 (d, J = 4.8 Hz, 1 H), 1.87-1.58 (m, 4 H), 1.23 (d, J = 6.5 Hz, 3 H). HRMS calcd for C$_{19}$H$_{23}$F$_3$N$_5$O$_2$S (M + H)$^+$ 442.1525, found: 422.1513 | 0.031 |

TABLE 12-continued

| Example | Compound | Characterization | IC$_{50}$ (µM) |
|---|---|---|---|
| 97 | (structure shown) | $^1$H NMR (400 MHz, Methanol-d$_4$) δ ppm 7.98 (s, 1 H), 7.21 (dd, J = 8.0, 1.4 Hz, 1 H), 7.08 (t, J = 8.0 Hz, 1 H), 6.77 (dd, J = 8.0, 1.4 Hz, 1 H), 4.27-4.10 (m, 3 H), 3.87 (d, J = 8.8 Hz, 1 H), 3.73 (d, J = 8.8 Hz, 1 H), 3.42-3.33 (m, 1 H), 3.27-3.23 (m, 1 H), 3.07 (d, J = 4.8 Hz, 1 H), 1.85-1.56 (m, 4 H), 1.23 (d, J = 6.5 Hz, 3 H). HRMS calcd for C$_{19}$H$_{23}$Cl$_2$N$_4$O$_2$S (M + H)$^+$ 441.0919, found 441.0924 | 0.009 |

Example 98

2-(4-(aminomethyl)-4-methylpiperidin-1-yl)-5-((2,3-dichlorophenyl)thio)-3-methylpyrimidin-4(3H)-one

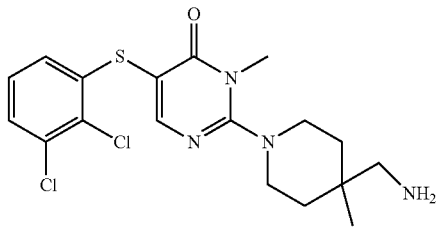 [SMILES: Cn1c(N2CCC(C)(CN)CC2)ncc(Sc2cccc(Cl)c2Cl)c1=O]

Step a: A mixture of tert-butyl ((1-(5-iodo-1-methyl-6-oxo-1,6-dihydropyrimidin-2-yl)-4-methylpiperidin-4-yl)methyl)carbamate (76.9 mg, 0.166 mmol), 2,3-dichlorobenzenethiol (44.7 mg, 0.249 mmol), 1,10-phenanthroline (12.0 mg, 0.067 mmol), Cu(I)I (6.3 mg, 0.033 mmol), and Cs$_2$CO$_3$ (108 mg, 0.333 mmol) in dioxane (3 mL) was stirred for 1 h at 100° C. After cooling to RT, the reaction was diluted with EtOAc and filtered through pad of Celite. The organic layer was washed with sat. aq. NH$_4$Cl (2×) followed by brine. The organic layer was dried over MgSO$_4$, filtered, and the volatiles were removed under reduced pressure. The residue was purified by silica chromatography (0 to 100% gradient of EtOAc/heptane) to give tert-butyl ((1-(5-((2,3-dichlorophenyl)thio)-1-methyl-6-oxo-1,6-dihydropyrimidin-2-yl)-4-methylpiperidin-4-yl)methyl)carbamate. MS m/z 513.0 (M+H)$^+$ Step b: A mixture of tert-butyl ((1-(5-((2,3-dichlorophenyl)thio)-1-methyl-6-oxo-1,6-dihydropyrimidin-2-yl)-4-methylpiperidin-4-yl)methyl)carbamate in DCM (3 mL) and TFA (1 mL) was stirred for 1 h at RT. The volatiles were removed under reduced pressure and the residue was purified by HPLC (gradient elution 15-40% MeCN in water, 0.1% TFA modifier) to give 2-(4-(aminomethyl)-4-methylpiperidin-1-yl)-5-((2,3-dichlorophenyl)thio)-3-methylpyrimidin-4(3H)-one (TFA salt, 36 mg).

The following compounds of Table 13 were synthesized using the above procedure or modifications to the above procedure using the corresponding thiol and iodo-pyrimidinone intermediate:

TABLE 13

| Example | Compound | Characterization | IC$_{50}$ (µM) |
|---|---|---|---|
| 98 | (structure shown) | $^1$H NMR (400 MHz, Methanol-d$_4$) δ ppm 8.12 (s, 1 H), 7.30 (dd, J = 8.0, 1.4 Hz, 1 H), 7.12 (t, J = 8.0 Hz, 1 H), 6.85 (dd, J = 8.0, 1.4 Hz, 1 H), 3.61-3.52 (m, 2 H), 3.50 (s, 3 H), 3.37-3.32 (m, 2 H), 2.93 (s, 2 H), 1.79-1.68 (m, 2 H), 1.67-1.56 (m, 2 H), 1.18 (s, 3 H). HRMS calcd for C$_{18}$H$_{23}$Cl$_2$N$_4$OS (M + H)$^+$ 413.0969, found 413.0881. | 0.068 |
| 99 | (structure shown) | $^1$H NMR (400 MHz, DMSO-d$_6$) δ ppm 8.09 (s, 1 H), 7.81 (s, 2 H), 7.45 (dd, J = 7.7, 1.5 Hz, 1 H), 7.25-7.12 (m, 2 H), 6.88 (dd, J = 7.7, 1.7 Hz, 1 H), 3.51-3.44 (m, 2 H), 3.39 (s, 3 H), 3.29-3.18 (m, 2 H), 2.86-2.77 (m, 2 H), 1.68-1.57 (m, 2 H), 1.53-1.42 (m, 2 H), 1.07 (s, 3 H). HRMS calcd for C$_{18}$H$_{24}$ClN$_4$OS (M + H)$^+$ 379.1359, found 379.0968. | 0.375 |

TABLE 13-continued

| Example | Compound | Characterization | IC$_{50}$ (μM) |
|---|---|---|---|
| 100 | | $^1$H NMR (400 MHz, Methanol-d$_4$) δ ppm 8.38 (d, J = 4.6 Hz, 1 H), 8.14 (d, J = 1.2 Hz, 1 H), 7.61 (d, J = 8.2 Hz, 1 H), 7.42 (dd, J = 8.2, 4.5 Hz, 1 H), 3.58-3.50 (m, 2 H), 3.48 (s, 3 H), 3.40-3.23 (m, 2 H), 2.67 (s, 2 H), 1.79-1.62 (m, 2 H), 1.60-1.46 (m, 2 H), 1.07 (d, J = 21.5 Hz, 3 H). HRMS calcd for C$_{18}$H$_{23}$F$_3$N$_5$OS (M + H)$^+$ 414.1575, found 414.1568. | 0.631 |
| 101 | | $^1$H NMR (400 MHz, Methanol-d$_4$) δ ppm 8.12 (s, 1 H), 7.31 (dd, J = 8.0, 1.3 Hz, 1 H), 7.12 (t, J = 8.0 Hz, 1 H), 6.86 (dd, J = 8.0, 1.3 Hz, 1 H), 4.18 (dd, J = 10.7, 5.5 Hz, 1 H), 3.96 (d, J = 9.2 Hz, 1 H), 3.92-3.76 (m, 2 H), 3.76-3.58 (m, 3 H), 3.52 (s, 3 H), 3.26-3.06 (m, 2 H), 2.01-1.70 (m, 4 H). HRMS calcd for C$_{19}$H$_{23}$Cl$_2$N$_4$O$_2$S (M + H)$^+$ 441.0919, found 441.0928. | 0.037 |
| 102 | | $^1$H NMR (400 MHz, Methanol-d$_4$) δ ppm 8.14 (s, 1 H), 7.75 (d, J = 5.5 Hz, 1 H), 6.42 (d, J = 5.5 Hz, 1 H), 4.38 (q, J = 7.1 Hz, 2 H), 4.28-4.16 (m, 1 H), 3.86 (d, J = 8.7 Hz, 1 H), 3.70 (d, J = 8.7 Hz, 1 H), 3.68-3.57 (m, 2 H), 3.52 (s, 3 H), 3.28-3.11 (m, 2 H), 3.04 (d, J = 5.0 Hz, 1 H), 2.00-1.83 (m, 2 H), 1.80-1.66 (m, 2 H), 1.39 (t, J = 7.1 Hz, 3 H), 1.22 (d, J = 6.5 Hz, 3 H). HRMS calcd for C$_{21}$H$_{29}$ClN$_5$O$_3$S (M + H)$^+$ 466.1680, found 466.1687. | 0.010 |
| 103 | | $^1$H NMR (400 MHz, Methanol-d$_4$) δ ppm 8.14 (s, 1H), 7.41 (dd, J = 8.0, 1.3 Hz, 1 H), 7.22 (t, J = 8.0 Hz, 1 H), 6.84 (dd, J = 8.1, 1.4 Hz, 1 H), 4.12-3.98 (m, 1 H), 3.66 (d, J = 8.5 Hz, 1 H), 3.54-3.44 (m, 3 H), 3.39 (s, 2 H), 3.28-3.10 (m, 2 H), 2.93 (d, J = 5.0 Hz, 1 H), 1.91-1.68 (m, 2 H), 1.64-1.46 (m, 3 H), 1.08 (d, J = 6.4 Hz, 3 H). HRMS calcd for C$_{20}$H$_{25}$Cl$_2$N$_4$O$_2$S (M + H)$^+$ 455.1075, found 455.1076. | 0.015 |

TABLE 13-continued

| Example | Compound | Characterization | IC$_{50}$ (μM) |
|---|---|---|---|
| 104 | | $^1$H NMR (400 MHz, DMSO-d$_6$) δ ppm 8.15 (s, 1 H), 7.98 (s, 3 H), 7.42 (dd, J = 8.0, 1.4 Hz, 1 H), 7.22 (t, J = 8.0 Hz, 1 H), 6.84 (dd, J = 8.1, 1.3 Hz, 1 H), 3.49-3.41 (m, 2 H), 3.38 (s, 3 H), 2.99 (dt, J = 58.9, 11.3 Hz, 2 H), 2.24-2.13 (m, 1 H), 2.06-1.90 (m, 2 H), 1.87-1.75 (m, 2 H), 1.74-1.56 (m, 4 H). TFA salt. HRMS calcd for C$_{19}$H$_{23}$Cl$_2$N$_4$OS: 425.0969, found 425.0994. | 0.109 |
| 105 | | $^1$H NMR (400 MHz, Methanol-d$_4$) δ ppm 8.14 (s, 1 H), 7.77 (d, J = 5.5 Hz, 1 H), 6.45 (d, J = 5.5 Hz, 1 H), 4.29-4.17 (m, 1 H), 3.96 (s, 3 H), 3.86 (d, J = 8.7 Hz, 1 H), 3.71 (d, J = 8.7 Hz, 1 H), 3.68-3.57 (m, 2 H), 3.52 (s, 3 H), 3.25-3.12 (m, 2 H), 3.05 (d, J = 5.0 Hz, 1 H), 2.01-1.84 (m, 2 H), 1.73 (t, J = 15.3 Hz, 2 H), 1.22 (d, J = 6.5 Hz, 3 H). HRMS calcd for C$_{20}$H$_{27}$ClN$_5$O$_3$S (M + H)$^+$ 452.1523, found 452.1496. | 0.008 |
| 106 | | $^1$H NMR (400 MHz, Methanol-d$_4$) δ ppm 8.03 (s, 1 H), 7.10 (t, J = 8.1 Hz, 1 H), 6.86 (dd, J = 8.3, 1.1 Hz, 1 H), 6.51 (dd, J = 8.0, 1.2 Hz, 1 H), 4.28-4.18 (m, 1 H), 3.86 (s, 3 H), 3.84 (s, 1 H), 3.70 (d, J = 8.7 Hz, 1 H), 3.62-3.53 (m, 2 H), 3.51 (s, 3 H), 3.26-3.08 (m, 2 H), 3.03 (d, J = 5.0 Hz, 1 H), 2.00-1.84 (m, 2 H), 1.78-1.65 (m, 2 H), 1.22 (d, J = 6.5 Hz, 3 H). HRMS calcd for C$_{21}$H$_{28}$ClN$_4$O$_3$S (M + H)$^+$ 451.1571, found 451.1589. | 0.030 |
| 107 | | $^1$H NMR (400 MHz, Methanol-d$_4$) δ ppm 8.12 (s, 1 H), 7.71 (d, J = 5.6 Hz, 1 H), 6.15 (d, J = 5.6 Hz, 1 H), 4.28-4.15 (m, 1 H), 3.86 (d, J = 8.7 Hz, 1 H), 3.70 (d, J = 8.7 Hz, 1 H), 3.67-3.58 (m, 2 H), 3.52 (s, 3 H), 3.33-3.32 (m, 1 H), 3.27-3.10 (m, 2 H), 3.04 (d, J = 5.0 Hz, 1 H), 2.65 (tt, J = 6.9, 3.7 Hz, 1 H), 2.01-1.84 (m, 2 H), 1.73 (t, J = 14.9 Hz, 2 H), 1.22 (d, J = 6.5 Hz, 3 H), 0.79 (td, J = 6.9, 5.0 Hz, 2 H), 0.58-0.50 (m, 2 H). HRMS calcd for C$_{22}$H$_{30}$ClN$_6$O$_2$S: 477.1839, obtained 477.1837. | 0.146 |

TABLE 13-continued

| Example | Compound | Characterization | IC$_{50}$ (µM) |
|---|---|---|---|
| 108 | | $^1$H NMR (400 MHz, DMSO-d$_6$) δ ppm 8.09 (s, 1 H), 7.83-7.70 (m, 4 H), 7.50 (t, J = 7.7 Hz, 1 H), 7.34 (t, J = 7.6 Hz, 1 H), 7.14 (d, J = 8.0 Hz, 1 H), 3.53-3.42 (m, 2 H), 3.38 (s, 3 H), 3.33-3.16 (m, 2 H), 2.87-2.73 (m, 2 H), 1.69-1.57 (m, 2 H), 1.55-1.41 (m, 2 H), 1.07 (s, 3 H). TFA salt.<br>HRMS calcd for C$_{19}$H$_{24}$F$_3$N$_4$OS: 413.1623, found 413.1320. | 0.500 |
| 109 | | $^1$H NMR (400 MHz, DMSO-d$_6$) δ ppm 8.13 (s, 1 H), 7.40 (dd, J = 8.0, 1.3 Hz, 1 H), 7.22 (t, J = 8.0 Hz, 1 H), 6.84 (dd, J = 8.1, 1.3 Hz, 1 H), 3.62 (t, J = 12.3 Hz, 2 H), 3.39 (s, 3 H), 3.07 (q, J = 10.4 Hz, 2 H), 2.72 (t, J = 7.3 Hz, 1 H), 1.91-1.43 (m, 6H), 1.42-1.16 (m, 4 H).<br>HRMS calcd for C$_{20}$H$_{25}$Cl$_2$N$_4$OS: 439.1126, found 439.1173. | 0.026 |
| 110 | | $^1$H NMR (400 MHz, Methanol-d$_4$) δ ppm 8.13 (s, 1 H), 7.71 (s, 1 H), 6.01 (s, 1 H), 3.78-3.62 (m, 2 H), 3.53 (s, 3 H), 3.34-3.32 (m, 1 H), 3.23-3.09 (m, 2 H), 2.87 (dd, J = 9.6, 6.4 Hz, 1 H), 2.22-2.11 (m, 1 H), 2.10-2.00 (m, 1 H), 1.96 (dd, J = 12.8, 8.2 Hz, 1 H), 1.87-1.76 (m, 2 H), 1.34-1.24 (m, 2 H), 1.20-1.10 (m, 1 H), 1.07 (d, J = 6.4 Hz, 3 H).<br>HRMS: calcd for C$_{20}$H$_{28}$ClN$_6$OS (M + H)$^+$ 435.1734, found 435.1736. | 0.016 |
| 111 | | $^1$H NMR (400 MHz, Methanol-d$_4$) δ ppm 8.40-8.36 (m, 1 H), 8.15 (s, 1 H), 7.63-7.58 (m, 1 H), 7.43 (dd, J = 8.2, 4.6 Hz, 1 H), 4.28-4.18 (m, 1 H), 3.85 (d, J = 8.7 Hz, 1 H), 3.70 (d, J = 8.7 Hz, 1 H), 3.65-3.54 (m, 2 H), 3.50 (s, 3 H), 3.29-3.11 (m, 2 H), 3.03 (d, J = 5.0 Hz, 1 H), 1.98-1.83 (m, 2 H), 1.79-1.66 (m, 2 H), 1.22 (d, J = 6.5 Hz, 3 H).<br>HRMS calcd for C$_{20}$H$_{25}$F$_3$N$_5$O$_2$S (M + H)$^+$ 456.1681, found 456.1718. | 0.041 |

TABLE 13-continued

| Example | Compound | Characterization | IC$_{50}$ (μM) |
|---|---|---|---|
| 112 | | $^1$H NMR (400 MHz, Methanol-d$_4$) δ ppm 8.04 (s, 1 H), 5.83 (s, 1 H), 4.18-4.06 (m, 1 H), 3.76 (d, J = 8.7 Hz, 1 H), 3.62 (s, 1 H), 3.57-3.49 (m, 2 H), 3.43 (s, 3 H), 3.19-3.03 (m, 2 H), 2.94 (d, J = 5.0 Hz, 1 H), 1.90-1.74 (m, 2 H), 1.63 (t, J = 14.6 Hz, 2 H), 1.12 (d, J = 6.5 Hz, 3 H). HRMS calcd for C$_{19}$H$_{25}$Cl$_2$N$_6$O$_2$S (M + H)$^+$ 471.1137, found 471.1121. | 0.019 |
| 113 | | $^1$H NMR (400 MHz, Methanol-d$_4$) δ ppm 8.13 (s, 1 H), 7.59 (d, J = 5.6 Hz, 1 H), 6.13 (d, J = 5.6 Hz, 1 H), 4.29-4.16 (m, 1 H), 3.85 (d, J = 8.7 Hz, 1 H), 3.70 (d, J = 8.7 Hz, 1 H), 3.67-3.57 (m, 2 H), 3.52 (s, 3 H), 3.27-3.12 (m, 2 H), 3.03 (d, J = 5.0 Hz, 1 H), 2.02-1.83 (m, 2 H), 1.73 (t, J = 14.7 Hz, 2 H), 1.22 (s, 3 H). HRMS calcd for C$_{19}$H$_{26}$ClN$_6$O$_2$S (M + H)$^+$ 437.1526, found 437.1544. | 0.035 |
| 114 | | $^1$H NMR (400 MHz, Chloroform-d) δ ppm 8.37 (d, J = 4.5 Hz, 1 H), 8.00 (s, 1 H), 7.53 (d, J = 8.0 Hz, 1 H), 7.23 (dd, J = 8.1, 4.6 Hz, 1 H), 3.47 (d, J = 14.3 Hz, 2 H), 3.41 (s, 3 H), 3.06-2.91 (m, 3 H), 2.16 (s, 1 H), 1.99 (d, J = 7.0 Hz, 1 H), 1.90-1.62 (m, 4 H), 1.42-1.08 (m, 5 H), 0.99 (d, J = 6.6 Hz, 3 H). HRMS calcd for C$_{21}$H$_{27}$F$_3$N$_5$OS (M + H)$^+$ 454.1888, found 454.1873. | 0.050 |
| 115 | | $^1$H NMR (400 MHz, DMSO-d$_6$) δ ppm 8.19 (s, 1 H), 8.11 (d, J = 5.3 Hz, 1 H), 7.75 (s, 3 H), 6.93 (d, J = 5.3 Hz, 1 H), 3.54-3.47 (m, 2 H), 3.40 (s, 3 H), 3.35-3.23 (m, 2 H), 2.82 (d, J = 5.8 Hz, 2 H), 1.68-1.41 (m, 4 H), 1.07 (s, 3 H). HRMS calcd for C$_{17}$H$_{22}$Cl$_2$N$_5$OS (M + H)$^+$ 414.0922, found 414.0923. | 0.083 |

Example 116

6-(4-(aminomethyl)-4-methylpiperidin-1-yl)-3-((2,3-dichlorophenyl)thio)-1-methylpyridin-2(1H)-one

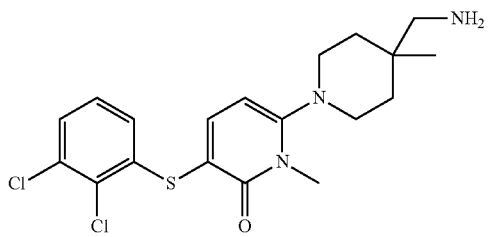 [SMILES: Cn1c(N2CCC(C)(CN)CC2)ccc(Sc2cccc(Cl)c2Cl)c1=O]

Step a: A mixture of tert-butyl ((1-(5-iodo-1-methyl-6-oxo-1,6-dihydropyridin-2-yl)-4-methylpiperidin-4-yl)methyl)carbamate (34.4 mg, 0.075 mmol), 2,3-dichlorobenzenethiol (20 mg, 0.112 mmol), 1,10-phenanthroline (5.4 mg, 0.030 mmol), Cu(I)I (2.8 mg, 0.015 mmol), and $Cs_2CO_3$ (48.6 mg, 0.149 mmol) in dioxane (3 mL) was stirred for 1 h at 100° C. After cooling to RT, the reaction was diluted with EtOAc and filtered through a pad of Celite. The organic layer was washed with sat. aq. $NH_4Cl$ (2×) followed by brine. The organic layer was dried over $MgSO_4$, filtered, and the volatiles were removed under reduced pressure. The residue was purified by silica chromatography (0 to 100% gradient of EtOAc/heptane) to give tert-butyl ((1-(5-((2,3-dichlorophenyl)thio)-1-methyl-6-oxo-1,6-dihydropyridin-2-yl)-4-methylpiperidin-4-yl)methyl)carbamate. MS m/z 512.0 $(M+H)^+$ Step b: A mixture of tert-butyl ((1-(5-((2,3-dichlorophenyl)thio)-1-methyl-6-oxo-1,6-dihydropyridin-2-yl)-4-methylpiperidin-4-yl)methyl)carbamate (see above) in DCM (3 mL) and TFA (1 mL) was stirred for 1 h at RT. The volatiles were removed under reduced pressure and the residue was purified by HPLC (gradient elution 15-40% MeCN in water, 0.1% TFA modifier) to give 6-(4-(aminomethyl)-4-methylpiperidin-1-yl)-3-((2,3-dichlorophenyl)thio)-1-methylpyridin-2(1H)-one (TFA salt, 5 mg).

The following compounds of Table 14 were synthesized using the above procedure or modifications to the above procedure using the corresponding starting materials and intermediates:

TABLE 14

| Example | Compound | Characterization | $IC_{50}$ (µM) |
|---|---|---|---|
| 116 | (structure shown: 3-((2,3-dichlorophenyl)thio)-6-(4-(aminomethyl)-4-methylpiperidin-1-yl)-1-methylpyridin-2(1H)-one) | $^1$H NMR (400 MHz, Methanol-$d_4$) δ ppm 7.73 (d, J = 7.9 Hz, 1 H), 7.32 (dd, J = 8.0, 1.4 Hz, 1 H), 7.12 (t, J = 8.0 Hz, 1 H), 6.82 (dd, J = 8.0, 1.4 Hz, 1 H), 6.16 (d, J = 8.0 Hz, 1 H), 3.58 (s, 3 H), 3.19-3.10 (m, 2 H), 3.09-2.99 (m, 2 H), 2.94 (s, 2 H), 1.81-1.71 (m, 2 H), 1.69-1.59 (m, 2 H), 1.18 (s, 3 H). HRMS calcd for $C_{19}H_{24}Cl_2N_3OS$ $(M + H)^+$ 412.1017, found 412.1023. | 1.623 |
| 117 | (structure shown: pyridinone with spirocyclic aminotetrahydrofuran-piperidine and 2-(trifluoromethyl)pyridin-3-ylthio substituent) | $^1$H NMR (400 MHz, Methanol-$d_4$) δ ppm 8.40-8.36 (m, 1 H), 7.80 (d, J = 8.0 Hz, 1 H), 7.54-7.48 (m, 1 H), 7.42 (dd, J = 8.2, 4.6 Hz, 1 H), 6.12 (d, J = 8.0 Hz, 1 H), 4.26-4.18 (m, 1 H), 3.85 (d, J = 8.7 Hz, 1 H), 3.70 (d, J = 8.7 Hz, 1 H), 3.58 (s, 3 H), 3.26-3.14 (m, 2 H), 3.04 (d, J = 4.9 Hz, 1 H), 2.90 (dt, J = 34.6, 10.4 Hz, 2 H), 2.03-1.87 (m, 2 H), 1.82-1.69 (m, 2 H), 1.22 (d, J = 6.5 Hz, 3 H). HRMS calcd for $C_{21}H_{26}F_3N_4O_2S$ 455.1729 $(M + H)^+$, found 455.1668. | 0.177 |

Example 118

6-(4-(aminomethyl)-4-methylpiperidin-1-yl)-3-((2,3-dichlorophenyl)thio)pyridin-2(1H)-one

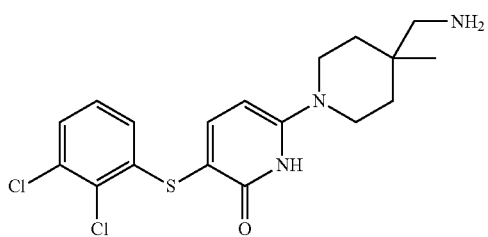 [SMILES: CC1(CN)CCN(c2ccc(Sc3cccc(Cl)c3Cl)c(=O)[nH]2)CC1]

Step a: A mixture of 2-chloro-5-((2,3-dichlorophenyl)thio)-4-methoxypyrimidine (81.6 mg, 0.255 mmol), DIPEA (89 μL, 0.509 mmol), and tert-butyl ((4-methylpiperidin-4-yl)methyl)carbamate (69.7 mg, 0.305 mmol) in DMF (1 mL) was radiated in a microwave reactor for 2 h at 140° C. After cooling to RT, the mixture was diluted with EtOAc. The organic layer was washed with sat. aq. NH$_4$Cl (2×) followed by brine. The organic layer was dried over MgSO$_4$, filtered, and the volatiles were removed under reduced pressure. The residue was purified by silica chromatography (0 to 100% gradient of EtOAc/heptane) to give tert-butyl ((1-(5-((2,3-dichlorophenyl)thio)-6-methoxypyridin-2-yl)-4-methylpiperidin-4-yl)methyl)carbamate (26.1 mg) as a white solid. $^1$H NMR (400 MHz, Methanol-d$_4$) δ ppm 7.53 (d, J=8.4 Hz, 1H), 7.21 (dd, J=8.0, 1.4 Hz, 1H), 7.04 (t, J=8.0 Hz, 1H), 6.51 (dd, J=8.1, 1.3 Hz, 1H), 6.38 (d, J=8.5 Hz, 1H), 3.96-3.87 (m, 2H), 3.82 (s, 3H), 3.49-3.39 (m, 4H), 3.01 (d, J=5.3 Hz, 2H), 1.59-1.47 (m, 3H), 1.44 (s, 9H), 1.42-1.33 (m, 2H), 1.00 (s, 3H). MS m/z 512.1 (M+H)$^+$.

Step b: A solution of tert-butyl ((1-(5-((2,3-dichlorophenyl)thio)-6-methoxypyridin-2-yl)-4-methylpiperidin-4-yl)methyl)carbamate (26.1 mg, 0.051 mmol) and BBr$_3$ (1 M in DCM, 0.153 mL, 0.153 mmol) in DCM (2 mL) was stirred for 1 h at 0° C. The volatiles were removed under reduced pressure to give tert-butyl ((1-(5-((2,3-dichlorophenyl)thio)-4-methoxypyrimidin-2-yl)-4-methylpiperidin-4-yl)methyl)carbamate (26.1 mg, 0.051 mmol). MS m/z 412.1 (M+H)$^+$.

Step c: A mixture of tert-butyl ((1-(5-((2,3-dichlorophenyl)thio)-4-methoxypyrimidin-2-yl)-4-methylpiperidin-4-yl)methyl)carbamate (26.1 mg, 0.051 mmol) and HCl (4 M in dioxane, 2 mL, 8 mmol) was stirred for 20 h at 90° C. After cooling to RT, the volatiles were removed under reduced pressure and the residue was purified by HPLC (gradient elution 15-40% MeCN in water, 0.1% TFA modifier) to give 2-(4-(aminomethyl)-4-methylpiperidin-1-yl)-5-((2,3-dichlorophenyl)thio)pyrimidin-4(3H)-one (TFA salt, 13.0 mg).

The following compounds of Table 15 were synthesized using the above procedure or modifications to the above procedure using the corresponding starting materials and intermediates:

TABLE 15

| Example | Compound | Characterization | IC$_{50}$ (μM) |
|---|---|---|---|
| 118 | | $^1$H NMR (400 MHz, DMSO-d$_6$) δ ppm 7.72 (s, 3 H), 7.60 (d, J = 8.3 Hz, 1 H), 7.37 (dd, J = 8.0, 1.4 Hz, 1 H), 7.22 (t, J = 8.0 Hz, 1 H), 6.62 (d, J = 6.8 Hz, 1 H), 3.83-3.65 (m, 2 H), 3.37-3.28 (m, 2 H), 2.79 (d, J = 5.8 Hz, 2 H), 1.57-1.36 (m, 4 H), 1.05 (s, 3H). HRMS calcd for C$_{18}$H$_{22}$Cl$_2$N$_3$OS: 398.0861, found 398.0558. | 0.108 |
| 119 | | $^1$H NMR (400 MHz, Methanol-d$_4$) δ ppm 7.80 (d, J = 5.5 Hz, 1 H), 7.49 (d, J = 8.8 Hz, 1 H), 6.29 (d, J = 5.5 Hz, 1 H), 6.17 (d, J = 8.8 Hz, 1 H), 4.22-4.11 (m, 1 H), 3.96 (s, 3 H), 3.74 (d, J = 8.7 Hz, 1 H), 3.60 (d, J = 8.7 Hz, 1 H), 3.56-3.44 (m, 2 H), 3.21-3.02 (m, 2 H), 2.92 (d, J = 4.8 Hz, 1 H), 1.77-1.61 (m, 2 H), 1.6-1.47 (m, 2 H), 1.17 (d, J = 6.5 Hz, 3 H). HRMS calcd for C$_{20}$H$_{26}$ClN$_4$O$_3$S (M + H)$^+$ 437.1414, found 437.1407 | 0.083 |

TABLE 15-continued

| Example | Compound | Characterization | IC$_{50}$ (μM) |
|---|---|---|---|
| 120 | | $^1$H NMR (400 MHz, Chloroform-d) ppm 7.57 (d, J = 8.4 Hz, 1 H), 7.18 (s, 1 H), 7.09 (dd, J = 7.9, 1.3 Hz, 1 H), 6.93 (t, J = 8.0 Hz, 1 H), 6.65 (dd, J = 8.0, 1.3 Hz, 1 H), 5.53 (d, J = 8.4 Hz, 1 H), 4.07-3.99 (m, 1 H), 3.59 (d, J = 8.8 Hz, 1 H), 3.47 (d, J = 8.8 Hz, 2 H), 3.16-2.93 (m, 2 H), 2.75 (d, J = 4.4 Hz, 1 H), 1.64 (dd, J = 16.3, 6.6 Hz, 2 H), 1.49-1.32 (m, 4 H), 1.18-1.16 (m, 3 H), 1.15 (s, 1 H). HRMS calcd for $C_{20}H_{24}Cl_2N_3O_2S$: 440.0966, found 440.0683 | 0.015 |

Example 121

5-((2-amino-3-chloropyridin-4-yl)thio)-2-((3S,4S)-4-amino-3-methyl-2-oxa-8-azaspiro[4.5]decan-8-yl)-3,6-dimethylpyrimidin-4(3H)-one

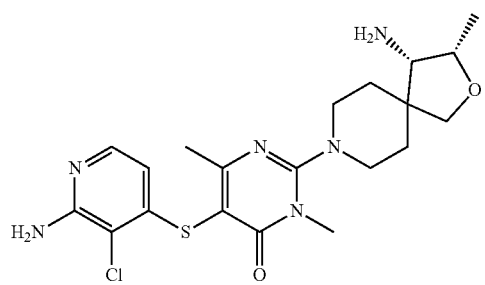 [SMILES: Cc1nc(N2CCC3(CC2)CO[C@@H](C)[C@H]3N)n(C)c(=O)c1Sc1ccnc(N)c1Cl]

Step a: To a mixture of tert-butyl ((3S,4S)-8-(5-bromo-1,4-dimethyl-6-oxo-1,6-dihydropyrimidin-2-yl)-3-methyl-2-oxa-8-azaspiro[4.5]decan-4-yl)carbamate (130 mg, 0.276 mmol), K$_3$PO$_4$ (176 mg, 0.827 mmol), sodium 2-amino-3-chloropyridine-4-thiolate (76 mg, 0.414 mmol), and Cu(I)I (10.50 mg, 0.055 mmol) in DMF under N$_2$ atmosphere in microwave vial was added TMEDA (0.017 mL, 0.110 mmol). The reaction mixture was radiated in a microwave at 150° C. for 1 h. The reaction mixture was diluted with water/EtOAc and extracted with EtOAc (2×) and DCM (2×). The combined organic layers were dried over Na$_2$SO$_4$, filtered off and concentrated under reduced pressure. The residue was purified by preparative TLC (silica gel, 1 mm, DCM/MeOH=95/5) providing tert-butyl ((3S,4S)-8-(5-((2-amino-3-chloropyridin-4-yl)thio)-1,4-dimethyl-6-oxo-1,6-dihydropyrimidin-2-yl)-3-methyl-2-oxa-8-azaspiro[4.5]decan-4-yl)carbamate. MS m/z 551.3 (M+H)$^+$.

Step b: tert-Butyl ((3S,4S)-8-(5-((2-amino-3-chloropyridin-4-yl)thio)-1,4-dimethyl-6-oxo-1,6-dihydropyrimidin-2-yl)-3-methyl-2-oxa-8-azaspiro[4.5]decan-4-yl)carbamate was dissolved/suspended in DCM (3 mL) and TFA (0.5 mL) was added. The mixture was stirred for ~20 min and concentrated under reduced pressure. To the residue was added MeCN (5% water containing) and solid NaHCO$_3$. The mixture was vigorously stirred for 5 min and filtered through a syringe filter (2 μm). The filtrate was concentrated under reduced pressure and purified by preparative TLC (silica gel, 1 mm, DCM/MeOH=90:10). The silica band was washed with DCM/MeOH and the filtrate was concentrated under reduced pressure. The residue was dissolved in MeCN, filtered through a syringe filter (2 μm) and lyophilized providing 5-((2-amino-3-chloropyridin-4-yl)thio)-2-((3S,4S)-4-amino-3-methyl-2-oxa-8-azaspiro[4.5]decan-8-yl)-3,6-dimethylpyrimidin-4(3H)-one (3.6 mg).

The following compounds of Table 16 were synthesized using the above procedure or modifications to the above procedure using the corresponding starting materials and intermediates:

TABLE 16

| Example | Compound | Characterization | IC$_{50}$ (μM) |
|---|---|---|---|
| 121 | | $^1$H NMR (400 MHz, Methanol-d$_4$) δ ppm 7.58 (d, J = 5.6 Hz, 1 H), 6.05 (d, J = 5.6 Hz, 1 H), 4.27-4.17 (m, 1 H), 3.86 (d, J = 8.7 Hz, 1 H), 3.71 (d, J = 8.8 Hz, 1 H), 3.66-3.53 (m, 2 H), 3.49 (s, 3 H), 3.22-3.11 (m, 2 H), 3.04 (d, J = 5.0 Hz, 1 H), 2.38 (s, 3 H), 1.98-1.85 (m, 2 H), 1.80-1.65 (m, 2 H), 1.22 (d, J = 6.5 Hz, 3 H). HRMS calcd for $C_{20}H_{28}ClN_6O_2S$ (M + H)$^+$ 451.1683, found 451.1660 | 0.060 |

TABLE 16-continued

| Example | Compound | Characterization | IC$_{50}$ (μM) |
|---|---|---|---|
| 122 | | $^1$H NMR (400 MHz, Methanol-d$_4$) δ ppm 8.35 (d, J = 3.4 Hz, 1 H), 7.47 (d, J = 7.4 Hz, 1 H), 7.40 (dd, J = 8.2, 4.5 Hz, 1 H), 4.28-4.14 (m, 1 H), 3.85 (d, J = 8.7 Hz, 1 H), 3.70 (d, J = 8.7 Hz, 1 H), 3.66-3.55 (m, 2 H), 3.48 (s, 3 H), 3.24-3.12 (m, 2 H), 3.04 (d, J = 5.0 Hz, 1 H), 2.39 (s, 3 H), 1.99-1.83 (m, 2 H), 1.79-1.66 (m, 2 H), 1.22 (d, J = 6.5 Hz, 3 H). HRMS calcd for C$_{21}$H$_{27}$F$_3$N$_5$O$_2$S (M + H)$^+$ 470.1838, found 470.1826. | 0.068 |

Example 123

6-amino-2-((3S,4S)-4-amino-3-methyl-2-oxa-8-azaspiro[4.5]decan-8-yl)-5-(3-chloro-4-methylphenyl)-3-methylpyrimidin-4(3H)-one

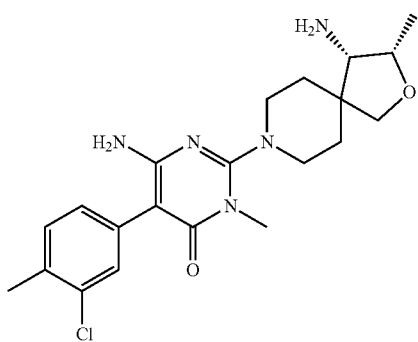

Step a: To a mixture of (3-chloro-4-methoxyphenyl)boronic acid (41.0 mg, 0.241 mmol), Cs$_2$CO$_3$ (182 mg, 0.558 mmol) and Pd(PPh$_3$)$_4$(16.69 mg, 0.014 mmol) in toluene (1 mL) was added under N$_2$ atmosphere a solution of tert-butyl ((3S,4S)-8-(4-amino-5-iodo-1-methyl-6-oxo-1,6-dihydropyrimidin-2-yl)-3-methyl-2-oxa-8-azaspiro[4.5]decan-4-yl) carbamate (50 mg, 0.096 mmol) in EtOH (1 mL). The mixture was radiated in a microwave reactor for 30 min at 100° C. The reaction mixture was diluted with water and EtOAc. The separated aq. layer was extracted with EtOAc (2×) and the combined organic layers were dried over Na$_2$SO$_4$, filtered off, and concentrated under reduced pressure providing crude tert-butyl ((3S,4S)-8-(4-amino-5-(3-chloro-4-methylphenyl)-1-methyl-6-oxo-1,6-dihydropyrimidin-2-yl)-3-methyl-2-oxa-8-azaspiro[4.5]decan-4-yl) carbamate (83 mg) as a brown solid which was directly used in next reaction without further purification. MS m/z 518.3 (M+H)$^+$.

Step b: To crude tert-butyl ((3S,4S)-8-(4-amino-5-(3-chloro-4-methylphenyl)-1-methyl-6-oxo-1,6-dihydropyrimidin-2-yl)-3-methyl-2-oxa-8-azaspiro[4.5]decan-4-yl) carbamate (83 mg) in DCM (1 mL) under N$_2$ atmosphere was added TFA (1 mL). The mixture was stirred for 1 h, diluted with toluene (1 mL) and concentrated under reduced pressure. The residue was dissolved in MeOH and basified with NH$_3$ (7 M in MeOH) and the mixture was concentrated under reduced pressure. The residue was dissolved in MeCN/water (2/1), filtered through a syringe filter (0.2 μm) and purified by HPLC (gradient elution 25-50% MeCN in water, 5 mM NH$_4$OH modifier) providing 6-amino-2-((3S,4S)-4-amino-3-methyl-2-oxa-8-azaspiro[4.5]decan-8-yl)-5-(3-chloro-4-methylphenyl)-3-methylpyrimidin-4(3H)-one (19 mg) as a white solid.

The following compounds of Table 17 were synthesized using the above procedure or modifications to the above procedure using the corresponding starting materials and intermediates:

TABLE 17

| Example | Compound | Characterization | IC$_{50}$ (μM) |
|---|---|---|---|
| 123 | | $^1$H NMR (400 MHz, Methanol-d$_4$) δ ppm 7.26-7.18 (m, 2 H), 7.10-7.01 (m, 1 H), 4.18-4.07 (m, 1 H), 3.74 (d, J = 8.7 Hz, 1 H), 3.60 (d, J = 8.7 Hz, 1 H), 3.37-3.28 (m, 5 H), 3.02-2.94 (m, 1 H), 2.94 (d, J = 5.0 Hz, 1 H), 2.92-2.84 (m, 1 H), 2.28 (s, 3 H), 1.89-1.72 (m, 2 H), 1.68-1.55 (m, 2 H), 1.12 (d, J = 6.5 Hz, 3 H). HRMS calcd for C$_{21}$H$_{29}$ClN$_5$O$_2$ (M + H)$^+$ 418.2010, found 418.2005. | 0.014 |

TABLE 17-continued

| Example | Compound | Characterization | IC$_{50}$ (µM) |
|---|---|---|---|
| 124 | | $^1$H NMR (400 MHz, Methanol-d$_4$) δ ppm 7.34-7.29 (m, 2 H), 7.17-7.11 (m, 1 H), 3.55-3.44 (m, 2 H), 3.42 (s, 3 H), 3.06-2.94 (m, 3 H), 2.37 (s, 3 H), 2.26-2.18 (m, 1 H), 2.13-2.05 (m, 1 H), 2.05-1.97 (m, 1 H), 1.87-1.69 (m, 2 H), 1.47 (d, J = 13.1 Hz, 2 H), 1.35-1.18 (m, 2 H), 1.09 (d, J = 6.4 Hz, 3 H).<br>HRMS calcd for C$_{22}$H$_{31}$ClN$_5$O (M + H)$^+$ 416.2217, found 416.2214. | 0.010 |
| 125 | | $^1$H NMR (400 MHz, Methanol-d$_4$) δ ppm 7.38 (t, J = 7.8 Hz, 1 H), 7.35 (s, 1 H), 7.30-7.23 (m, 2 H), 3.55-3.43 (m, 2 H), 3.42 (s, 3 H), 3.06-2.95 (m, 2 H), 2.91 (dd, J = 9.5, 6.4 Hz, 1 H), 2.23-2.12 (m, 1 H), 2.11-2.00 (m, 1 H), 1.99-1.90 (m, 1 H), 1.87-1.73 (m, 2 H), 1.50-1.38 (m, 2 H), 1.28 (dd, J = 12.9, 9.3 Hz, 1 H), 1.21-1.10 (m, 1 H), 1.07 (d, J = 6.5 Hz, 3 H).<br>HRMS calcd for C$_{21}$H$_{29}$ClN$_5$O (M + H)$^+$ 402.2061, found 402.2056. | 0.012 |
| 126 | | $^1$H NMR (400 MHz, Methanol-d$_4$) δ ppm 7.25-7.13 (m, 2 H), 7.11-7.03 (m, 1 H), 3.57-3.45 (m, 2 H), 3.43 (s, 3 H), 3.08-2.96 (m, 2 H), 2.96-2.87 (m, 1 H), 2.23-2.12 (m, 1 H), 2.12-1.98 (m, 1 H), 2.01-1.91 (m, 1 H), 1.87-1.73 (m, 2 H), 1.48-1.38 (m, 2 H), 1.29 (dd, J = 12.8, 9.3 Hz, 1 H), 1.23-1.10 (m, 1 H), 1.07 (d, J = 6.5 Hz, 3 H).<br>HRMS calcd for C$_{21}$H$_{28}$F$_2$N$_5$O (M + H)$^+$ 404.2262, found 404.2258. | 0.012 |
| 127 | | $^1$H NMR (400 MHz, Methanol-d$_4$) δ ppm 7.31-7.17 (m, 2 H), 7.13-7.05 (m, 1 H), 3.54-3.43 (m, 2 H), 3.42 (s, 3 H), 3.05-2.94 (m, 2 H), 2.95-2.88 (m, 1 H), 2.21-2.13 (m, 1 H), 2.11-2.00 (m, 1 H), 2.00-1.91 (m, 1 H), 1.85-1.74 (m, 2 H), 1.49-1.38 (m, 2 H), 1.28 (dd, J = 12.9, 9.3 Hz, 1 H), 1.21-1.10 (m, 1 H), 1.07 (d, J = 6.5 Hz, 3 H).<br>HRMS calcd for C$_{21}$H$_{28}$F$_2$N$_5$O (M + H)$^+$ 404.2262, found 404.2265. | 0.014 |

TABLE 17-continued

| Example | Compound | Characterization | IC$_{50}$ (µM) |
|---|---|---|---|
| 129 | | $^1$H NMR (400 MHz, Methanol-d$_4$) δ ppm 7.51 (dd, J = 8.0, 1.6 Hz, 1 H), 7.32 (t, J = 7.8 Hz, 1 H), 7.21 (dd, J = 7.6, 1.6 Hz, 1 H), 3.62-3.47 (m, 2 H), 3.43 (s, 3 H), 3.21-3.14 (m, 1 H), 3.11-2.97 (m, 2 H), 2.29 (dt, J = 12.6, 7.2 Hz, 1 H), 2.19-2.07 (m, 2 H), 1.80 (dddd, J = 28.9, 12.6, 8.7, 4.1 Hz, 2 H), 1.62-1.48 (m, 2 H), 1.36-1.25 (m, 2 H), 1.11 (d, J = 6.1 Hz, 3 H). HRMS calcd for C$_{21}$H$_{28}$Cl$_2$N$_5$O (M + H)$^+$ 436.1671, found 436.1719. | 0.014 |
| 130 | | $^1$H NMR (400 MHz, Methanol-d$_4$) δ ppm 7.71 (d, J = 8.2 Hz, 2 H), 7.50-7.47 (m, 2 H), 4.26-4.18 (m, 1 H), 3.84 (d, J = 8.6 Hz, 1 H), 3.70 (d, J = 8.7 Hz, 1 H), 3.46 (s, 1 H), 3.43 (s, 3 H), 3.41 (s, 1 H), 3.12-3.04 (m, 1 H), 3.03 (d, J = 4.8 Hz, 1 H), 3.01-2.95 (m, 1 H), 1.99-1.85 (m, 2 H), 1.77-1.66 (m, 2 H), 1.22 (d, J = 6.5 Hz, 3 H). HRMS calcd for C$_{21}$H$_{27}$F$_3$N$_5$O$_2$S (M + H)$^+$ 470.1838, found 470.1828. | 0.014 |
| 131 | | $^1$H NMR (400 MHz, Methanol-d$_4$) δ ppm 7.29 (d, J = 8.1 Hz, 2 H), 7.24 (d, 2 H), 4.27-4.19 (m, 1 H), 3.84 (d, J = 8.7 Hz, 1 H), 3.70 (d, J = 8.7 Hz, 1 H), 3.43 (s, 3 H), 3.43-3.37 (m, 2 H), 3.11-3.05 (m, 1 H), 3.04 (d, J = 4.9 Hz, 1 H), 3.02-2.95 (m, 1 H), 2.95-2.89 (m, 1 H), 1.99-1.82 (m, 2 H), 1.78-1.65 (m, 2 H), 1.27 (d, 3H), 1.25-1.19 (m, 6 H). HRMS calcd for C$_{23}$H$_{34}$N$_5$O$_2$ (M + H)$^+$ 412.2713, found 412.2698. | 0.016 |
| 132 | | $^1$H NMR (400 MHz, Methanol-d$_4$) δ ppm 7.51 (dd, J = 8.0, 1.6 Hz, 1 H), 7.32 (t, J = 7.8 Hz, 1 H), 7.22 (dd, J = 7.6, 1.6 Hz, 1 H), 4.30-4.17 (m, 1 H), 3.85 (d, J = 8.7 Hz, 1 H), 3.71 (d, J = 8.7 Hz, 1 H), 3.51-3.39 (m, 5 H), 3.13-2.96 (m, 3 H), 2.00-1.81 (m, 2 H), 1.80-1.63 (m, 2 H), 1.22 (d, J = 6.5 Hz, 3 H). HRMS calcd for C$_{20}$H$_{26}$Cl$_2$N$_5$O$_2$ (M + H)$^+$ 438.1464, found 438.1464. | 0.016 |

TABLE 17-continued

| Example | Compound | Characterization | IC$_{50}$ (μM) |
|---|---|---|---|
| 133 | (structure) | $^1$H NMR (400 MHz, Methanol-d$_4$) δ ppm 7.30-7.23 (m, 1 H), 7.23-7.17 (m, 1 H), 7.14-7.07 (m, 1 H), 4.26-4.17 (m, 1 H), 3.84 (d, J = 8.7 Hz, 1 H), 3.69 (d, J = 8.7 Hz, 1 H), 3.46-3.43 (m, 1 H), 3.42 (s, 3 H), 3.41-3.38 (m, 1 H), 3.12-3.04 (m, 1 H), 3.03 (d, J = 5.0 Hz, 1 H), 3.02-2.94 (m, 1 H), 1.99-1.82 (m, 2 H), 1.78-1.64 (m, 2 H), 1.22 (d, J = 6.5 Hz, 3 H). HRMS calcd for C$_{20}$H$_{26}$F$_2$N$_5$O$_2$ (M + H)$^+$ 406.2055, found 406.1936. | 0.017 |
| 134 | (structure) | $^1$H NMR (400 MHz, Methanol-d$_4$) δ ppm 7.75-7.68 (m, 2 H), 7.53-7.46 (m, 2 H), 3.57-3.45 (m, 2 H), 3.42 (s, 3 H), 3.08-2.96 (m, 3 H), 2.26-2.17 (m, 1 H), 2.15-2.04 (m, 1 H), 2.04-1.97 (m, 1 H), 1.88-1.74 (m, 2 H), 1.47 (d, J = 13.3 Hz, 2 H), 1.34-1.25 (m, 1 H), 1.25-1.16 (m, 1 H), 1.09 (d, J = 6.4 Hz, 3 H). HRMS calcd for C$_{22}$H$_{29}$F$_3$N$_5$OS (M + H)$^+$ 468.2045, found 468.2039. | 0.019 |
| 135 | (structure) | $^1$H NMR (400 MHz, Methanol-d$_4$) δ ppm 7.44-7.33 (m, 2 H), 7.33-7.20 (m, 2 H), 4.31-4.16 (m, 1 H), 3.84 (d, J = 8.7 Hz, 1 H), 3.70 (d, J = 8.7 Hz, 1 H), 3.55-3.37 (m, 5 H), 3.16-2.91 (m, 3 H), 2.01-1.82 (m, 2 H), 1.81-1.62 (m, 2 H), 1.22 (d, J = 6.5 Hz, 3 H). HRMS calcd for C$_{20}$H$_{27}$ClN$_5$O$_2$ (M + H)$^+$ 404.1853, found 404.1842. | 0.019 |
| 136 | (structure) | $^1$H NMR (400 MHz, Methanol-d$_4$) δ ppm 7.33-7.27 (m, 2 H), 7.24-7.18 (m, 2 H), 4.17-4.08 (m, 1 H), 3.75 (d, J = 8.7 Hz, 1 H), 3.60 (d, J = 8.7 Hz, 1 H), 3.37-3.28 (m, 5 H), 3.02-2.95 (m, 1 H), 2.94 (d, J = 4.9 Hz, 1 H), 2.93-2.83 (m, 1 H), 1.89-1.73 (m, 2 H), 1.69-1.54 (m, 2 H), 1.12 (d, J = 6.5 Hz, 3 H). HRMS calcd for C$_{20}$H$_{27}$ClN$_5$O$_2$ (M + H)$^+$ 404.1853, found 404.1848. | 0.020 |

TABLE 17-continued

| Example | Compound | Characterization | IC$_{50}$ (μM) |
| --- | --- | --- | --- |
| 137 | | $^1$H NMR (400 MHz, Methanol-d$_4$) δ ppm 7.51 (dd, J = 8.0, 1.6 Hz, 1 H), 7.32 (t, J = 7.8 Hz, 1 H), 7.22 (dd, J = 7.6, 1.6 Hz, 1 H), 3.63-3.49 (m, 2 H), 3.43 (s, 3 H), 3.14-3.06 (m, 1 H), 3.06-2.89 (m, 2 H), 2.56-2.38 (m, 2 H), 2.16-1.92 (m, 3 H), 1.92-1.80 (m, 1 H), 1.55 (d, J = 10.9 Hz, 1 H), 1.45 (d, J = 13.2 Hz, 1 H). HRMS calcd for C$_{20}$H$_{24}$Cl$_2$F$_2$N$_5$O (M + H)$^+$ 458.1326, found 458.1336. | 0.022 |
| 138 | | $^1$H NMR (400 MHz, Methanol-d$_4$) δ ppm 7.44-7.37 (m, 2 H), 7.34-7.30 (m, 2 H), 7.30-7.25 (m, 1 H), 4.27-4.19 (m, 1 H), 3.84 (d, J = 8.7 Hz, 1 H), 3.70 (d, J = 8.7 Hz, 1 H), 3.44 (s, 3 H), 3.43-3.37 (m, 2 H), 3.12-3.05 (m, 1 H), 3.03 (d, J = 5.0 Hz, 1 H), 3.02-2.94 (m, 1 H), 1.99-1.83 (m, 2 H), 1.78-1.66 (m, 2 H), 1.22 (d, J = 6.5 Hz, 3 H). HRMS calcd for C$_{20}$H$_{28}$N$_5$O$_2$ (M + H)$^+$ 370.2243, found 370.2246. | 0.024 |
| 139 | | $^1$H NMR (400 MHz, Methanol-d$_4$) δ 7.22 (d, 1 H), 7.10 (d, J = 4.5 Hz, 1 H), 6.86 (d, 1 H), 6.68 (d, J = 4.3 Hz, 1 H), 4.27-4.19 (m, 1 H), 3.84 (d, J = 8.7 Hz, 1 H), 3.71 (d, 1 H), 3.69-3.64 (m, 1 H), 3.43 (s, 3 H), 3.43-3.38 (m, 2 H), 3.12-3.05 (m, 1 H), 3.04 (d, J = 4.9 Hz, 1 H), 3.02-2.93 (m, 1 H), 1.98-1.83 (m, 2 H), 1.78-1.63 (m, 2 H), 1.22 (d, J = 6.5 Hz, 3 H), 0.78-0.71 (m, 2 H), 0.68-0.63 (m, 2 H). HRMS calcd for C$_{23}$H$_{32}$N$_5$O$_3$ (M + H)$^+$ 426.2505, found 426.2495. | 0.025 |
| 140 | | $^1$H NMR (400 MHz, Methanol-d$_4$) δ ppm 7.44-7.37 (m, 2 H), 7.35-7.24 (m, 3 H), 3.53-3.43 (m, 2 H), 3.43 (s, 3 H), 3.05-2.94 (m, 2 H), 2.86 (dd, J = 9.6, 6.4 Hz, 1 H), 2.15 (dt, J = 12.7, 6.5 Hz, 1 H), 2.10-1.98 (m, 1 H), 1.92 (dd, J = 13.0, 8.1 Hz, 1 H), 1.81 (td, J = 12.5, 3.5 Hz, 2 H), 1.46-1.36 (m, 2 H), 1.28 (dd, J = 13.0, 9.1 Hz, 1 H), 1.21-1.09 (m, 1 H), 1.07 (d, J = 6.5 Hz, 3 H). HRMS calcd for C$_{21}$H$_{30}$N$_5$O (M + H)$^+$ 368.2450, found 368.2484. | 0.025 |
| 141 | | $^1$H NMR (400 MHz, Methanol-d$_4$) δ ppm 7.47 (t, J = 8.1 Hz, 1 H), 7.22 (dd, J = 10.5, 1.9 Hz, 1 H), 7.14 (dd, 1 H), 4.27-4.18 (m, 1 H), 3.84 (d, J = 8.7 Hz, 1 H), 3.69 (d, J = 8.7 Hz, 1 H), 3.47-3.43 (m, 1 H), 3.42 (s, 3 H), 3.41-3.38 (m, 1 H), 3.12-3.04 (m, 1 H), 3.02 (d, J = 4.9 Hz, 1 H), 3.01-2.94 (m, 1 H), 1.98-1.80 (m, 2 H), 1.79-1.62 (m, 2 H), 1.22 (d, J = 6.5 Hz, 3 H). HRMS calcd for C$_{20}$H$_{26}$ClFN$_5$O$_2$ (M + H)$^+$ 422.1759, found 422.1754. | 0.026 |

TABLE 17-continued

| Example | Compound | Characterization | IC$_{50}$ (µM) |
|---|---|---|---|
| 142 | | $^1$H NMR (400 MHz, Methanol-d$_4$) δ ppm 7.38-7.32 (m, 2 H), 7.32-7.26 (m, 2 H), 7.13-7.07 (m, 1 H), 7.06-6.99 (m, 4 H), 4.27-4.19 (m, 1 H), 3.84 (d, J = 8.7 Hz, 1 H), 3.70 (d, J = 8.7 Hz, 1 H), 3.44 (s, 3 H), 3.43-3.37 (m, 2 H), 3.11-3.04 (m, 1 H), 3.03 (d, J = 4.9 Hz, 1 H), 3.02-2.93 (m, 1 H), 1.98-1.83 (m, 2 H), 1.78-1.65 (m, 2 H), 1.22 (d, J = 6.5 Hz, 3 H). HRMS calcd for C$_{26}$H$_{32}$N$_5$O$_3$ (M + H)$^+$ 462.2505, found 462.2501. | 0.027 |
| 143 | | $^1$H NMR (400 MHz, Methanol-d$_4$) δ 7.25-7.19 (m, 1 H), 7.19-7.13 (m, 1 H), 7.11-7.04 (m, 1 H), 4.26-4.18 (m, 1 H), 3.84 (d, J = 8.7 Hz, 1 H), 3.70 (d, J = 8.7 Hz, 1 H), 3.50-3.43 (m, 2 H), 3.43 (s, 3 H), 3.11-3.04 (m, 1 H), 3.03 (d, J = 5.0 Hz, 1 H), 3.02-2.95 (m, 1 H), 2.00-1.81 (m, 2 H), 1.77-1.66 (m, 2 H), 1.22 (d, J = 6.5 Hz, 3 H). HRMS calcd for C$_{20}$H$_{26}$F$_2$N$_5$O$_2$ (M + H)$^+$ 406.2055, found 406.1907. | 0.028 |
| 144 | | $^1$H NMR (400 MHz, Methanol-d$_4$) δ 7.43-7.38 (m, 2 H), 7.33-7.30 (m, 2 H), 7.30-7.25 (m, 1 H), 3.97-3.91 (m, 1 H), 3.81 (d, J = 8.7 Hz, 1 H), 3.73 (d, J = 8.7 Hz, 1 H), 3.44 (s, 3 H), 3.42-3.37 (m, 2 H), 3.12-3.08 (m, 1 H), 3.08 (d, J = 4.5 Hz, 1 H), 3.03-2.93 (m, 1 H), 1.97-1.82 (m, 2 H), 1.80-1.67 (m, 2 H), 1.65-1.55 (m, 2 H), 1.01 (t, J = 7.4 Hz, 3 H). HRMS calcd for C$_{21}$H$_{30}$N$_5$O$_2$ (M + H)$^+$ 384.2400, found 384.2404. | 0.034 |
| 145 | | $^1$H NMR (400 MHz, Methanol-d$_4$) δ ppm 7.38-7.30 (m, 2 H), 7.18 (d, J = 8.6 Hz, 2 H), 6.82 (t, J = 74.3 Hz, 1 H), 4.27-4.16 (m, 1 H), 3.84 (d, J = 8.7 Hz, 1 H), 3.69 (d, J = 8.7 Hz, 1 H), 3.42 (d, J = 9.1 Hz, 5 H), 3.08 (ddd, J = 13.3, 10.2, 2.9 Hz, 1 H), 3.02 (d, J = 5.0 Hz, 1 H), 3.01-2.95 (m, 1 H), 1.99-1.81 (m, 2 H), 1.77-1.64 (m, 2 H), 1.22 (d, J = 6.5 Hz, 3 H). HRMS calcd for C$_{21}$H$_{28}$F$_2$N$_5$O$_3$ (M + H)$^+$ 436.2160, found 436.2142. | 0.034 |
| 146 | | $^1$H NMR (400 MHz, Methanol-d$_4$) δ ppm 7.25-7.18 (m, 2 H), 7.07-6.99 (m, 2 H), 4.17-4.09 (m, 1 H), 3.74 (d, J = 8.7 Hz, 1 H), 3.60 (d, J = 8.7 Hz, 1 H), 3.33 (s, 3 H), 3.33-3.27 (m, 2 H), 3.02-2.94 (m, 1 H), 2.93 (d, J = 5.0 Hz, 1 H), 2.92-2.84 (m, 1 H), 1.89-1.73 (m, 2 H), 1.69-1.55 (m, 2 H), 1.12 (d, J = 6.5 Hz, 3 H). HRMS calcd for C$_{20}$H$_{27}$FN$_5$O$_2$ (M + H)$^+$ 388.2149, found 388.2142. | 0.038 |

TABLE 17-continued

| Example | Compound | Characterization | IC$_{50}$ (μM) |
| --- | --- | --- | --- |
| 147 | | $^1$H NMR (400 MHz, Methanol-d$_4$) δ 7.23-7.17 (m, 2 H), 6.98-6.93 (m, 2 H), 4.26-4.19 (m, 1 H), 3.86 (d, 1 H), 3.83 (d, J = 4.7 Hz, 2 H), 3.71 (d, J = 8.7 Hz, 1 H), 3.43 (s, 3 H), 3.41-3.38 (m, 2 H), 3.10-3.01 (m, 2 H), 3.01-2.92 (m, 1 H), 1.98-1.83 (m, 2 H), 1.79-1.65 (m, 2 H), 1.30-1.26 (m, 1 H), 1.22 (d, J = 6.5 Hz, 3 H), 0.65-0.55 (m, 2 H), 0.39-0.29 (m, 2 H). HRMS calcd for C$_{24}$H$_{34}$N$_5$O$_3$ (M + H)$^+$ 440.2662, found 440.2651. | 0.039 |
| 148 | | $^1$H NMR (400 MHz, Methanol-d$_4$) δ 7.51 (dd, J = 8.0, 1.6 Hz, 1 H), 7.32 (t, J = 7.8 Hz, 1 H), 7.24-7.19 (m, 1 H), 3.57-3.45 (m, 2 H), 3.43 (s, 3 H), 3.11-2.97 (m, 2 H), 2.97-2.91 (m, 1 H), 2.91-2.77 (m, 1 H), 2.27-2.17 (m, 1 H), 1.89 (d, J = 9.0 Hz, 2 H), 1.88-1.76 (m, 2 H), 1.68-1.58 (m, 1 H), 1.52-1.36 (m, 2 H). HRMS calcd for C$_{21}$H$_{25}$Cl$_2$F$_3$N$_5$O (M + H)$^+$ 490.1388, found 490.1361. | 0.043 |
| 149 | | $^1$H NMR (400 MHz, Methanol-d$_4$) δ ppm 7.47-7.41 (m, 2 H), 7.40-7.33 (m, 2 H), 7.33-7.27 (m, 1 H), 7.24-7.19 (m, 2 H), 7.07-7.01 (m, 2 H), 5.11 (s, 2 H), 4.27-4.17 (m, 1 H), 3.84 (d, J = 8.7 Hz, 1 H), 3.70 (d, J = 8.7 Hz, 1 H), 3.42 (s, 3 H), 3.42-3.36 (m, 2 H), 3.10-3.04 (m, 1 H), 3.03 (d, J = 4.9 Hz, 1 H), 3.01-2.92 (m, 1 H), 1.98-1.83 (m, 2 H), 1.80-1.64 (m, 2 H), 1.22 (d, J = 6.5 Hz, 3 H). HRMS calcd for C$_{27}$H$_{34}$N$_5$O$_3$ (M + H)$^+$ 476.2662, found 476.2656. | 0.043 |
| 150 | | $^1$H NMR (400 MHz, Methanol-d$_4$) δ ppm 7.44-7.36 (m, 2 H), 7.35-7.25 (m, 3 H), 3.59-3.45 (m, 2 H), 3.43 (s, 3 H), 3.13-3.06 (m, 1 H), 3.04-2.87 (m, 2 H), 2.56-2.37 (m, 2 H), 2.17-1.93 (m, 3 H), 1.91-1.80 (m, 1 H), 1.55 (d, J = 13.4 Hz, 1 H), 1.45 (d, J = 13.5 Hz, 1 H). HRMS calcd for C$_{20}$H$_{26}$F$_2$N$_5$O (M + H)$^+$ 390.2105, found 390.2070. | 0.044 |

TABLE 17-continued

| Example | Compound | Characterization | IC$_{50}$ (μM) |
| --- | --- | --- | --- |
| 151 | | $^1$H NMR (400 MHz, Methanol-d$_4$) δ 7.44-7.37 (m, 1 H), 7.17-7.12 (m, 1 H), 7.10-7.05 (m, 1 H), 7.04-6.96 (m, 1 H), 4.27-4.18 (m, 1 H), 3.84 (d, J = 8.7 Hz, 1 H), 3.70 (d, J = 8.7 Hz, 1 H), 3.48-3.44 (m, 1 H), 3.43 (s, 3 H), 3.42-3.38 (m, 1 H), 3.12-3.04 (m, 1 H), 3.03 (d, J = 4.9 Hz, 1 H), 3.02-2.93 (m, 1 H), 1.98-1.83 (m, 2 H), 1.79-1.65 (m, 2 H), 1.22 (d, J = 6.5 Hz, 3 H). HRMS calcd for C$_{20}$H$_{27}$FN$_5$O$_2$ (M + H)$^+$ 388.2149, found 388.2141. | 0.044 |
| 152 | | $^1$H NMR (400 MHz, Methanol-d$_4$) δ ppm 7.52-7.48 (m, 1 H), 7.36-7.31 (m, 2 H), 7.31-7.26 (m, 1 H), 4.29-4.18 (m, 1 H), 3.84 (d, J = 8.7 Hz, 1 H), 3.70 (d, J = 8.7 Hz, 1 H), 3.50-3.38 (m, 5 H), 3.14-2.95 (m, 3 H), 2.00-1.84 (m, 2 H), 1.78-1.64 (m, 2 H), 1.22 (d, J = 6.5 Hz, 3 H). HRMS calcd for C$_{20}$H$_{27}$ClN$_5$O$_2$ (M + H)$^+$ 404.1834, found 404.1853. | 0.045 |
| 153 | | $^1$H NMR (400 MHz, Methanol-d$_4$) δ ppm 7.38-7.31 (m, 1 H), 7.29 (dd, J = 7.4, 1.8 Hz, 1 H), 7.21 (td, J = 7.5, 1.2 Hz, 1 H), 7.15 (ddd, J = 9.5, 8.3, 1.0 Hz, 1 H), 4.27-4.17 (m, 1 H), 3.84 (d, J = 8.7 Hz, 1 H), 3.70 (d, J = 8.7 Hz, 1 H), 3.49-3.38 (m, 5 H), 3.15-2.95 (m, 3 H), 2.00-1.83 (m, 2 H), 1.79-1.65 (m, 2 H), 1.22 (d, J = 6.5 Hz, 3 H). HRMS calcd for C$_{20}$H$_{27}$FN$_5$O$_2$ (M + H)$^+$ 388.2149, found 388.2169. | 0.046 |
| 154 | | $^1$H NMR (400 MHz, Methanol-d$_4$) δ ppm 7.44-7.38 (m, 2 H), 7.34-7.26 (m, 3 H), 5.13 (dt, J = 54.3, 5.8 Hz, 1 H), 3.56-3.46 (m, 2 H), 3.44 (s, 3 H), 3.21-3.14 (m, 1 H), 3.05-2.92 (m, 2 H), 2.33-2.12 (m, 2 H), 2.00-1.72 (m, 4 H), 1.50 (d, J = 11.1 Hz, 1 H), 1.35 (d, J = 11.4 Hz, 1 H). HRMS calcd for C$_{20}$H$_{27}$FN$_5$O (M + H)$^+$ 372.2200, found 372.2205. | 0.046 |
| 155 | | $^1$H NMR (400 MHz, Methanol-d$_4$) δ ppm 7.51 (dd, J = 8.0, 1.6 Hz, 1 H), 7.32 (t, J = 7.8 Hz, 1 H), 7.22 (dd, J = 7.6, 1.6 Hz, 1 H), 5.20 (dt, 1 H), 3.52 (s, 2 H), 3.43 (s, 3 H), 3.22-3.15 (m, 1 H), 3.08-2.89 (m, 2 H), 2.35-2.13 (m, 2 H), 2.01-1.72 (m, 4 H), 1.51 (d, J = 13.9 Hz, 1 H), 1.36 (d, J = 10.5 Hz, 1 H). HRMS calcd for C$_{20}$H$_{25}$Cl$_2$FN$_5$O (M + H)$^+$ 440.1420, found 440.1449. | 0.048 |

TABLE 17-continued

| Example | Compound | Characterization | IC$_{50}$ (μM) |
|---|---|---|---|
| 156 | | $^1$H NMR (400 MHz, Methanol-d$_4$) δ ppm 7.34-7.25 (m, 1 H), 7.03-6.94 (m, 2 H), 4.27-4.19 (m, 1 H), 3.84 (d, J = 8.7 Hz, 1 H), 3.70 (d, J = 8.7 Hz, 1 H), 3.46-3.44 (m, 1 H), 3.43 (s, 3 H), 3.42-3.38 (m, 1 H), 3.13-3.05 (m, 1 H), 3.03 (d, J = 4.9 Hz, 1 H), 2.99 (d, J = 12.7 Hz, 1 H), 1.99-1.82 (m, 2 H), 1.78-1.65 (m, 2 H), 1.22 (d, J = 6.5 Hz, 3 H). HRMS calcd for C$_{20}$H$_{26}$F$_2$N$_5$O$_2$ (M + H)$^+$ 406.2055, found 406.2050. | 0.048 |
| 157 | | $^1$H NMR (400 MHz, Methanol-d$_4$) δ ppm 7.12 (t, J = 8.5 Hz, 1 H), 7.08-7.02 (m, 2 H), 4.27-4.18 (m, 1 H), 3.88 (s, 3 H), 3.84 (d, J = 8.7 Hz, 1 H), 3.70 (d, J = 8.7 Hz, 1 H), 3.46-3.37 (m, 5 H), 3.11-2.94 (m, 3 H), 1.90 (ddd, J = 22.6, 11.8, 8.4 Hz, 2 H), 1.77-1.65 (m, 2 H), 1.22 (d, J = 6.5 Hz, 3 H). HRMS calcd for C$_{21}$H$_{29}$FN$_5$O$_3$ (M + H)$^+$ 418.2254, found 418.2232. | 0.052 |
| 158 | | $^1$H NMR (400 MHz, Methanol-d$_4$) δ ppm 7.44-7.40 (m, 1 H), 7.25 (dd, J = 6.5, 1.4 Hz, 2 H), 4.29-4.16 (m, 1 H), 3.84 (d, J = 8.7 Hz, 1 H), 3.69 (d, J = 8.7 Hz, 1 H), 3.47-3.43 (m, 1 H), 3.42 (s, 3 H), 3.41-3.38 (m, 1 H), 3.12-3.04 (m, 1 H), 3.03 (d, J = 4.9 Hz, 1 H), 3.01-2.95 (m, 1 H), 2.01-1.81 (m, 2 H), 1.79-1.63 (m, 2 H), 1.22 (d, J = 6.5 Hz, 3 H). HRMS calcd for C$_{20}$H$_{26}$ClFN$_5$O$_2$ (M + H)$^+$ 422.1759, found 422.1714. | 0.053 |
| 159 | | $^1$H NMR (400 MHz, Methanol-d$_4$) δ ppm 7.15-7.08 (m, 2 H), 6.91-6.85 (m, 2 H), 4.17-4.09 (m, 1 H), 3.74 (d, J = 8.7 Hz, 1 H), 3.71 (s, 3 H), 3.60 (d, J = 8.7 Hz, 1 H), 3.33 (s, 3 H), 3.33-3.26 (m, 2 H), 3.01-2.94 (m, 1 H), 2.93 (d, J = 5.0 Hz, 1 H), 2.92-2.84 (m, 1 H), 1.90-1.73 (m, 2 H), 1.68-1.50 (m, 2 H), 1.12 (d, J = 6.5 Hz, 3 H). HRMS calcd for C$_{21}$H$_{30}$N$_5$O$_3$ (M + H)$^+$ 400.2349, found 400.2346. | 0.056 |

TABLE 17-continued

| Example | Compound | Characterization | IC$_{50}$ (µM) |
|---|---|---|---|
| 160 | | $^1$H NMR (400 MHz, Methanol-d$_4$) δ ppm 7.19 (d, 2 H), 7.12 (d, J = 8.3 Hz, 2 H), 4.26-4.18 (m, 1 H), 3.84 (d, J = 8.7 Hz, 1 H), 3.70 (d, J = 8.7 Hz, 1 H), 3.43 (s, 3 H), 3.42-3.36 (m, 2 H), 3.11-3.04 (m, 1 H), 3.03 (d, J = 5.0 Hz, 1 H), 3.01-2.92 (m, 1 H), 1.98-1.89 (m, 2 H), 1.89-1.83 (m, 1 H), 1.78-1.63 (m, 2 H), 1.22 (d, J = 6.5 Hz, 3 H), 1.01-0.92 (m, 2 H), 0.76-0.58 (m, 2 H).<br>HRMS calcd for C$_{23}$H$_{32}$N$_5$O$_2$ (M + H)$^+$ 410.2556, found 410.2509. | 0.063 |
| 161 | | $^1$H NMR (400 MHz, Methanol-d$_4$) δ ppm 7.44-7.38 (m, 2 H), 7.34-7.25 (m, 3 H), 3.56-3.45 (m, 2 H), 3.43 (s, 3 H), 3.06-2.92 (m, 3 H), 2.92-2.78 (m, 1 H), 2.29-2.17 (m, 1 H), 1.90 (d, J = 9.0 Hz, 2 H), 1.88-1.76 (m, 2 H), 1.70-1.57 (m, 1 H), 1.53-1.38 (m, 2 H).<br>HRMS calcd for C$_{21}$H$_{27}$F$_3$N$_5$O (M + H)$^+$ 422.2168, found 422.2149. | 0.063 |
| 162 | | $^1$H NMR (400 MHz, Methanol-d$_4$) δ ppm 7.22 (d, J = 2.1 Hz, 1 H), 7.14-7.08 (m, 1 H), 7.01 (d, J = 8.5 Hz, 1 H), 4.17-4.09 (m, 1 H), 3.80 (s, 3 H), 3.74 (d, J = 8.7 Hz, 1 H), 3.60 (d, J = 8.7 Hz, 1 H), 3.33 (s, 3 H), 3.32-3.27 (m, 2 H), 3.02-2.94 (m, 1 H), 2.93 (d, J = 5.0 Hz, 1 H), 2.92-2.84 (m, 1 H), 1.89-1.73 (m, 2 H), 1.70-1.54 (m, 2 H), 1.12 (d, J = 6.5 Hz, 3 H).<br>HRMS calcd for C$_{21}$H$_{29}$ClN$_5$O$_3$ (M + H)$^+$ 434.1959, found 434.1948. | 0.066 |
| 163 | | $^1$H NMR (400 MHz, Methanol-d$_4$) δ ppm 7.20-7.09 (m, 4 H), 4.17-4.08 (m, 1 H), 3.74 (d, J = 8.7 Hz, 1 H), 3.60 (d, J = 8.7 Hz, 1 H), 3.33 (s, 3 H), 3.33-3.27 (m, 2 H), 3.02-2.95 (m, 1 H), 2.94 (d, J = 4.8 Hz, 1 H), 2.93-2.84 (m, 1 H), 2.49-2.33 (m, 1 H), 1.89-1.78 (m, 2 H), 1.76 (d, J = 9.3 Hz, 4 H), 1.70-1.57 (m, 3 H), 1.42-1.31 (m, 4 H), 1.24-1.18 (m, 1 H), 1.12 (d, J = 6.5 Hz, 3 H).<br>HRMS calcd for C$_{26}$H$_{38}$N$_5$O$_2$ (M + H)$^+$ 452.3026, found 452.3017. | 0.073 |

TABLE 17-continued

| Example | Compound | Characterization | IC$_{50}$ (µM) |
|---|---|---|---|
| 164 | | $^1$H NMR (400 MHz, Methanol-d$_4$) δ ppm 6.97-6.94 (m, 1 H), 6.94-6.91 (m, 1 H), 6.86-6.79 (m, 1 H), 4.26-4.18 (m, 1 H), 3.84 (d, J = 8.7 Hz, 1 H), 3.70 (d, J = 8.7 Hz, 1 H), 3.46-3.43 (m, 1 H), 3.42 (s, 3 H), 3.42-3.39 (m, 1 H), 3.12-3.05 (m, 1 H), 3.03 (d, J = 5.0 Hz, 1 H), 3.01-2.95 (m, 1 H), 1.98-1.80 (m, 2 H), 1.78-1.63 (m, 2 H), 1.22 (d, J = 6.5 Hz, 3 H). HRMS calcd for C$_{20}$H$_{26}$F$_2$N$_5$O$_2$ (M + H)$^+$ 406.2055, found 406.2041. | 0.075 |
| 165 | | $^1$H NMR (400 MHz, Methanol-d$_4$) δ ppm 7.43-7.37 (m, 2 H), 7.34-7.25 (m, 3 H), 3.52-3.45 (m, 2 H), 3.43 (s, 3 H), 3.06-2.87 (m, 3 H), 2.44-2.23 (m, 1 H), 2.10 (dd, J = 13.1, 9.4 Hz, 1 H), 1.99 (td, J = 12.8, 3.9 Hz, 1 H), 1.86 (td, J = 12.8, 4.0 Hz, 1 H), 1.49 (dd, J = 13.2, 2.3 Hz, 1 H), 1.42-1.25 (m, 2 H), 1.08 (d, J = 6.8 Hz, 3 H). HRMS calcd for C$_{21}$H$_{28}$F$_2$N$_5$O (M + H)$^+$ 404.2262, found 404.2241. | 0.078 |
| 166 | | $^1$H NMR (400 MHz, Methanol-d$_4$) δ ppm 7.08-7.03 (m, 2 H), 6.77-6.70 (m, 2 H), 4.18-4.09 (m, 1 H), 3.75 (d, J = 8.7 Hz, 1 H), 3.62 (d, J = 8.7 Hz, 1 H), 3.34 (s, 3 H), 3.33-3.26 (m, 2 H), 2.98 (d, J = 4.8 Hz, 1 H), 2.96-2.89 (m, 1 H), 2.88-2.85 (m, 1 H), 2.84 (s, 6 H), 1.89-1.73 (m, 2 H), 1.70-1.55 (m, 2 H), 1.13 (d, J = 6.5 Hz, 3 H). HRMS calcd for C$_{22}$H$_{33}$N$_6$O$_2$ (M + H)$^+$ 413.2665, found 413.2651. | 0.088 |
| 167 | | $^1$H NMR (400 MHz, Methanol-d$_4$) δ ppm 7.51 (dd, J = 8.0, 1.6 Hz, 1 H), 7.31 (t, J = 7.8 Hz, 1 H), 7.22 (dd, J = 7.6, 1.6 Hz, 1 H), 3.53 (d, J = 13.0 Hz, 2 H), 3.43 (s, 3 H), 3.08-2.91 (m, 3 H), 2.45-2.25 (m, 1 H), 2.10 (dd, J = 13.2, 9.5 Hz, 1 H), 2.05-1.94 (m, 1 H), 1.93-1.79 (m, 1 H), 1.53-1.45 (m, 1 H), 1.43-1.26 (m, 2 H), 1.08 (d, J = 6.8 Hz, 3 H). HRMS calcd for C$_{21}$H$_{26}$Cl$_2$F$_2$N$_5$O (M + H)$^+$ 472.1482, found 472.1451. | 0.089 |

TABLE 17-continued

| Example | Compound | Characterization | IC$_{50}$ (μM) |
|---|---|---|---|
| 168 | (biphenyl-substituted pyrimidinone with methyl-oxa-spiro piperidine and amino groups) | $^1$H NMR (400 MHz, Methanol-d$_4$) δ ppm 7.71-7.61 (m, 5 H), 7.44-7.39 (m, 4 H), 4.27-4.20 (m, 1 H), 3.85 (d, J = 8.7 Hz, 1 H), 3.71 (d, J = 8.7 Hz, 1 H), 3.45 (s, 3 H), 3.45-3.39 (m, 2 H), 3.12-3.07 (m, 1 H), 3.05 (d, J = 4.8 Hz, 1 H), 3.03-2.96 (m, 1 H), 1.97-1.85 (m, 2 H), 1.79-1.67 (m, 2 H), 1.23 (d, J = 6.5 Hz, 3 H). HRMS calcd for C$_{26}$H$_{32}$N$_5$O$_2$ (M + H)$^+$ 446.2556, found 446.2549. | 0.107 |
| 169 | (4-trifluoromethoxyphenyl pyrimidinone analog) | $^1$H NMR (400 MHz, Methanol-d$_4$) δ ppm 7.46-7.39 (m, 2 H), 7.30 (d, J = 8.0 Hz, 2 H), 4.29-4.18 (m, 1 H), 3.84 (d, J = 8.7 Hz, 1 H), 3.70 (d, J = 8.7 Hz, 1 H), 3.43 (s, 5 H), 3.12-3.04 (m, 1 H), 3.03 (d, J = 5.0 Hz, 1 H), 2.98 (d, J = 10.4 Hz, 1 H), 1.99-1.82 (m, 2 H), 1.77-1.64 (m, 2 H), 1.22 (d, J = 6.5 Hz, 3 H). HRMS calcd for C$_{21}$H$_{27}$F$_3$N$_5$O$_3$ (M + H)$^+$ 454.2037, found 454.2065. | 0.119 |
| 170 | (4-(2-methoxyethoxy)phenyl pyrimidinone analog) | $^1$H NMR (400 MHz, Methanol-d$_4$) δ ppm 7.26-7.18 (m, 2 H), 7.02-6.96 (m, 2 H), 4.27-4.19 (m, 1 H), 4.17-4.09 (m, 2 H), 3.84 (d, J = 8.7 Hz, 1 H), 3.77-3.73 (m, 2 H), 3.70 (d, J = 8.7 Hz, 1 H), 3.43 (s, 3 H), 3.43 (s, 3 H), 3.42-3.36 (m, 2 H), 3.11-3.04 (m, 1 H), 3.03 (d, J = 4.9 Hz, 1 H), 3.01-2.93 (m, 1 H), 1.99-1.81 (m, 2 H), 1.77-1.64 (m, 2 H), 1.22 (d, J = 6.5 Hz, 3 H). HRMS calcd for C$_{23}$H$_{34}$N$_5$O$_4$ (M + H)$^+$ 444.2611, found 444.2612. | 0.169 |
| 171 | (5-chloropyridin-3-yl pyrimidinone analog) | $^1$H NMR (400 MHz, Methanol-d$_4$) δ ppm 8.43 (d, J = 1.8 Hz, 1 H), 8.41 (d, J = 2.4 Hz, 1 H), 7.88-7.83 (m, 1 H), 4.27-4.18 (m, 1 H), 3.84 (d, J = 8.7 Hz, 1 H), 3.70 (d, J = 8.7 Hz, 1 H), 3.51-3.43 (m, 2 H), 3.42 (s, 3 H), 3.15-3.06 (m, 1 H), 3.06-3.02 (m, 1 H), 3.02 (s, 1 H), 1.99-1.83 (m, 2 H), 1.77-1.65 (m, 2 H), 1.22 (d, J = 6.5 Hz, 3 H). HRMS calcd for C$_{19}$H$_{26}$ClN$_6$O$_2$ (M + H)$^+$ 405.1806, found 405.1830. | 0.172 |

TABLE 17-continued

| Example | Compound | Characterization | IC$_{50}$ (μM) |
|---|---|---|---|
| 172 | | $^1$H NMR (400 MHz, Methanol-d$_4$) δ ppm 7.43-7.37 (m, 2 H), 7.34-7.28 (m, 2 H), 3.56-3.43 (m, 2 H), 3.42 (s, 3 H), 3.07-2.94 (m, 3 H), 2.28-2.17 (m, 1 H), 2.16-2.05 (m, 1 H), 2.05-1.96 (m, 1 H), 1.88-1.72 (m, 2 H), 1.47 (d, J = 13.0 Hz, 2 H), 1.34-1.15 (m, 2 H), 1.09 (d, J = 6.4 Hz, 3 H). HRMS calcd for C$_{21}$H$_{29}$ClN$_5$O (M + H)$^+$ 402.2061, found 402.2054. | 0.174 |
| 173 | | $^1$H NMR (400 MHz, Methanol-d$_4$) δ ppm 7.10-7.04 (m, 2 H), 6.94 (d, J = 8.3 Hz, 1 H), 4.28-4.17 (m, 1 H), 3.84 (d, J = 8.7 Hz, 1 H), 3.83 (s, 3 H), 3.70 (d, J = 8.7 Hz, 1 H), 3.43 (s, 3 H), 3.42-3.36 (m, 2 H), 3.10-3.04 (m, 1 H), 3.03 (d, J = 4.8 Hz, 1 H), 3.01-2.92 (m, 1 H), 2.19 (s, 3 H), 1.98-1.82 (m, 2 H), 1.78-1.64 (m, 2 H), 1.22 (d, J = 6.5 Hz, 3 H). HRMS calcd for C$_{22}$H$_{32}$N$_5$O$_3$ (M + H)$^+$ 414.2505, found 414.2498. | 0.175 |
| 174 | | $^1$H NMR (400 MHz, Methanol-d$_4$) δ ppm 7.47-7.45 (m, 2 H), 7.26-7.23 (m, 2 H), 4.27-4.19 (m, 1 H), 3.84 (d, J = 8.7 Hz, 1 H), 3.70 (d, J = 8.7 Hz, 1 H), 3.43 (s, 3 H), 3.42-3.37 (m, 2 H), 3.11-3.04 (m, 1 H), 3.04 (d, J = 4.8 Hz, 1 H), 3.02-2.94 (m, 1 H), 1.96-1.83 (m, 2 H), 1.78-1.66 (m, 2 H), 1.34 (s, 9 H), 1.22 (d, J = 6.5 Hz, 3 H). HRMS calcd for C$_{24}$H$_{36}$N$_5$O$_2$ (M + H)$^+$ 426.2869, found 426.2864. | 0.183 |
| 175 | | $^1$H NMR (400 MHz, Methanol-d$_4$) δ ppm 7.75-7.71 (m, 2 H), 7.58-7.52 (m, 2 H), 4.27-4.18 (m, 1 H), 3.84 (d, J = 8.7 Hz, 1 H), 3.70 (d, J = 8.7 Hz, 1 H), 3.50-3.44 (m, 1 H), 3.42 (s, 3 H), 3.42-3.40 (m, 1 H), 3.14-3.05 (m, 1 H), 3.03 (d, J = 4.9 Hz, 1 H), 3.02-2.96 (m, 1 H), 1.98-1.83 (m, 2 H), 1.77-1.64 (m, 2 H), 1.22 (d, J = 6.5 Hz, 3 H). HRMS calcd for C$_{21}$H$_{27}$N$_6$O$_2$ (M + H)$^+$ 395.2195, found 395.2188. | 0.256 |
| 176 | | $^1$H NMR (400 MHz, Methanol-d$_4$) δ ppm 7.31-7.27 (m, 1 H), 7.26-7.19 (m, 2 H), 7.15-7.10 (m, 1 H), 4.23 (dd, J = 6.5, 5.1 Hz, 1 H), 3.85 (d, J = 8.7 Hz, 1 H), 3.70 (d, J = 8.7 Hz, 1 H), 3.45-3.39 (m, 5 H), 3.12-2.95 (m, 3 H), 2.15 (s, 3 H), 1.99-1.85 (m, 2 H), 1.79-1.66 (m, 2 H), 1.22 (d, J = 6.5 Hz, 3 H). HRMS calcd for C$_{21}$H$_{30}$N$_5$O$_2$ (M + H)$^+$ 384.2400, found 384.2215. | 0.271 |

TABLE 17-continued

| Example | Compound | Characterization | IC$_{50}$ (μM) |
|---|---|---|---|
| 177 | | $^1$H NMR (400 MHz, Methanol-d$_4$) δ ppm 7.52 (d, J = 8.3 Hz, 1 H), 7.49 (d, J = 2.0 Hz, 1 H), 7.25 (dd, J = 8.3, 2.0 Hz, 1 H), 4.28-4.14 (m, 1 H), 3.83 (d, J = 8.7 Hz, 1 H), 3.69 (d, J = 8.7 Hz, 1 H), 3.47-3.37 (m, 5 H), 3.12-3.05 (m, 1 H), 3.02 (d, J = 5.0 Hz, 1 H), 2.98 (d, J = 10.6 Hz, 1 H), 2.00-1.79 (m, 2 H), 1.77-1.59 (m, 2 H), 1.21 (d, J = 6.5 Hz, 3 H). HRMS calcd for C$_{20}$H$_{26}$Cl$_2$N$_5$O$_2$ (M + H)$^+$ 438.1464, found 438.1476. | 0.309 |
| 178 | | $^1$H NMR (400 MHz, Methanol-d$_4$) δ ppm 7.24-7.14 (m, 4 H), 4.17-4.09 (m, 1 H), 3.99-3.91 (m, 2 H), 3.75 (d, J = 8.7 Hz, 1 H), 3.60 (d, J = 8.7 Hz, 1 H), 3.52-3.43 (m, 2 H), 3.33 (s, 3 H), 3.33-3.27 (m, 2 H), 3.02-2.95 (m, 1 H), 2.95 (d, J = 4.9 Hz, 1 H), 2.93-2.83 (m, 1 H), 2.78-2.67 (m, 1 H), 1.88-1.74 (m, 2 H), 1.74-1.55 (m, 6 H), 1.13 (d, J = 6.5 Hz, 3 H). HRMS calcd for C$_{25}$H$_{36}$N$_5$O$_3$ (M + H)$^+$ 454.2818, found 454.2805. | 0.412 |
| 179 | | $^1$H NMR (400 MHz, Methanol-d$_4$) δ ppm 7.33 (t, J = 1.9 Hz, 1 H), 7.30 (d, J = 1.9 Hz, 2 H), 4.27-4.15 (m, 1 H), 3.84 (d, J = 8.7 Hz, 1 H), 3.69 (d, J = 8.7 Hz, 1 H), 3.49-3.38 (m, 5 H), 3.13-3.04 (m, 1 H), 3.03 (d, J = 4.9 Hz, 1 H), 3.02-2.96 (m, 1 H), 1.97-1.83 (m, 2 H), 1.78-1.62 (m, 2 H), 1.22 (d, J = 6.5 Hz, 3 H). HRMS calcd for C$_{20}$H$_{26}$Cl$_2$N$_5$O$_2$ (M + H)$^+$ 438.1464, found 438.1479. | 0.421 |
| 180 | | $^1$H NMR (400 MHz, Methanol-d$_4$) δ ppm 7.58 (d, J = 2.5 Hz, 1 H), 7.25 (d, J = 2.5 Hz, 1 H), 4.27-4.15 (m, 1 H), 3.84 (d, J = 8.7 Hz, 1 H), 3.70 (d, J = 8.7 Hz, 1 H), 3.50-3.44 (m, 2 H), 3.42 (s, 3 H), 3.12-2.97 (m, 3 H), 2.00-1.83 (m, 2 H), 1.78-1.65 (m, 2 H), 1.22 (d, J = 6.5 Hz, 3 H). HRMS calcd for C$_{20}$H$_{25}$Cl$_3$N$_5$O$_2$ (M + H)$^+$ 472.1074, found 472.1054. | 0.515 |

TABLE 17-continued

| Example | Compound | Characterization | IC$_{50}$ (μM) |
|---|---|---|---|
| 181 | | $^1$H NMR (400 MHz, Methanol-d$_4$) δ ppm 7.36-7.30 (m, 1 H), 7.15 (dd, J = 7.5, 1.7 Hz, 1 H), 7.06 (d, J = 7.7 Hz, 1 H), 6.99 (td, J = 7.4, 1.0 Hz, 1 H), 4.29 (dd, J = 6.5, 4.2 Hz, 1 H), 3.94 (d, J = 9.1 Hz, 1 H), 3.83 (d, J = 9.2 Hz, 1 H), 3.76 (s, 3 H), 3.58-3.38 (m, 6 H), 2.97 (dt, J = 24.9, 12.3 Hz, 2 H), 2.06-1.83 (m, 4 H), 1.32 (d, J = 6.5 Hz, 3 H). One proton signal buried under solvent peak. HRMS calcd for C$_{21}$H$_{30}$N$_5$O$_3$ (M + H)$^+$ 400.2349, found 400.2336. | 0.840 |
| 182 | | $^1$H NMR (400 MHz, Methanol-d$_4$) δ ppm 8.55-8.49 (m, 1 H), 8.30 (d, J = 8.4 Hz, 1 H), 7.98-7.87 (m, 1 H), 7.34-7.18 (m, 1 H), 4.29 (dd, J = 6.6, 4.1 Hz, 1 H), 3.95 (d, J = 9.3 Hz, 1 H), 3.84 (d, J = 9.2 Hz, 1 H), 3.71-3.60 (m, 2 H), 3.46-3.41 (m, 4 H), 3.04 (dd, J = 22.9, 11.3 Hz, 2 H), 2.00-1.85 (m, 3 H), 1.72 (d, J = 13.0 Hz, 1 H), 1.32 (d, J = 6.6 Hz, 2 H). HRMS calcd for C$_{19}$H$_{27}$N$_6$O$_2$ (M + H)$^+$ 370.2117, found 370.2117. | 1.063 |
| 183 | | $^1$H NMR (400 MHz, Methanol-d$_4$) δ ppm 8.37 (dd, J = 5.0, 1.7 Hz, 1 H), 7.59 (dd, J = 7.7, 1.7 Hz, 1 H), 7.30 (dd, J = 7.6, 5.0 Hz, 1 H), 4.27-4.18 (m, 1 H), 3.85 (d, J = 8.7 Hz, 1 H), 3.70 (d, J = 8.7 Hz, 1 H), 3.49-3.40 (m, 5 H), 3.16-2.95 (m, 3 H), 2.38 (s, 3 H), 2.00-1.83 (m, 2 H), 1.80-1.66 (m, 2 H), 1.22 (d, J = 6.5 Hz, 3 H). HRMS calcd for C$_{20}$H$_{29}$N$_6$O$_2$ (M + H)$^+$ 385.2352, found 385.2341. | 1.594 |
| 184 | | $^1$H NMR (400 MHz, Methanol-d$_4$) δ ppm 7.64 (s, 1 H), 7.61-7.53 (m, 3 H), 4.27-4.18 (m, 1 H), 3.84 (d, J = 8.7 Hz, 1 H), 3.70 (d, J = 8.7 Hz, 1 H), 3.47-3.39 (m, 5 H), 3.13-3.05 (m, 1 H), 3.04 (d, J = 4.8 Hz, 1 H), 3.02-2.97 (m, 1 H), 1.99-1.83 (m, 2 H), 1.79-1.62 (m, 2 H), 1.22 (d, J = 6.5 Hz, 3 H). HRMS calcd for C$_{21}$H$_{27}$F$_3$N$_5$O$_2$ (M + H)$^+$ 436.2117, found 438.2083 | 1.690 |

TABLE 17-continued

| Example | Compound | Characterization | IC$_{50}$ (μM) |
|---|---|---|---|
| 185 | 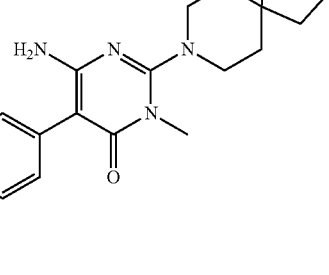 | $^1$H NMR (400 MHz, Methanol-d$_4$) δ ppm 7.14-7.09 (m, 2 H), 6.95-6.90 (m, 2 H), 4.16-4.09 (m, 1 H), 3.77-3.71 (m, 5 H), 3.60 (d, J = 8.7 Hz, 1 H), 3.33 (s, 3 H), 3.33-3.26 (m, 2 H), 3.08-3.04 (m, 4 H), 3.01-2.95 (m, 1 H), 2.94 (d, J = 5.0 Hz, 1 H), 2.93-2.81 (m, 1 H), 1.90-1.72 (m, 2 H), 1.69-1.54 (m, 2 H), 1.12 (d, J = 6.5 Hz, 3 H). HRMS calcd for C$_{24}$H$_{35}$N$_6$O$_3$ (M + H)$^+$ 455.2771, found 455.2767. | 2.116 |
| 186 | 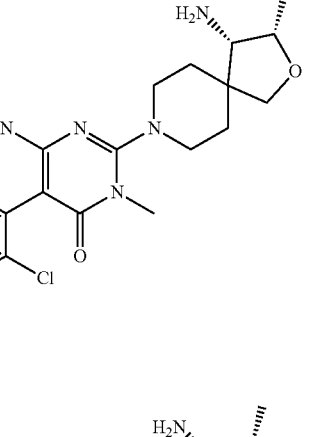 | $^1$H NMR (400 MHz, Methanol-d$_4$) δ ppm 7.48 (d, J = 8.5 Hz, 1 H), 7.33 (dd, J = 8.5, 2.6 Hz, 1 H), 7.29 (d, J = 2.5 Hz, 1 H), 4.27-4.16 (m, 1 H), 3.84 (d, J = 8.7 Hz, 1 H), 3.70 (d, J = 8.6 Hz, 1 H), 3.51-3.44 (m, 1 H), 3.43 (s, 3 H), 3.42-3.40 (m, 1 H), 3.14-3.06 (m, 1 H), 3.04 (d, J = 5.0 Hz, 1 H), 3.02-2.96 (m, 1 H), 2.00-1.81 (m, 2 H), 1.79-1.63 (m, 2 H), 1.22 (d, J = 6.5 Hz, 3 H). HRMS calcd for C$_{20}$H$_{26}$Cl$_2$N$_5$O$_2$ (M + H)$^+$ 438.1464, found 438.1527. | 2.233 |
| 187 | 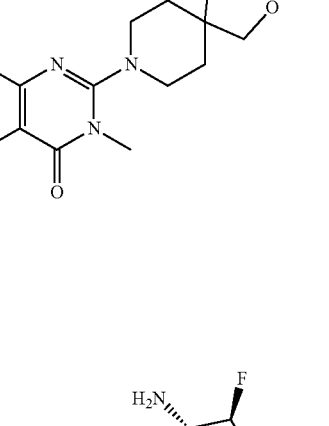 | $^1$H NMR (400 MHz, Methanol-d$_4$) δ ppm 8.30 (d, J = 5.3 Hz, 1 H), 7.53 (s, 1 H), 7.49-7.37 (m, 1 H), 4.64-4.50 (m, 1 H), 3.84 (d, J = 8.7 Hz, 1 H), 3.70 (d, J = 8.7 Hz, 1 H), 3.46-3.38 (m, 5 H), 3.18-2.97 (m, 3 H), 2.02-1.61 (m, 4 H), 1.22 (d, J = 6.4 Hz, 3 H). HRMS calcd for C$_{19}$H$_{26}$ClN$_6$O$_2$ (M + H)$^+$ 405.1806, found 405.1796. | 2.951 |
| 188 | 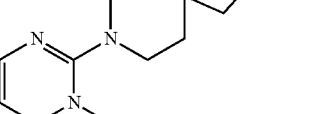 | $^1$H NMR (400 MHz, Methanol-d$_4$) δ ppm 7.46-7.39 (m, 2 H), 7.36-7.28 (m, 3 H), 4.23 (dt, J = 55.2, 8.1 Hz, 1 H), 3.52-3.46 (m, 2 H), 3.45 (s, 3 H), 3.08-2.94 (m, 2 H), 2.94-2.85 (m, 1 H), 2.20-2.02 (m, 2 H), 2.02-1.83 (m, 2 H), 1.55-1.46 (m, 1 H), 1.40-1.26 (m, 2 H), 1.16 (d, J = 6.4 Hz, 3 H). HRMS calcd for C$_{21}$H$_{29}$FN$_5$O (M + H)$^+$ 386.2356, found 386.2363. | 0.015 |

TABLE 17-continued

| Example | Compound | Characterization | IC$_{50}$ (μM) |
|---|---|---|---|
| 189 | | $^1$H NMR (400 MHz, Methanol-d$_4$) δ ppm 7.46-7.40 (m, 2 H), 7.36-7.27 (m, 3 H), 4.14 (dd, J = 9.0, 6.5 Hz, 1 H), 3.85 (d, J = 8.7 Hz, 1 H), 3.79 (d, J = 8.7 Hz, 1 H), 3.56-3.47 (m, 3 H), 3.46 (s, 3 H), 3.23-3.18 (m, 1 H), 3.08-3.03 (m, 1 H), 3.03-2.97 (m, 1 H), 1.98-1.82 (m, 2 H), 1.65 (t, J = 15.0 Hz, 2 H).<br>HRMS calcd for C$_{19}$H$_{26}$N$_5$O$_2$ (M + H)$^+$ 356.2087, found 356.2085. | 0.041 |
| 190 | | $^1$H NMR (400 MHz, Methanol-d$_4$) δ ppm 7.41 (dd, J = 8.0, 1.6 Hz, 1 H), 7.22 (t, J = 7.8 Hz, 1 H), 7.13 (dd, J = 7.6, 1.6 Hz, 1 H), 4.03 (dd, J = 9.0, 6.5 Hz, 1 H), 3.74 (d, J = 8.7 Hz, 1 H), 3.68 (d, J = 8.8 Hz, 1 H), 3.46-3.35 (m, 3 H), 3.34 (s, 3 H), 3.12-3.06 (m, 1 H), 2.99-2.93 (m, 1 H), 2.93-2.87 (m, 1 H), 1.87-1.68 (m, 2 H), 1.62-1.45 (m, 2 H).<br>HRMS calcd for C$_{19}$H$_{24}$Cl$_2$N$_5$O$_2$ (M + H)$^+$ 424.1307, found 424.1344. | 0.069 |
| 191 | | $^1$H NMR (400 MHz, Methanol-d$_4$) δ ppm 7.35-7.27 (m, 2 H), 7.25-7.18 (m, 3 H), 3.41-3.35 (m, 2 H), 3.34 (s, 3 H), 2.98-2.93 (m, 1 H), 2.93-2.85 (m, 2 H), 2.05-1.94 (m, 1 H), 1.81-1.68 (m, 3 H), 1.68-1.60 (m, 2 H), 1.59-1.45 (m, 2 H), 1.40-1.29 (m, 2 H).<br>HRMS calcd for C$_{20}$H$_{28}$N$_5$O (M + H)$^+$ 354.2294, found 354.2286. | 0.027 |
| 192 | | $^1$H NMR (400 MHz, Methanol-d$_4$) δ ppm 7.41 (dd, J = 8.0, 1.6 Hz, 1 H), 7.22 (t, J = 7.8 Hz, 1 H), 7.13 (dd, J = 7.6, 1.6 Hz, 1 H), 3.46-3.36 (m, 2 H), 3.33 (s, 3 H), 2.99-2.87 (m, 2 H), 2.80 (t, J = 7.4 Hz, 1 H), 2.03-1.89 (m, 1 H), 1.82-1.72 (m, 2 H), 1.71-1.62 (m, 2 H), 1.61-1.53 (m, 1 H), 1.53-1.46 (m, 1 H), 1.46-1.39 (m, 1 H), 1.38-1.25 (m, 2 H).<br>HRMS calcd for C$_{20}$H$_{26}$Cl$_2$N$_5$O (M + H)$^+$ 422.1514, found 422.1505. | 0.021 |
| 193 | | $^1$H NMR (400 MHz, Methanol-d$_4$) δ ppm 7.42 (dd, J = 8.0, 1.6 Hz, 1 H), 7.23 (t, J = 7.8 Hz, 1 H), 7.12 (dd, J = 7.6, 1.6 Hz, 1 H), 3.32 (s, 3 H), 3.31-3.26 (m, 2 H), 3.14-3.06 (m, 2 H), 2.78 (s, 2 H), 1.68-1.56 (m, 2 H), 1.49 (d, J = 13.4 Hz, 2H), 1.06 (s, 3H).<br>HRMS calcd for C$_{18}$H$_{24}$Cl$_2$N$_5$O (M + H)$^+$ 396.1358, found 396.1342. | 0.040 |

TABLE 17-continued

| Example | Compound | Characterization | IC$_{50}$ (μM) |
|---|---|---|---|
| 194 | | $^1$H NMR (400 MHz, Methanol-d$_4$) δ ppm 7.44-7.38 (m, 2 H), 7.34-7.25 (m, 3 H), 3.42 (s, 3 H), 3.40-3.33 (m, 2 H), 3.25-3.15 (m, 2 H), 1.79-1.68 (m, 4 H), 1.26 (s, 3 H). HRMS calcd for C$_{17}$H$_{24}$N$_5$O (M + H)$^+$ 314.1981, found 314.1946. | |
| 195 | | $^1$H NMR (400 MHz, Methanol-d$_4$) δ ppm 7.51 (dd, J = 8.0, 1.6 Hz, 1 H), 7.32 (t, J = 7.8 Hz, 1 H), 7.22 (dd, J = 7.6, 1.6 Hz, 1 H), 3.42 (s, 3 H), 3.41-3.34 (m, 2 H), 3.27-3.19 (m, 2 H), 1.73 (q, J = 6.9, 6.2 Hz, 4 H), 1.26 (s, 3 H). HRMS calcd for C$_{17}$H$_{22}$Cl$_2$N$_5$O (M + H)$^+$ 382.1201, found 382.1191. | |
| 197 | | $^1$H NMR (400 MHz, Methanol-d$_4$) δ ppm 7.43-7.37 (m, 2 H), 7.36-7.29 (m, 1 H), 7.25-7.18 (m, 2 H), 4.27-4.19 (m, 1 H), 3.85 (d, J = 8.7 Hz, 1 H), 3.70 (d, J = 8.7 Hz, 1 H), 3.51 (s, 3 H), 3.46-3.39 (m, 2 H), 3.11 (ddd, J = 13.2, 9.9, 2.5 Hz, 1 H), 3.04 (d, J = 5.0 Hz, 1 H), 3.05-2.97 (m, 1 H), 2.08 (s, 3 H), 2.00-1.85 (m, 2 H), 1.81-1.66 (m, 2 H), 1.22 (d, J = 6.5 Hz, 3 H). HRMS calcd for C$_{21}$H$_{29}$N$_4$O$_2$ (M + H)$^+$ 369.2291, found 369.2281. | 0.369 |

Example 198

2-(4-(aminomethyl)-4-methylpiperidin-1-yl)-5-(2,3-dichlorophenyl)pyrimidin-4(3H)-one

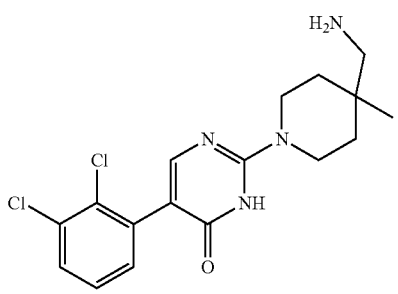 [SMILES: CC1(CN)CCN(c2ncc(-c3cccc(Cl)c3Cl)c(=O)[nH]2)CC1]

Step a: A suspension of tert-butyl ((1-(5-bromo-4-methoxypyrimidin-2-yl)-4-methylpiperidin-4-yl)methyl)carbamate (105 mg, 0.225 mmol), (2,3-dichlorophenyl)boronic acid (42.9 mg, 0.225 mmol), PdCl$_2$(dppf) CH$_2$Cl$_2$ adduct (18.4 mg, 0.023 mmol) and K$_2$CO$_3$ (124 mg, 0.900 mmol) in THF (1.88 mL) and water (0.375 mL) was degassed with a stream of N$_2$ for 5 min., heated to 50° C. for 4 h. The reaction mixture was partioned between EtOAc (100 mL) and water (50 mL). The separated organic layer was washed with brine (50 mL), dried over Na$_2$SO$_4$, filtered and concentrated under reduced pressure. The residue was purified by column chromatography (silica gel, 0 to 30% gradient of EtOAc/heptane) providing tert-butyl ((1-(5-(2,3-dichlorophenyl)-4-methoxypyrimidin-2-yl)-4-methylpiperidin-4-yl)methyl)carbamate (17 mg) as a colorless solid. MS m/z 481.3 (M+H).

Step b: tert-Butyl ((1-(5-(2,3-dichlorophenyl)-4-methoxypyrimidin-2-yl)-4-methylpiperidin-4-yl)methyl) carbamate (17 mg, 0.028 mmol) was dissolved in HBr (33% in AcOH, 0.4 mL) and the mixture was stirred at 90° C. for 1 h. The reaction mixture was concentrated under reduced pressure. The residue was dissolved in MeOH and basified with NH$_3$ (7 M in MeOH) and the mixture was concentrated under reduced pressure. The residue was dissolved in MeCN/water (2:1), filtered through a syringe filter (0.2 μm) and purified by HPLC (gradient elution 15-40% MeCN in water, 5 mM NH$_4$OH modifier) providing 2-(4-(aminomethyl)-4-methylpiperidin-1-yl)-5-(2,3-dichlorophenyl)pyrimidin-4(3H)-one (6 mg) as a white solid.

Example 199

2-((3S,4S)-4-amino-3-methyl-2-oxa-8-azaspiro[4.5]decan-8-yl)-5-(2,3-dichlorophenyl)pyrimidin-4(3H)-one

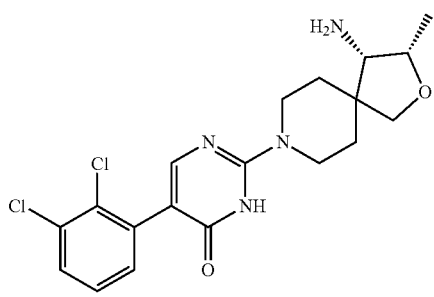 [SMILES: C[C@@H]1OCC2(CCN(c3ncc(-c4cccc(Cl)c4Cl)c(=O)[nH]3)CC2)[C@@H]1N]

Step a: A mixture of 2-chloro-5-(2,3-dichlorophenyl)-4-methoxypyrimidine (55 mg, 0.177 mmol) and (3S,4S)-3-methyl-2-oxa-8-azaspiro[4.5]decan-4-amine bis-hydrochloride salt (47.3 mg, 0.194 mmol) in DMSO (1.18 mL) and DIPEA (0.59 mL) under $N_2$ atmosphere was heated to 120° C. for 2 h. The reaction mixture was allowed to cool to RT, diluted with EtOAc (50 mL), and washed with brine (25 mL). The separated aq. layer was extracted with EtOAc (25 mL). The combined organic layers were dried over $Na_2SO_4$, filtered and concentrated under reduced pressure providing crude (3S,4S)-8-(5-(2,3-dichlorophenyl)-4-methoxypyrimidin-2-yl)-3-methyl-2-oxa-8-azaspiro[4.5]decan-4-amine (67 mg) as a brown-orange solid, which was directly used without further purification. MS m/z 423.2 $(M+H)^+$.

Step b: (3S,4S)-8-(5-(2,3-dichlorophenyl)-4-methoxypyrimidin-2-yl)-3-methyl-2-oxa-8-azaspiro[4.5]decan-4-amine (67 mg, 0.158 mmol) was dissolved in HBr (33% in AcOH, 1 mL) and the mixture was stirred at 90° C. for 1 h. The reaction mixture was concentrated under reduced pressure. The residue was dissolved in MeOH and basified with $NH_3$ (7 M in MeOH) and the mixture was concentrated under reduced pressure. The residue was dissolved in MeCN/water (2:1), filtered through a syringe filter (0.2 μm) and purified by HPLC (gradient elution 10-30% MeCN in water, 5 mM $NH_4OH$ modifier) providing 2-((3S,4S)-4-amino-3-methyl-2-oxa-8-azaspiro[4.5]decan-8-yl)-5-(2,3-dichlorophenyl)pyrimidin-4(3H)-one (20 mg) as a white solid.

The following compounds of Table 18 were synthesized using the above procedure or modifications to the above procedure using the corresponding starting materials and intermediates:

TABLE 18

| Example | Compound | Characterization | $IC_{50}$ (μM) |
|---|---|---|---|
| 200 | | $^1$H NMR (400 MHz, Methanol-$d_4$) δ ppm 7.63 (s, 1 H), 7.49-7.46 (m, 1 H), 7.28-7.25 (m, 2 H), 4.04-3.95 (m, 2 H), 3.49-3.42 (m, 2 H), 2.64 (s, 2 H), 1.60-1.52 (m, 2 H), 1.49-1.43 (m, 2 H), 1.09 (s, 3 H). HRMS calcd for $C_{17}H_{21}Cl_2N_4O$ $(M + H)+$ 367.1092, found 367.1089. | >100 |
| 201 | | $^1$H NMR (400 MHz, Methanol-$d_4$) δ ppm 7.66 (s, 1 H), 7.50 (dd, J = 7.7, 1.9 Hz, 1 H), 7.30 (t, J = 7.7 Hz, 1 H), 7.26 (dd, J = 7.7, 2.0 Hz, 1 H), 4.28-4.17 (m, 1 H), 4.12-3.99 (m, 2 H), 3.87 (d, J = 8.8 Hz, 1 H), 3.71 (d, J = 8.8 Hz, 1 H), 3.46-3.32 (m, 2 H), 3.05 (d, J = 5.0 Hz, 1 H), 1.89-1.74 (m, 2 H), 1.74-1.61 (m, 2 H), 1.22 (d, J = 6.5 Hz, 3 H). HRMS calcd for $C_{19}H_{23}Cl_2N_4O_2$ $(M + H)^+$ 409.1198, found 409.1186. | 3.339 |
| 202 | | $^1$H NMR (400 MHz, Methanol-$d_4$) δ ppm 7.62 (s, 1 H), 7.47 (dd, J = 7.2, 2.4 Hz, 1 H), 7.31-7.23 (m, 2 H), 4.38-4.23 (m, 2 H), 3.21-3.10 (m, 2 H), 2.93 (t, J = 7.4 Hz, 1 H), 2.14-2.03 (m, 1 H), 1.94-1.85 (m, 1 H), 1.85-1.76 (m, 1 H), 1.76-1.48 (m, 5 H), 1.48-1.33 (m, 2 H). HRMS calcd for $C_{19}H_{23}Cl_2N_4O_2$ $(M + H)^+$ 393.1249, found 393.1244. | 0.782 |

Assays

Compounds of the invention were assessed for their ability to selectively inhibit SHP2 activity. The inhibitory properties of the compounds of the invention described herein can be evidenced by testing in any one of the following assays.

SHP2 Allosteric Inhibition Assay

SHP2 is allosterically activated through binding of bis-tyrosyl-phosphorylated peptides to its Src Homology 2 (SH2) domains. The latter activation step leads to the release of the auto-inhibitory interface of SHP2, which in turn renders the SHP2 protein tyrosine phosphatase (PTP) active and available for substrate recognition and reaction catalysis. The catalytic activity of SHP2 was monitored using the surrogate substrate DiFMUP in a prompt fluorescence assay format.

More specifically, the phosphatase reactions were performed at room temperature in 384-well black polystyrene plate, flat bottom, low flange, non-binding surface (Corning, Cat#3575) using a final reaction volume of 25 µL and the following assay buffer conditions: 60 mM HEPES, pH 7.2, 75 mM NaCl, 75 mM KCl, 1 mM EDTA, 0.05% P-20, 5 mM DTT.

The inhibition of SHP2 by compounds of the invention (concentrations varying from 0.003-100 µM) was monitored using an assay in which 0.5 nM of SHP2 was incubated with of 0.5 µM of peptide IRS1_pY1172(dPEG8)pY1222 (sequence: H2N-LN(pY)IDLDLV(dPEG8)LST(pY)ASIN-FQK-amide) (SEQ ID NO:1). After 30-60 minutes incubation at 25° C., the surrogate substrate DiFMUP (Invitrogen, cat# D6567) was added to the reaction and incubated at 25° C. for 30 minutes. The reaction was then carefully diluted by the addition of 5 µL of a 160 µM solution of bpV(Phen) (Enzo Life Sciences cat# ALX-270-204). The fluorescence signal was monitored using a microplate reader (Envision, Perki-Elmer) using excitation and emission wavelengths of 340 nm and 450 nm, respectively. The inhibitor dose response curves were analyzed using normalized $IC_{50}$ regression curve fitting with control based normalization. $IC_{50}$ results for compounds of the invention are shown in examples and tables 1-7, above.

p-ERK Cellular Assay p-ERK cellular assay using the AlphaScreen® SureFire™ Phospho-ERK 1/2 Kit (PerkinElmer): KYSE-520 cells (30,000 cells/well) were grown in 96-well plate culture overnight and treated with Shp2 inhibitors at concentrations of 20, 6.6, 2.2, 0.74, 0.24, 0.08, 0.027 µM for 2 hrs at 37° C. Incubations were terminated by addition of 30 µL of lysis buffer (PerkinElmer) supplied with the SureFire phospho-extracellular signal-regulated kinase (pERK) assay kit (PerkinElmer). Samples were processed according to the manufacturer's directions. The fluorescence signal from pERK was measured in duplicate using a 2101 multilabel reader (Perkin Elmer Envision). The percentage of inhibition was normalized by the total ERK signal and compared with the DMSO vehicle control.

Colony Formation Assay and Cell Proliferation Assay

KYSE-520 Cells (1500 cells/well) were plated onto 24-well plates in 300 µL medium (RPMI-1640 containing 10% FBS, Lonza). For drug treatment, compounds of the invention at various concentrations (20, 10, 5, 2.5, 1.25 µM) were added 24 hours and 5 days after cell plating. At day 11, colonies were stained with 0.2% crystal violet (MP Biomedicals) and subsequently dissolved in 20% AcOH for quantitation using a Spectramax reader (Thermo Scientific). In cell proliferation assay, cells (1500-cells/well) were plated onto 96-well plates in 100 µL medium (RPMI-1640 containing 10% FBS, Lonza). At day 6, 50 µL Celltiter-Glo reagent (Promega) was added, and the luminescent signal was determined according to the supplier's instruction (Promega).

It is understood that the examples and embodiments described herein are for illustrative purposes only and that various modifications or changes in light thereof will be suggested to persons skilled in the art and are to be included within the spirit and purview of this application and scope of the appended claims.

We claim:

1. A compound of formula I:

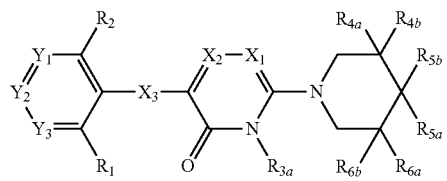

in which:

$X_1$ is selected from N and CH;

$X_2$ is $CR_{3b}$;

$X_3$ is selected from S and a bond;

$Y_1$ is selected from N and $CR_7$; wherein $R_7$ is selected from hydrogen, amino, halo, $C_{1-3}$alkyl, $C_{1-3}$alkoxy and hydroxy;

$Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy;

$Y_3$ is selected from N and $CR_9$; wherein $R_9$ is selected from hydrogen, amino, halo, $C_{1-3}$alkyl, —NH($C_{3-5}$cycloalkyl), $C_{1-3}$alkoxy and hydroxy;

$R_1$ is selected from hydrogen, halo, halo-substituted-$C_{1-2}$alkyl, halo-substituted-$C_{1-2}$alkoxy, $C_{1-2}$alkyl-hydroxy and cyano; or $R_1$ and $R_8$ together with the carbon atoms to which $R_1$ and $R_8$ are attached form a ring selected from 1,3-dioxole, phenyl, pyridine, cyclopentene, dihydrofuran, dihydropyrane; wherein said 1,3-dioxole, phenyl, pyridine, cyclopentene, 2,3-dihydrofuran, 2,3-dihydropyrrole, or dihydropyrane can be unsubstituted or substituted 1 to 2 halo groups;

$R_2$ is selected from hydrogen and halo;

$R_{3a}$ is selected from hydrogen, methyl and halo-substituted-$C_{1-2}$alkyl;

$R_{3b}$ is selected from hydrogen, methyl and amino;

$R_{4a}$ and $R_{4b}$ are each independently selected from hydrogen, hydroxy and fluoro; with proviso that $R_{4a}$ and $R_{4b}$ cannot both be OH; with the proviso that $R_{4a}$ and $R_{4b}$ cannot be OH and F simultaneously;

$R_{5a}$ is selected from amino and amino-methyl;

$R_{5b}$ is selected from OH, amino, fluoro, $C_{1-6}$alkyl, methoxy-carbonyl, $C_{3-6}$cycloalkyl-$C_{1-3}$alkyl, hydroxy-substituted $C_{1-3}$alkyl, $C_{1-2}$alkoxy-substituted $C_{1-3}$alkyl and a 5 to 6 member heteroaryl ring containing 1 to 4 heteroatoms selected from O, S and N; wherein said $C_{1-6}$alkyl or $C_{1-2}$alkoxy-substituted $C_{1-3}$alkyl of $R_{5b}$ is unsubstituted or substituted with 1-3 fluorines; with the proviso that if $R_{5a}$ is amino, $R_{5b}$ cannot be OH, amino or fluoro; or $R_{5a}$ and $R_{5b}$, together with the carbon atom to which $R_{5a}$ and $R_{5b}$ are attached, form a group selected from:

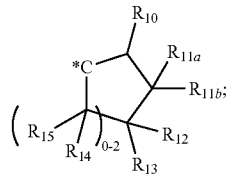 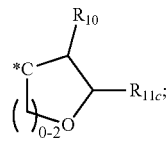

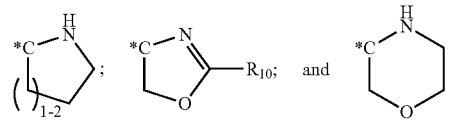

wherein *C represents the carbon atom to which $R_{5a}$ and $R_{5b}$ are attached; $R_{10}$ is amino; $R_{11a}$ is selected from hydrogen, hydroxy, fluoro, $C_{1-3}$alkyl and hydroxymethyl; $R_{11b}$ is selected from fluoro, methyl and hydrogen; with proviso that $R_{11a}$ and $R_{11b}$ cannot both be OH and fluoro simultaneously; $R_{11c}$ is selected from hydrogen, $C_{1-3}$alkyl and hydroxy-methyl; $R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy; $R_{13}$ is selected from hydrogen, halo and $C_{1-3}$alkyl; $R_{14}$ is selected from hydrogen and fluoro; with proviso that $R_{12}$ and $R_{13}$ cannot both be OH and fluoro simultaneously; $R_{15}$ is selected from hydrogen and fluoro; and $R_{6a}$ and $R_{6b}$ are each independently selected from hydrogen, hydroxy and fluoro; with proviso that $R_{6a}$ and $R_{6b}$ cannot both be OH; with proviso that $R_{6a}$ and $R_{6b}$ cannot both be OH and fluoro simultaneously; or the pharmaceutically acceptable salts thereof; with the proviso that a compound of formula I does not include a compound selected from:

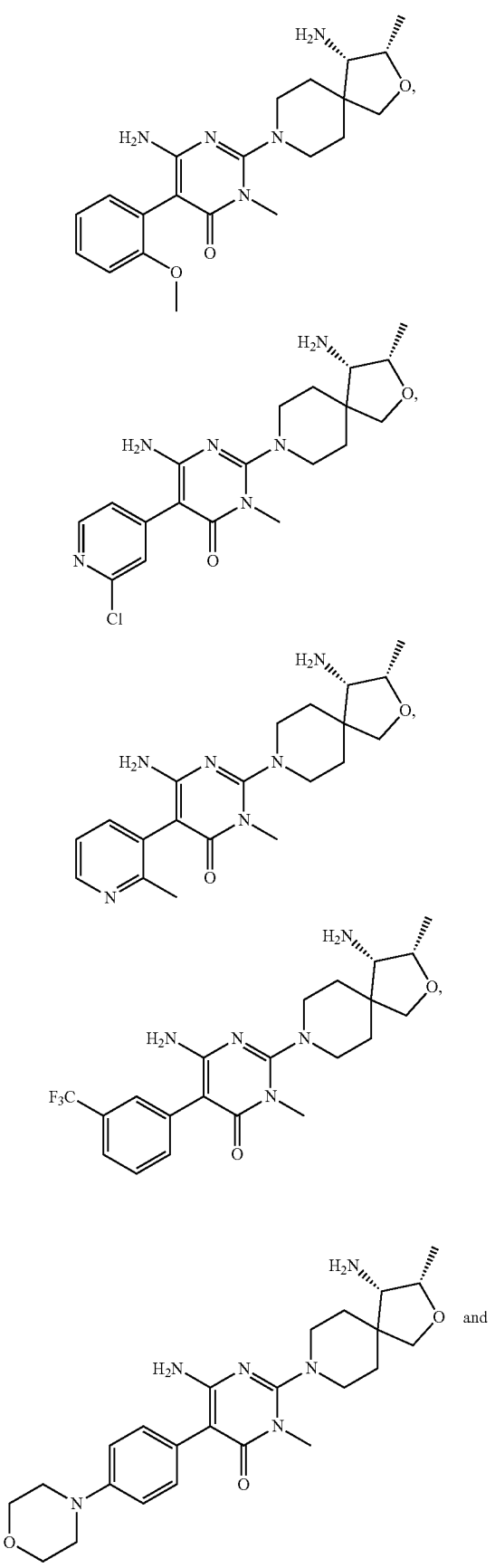

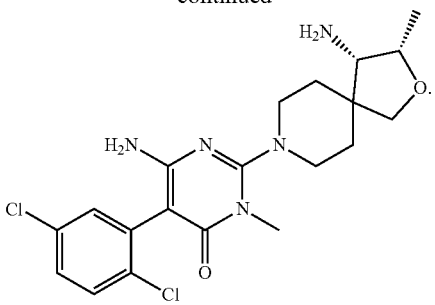

2. The compound of claim 1 of formula Ia:

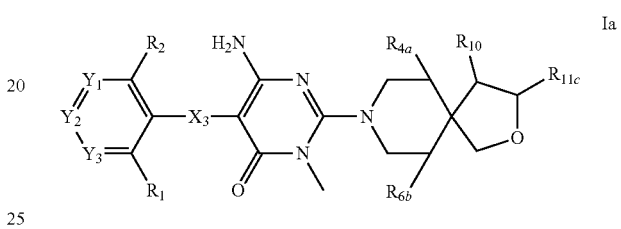

in which:

$X_3$ is selected from S;

$Y_1$ is selected from N and $CR_7$; wherein $R_7$ is selected from hydrogen, amino, halo, $C_{1-3}$alkyl, and $C_{1-3}$alkoxy;

$Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole;

$Y_3$ is selected from N and $CR_9$; wherein $R_9$ is selected from hydrogen, amino, halo, $C_{1-3}$alkyl, $C_{1-3}$alkoxy and hydroxy;

$R_1$ is selected from hydrogen, halo, halo-substituted-$C_{1-2}$alkyl;

$R_2$ is selected from hydrogen and chloro;

$R_{4a}$ is selected from hydrogen, hydroxy and fluoro;

$R_{6b}$ is selected from hydrogen, hydroxy and fluoro;

$R_{10}$ is amino; and $R_{11c}$ is selected from hydrogen and $C_{1-3}$alkyl; or the pharmaceutically acceptable salts thereof.

3. The compound of claim 2 in which:

$Y_1$ is selected from N and $CR_7$; wherein $R_7$ is selected from hydrogen, halo and amino;

$Y_2$ is selected from N and $CR_8$; wherein $R_8$ is selected from hydrogen, halo, amino, dimethyl-amino, cyano, halo-substituted-$C_{1-2}$alkyl, $C_{1-2}$alkoxy, cyclopropyl, cyclopentyl, cyclopentyl-methoxy, halo-substituted-$C_{1-2}$alkoxy, phenyl, methoxy-ethoxy, tetrahydro-2H-pyran-4-yl, morpholino, phenoxy and benzoxy;

$Y_3$ is selected from N and $CR_9$; wherein $R_9$ is selected from hydrogen, amino, halo, $C_{1-2}$alkoxy, cyclopropyl, trifluoromethyl, trifluoromethyl-sulfanyl, isopropyl and hydroxy;

$R_1$ is selected from hydrogen, halo, trifluoromethyl, trifluoromethoxy, $C_{1-2}$alkyl and cyano;

$R_2$ is selected from hydrogen, fluoro and chloro;

$R_{4a}$ is hydrogen;

$R_{6b}$ is hydrogen;
$R_{10}$ is amino; and
$R_{11c}$ is selected from hydrogen, methyl and ethyl; or the pharmaceutically acceptable salts thereof.
4. The compound of claim 3, or a pharmaceutically acceptable salt thereof, selected from:
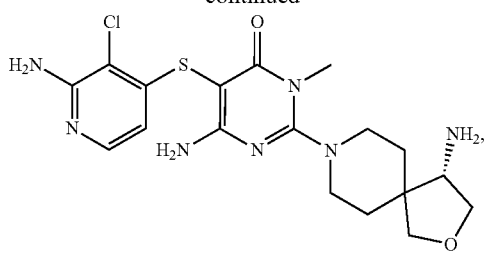
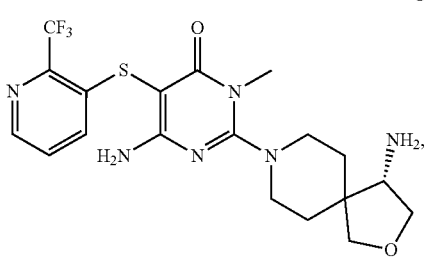
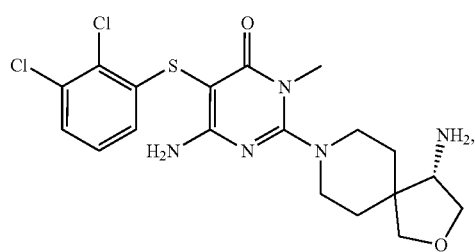
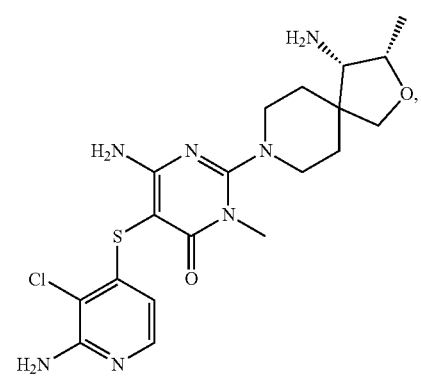
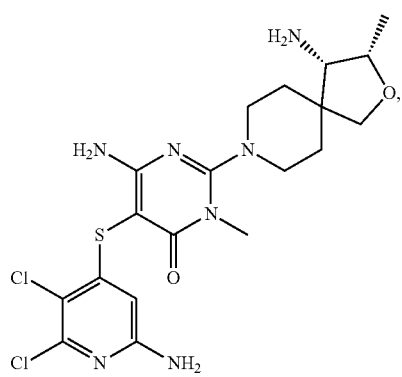
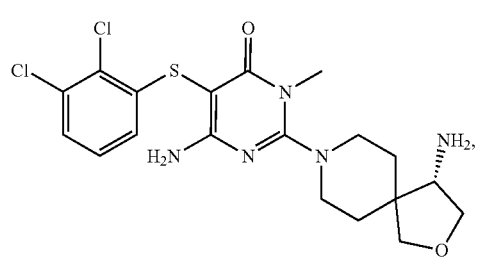
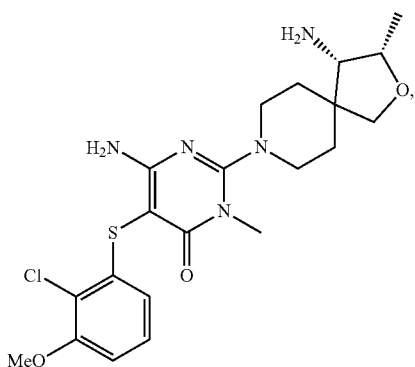

245
-continued
246
-continued
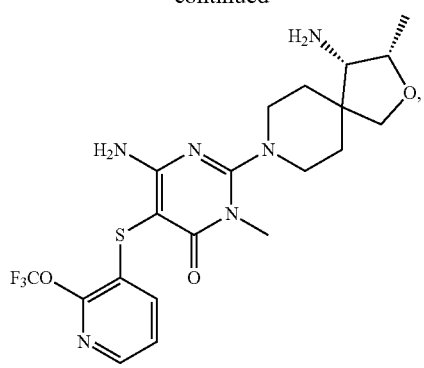
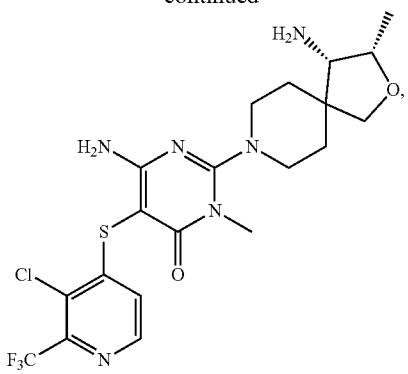

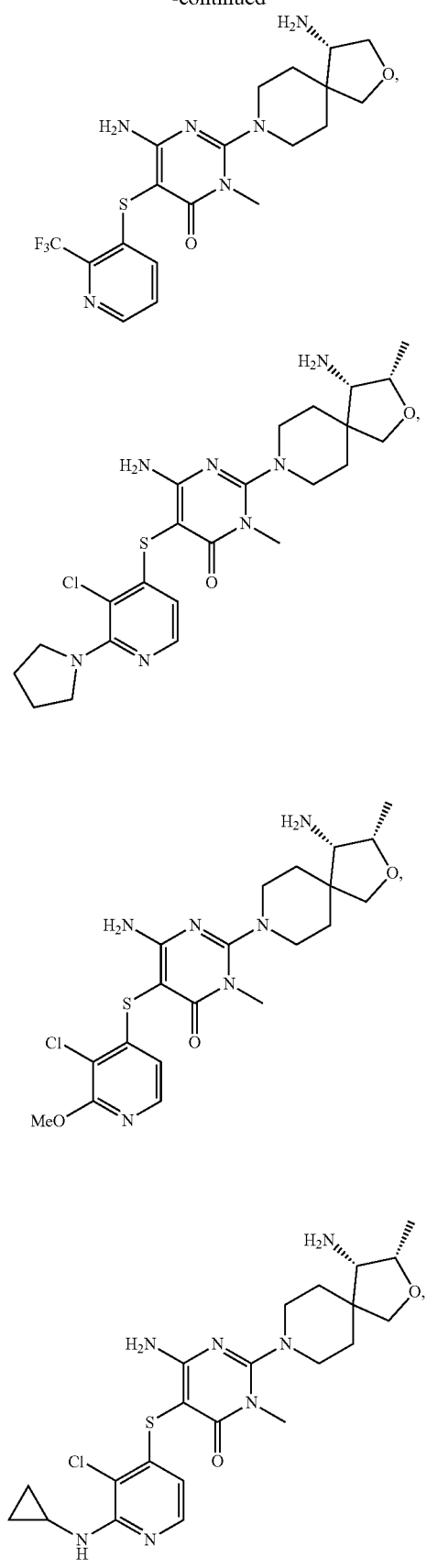
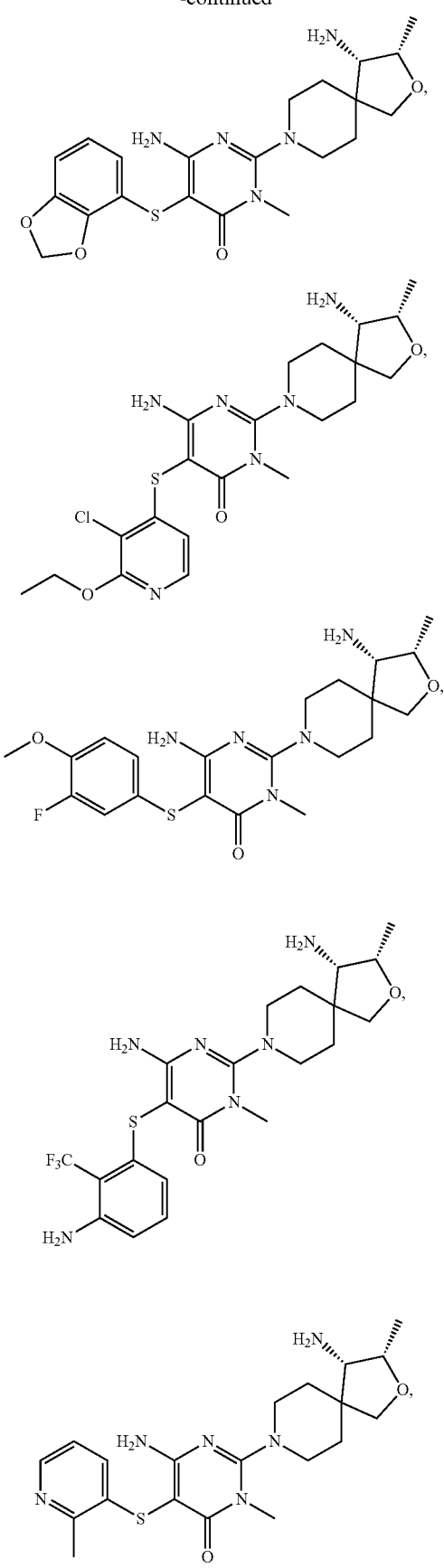

-continued

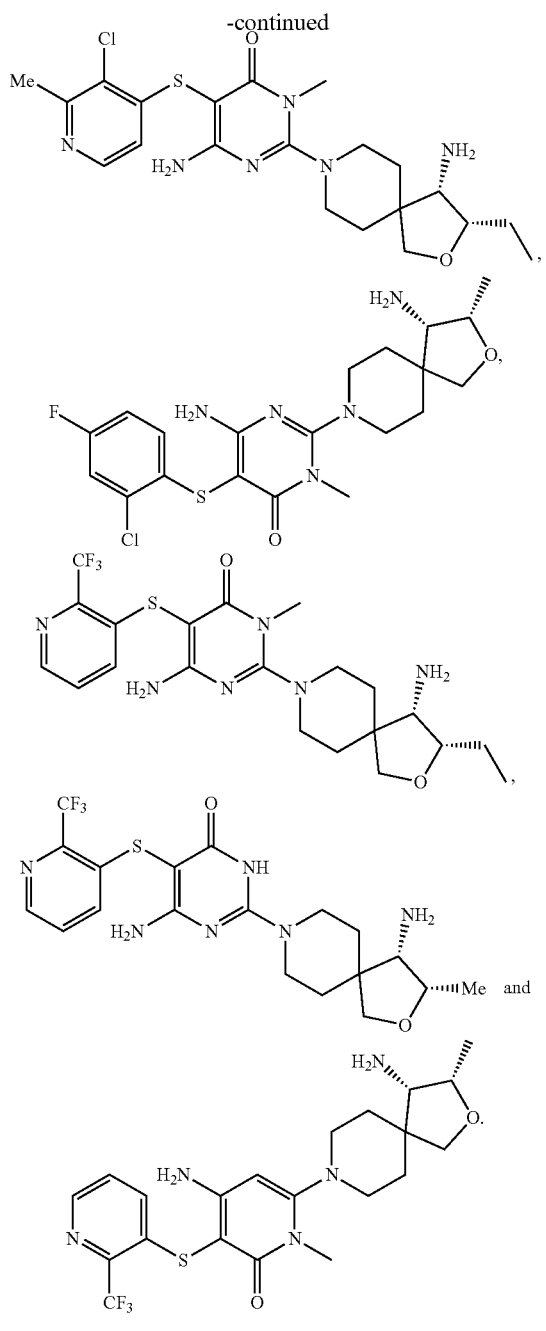

5. The compound of claim 1 of formula Ia:

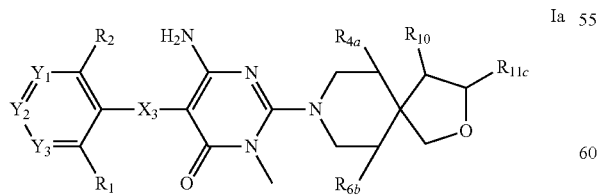

in which:
X₃ is a bond;
Y₁ is CR₇; wherein R₇ is selected from hydrogen, chloro and fluoro;

Y₂ is CR₈; wherein R₈ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_6$aryl and $C_6$aryl-$C_{0-1}$alkoxy;

Y₃ is selected from CR₉; wherein R₉ is selected from hydrogen, chloro, fluoro and methyl;

R₁ is selected from hydrogen, chloro, fluoro;

R₂ is hydrogen;

R₄ₐ is selected from hydrogen, hydroxy and fluoro;

R₆ᵦ is selected from hydrogen, hydroxy and fluoro;

R₁₀ is amino; and

R₁₁c is selected from hydrogen, $C_{1-3}$alkyl and hydroxymethyl; or the pharmaceutically acceptable salts thereof.

6. The compound of claim 5, or a pharmaceutically acceptable salt thereof, selected from:

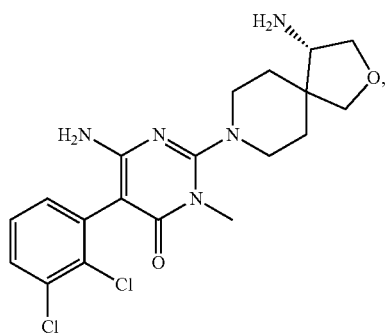

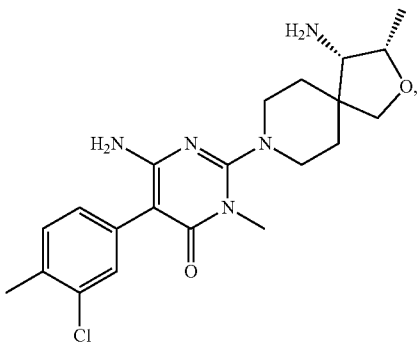

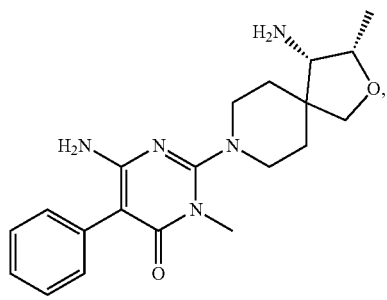

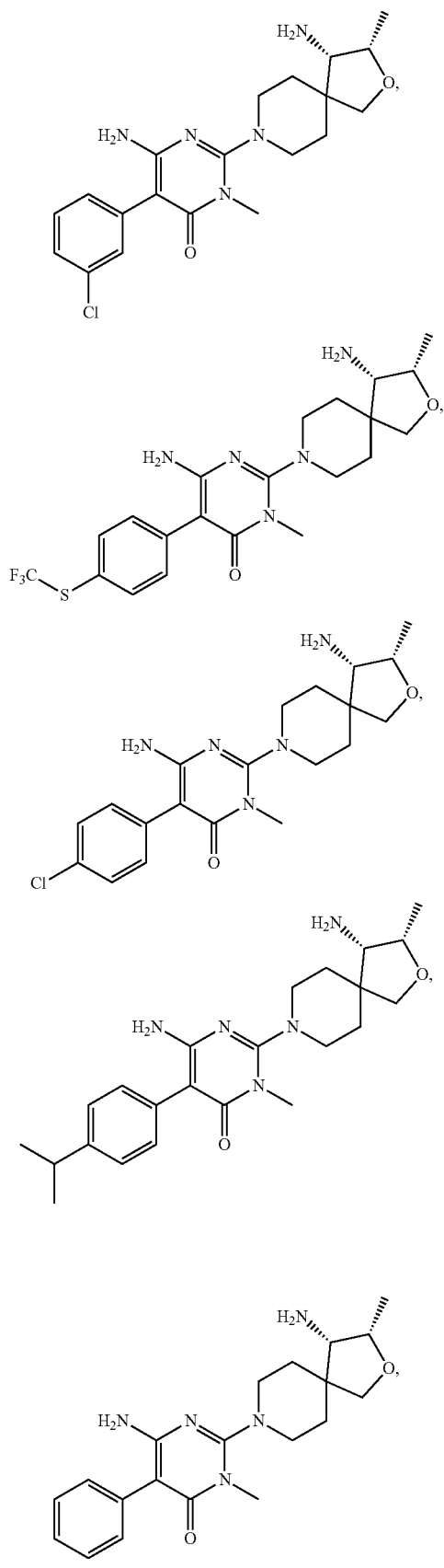
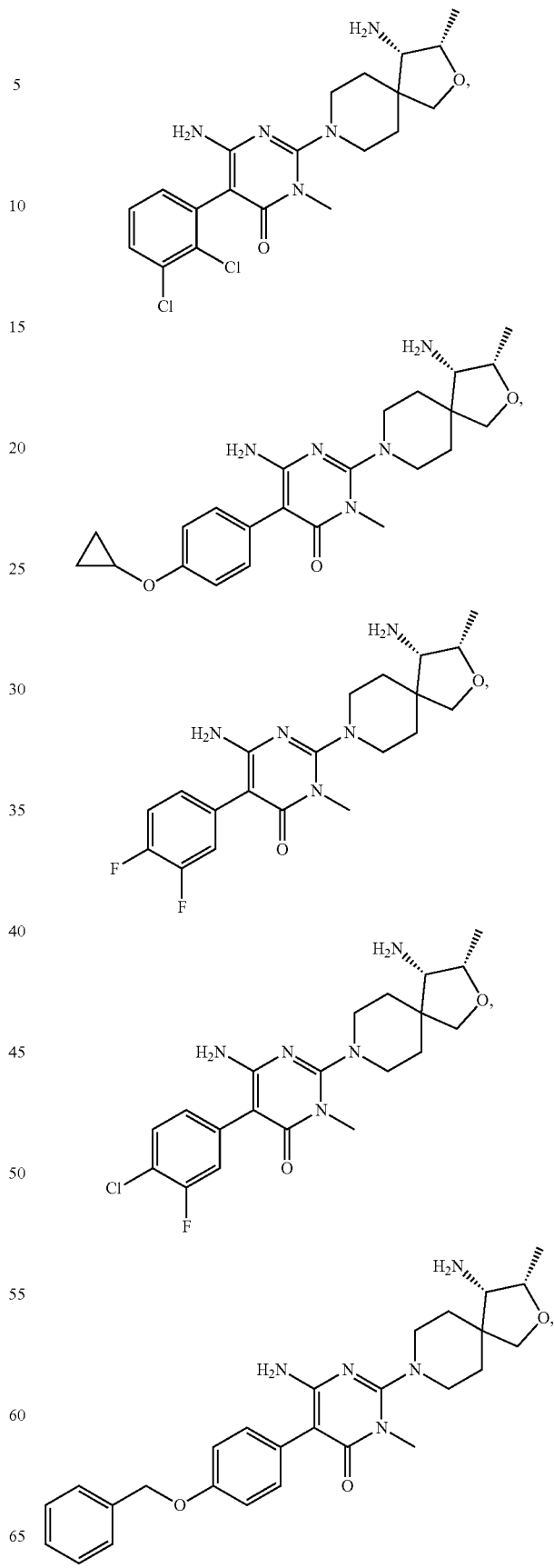

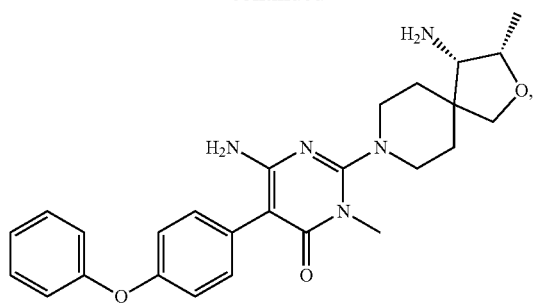
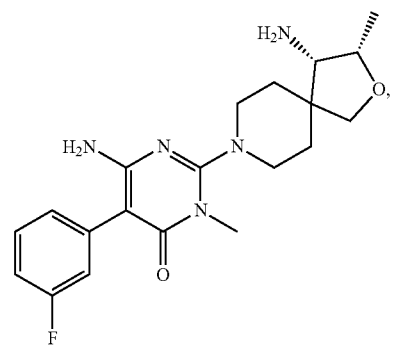
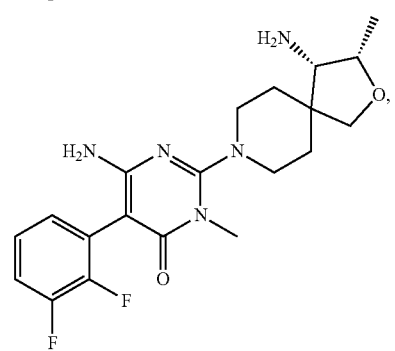
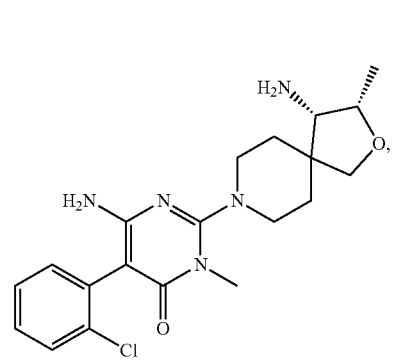
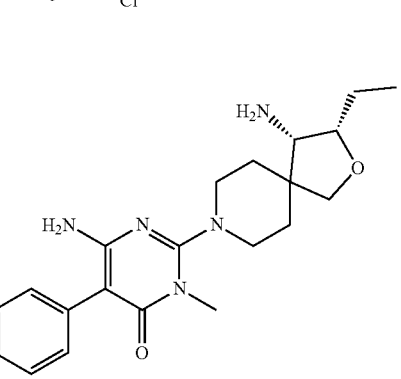
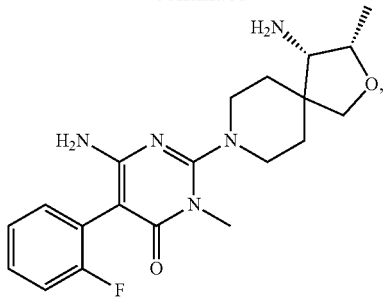
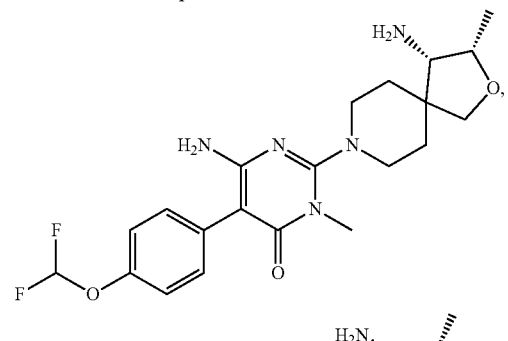
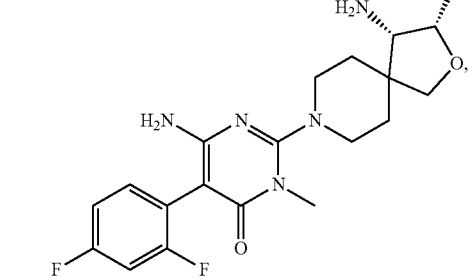
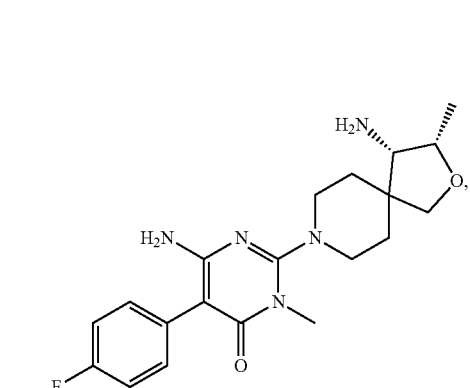
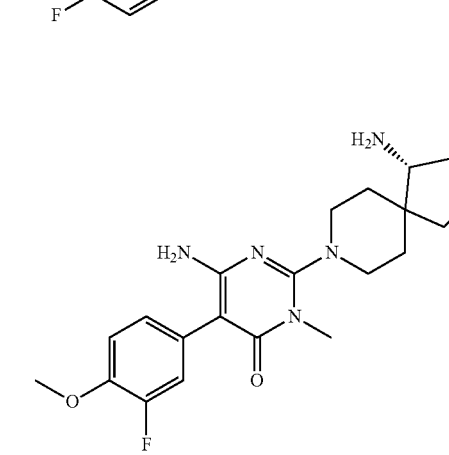

255
-continued
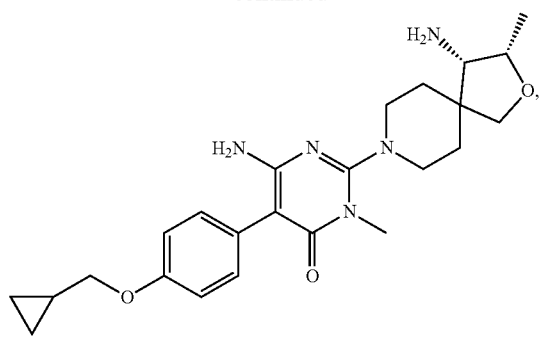
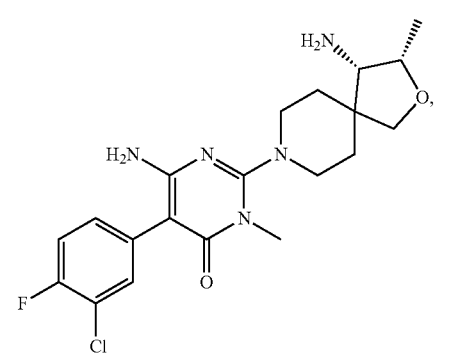
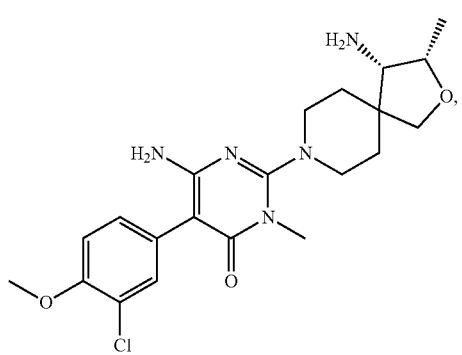
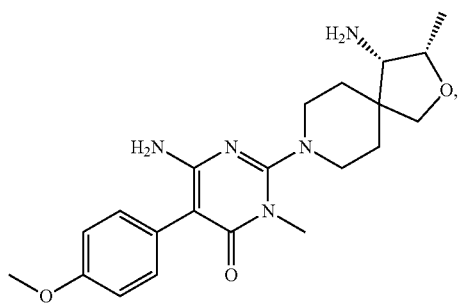
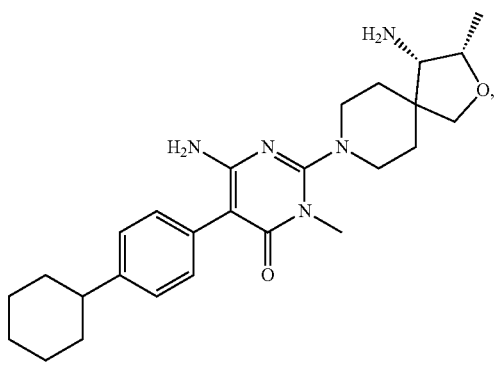
256
-continued
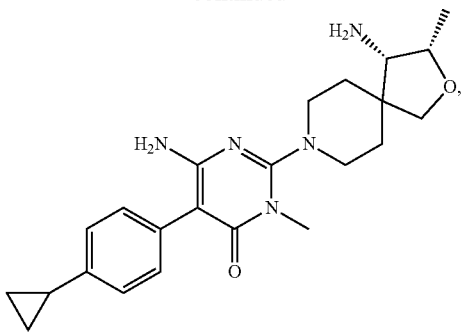
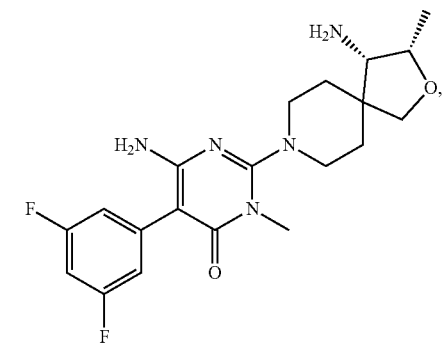
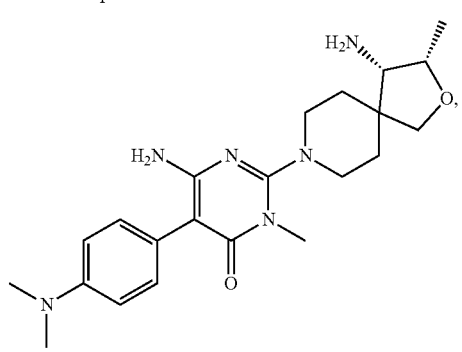
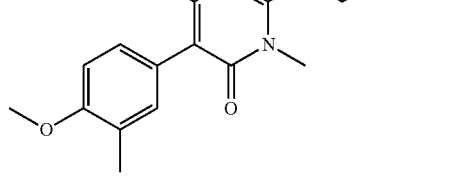
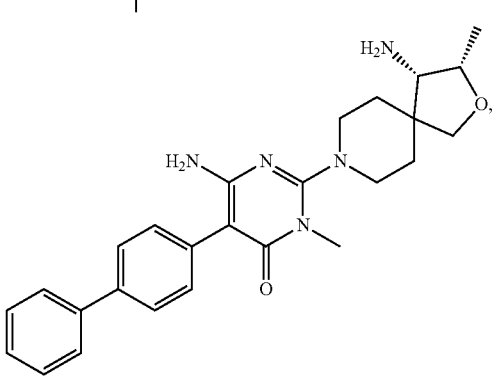

257
-continued
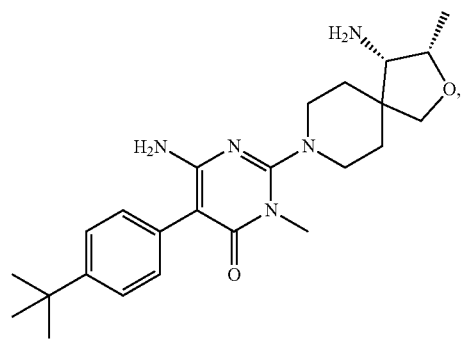
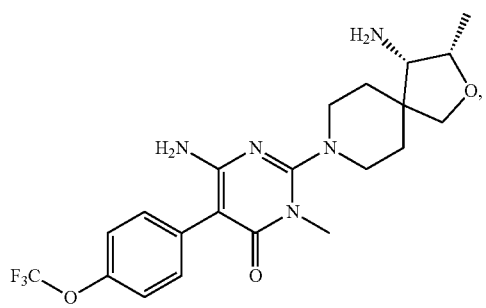
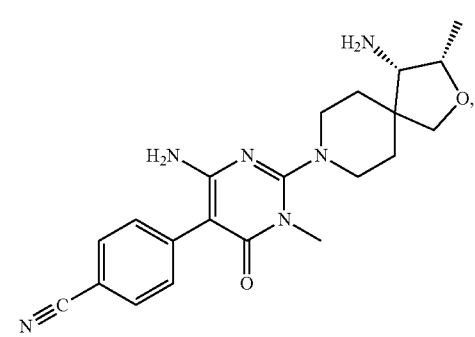
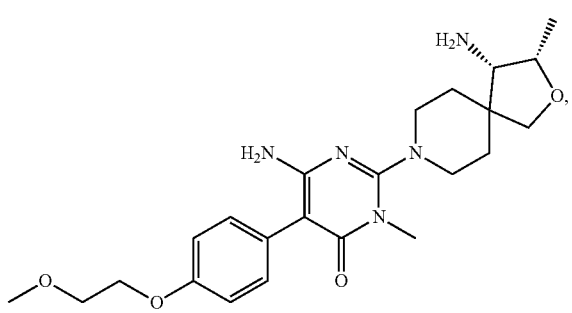
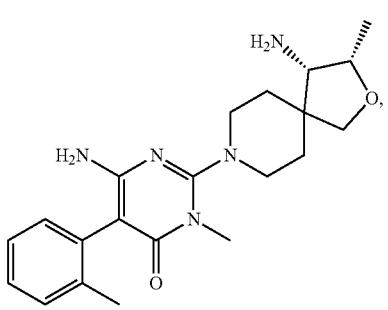
258
-continued
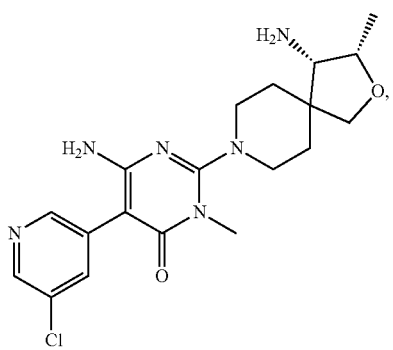
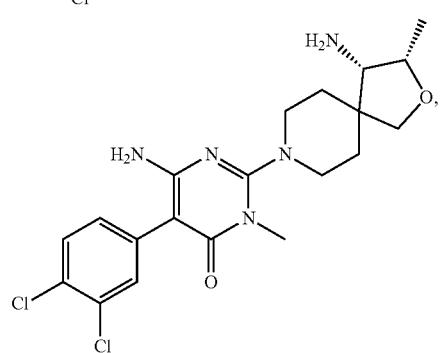
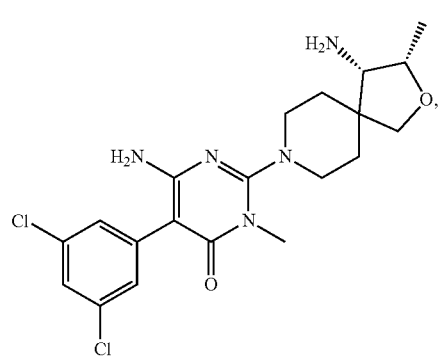
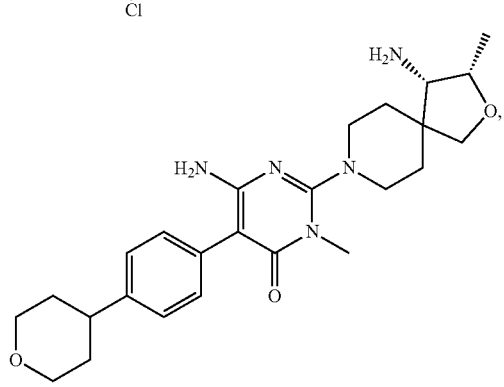
and -continued

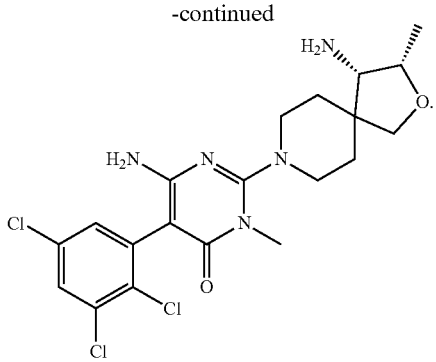

7. The compound of claim 1 of formula Ib:

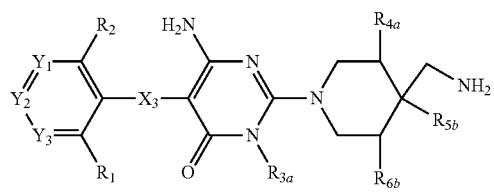

in which:
X₃ is S;
Y₁ is selected from N and CR₇; wherein R₇ is selected from hydrogen, amino, halo, $C_{1-3}$alkyl, and $C_{1-3}$alkoxy;
Y₂ is selected from N and CR₈; wherein R₈ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or R₁ and R₈ together with the carbon atoms to which R₁ and R₈ are attached form a ring selected from, cyclopentene, 2,3-dihydrofuran, 2,3-dihydropyrrole;
Y₃ is selected from N and CR₉; wherein R₉ is selected from hydrogen, amino, halo, $C_{1-3}$alkyl, $C_{1-3}$alkoxy and hydroxy;
R₁ is selected from hydrogen, halo, halo-substituted-$C_{1-2}$alkyl;
R₂ is selected from hydrogen and halo;
$R_{3a}$ is selected from hydrogen and methyl;
$R_{4a}$ is selected from hydrogen, hydroxy and fluoro;
$R_{5b}$ is $C_{1-6}$alkyl;
$R_{6b}$ is selected from hydrogen, hydroxy and fluoro; or the pharmaceutically acceptable salts thereof.

8. The compound of claim 7 in which:
Y₁ is selected from N and CR₇; wherein R₇ is selected from hydrogen, halo and amino;
Y₂ is selected from N and CR₈; wherein R₈ is selected from hydrogen, halo, amino, cyano, halo-substituted-$C_{1-2}$alkyl, $C_{1-2}$alkoxy and halo-substituted-$C_{1-2}$alkoxy;
Y₃ is selected from N and CR₉; wherein R₉ is selected from hydrogen, amino, halo, $C_{1-2}$alkoxy and hydroxy;
R₁ is selected from halo, trifluoromethyl, trifluoromethoxy, $C_{1-2}$alkyl, nitro, hydroxy and cyano; or R₁ and R₈ together with the carbon atoms to which R₁ and R₈ are attached form a ring selected from 1,3-dioxolane and pyridine; wherein said 1,3-dioxolane or pyridine can be unsubstituted or substituted 1 to 2 halo groups;
R₂ is selected from hydrogen, fluoro and chloro;
R₃ is selected from hydrogen and methyl;
$R_{4a}$ is hydrogen;
$R_{5b}$ is methyl;
$R_{6b}$ is hydrogen; or the pharmaceutically acceptable salts thereof.

9. The compound of claim 8, or a pharmaceutically acceptable salt thereof, selected from:

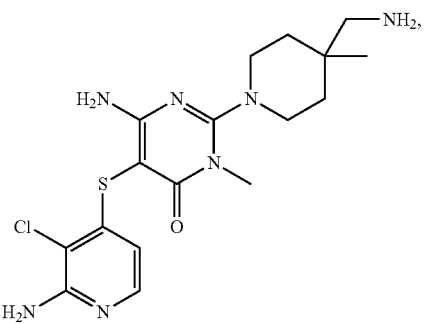

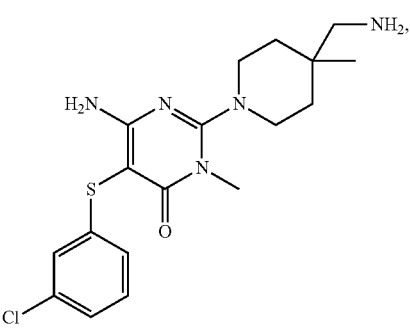

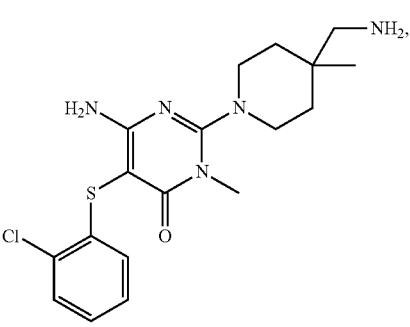

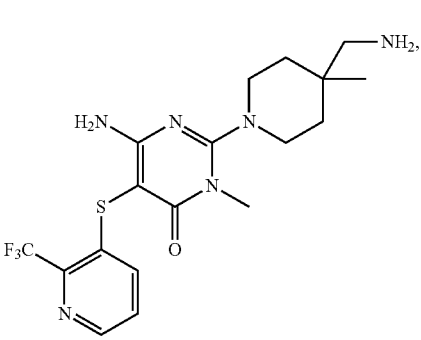

261
-continued
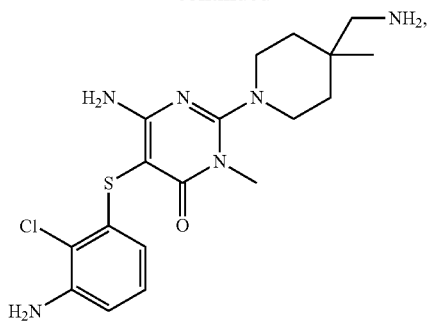
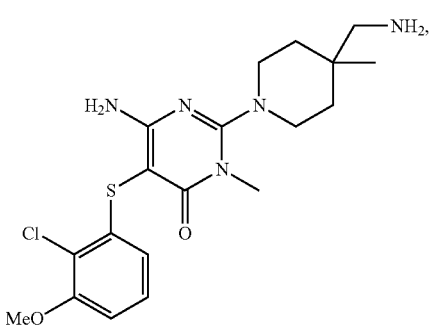
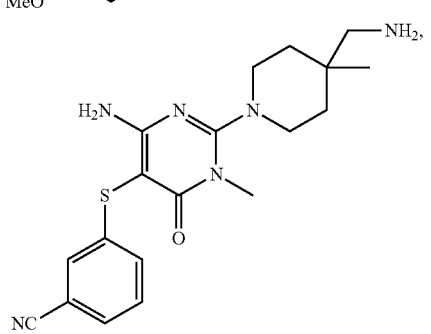
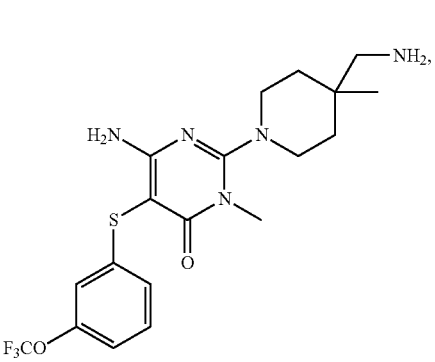
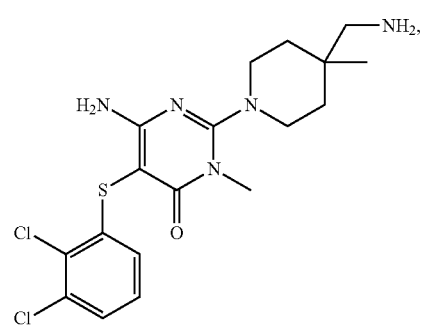
262
-continued
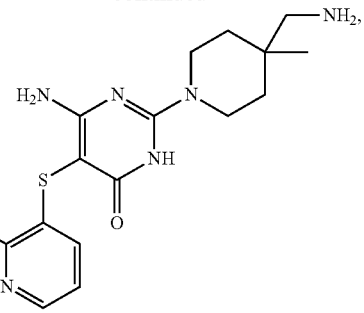
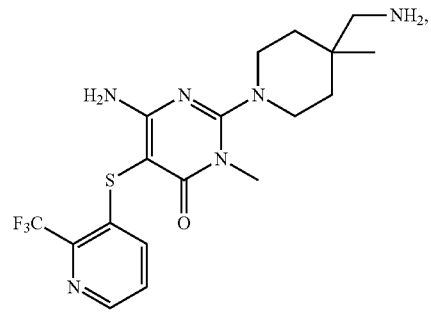 [SMILES: Cn1c(N2CCC(C)(CN)CC2)nc(N)c(Sc2ccccc2O)c1=O]
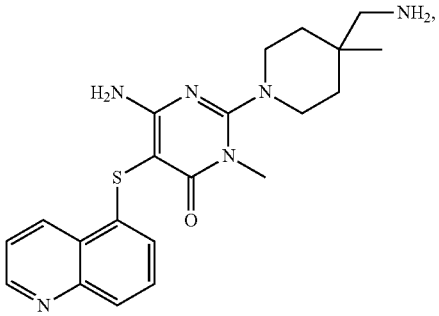
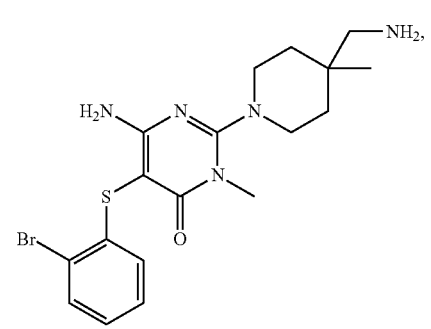
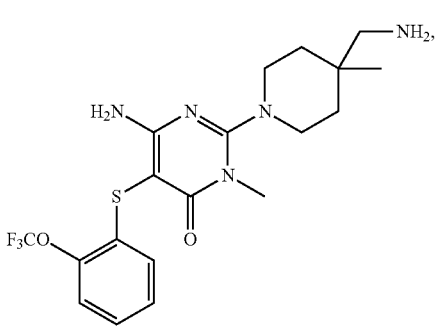

263
-continued
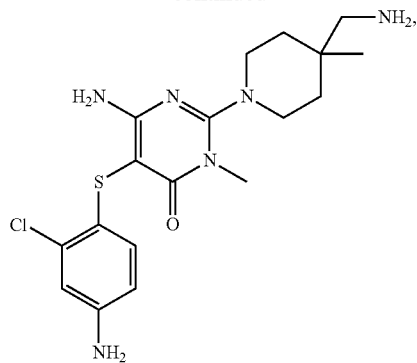
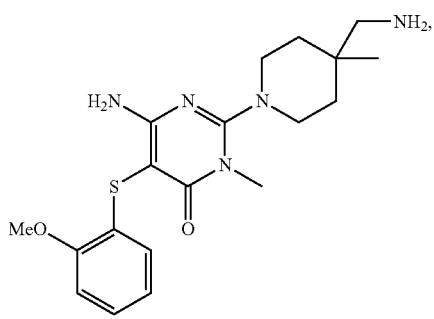
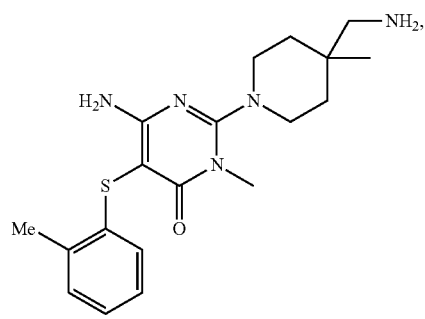
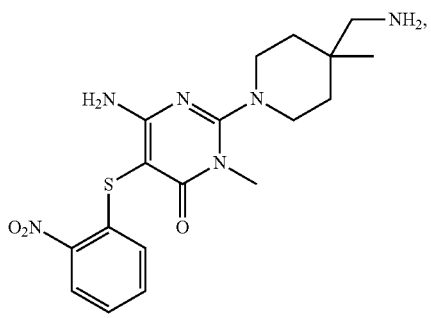
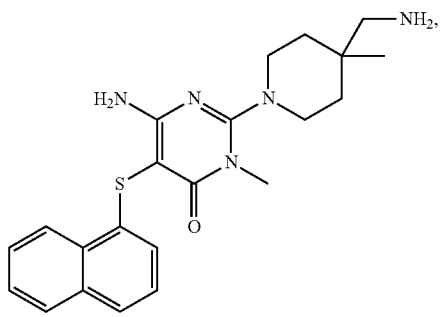
264
-continued
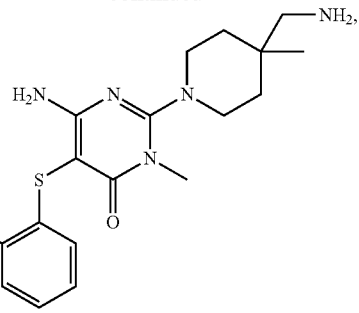
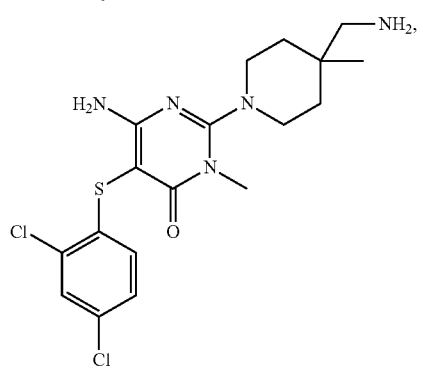
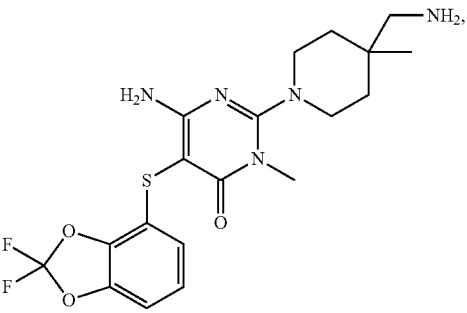
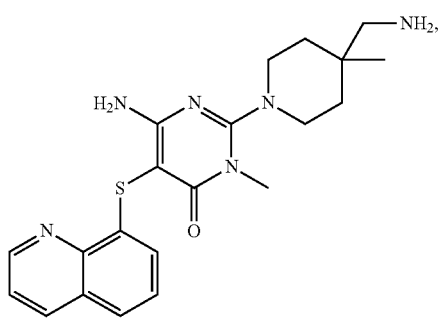
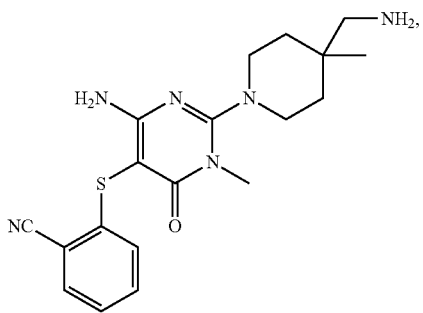

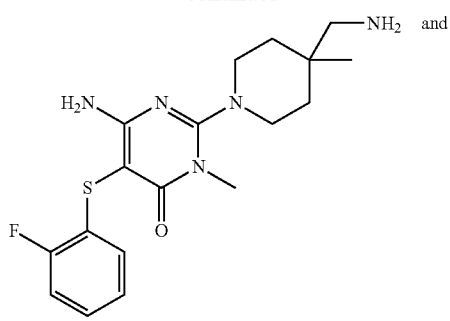

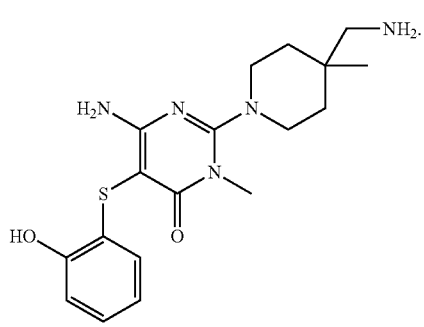

10. The compound of claim 1 of formula Ib:

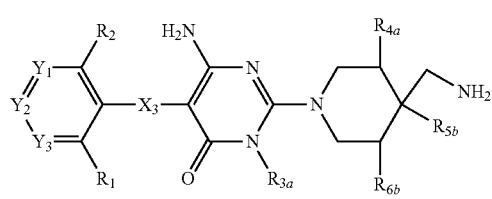

in which:

$X_3$ is a bond;

$Y_1$ is $CR_7$; wherein $R_7$ is selected from hydrogen, chloro and fluoro;

$Y_2$ is $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_6$aryl and $C_6$aryl-$C_{0-1}$alkoxy;

$Y_3$ is selected from $CR_9$; wherein $R_9$ is selected from hydrogen, chloro, fluoro and methyl;

$R_1$ is selected from hydrogen, chloro, fluoro;

$R_2$ is hydrogen;

$R_{4a}$ is selected from hydrogen, hydroxy and fluoro;

$R_{5b}$ is $C_{1-6}$alkyl;

$R_{6b}$ is selected from hydrogen, hydroxy and fluoro; or the pharmaceutically acceptable salts thereof.

11. The compound of claim 10, or a pharmaceutically acceptable salt thereof, selected from:

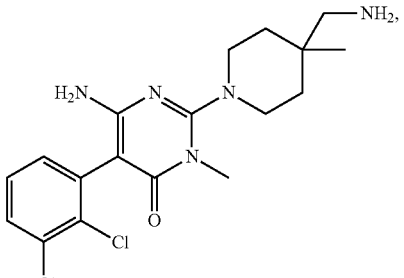

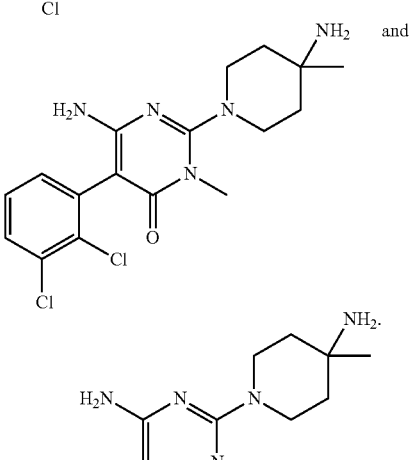

12. The compound of claim 1 of formula Ic:

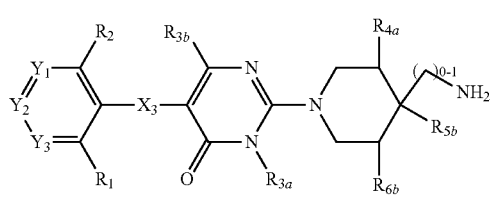

in which:

$X_1$ is selected from N and CH;

$X_3$ is S;

$Y_1$ is selected from N and $CR_7$; wherein $R_7$ is selected from hydrogen, amino, halo, $C_{1-3}$alkyl, $C_{1-3}$alkoxy;

$Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole;

$Y_3$ is selected from N and $CR_9$; wherein $R_9$ is selected from hydrogen, amino, halo, $C_{1-3}$alkyl, $C_{1-3}$alkoxy and hydroxy;

$R_1$ is selected from hydrogen, halo, halo-substituted-$C_{1-2}$alkyl and halo-substituted-$C_{1-2}$alkoxy;

$R_2$ is selected from hydrogen and halo;

$R_{3a}$ is selected from hydrogen and methyl;

$R_{3b}$ is selected from hydrogen and methyl;

$R_{4a}$ is selected from hydrogen, hydroxy and fluoro;

$R_{5b}$ is $C_{1-6}$alkyl;

$R_{6b}$ is selected from hydrogen, hydroxy and fluoro.

13. The compound of claim 12 in which:

$Y_1$ is selected from N and $CR_7$; wherein $R_7$ is selected from hydrogen, halo and amino;

$Y_2$ is selected from N and $CR_8$; wherein $R_8$ is selected from hydrogen, halo, amino, cyano, halo-substituted-$C_{1-2}$alkyl, $C_{1-2}$alkoxy and halo-substituted-$C_{1-2}$alkoxy;

$Y_3$ is selected from N and $CR_9$; wherein $R_9$ is selected from hydrogen, amino, halo, $C_{1-2}$alkoxy and hydroxy;

$R_1$ is selected from halo, trifluoromethyl, trifluoromethoxy, $C_{1-2}$alkyl and cyano;

$R_2$ is selected from hydrogen, fluoro and chloro;

$R_3$ is selected from hydrogen and methyl;

$R_{4a}$ is hydrogen;

$R_{6b}$ is hydrogen; or the pharmaceutically acceptable salts thereof.

14. The compound of claim 13, or a pharmaceutically acceptable salt thereof, selected from:

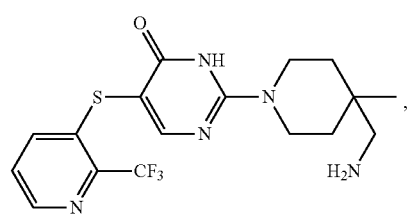

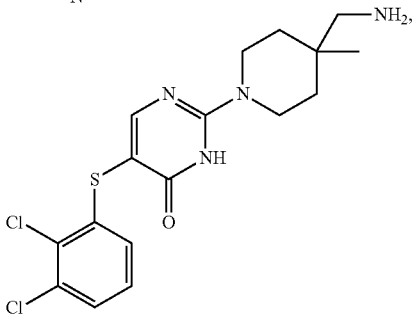

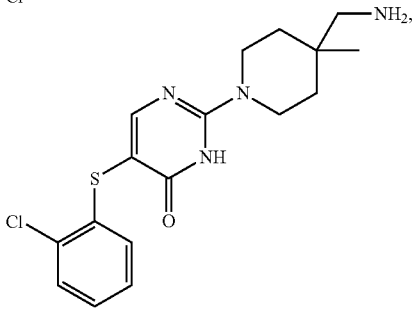

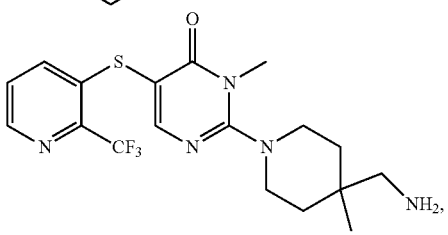

-continued

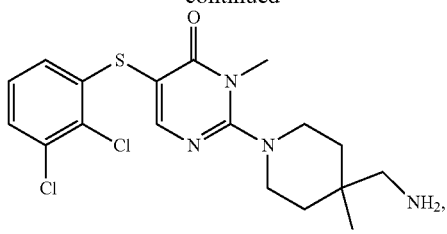

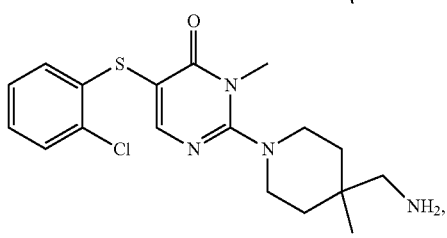

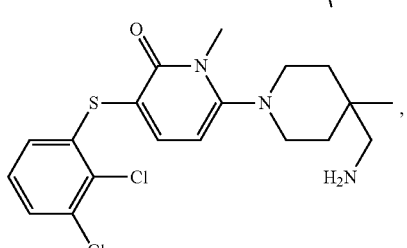

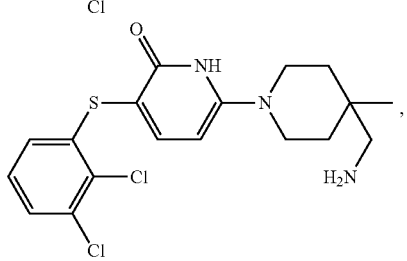

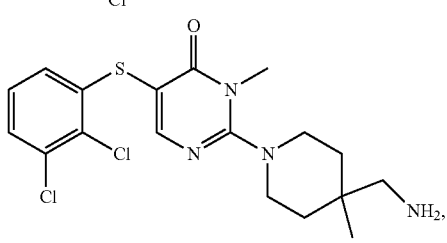

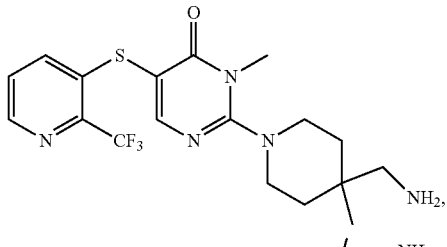

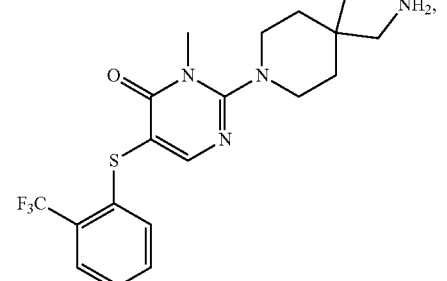

-continued

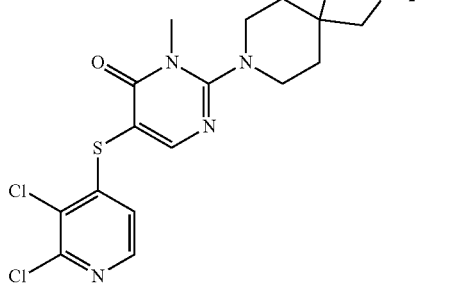 and

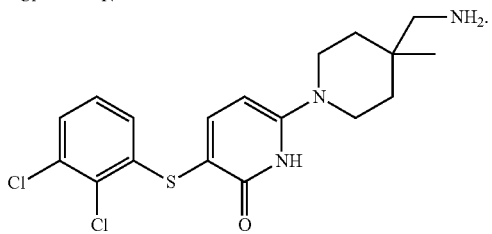

15. The compound of claim 1 of formula Id:

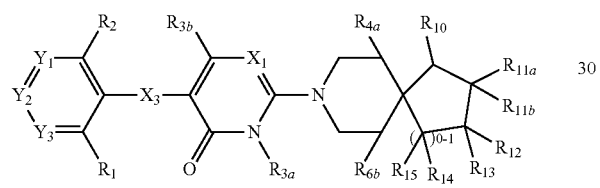

in which:
$X_1$ is selected from N and CH;
$X_3$ is S;
$Y_1$ is selected from N and $CR_7$; wherein $R_7$ is selected from hydrogen, amino, halo, $C_{1-3}$alkyl, and $C_{1-3}$alkoxy;
$Y_2$ is selected from N and $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_{6-10}$aryl and $C_{6-10}$aryl-$C_{0-1}$alkoxy; or $R_1$ and $R_8$ together with the carbon atoms to which $R_1$ and $R_8$ are attached form a ring selected from, cyclopentene, 2,3-dihydrofuran, 2,3-dihydropyrrole;
$Y_3$ is selected from N and $CR_9$; wherein $R_9$ is selected from hydrogen, amino, halo, $C_{1-3}$alkyl, $C_{1-3}$alkoxy and hydroxy;
$R_1$ is selected from hydrogen, halo, halo-substituted-$C_{1-2}$alkyl and cyano;
$R_2$ is selected from hydrogen and halo;
$R_{3a}$ is selected from hydrogen, methyl and halo-substituted-$C_{1-2}$alkyl;
$R_{4a}$ is selected from hydrogen, hydroxy and fluoro;
$R_{6b}$ is selected from hydrogen, hydroxy and fluoro;
$R_{10}$ is amino;
$R_{11a}$ is selected from hydrogen, hydroxy, fluoro, $C_{1-3}$alkyl and hydroxy-methyl;
$R_{11b}$ is selected from fluoro, methyl and hydrogen; with proviso that $R_{11a}$ and $R_{11b}$ cannot both be OH and fluoro simultaneously;

$R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy;
$R_{13}$ is selected from hydrogen, halo and $C_{1-3}$alkyl; with proviso that $R_{12}$ and $R_{13}$ cannot both be OH and fluoro simultaneously;
$R_{14}$ is selected from hydrogen and fluoro;
$R_{15}$ is selected from hydrogen and fluoro; or the pharmaceutically acceptable salts thereof.

16. The compound of claim 15, or a pharmaceutically acceptable salt thereof, selected from:

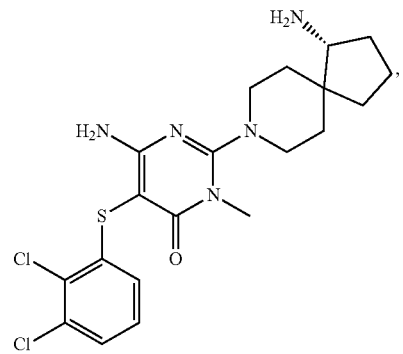

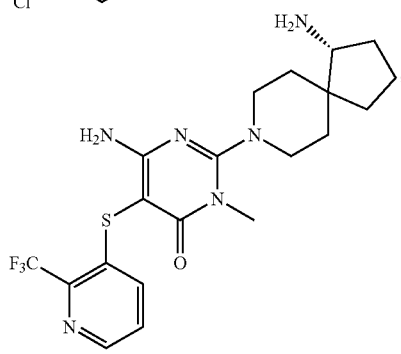

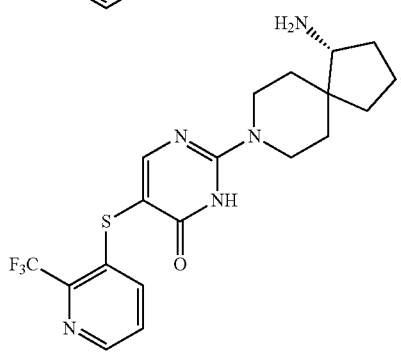

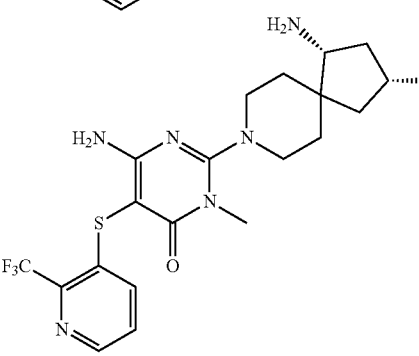

271
-continued
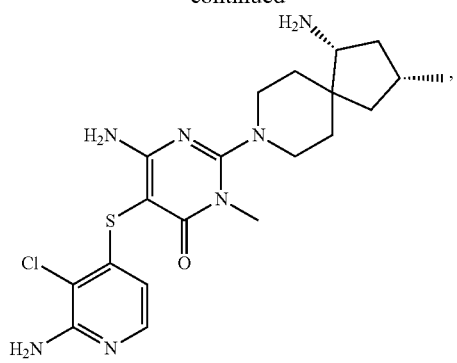
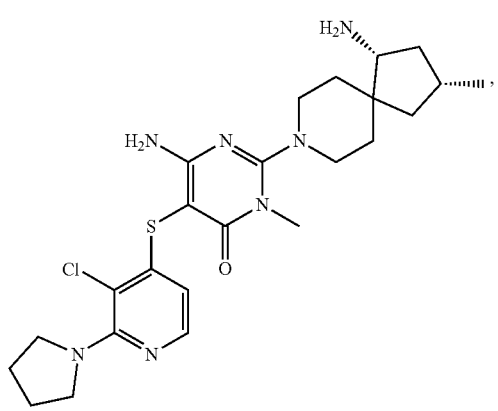
272
-continued
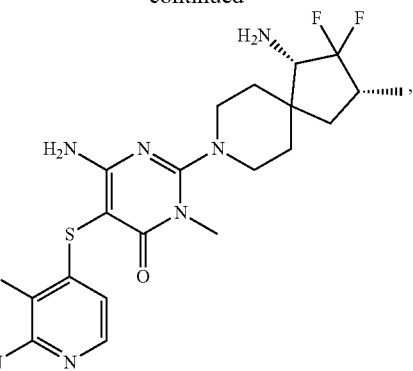
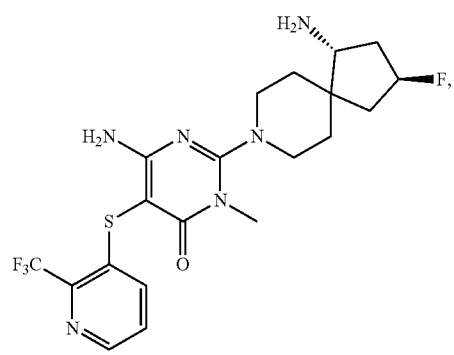
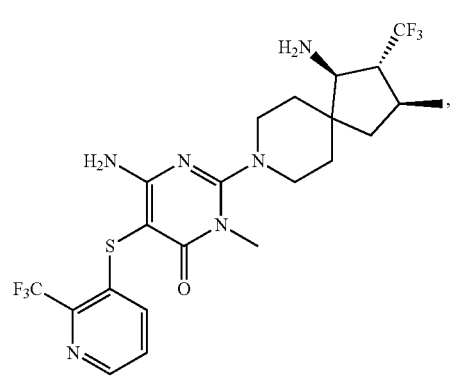

273
-continued
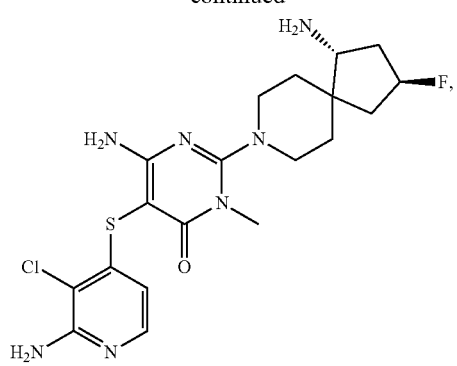
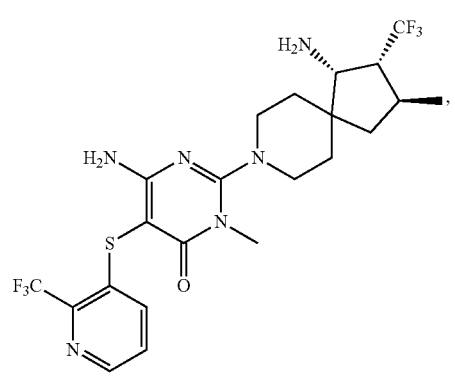
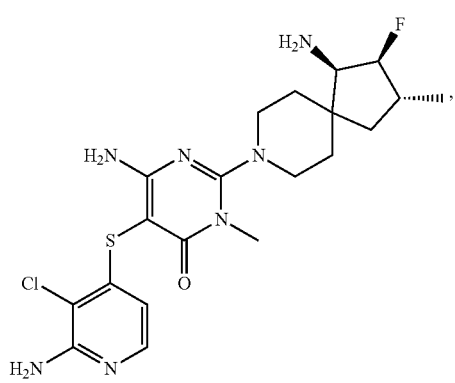
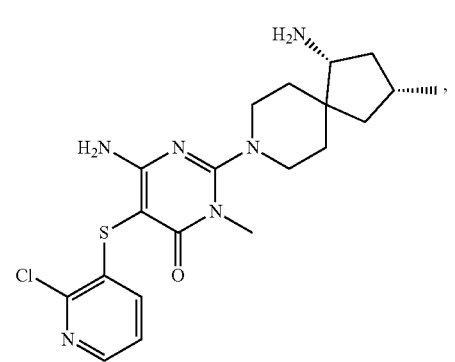
274
-continued
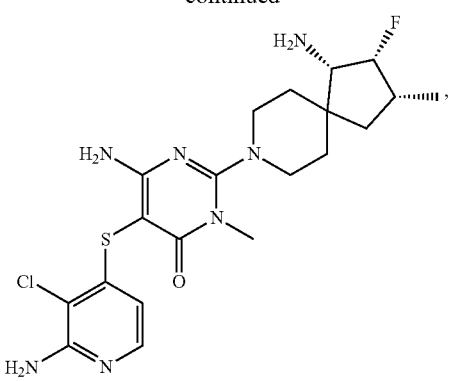
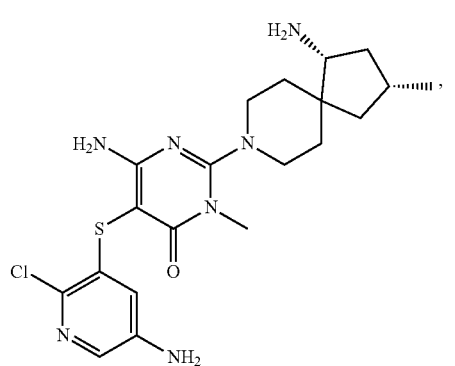
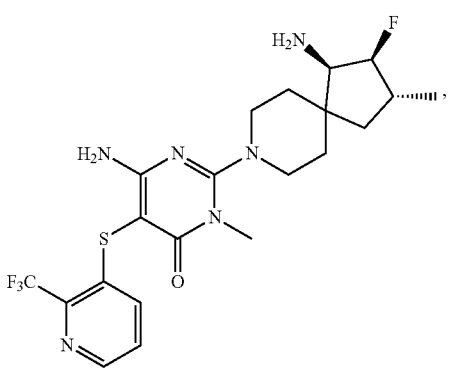
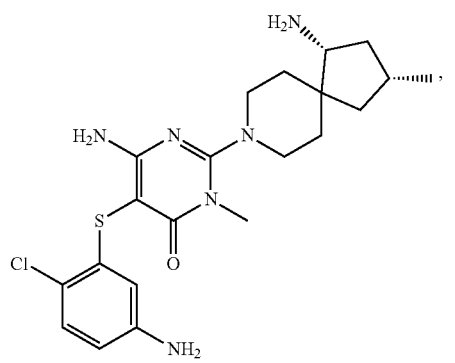

275
-continued
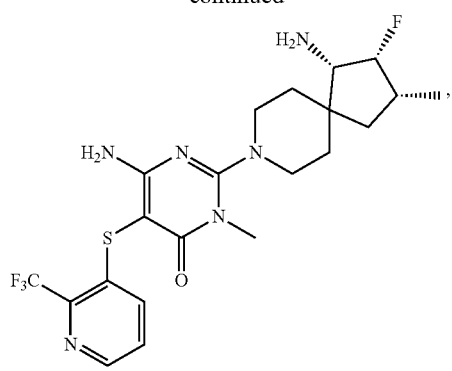
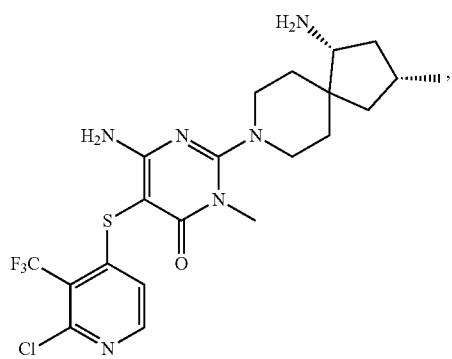
276
-continued
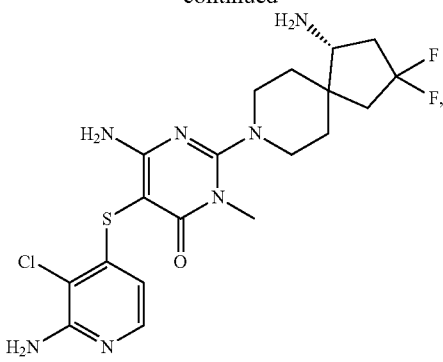
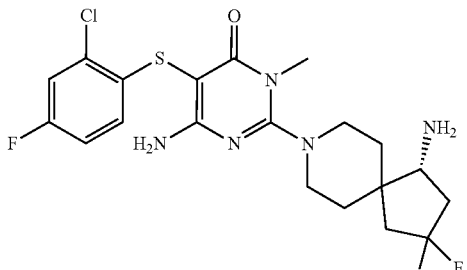
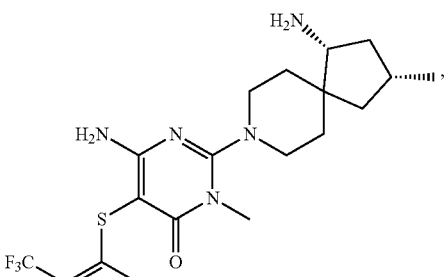
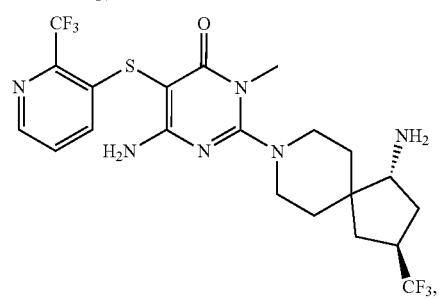

-continued

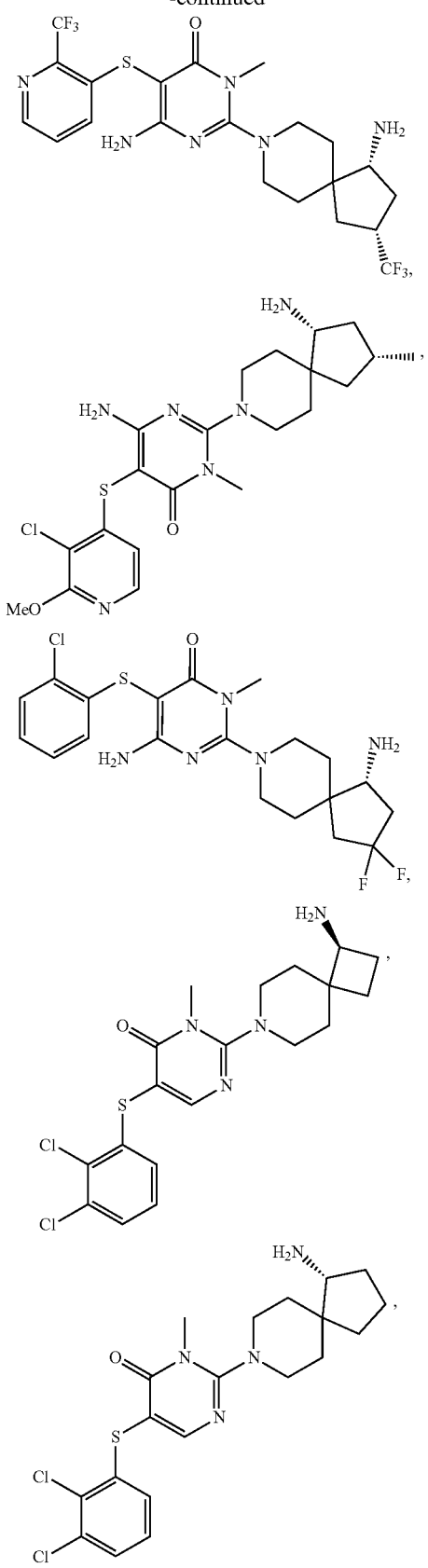

-continued

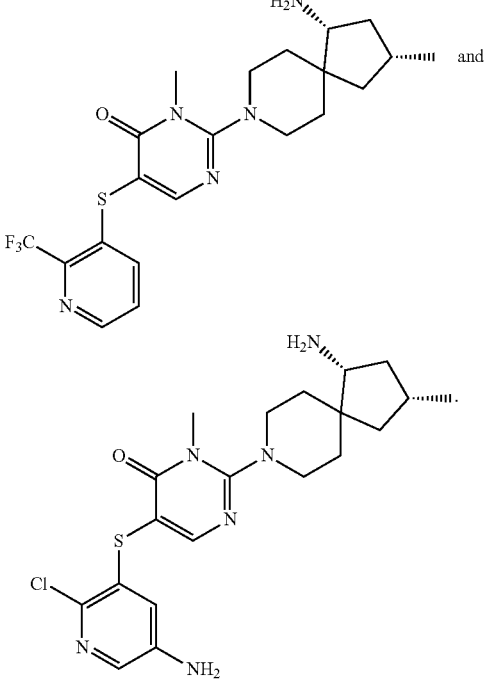

17. The compound of claim 1 of formula Id:

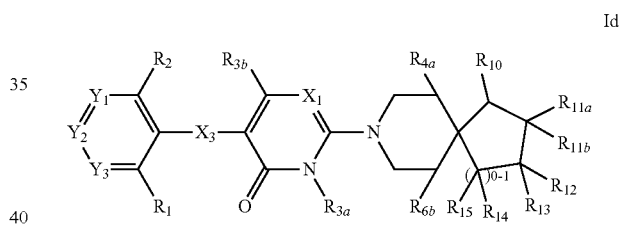

in which:
$X_1$ is selected from N and CH;
$X_3$ is a bond;
$Y_1$ is $CR_7$; wherein $R_7$ is selected from hydrogen, chloro and fluoro;
$Y_2$ is $CR_8$; wherein $R_8$ is selected from hydrogen, halo, amino, dimethyl-amino, cyano, $C_{3-6}$cycloalkyl, $C_{1-4}$alkyl, halo-substituted-$C_{1-3}$alkyl, halo-substituted-$C_{1-3}$alkyl-sulfanyl, $C_{1-3}$alkoxy, halo-substituted-$C_{1-3}$alkoxy, $C_{1-3}$alkoxy-$C_{1-3}$alkoxy, $C_6$aryl and $C_6$aryl-$C_{0-1}$alkoxy;
$Y_3$ is selected from $CR_9$; wherein $R_9$ is selected from hydrogen, chloro, fluoro and methyl;
$R_1$ is selected from hydrogen, chloro, and fluoro;
$R_2$ is hydrogen;
$R_{3a}$ is methyl;
$R_{3b}$ is amino;
$R_{4a}$ is selected from hydrogen, hydroxy and fluoro;
$R_{6b}$ is selected from hydrogen, hydroxy and fluoro;
$R_{10}$ is amino;
$R_{11a}$ is selected from hydrogen, hydroxy, fluoro, $C_{1-3}$alkyl and hydroxy-methyl;
$R_{11b}$ is selected from fluoro, methyl and hydrogen; with proviso that $R_{11a}$ and $R_{11b}$ cannot both be OH and fluoro simultaneously;

$R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy;

$R_{13}$ is selected from hydrogen, halo and $C_{1-3}$alkyl; with proviso that $R_{12}$ and $R_{13}$ cannot both be OH and fluoro simultaneously;

$R_{14}$ is selected from hydrogen and fluoro;

$R_{15}$ is selected from hydrogen and fluoro; or the pharmaceutically acceptable salts thereof.

18. The compound of claim 17, or a pharmaceutically acceptable salt thereof, selected from:

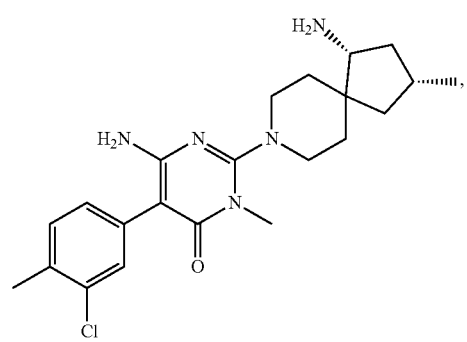

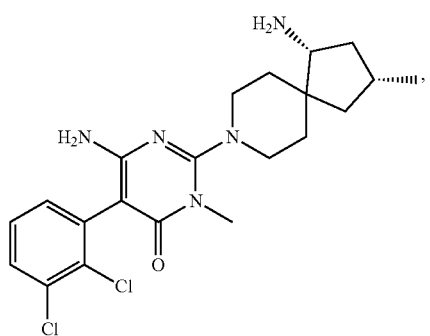

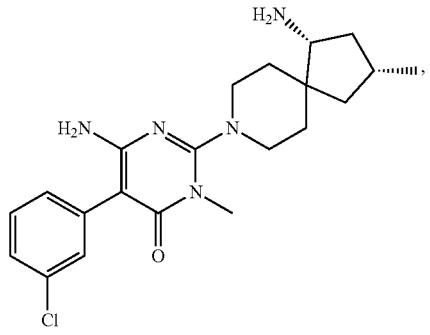

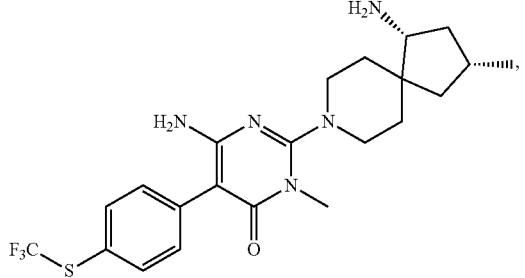

-continued

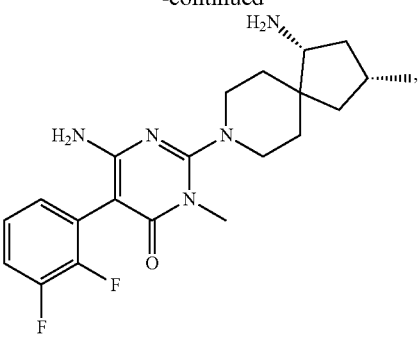

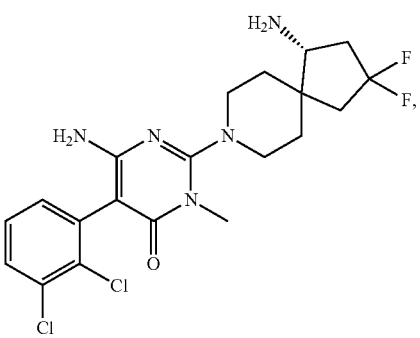

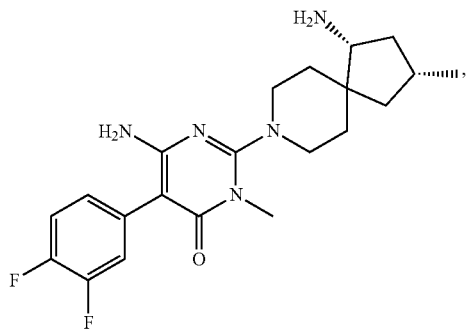

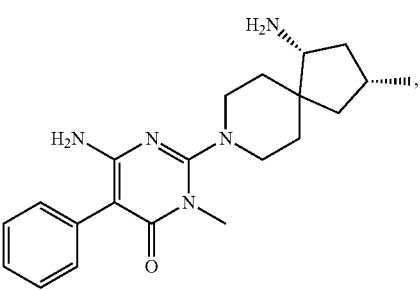

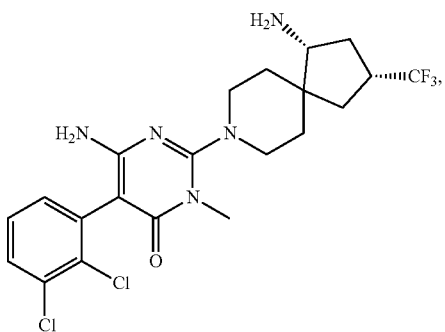

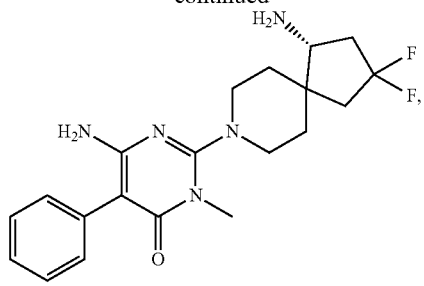
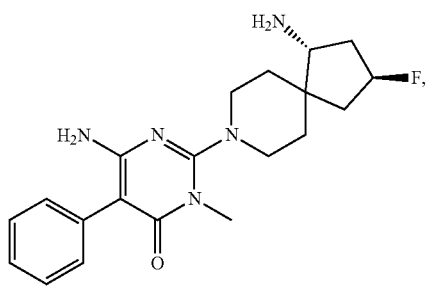
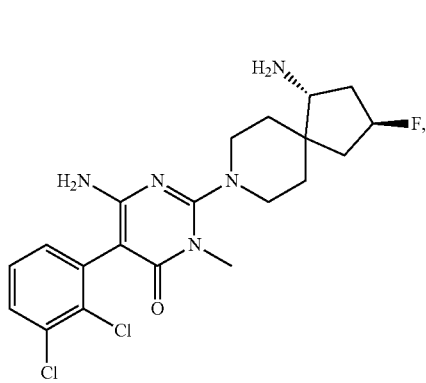
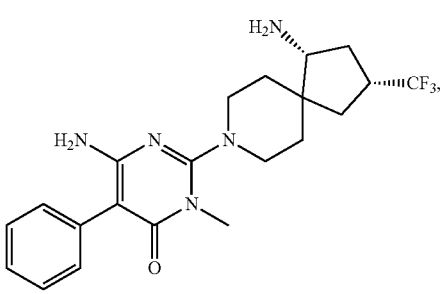
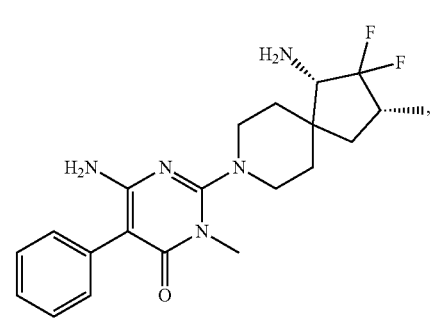
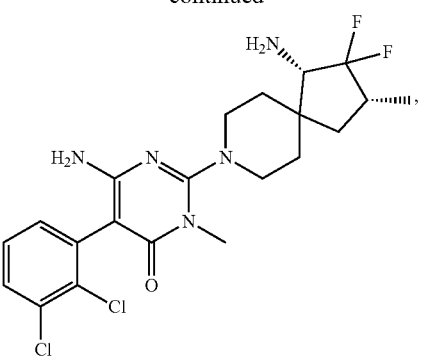
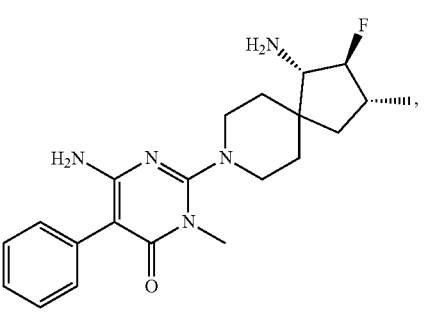
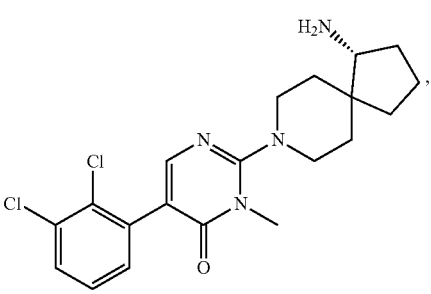
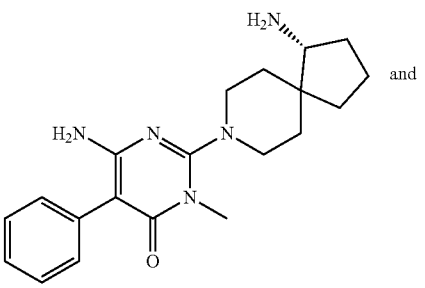

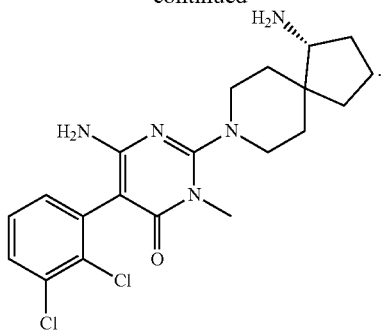

19. The compound of claim 1 of formula Ie:

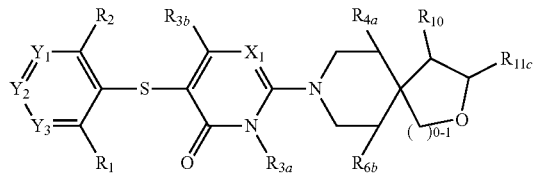

in which:

$X_1$ is selected from N and CH;

$Y_1$ is selected from $CR_7$; wherein $R_7$ is selected from hydrogen, halo and amino;

$Y_2$ is $CR_8$; wherein $R_8$ is selected from hydrogen, halo, amino, cyano, halo-substituted-$C_{1-3}$alkyl, $C_{1-3}$alkoxy and halo-substituted-$C_{1-3}$alkoxy;

$Y_3$ is selected from $CR_9$; wherein $R_9$ is selected from hydrogen, amino, halo, $C_{1-3}$alkoxy, and hydroxy;

$R_1$ is selected from halo-substituted-$C_{1-2}$alkyl, halo-substituted-$C_{1-2}$alkoxy, $C_{1-2}$alkyl and cyano;

$R_2$ is selected from hydrogen and halo;

$R_{3a}$ is selected from hydrogen, and methyl;

$R_{3b}$ is selected from hydrogen and methyl;

$R_{4a}$ is selected from hydrogen, hydroxy and fluoro; $R_{6b}$ is selected from hydrogen, hydroxy and fluoro;

$R_{10}$ is amino;

$R_{11a}$ is selected from hydrogen, hydroxy, fluoro, $C_{1-3}$alkyl and hydroxy-methyl;

$R_{11b}$ is selected from fluoro, methyl and hydrogen;

$R_{11c}$ is selected from hydrogen, $C_{1-3}$alkyl and hydroxy-methyl;

$R_{12}$ is selected from hydrogen, halo, hydroxy, $C_{1-3}$alkyl, halo-substituted-$C_{1-3}$alkyl, halo-substituted-$C_{1-3}$alkoxy and $C_{1-3}$alkoxy;

$R_{13}$ is selected from hydrogen, halo and $C_{1-3}$alkyl; with proviso that $R_{12}$ and $R_{13}$ cannot both be OH and fluoro simultaneously; or the pharmaceutically acceptable salts thereof.

20. The compound of claim 19, or a pharmaceutically acceptable salt thereof, selected from:

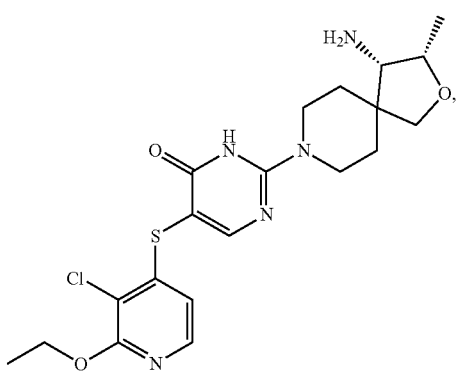

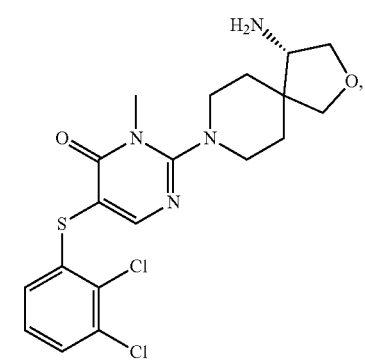

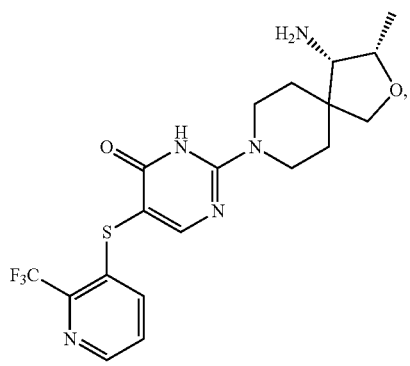

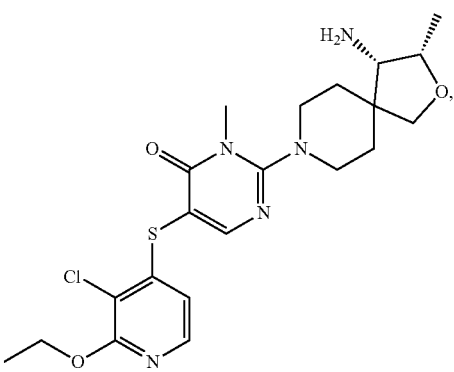

-continued

287
-continued
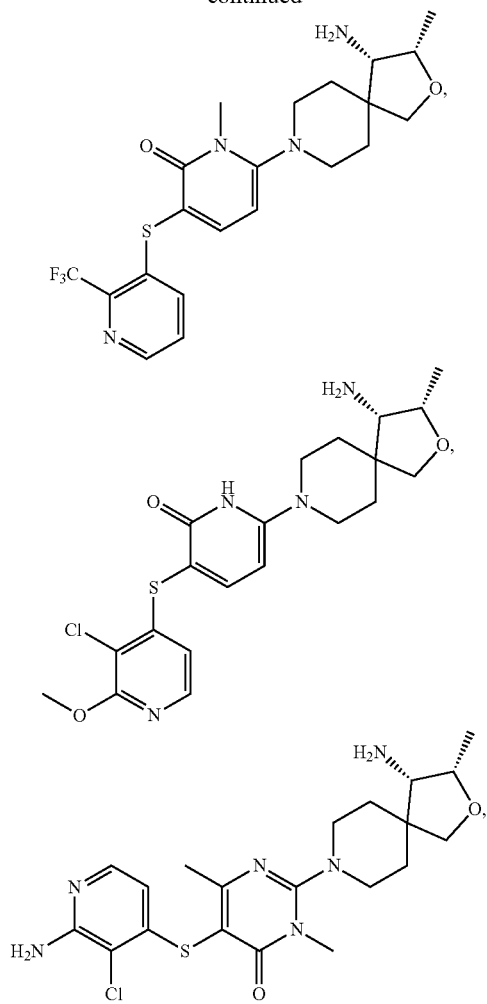
288
-continued
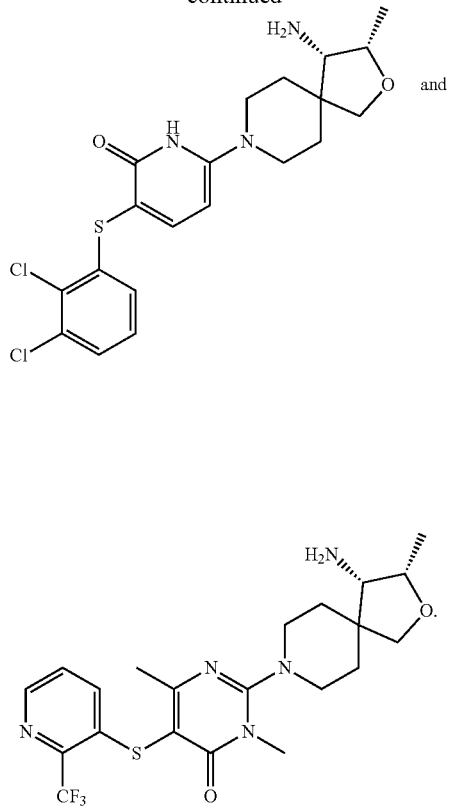
* * * * *

SEQUENCE LISTING

```
<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: biphosphorylated peptide derived from insulin
      receptor substrate-1 (IRS-1)
<220> FEATURE:
<221> NAME/KEY: MOD_RES
<222> LOCATION: (3)..(3)
<223> OTHER INFORMATION: PHOSPHORYLATED TYROSINE
<220> FEATURE:
<221> NAME/KEY: MOD_RES
<222> LOCATION: (9)..(9)
<223> OTHER INFORMATION: dPEG8 from valine residue 9 to leucine residue
      10
<220> FEATURE:
<221> NAME/KEY: MOD_RES
<222> LOCATION: (10)..(10)
<223> OTHER INFORMATION: dPEG8 from leucine residue 10 to valine residue
      9
<220> FEATURE:
<221> NAME/KEY: MOD_RES
<222> LOCATION: (14)..(14)
<223> OTHER INFORMATION: PHOSPHORYLATED TYROSINE
<220> FEATURE:
```

```
<221> NAME/KEY: MOD_RES
<222> LOCATION: (20)..(20)
<223> OTHER INFORMATION: AMIDATED LYSINE

<400> SEQUENCE: 1

Leu Asn Tyr Ile Asp Leu Asp Leu Val Leu Ser Thr Tyr Ala Ser Ile
1               5                   10                  15

Asn Phe Gln Lys
            20
```